United States Patent
Moniz et al.

(10) Patent No.: US 11,992,527 B2
(45) Date of Patent: May 28, 2024

(54) EXTRACELLULAR VESICLES FOR VACCINE DELIVERY

(71) Applicant: LONZA SALES AG, Basel (CH)

(72) Inventors: Raymond J. Moniz, Brighton, MA (US); Russell E. McConnell, Cambridge, MA (US); Nikki Ross, Philadelphia, PA (US); Christine McCoy, Cambridge, MA (US); Timothy J. Soos, Boston, MA (US); Ke Xu, Belmont, MA (US)

(73) Assignee: LONZA SALES AG, Basel (CH)

( * ) Notice: Subject to any disclaimer, the term of this patent is extended or adjusted under 35 U.S.C. 154(b) by 0 days.

(21) Appl. No.: 18/050,027

(22) Filed: Oct. 26, 2022

(65) Prior Publication Data

US 2023/0263885 A1 Aug. 24, 2023

Related U.S. Application Data

(62) Division of application No. 17/441,524, filed as application No. PCT/US2020/024023 on Mar. 20, 2020.

(60) Provisional application No. 62/984,146, filed on Mar. 2, 2020, provisional application No. 62/946,280, filed on Dec. 10, 2019, provisional application No. 62/901,166, filed on Sep. 16, 2019, provisional application No. 62/891,048, filed on Aug. 23, 2019, provisional application No. 62/840,348, filed on Apr. 29, 2019, provisional application No. 62/835,437, filed on Apr. 17, 2019, provisional application No. 62/822,008, filed on Mar. 21, 2019.

(51) Int. Cl.
| | |
|---|---|
| *A61P 35/00* | (2006.01) |
| *A61K 39/385* | (2006.01) |
| *A61P 31/00* | (2006.01) |
| *A61P 31/12* | (2006.01) |
| *A61P 35/04* | (2006.01) |
| *A61P 37/04* | (2006.01) |
| *A61K 39/00* | (2006.01) |

(52) U.S. Cl.
CPC .......... *A61K 39/385* (2013.01); *A61P 37/04* (2018.01); *A61K 2039/60* (2013.01)

(58) Field of Classification Search
CPC .......... A61P 35/00; A61P 11/00; A61P 25/00; A61P 31/12; A61P 37/04
See application file for complete search history.

(56) References Cited

FOREIGN PATENT DOCUMENTS

WO WO-2016184860 A1 11/2016

OTHER PUBLICATIONS

Chen, R., et al., "Exosomes in hepatocellular carcinoma: a new horizon," Cell Commun Signal 17(1):1, Biomed Central, United Kingdom (Jan. 2019).
Fantappie, L., et al., "Antibody-mediated immunity induced by engineered *Escherichia coli* OMVs carrying heterologous antigens in their lumen," J Extracell Vesicles 3(1), John Wiley & Sons, United States (Aug. 2014).
Gnopo, Y.M.D., et al., "Designer outer membrane vesicles as immunomodulatory systems—Reprogramming bacteria for vaccine delivery," Adv Drug Deliv Rev 114:132-142, Elsevier, Netherlands (May 2017).
Grandi, A., et al., "Synergistic Protective Activity of Tumor-Specific Epitopes Engineered in Bacterial Outer Membrane Vesicles," Front Oncol 7:253, Frontiers Media, S.A., Switzerland (Nov. 2017).
He, Y., et al., "Engineering α-fetoprotein-based gene vaccines to prevent and treat hepatocellular carcinoma: review and future prospects," Immunotherapy 6(6):725-736, Future Medicine, United Kingdom (Jun. 2014).
International Search Report and Written Opinion for International Application No. PCT/US2020/024023, European Patent Office, Netherlands, mailed on Sep. 23, 2020, 31 pages.
Kato, K., et al., "Cyclic GMP-AMP as an Endogenous Second Messenger in Innate Immune Signaling by Cytosolic DNA," Annu Rev Biochem 86:541-566, Annual Reviews, United States (Jun. 2017).
Kitai, Y., et al., "DNA-Containing Exosomes Derived from Cancer Cells Treated with Topotecan Activate a STING-Dependent Pathway and Reinforce Antitumor Immunity," J Immunol 198(4):1649-1659, American Association of Immunologists, United States (Feb. 2017).
Koshy, S.T., et al., "Liposomal Delivery Enhances Immune Activation by STING Agonists for Cancer Immunotherapy," Adv Biosyst 1(1-2):1600013, Wiley, United States (Feb. 2017).
Ma, F., et al., "Positive feedback regulation of type I interferon by the interferon-stimulated gene STING," EMBO Rep 16(2):202-212, Nature Portfolio, Germany (Feb. 2015).
Miyabe, H., et al., "A new adjuvant delivery system 'cyclic di-GMP/YSK05 liposome' for cancer immunotherapy," J Control Release 184:20-27, Elsevier, Netherlands (Jun. 2014).
Tan, K., et al., "Outer Membrane Vesicles: Current Status and Future Direction of These Novel Vaccine Adjuvants," Front Microbiol 9:783, Frontiers Media S.A., Switzerland (Apr. 2018).

*Primary Examiner* — Barry A Chestnut
(74) *Attorney, Agent, or Firm* — MEDLER FERRO WOODHOUSE & MILLS PLLC

(57) ABSTRACT

The present disclosure relates to extracellular vesicles (EVs), e.g., exosomes, comprising a payload (e.g., an antigen, adjuvant, and/or immune modulator) and/or a targeting moiety. Also provided herein are methods for producing the EVs (e.g., exosomes) and methods for using the EVs (e.g., exosomes) to treat and/or prevent diseases or disorders, e.g., cancer, graft-versus-host disease (GvHD), autoimmune disease, infectious diseases, or fibrotic diseases.

20 Claims, 46 Drawing Sheets

Specification includes a Sequence Listing.

⊗ inoculation   ◉ RX dosing   ⦿ uptake dosing   ○ sacrifice

| group | Rx | route | N | 0 | 7 | 14 | 21 | | |
|---|---|---|---|---|---|---|---|---|---|
| 1 | IgG-Px-OVA + CL656 | IN | 10 | ◉ | ⦿ | | ○ | | |
| 2 | IgG-Px-OVA exoVACC | IN | 10 | ◉ | ⦿ | | ○ | | |
| 3 | aCLEC9A-Px-OVA + CL656 | IN | 10 | ◉ | ⦿ | | ○ | | |
| 4 | aCLEC9A-Px-OVA exoVACC | IN | 10 | ◉ | ⦿ | | ○ | | |
| 5 | PyOVA exoVACC | IN | 10 | ◉ | ⦿ | | ○ | | |
| | TOTAL | | 50 | | | | | | |

Aims:
1. Determine whether there is a benefit to targeting CLEC9A+ cells in exoVACC.

Endpoints:
1. FACS analysis of T cell responses in the spleen and lung following intranasal vaccination, 7 days after prime
2. 14 days after boost, serum and T cell analysis

FIG. 6

| Group | Rx | Dose | # Doses | Route | N | 0 | 1 | 2 | 3 | 4 | 5 | 6 | 7 | 8 | 9 | 10 | 11 | 12 | 13 |
|---|---|---|---|---|---|---|---|---|---|---|---|---|---|---|---|---|---|---|---|
| 1 | PBS | | 1 | SQ | 9 | ◉ | | | | | | | ○ | | | | | | |
| 2 | exoVACC | OVA (0.5 ug) | 1 | IN | 9 | ● | | | | | | | ○ | | | | | | |
| 3 | exoVACC | OVA (0.5 ug) | 1 | SQ | 9 | ◉ | | | | | | | ○ | | | | | | |
| 4 | OVA +Poly:C | OVA (0.5 ug) + Poly:C (5 ug) | 1 | IN | 9 | ● | | | | | | | ○ | | | | | | |
| 5 | OVA +Poly:C | OVA (0.5 ug) + Poly:C (50 ug) | 1 | SQ | 9 | ◉ | | | | | | | ○ | | | | | | |

Key:
○ Tumor Inoculation (SC)   ⊕ Dosing (IP)
◉ Dosing (SC)   ● Dosing (IN)
⊗ Dosing (IT)   ⊘ Dosing (IV)
⊛ Sacrifice   ◐ Dosing (other)

FIG. 14A

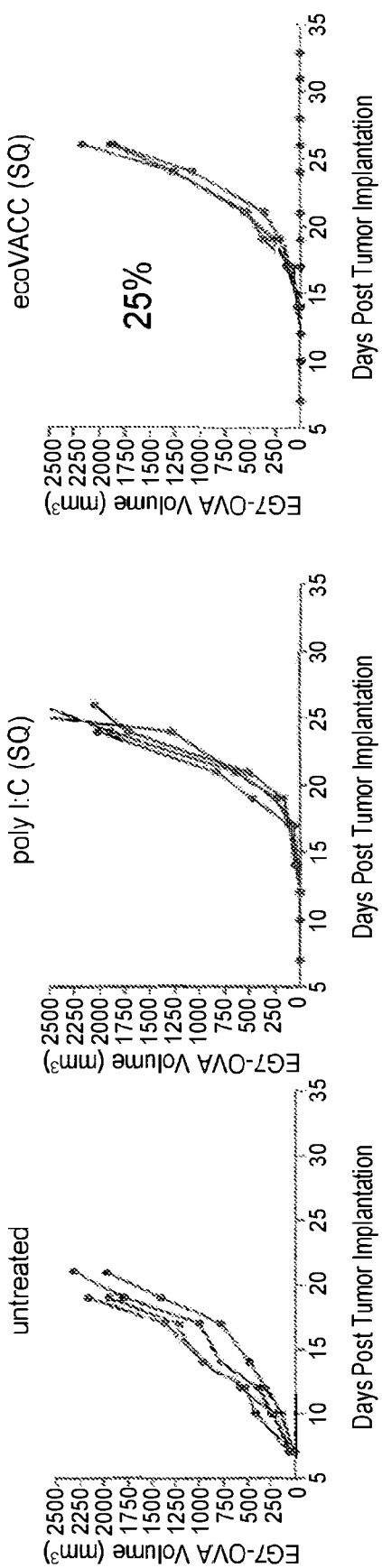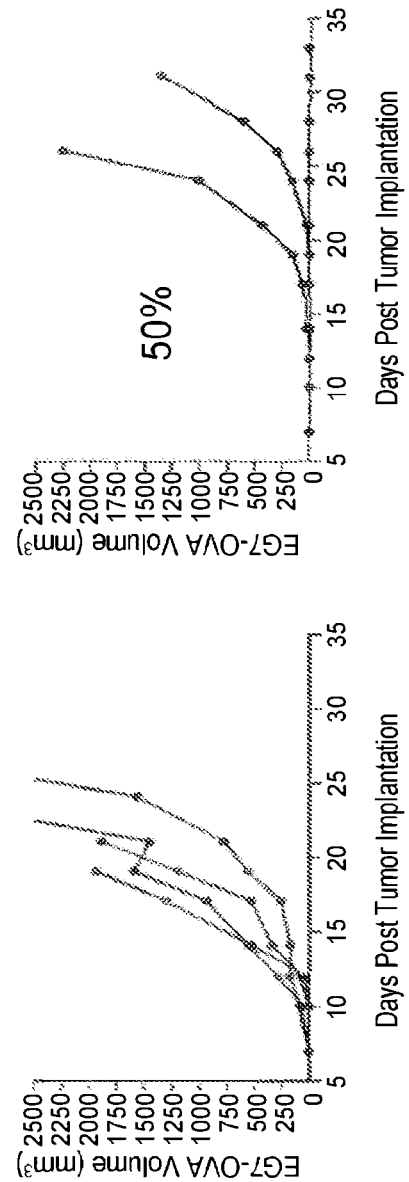
FIG. 14C   FIG. 14D   FIG. 14E   FIG. 14F   FIG. 14G

| | Composition | Dose | Molec. STING/exo | 0 | 7 | 14 |
|---|---|---|---|---|---|---|
| 1 | PBS | 0.1 mL | NA | ○ | ○ | ● |
| 2 | exo – Lama4+CL656 | Equal STING agonist | 2991 | ○ | ○ | ● |
| 3 | exo – Itgb1+CL656 | | 2158 | ○ | ○ | ● |
| 4 | exo – Lama4+Itgb1+CL656 | | 4372 | ○ | ○ | ● |

FIG. 16A

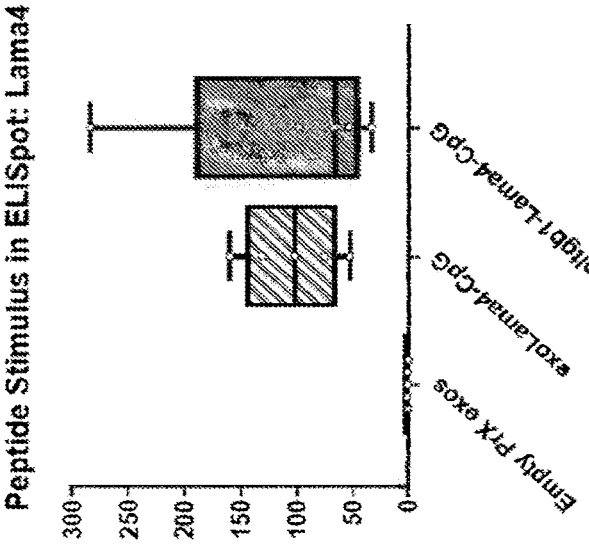
FIG. 17A
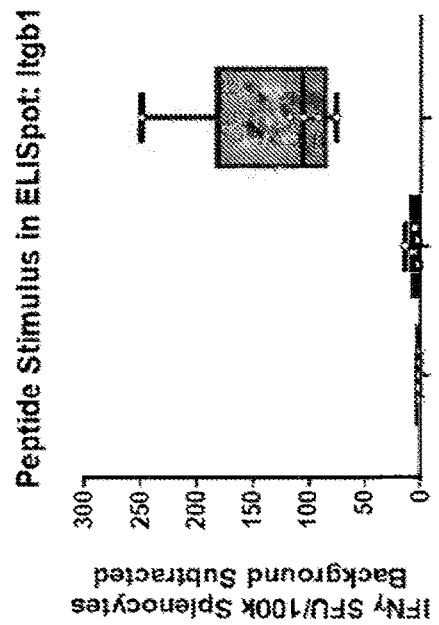
FIG. 17B
FIG. 17C

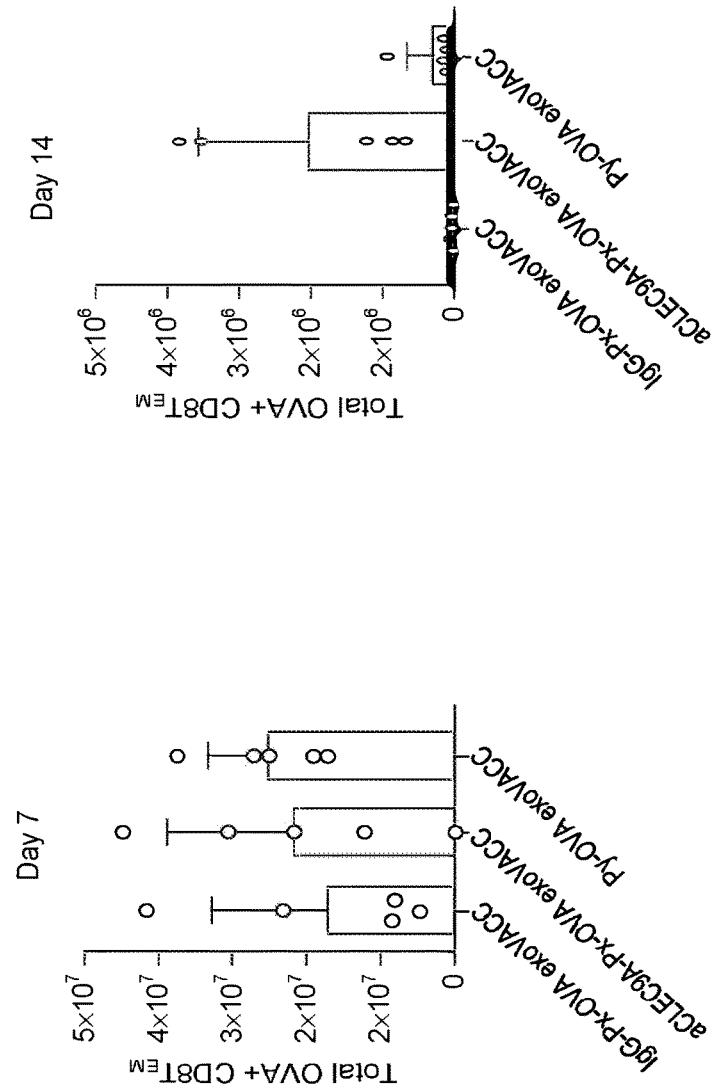

FIG. 22

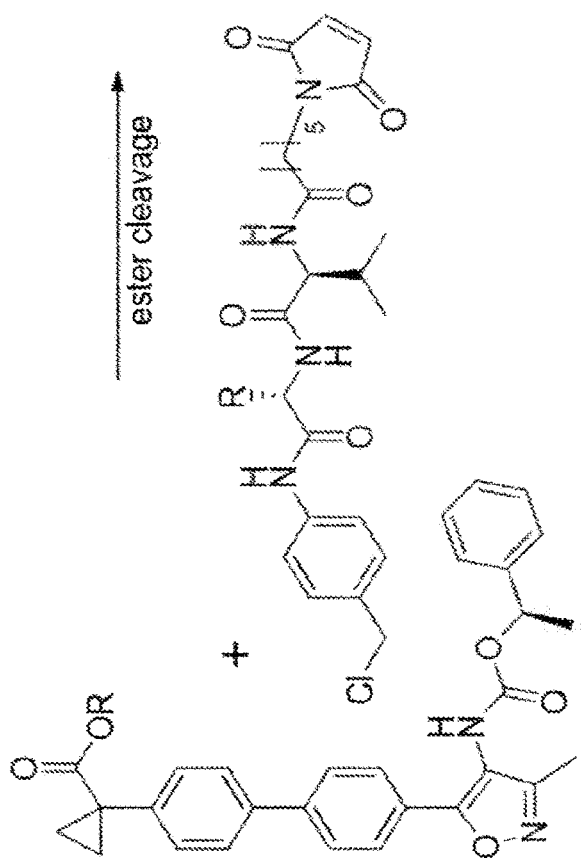
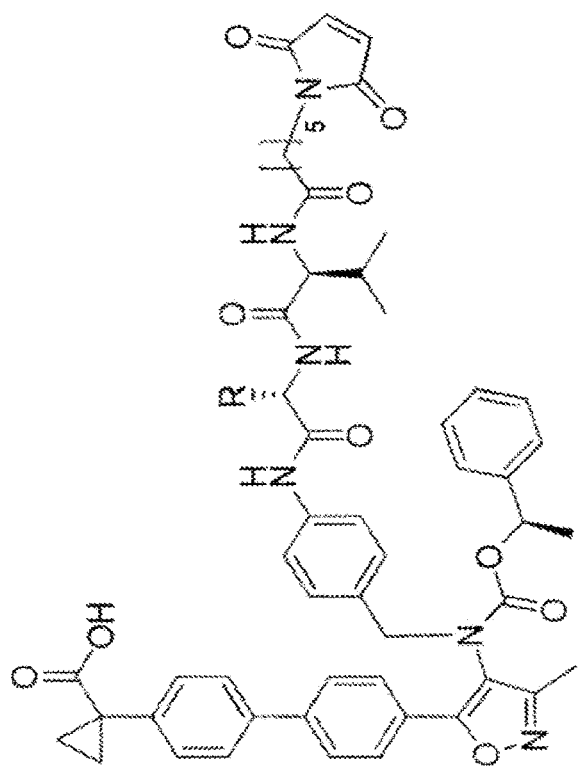
FIG. 28

EXTRACELLULAR VESICLES FOR VACCINE DELIVERY

CROSS-REFERENCE TO RELATED APPLICATIONS

This application is a division of U.S. application Ser. No. 17/441,524, filed Sep. 21, 2021, which is a U.S. National Phase application of PCT Application No. PCT/US2020/024023, filed Mar. 20, 2020, which claims the priority benefit of U.S. Provisional Application Nos. 62/822,008, filed Mar. 21, 2019; 62/835,437, filed Apr. 17, 2019; 62/840,348, filed Apr. 29, 2019; 62/891,048, filed Aug. 23, 2019; 62/901,166, filed Sep. 16, 2019; 62/946,280, filed Dec. 10, 2019; and 62/984,146, filed Mar. 2, 2020, each of which is herein incorporated by reference in its entirety.

REFERENCE TO SEQUENCE LISTING SUBMITTED ELECTRONICALLY VIA EFS-WEB

The content of the electronically submitted sequence listing in XML filed (Name: 4000_0320008_Sequence-Listing_ST26, Size: 413,475 bytes; and Date of Creation: May 12, 2023) submitted in this application is incorporated herein by reference in its entirety.

FIELD OF DISCLOSURE

The present disclosure relates to modified extracellular vesicles, e.g., exosomes (e.g., comprises one or more payloads, e.g., an antigen and adjuvant/immune modulator) that is useful as a vaccine that can be used to treat and/or prevent a range of medical disorders, including, but not limited to, cancer, graft-versus-host disease (GvHD), autoimmune disease, infectious diseases, and fibrotic diseases. The present disclosure also relates to methods of producing such EVs, e.g., exosomes, and uses thereof.

BACKGROUND

EVs, e.g., exosomes, are important mediators of intercellular communication. They are also important biomarkers in the diagnosis and prognosis of many diseases, such as cancer. As drug delivery vehicles, EVs, e.g., exosomes, offer many advantages over traditional drug delivery methods (e.g., peptide immunization, DNA vaccines) as a new treatment modality in many therapeutic areas. However, despite its advantages, many EVs, e.g., exosomes, have had limited clinical efficacy. For example, dendritic-cell derived exosomes (DEX) were investigated in a Phase II clinical trial as maintenance immunotherapy after first line chemotherapy in patients with inoperable non-small cell lung cancer (NSCLC). However, the trial was terminated because the primary endpoint (at least 50% of patients with progression-free survival (PFS) at 4 months after chemotherapy cessation) was not reached. Besse, B., et al., *Oncoimmunology* 5(4):e1071008 (2015).

Accordingly, new and more effective engineered-EVs, e.g., exosomes, are necessary to better enable therapeutic use and other applications of EV-based technologies.

SUMMARY OF DISCLOSURE

Provided herein are isolated EVs, e.g., exosomes, comprising (i) at least one antigen and (ii) at least one adjuvant. In some aspects, the EV comprises at least 2, 3, 4, 5, 6, 7, 8, 9, 10 or more different antigens. In some aspects, the EV comprises at least at least 2, 3, 4, 5, 6, 7, 8, 9, 10 or more different adjuvants. In some aspects, the antigen is not presented on MHC class I and/or II molecules In some aspects, an EV, e.g., exosome, is not derived from a naturally-existing antigen-presenting cell. In certain aspects, an EV, e.g., exosome, is not derived from a naturally-existing dendritic cell, a naturally-existing B cell, a naturally-existing mast cell, a naturally-existing macrophage, a naturally-existing neutrophil, naturally-existing Kupffer-Browicz cell, cell derived from any of these cells, or any combination thereof.

In some aspects, an EV, e.g., exosome, induces a cellular immune response, a humoral immune response, or both cellular and humoral immune responses. In certain aspects, the induction of the cellular immune response, the humoral immune response, or both cellular and humor immune responses is increased by at least about 5%, at least about 10%, at least about 20%, at least about 30%, at least about 40%, at least about 50%, at least about 60%, at least about 70%, at least about 80%, at least about 90%, at least about 100% or more, compared to (i) a corresponding EV, e.g., exosome, that does not comprise the adjuvant or the antigen or (ii) the adjuvant or the antigen without the EV (i.e., non-EV delivery vehicle).

In some aspects, an EV, e.g., exosome, described herein induces a CD4+ T cell response, a CD8+ T cell response, or both CD4+ and CD8+ T cell responses. In certain aspects, an EV, e.g., exosome, does not directly interact with T Cell Receptors (TCRs) of T cells.

In some aspects, an EV, e.g., exosome, of the present disclosure further comprises a first scaffold moiety. In certain aspects, the antigen is linked to the first scaffold moiety. In some aspects, the adjuvant is linked to the first scaffold moiety. In some aspects, an EV, e.g., exosome, further comprises a second scaffold moiety. In certain aspects, the antigen is linked to the first scaffold moiety, and the adjuvant is linked to the second scaffold moiety. In some aspects, the first scaffold moiety and the second scaffold moiety are the same. In other aspects, the first scaffold moiety and the second scaffold moiety are different.

In some aspects, a first scaffold moiety is a Scaffold X. In other aspects, a first scaffold moiety is a Scaffold Y. In some aspects, a second scaffold moiety is a Scaffold X. In certain aspects, a second scaffold moiety is a Scaffold Y.

In some aspects, Scaffold X is capable of: (i) anchoring the antigen to the luminal surface of the EV, e.g., exosome; (ii) anchoring the antigen on the exterior surface of the EV, e.g., exosome; (iii) anchoring the adjuvant to the luminal surface of the EV, e.g., exosome; (iv) anchoring the adjuvant on the exterior surface of the EV, e.g., exosome; or (v) combinations thereof. In certain aspects, Scaffold X is selected from the group consisting of prostaglandin F2 receptor negative regulator (the PTGFRN protein); basigin (the BSG protein); immunoglobulin superfamily member 2 (the IGSF2 protein); immunoglobulin superfamily member 3 (the IGSF3 protein); immunoglobulin superfamily member 8 (the IGSF8 protein); integrin beta-1 (the ITGB1 protein); integrin alpha-4 (the ITGA4 protein); 4F2 cell-surface antigen heavy chain (the SLC3A2 protein); a class of ATP transporter proteins (the ATP1A1, ATP1A2, ATP1A3, ATP1A4, ATP1B3, ATP2B1, ATP2B2, ATP2B3, ATP2B4 proteins), and any combination thereof.

In some aspects, Scaffold Y is capable of: (i) anchoring the antigen to the luminal surface of the EV, e.g., exosome; (ii) anchoring the adjuvant to the luminal surface of the EV, e.g., exosome; or (iii) both. In certain aspects, the Scaffold Y is selected from the group consisting of myristoylated alanine rich Protein Kinase C substrate (the MARCKS protein); myristoylated alanine rich Protein Kinase C substrate like 1 (the MARCKSL1 protein); brain acid soluble protein 1 (the BASP1 protein), and any combination thereof.

In some aspects, the antigen is linked to a first scaffold moiety on the luminal surface of the EV, e.g., exosome, (e.g., those described herein), and the adjuvant is linked to a second scaffold moiety on the luminal surface of the EV, e.g., exosome, (e.g., those described herein). In some of such aspects, (a) each of the first scaffold moiety and the second scaffold moiety is Scaffold Y; (b) the first scaffold moiety is Scaffold Y, and the second scaffold moiety is Scaffold X; (c) the first scaffold moiety is Scaffold X, and the second scaffold moiety is Scaffold Y; or (d) each of the first scaffold moiety and the second scaffold moiety is Scaffold X.

In some aspects, the antigen is linked to a first scaffold moiety on the luminal surface of the EV, e.g., exosome, and the adjuvant is in the lumen of the EV. In certain aspects, the antigen is in the lumen of the EV, e.g., exosome, and the adjuvant is linked to a first scaffold moiety on the luminal surface of the EV. In further aspects, the antigen is linked to a first scaffold moiety on the luminal surface of the EV, e.g., exosome, and the adjuvant is linked to a second scaffold moiety on the exterior surface of the exosome. In some of these aspects, (a) the first scaffold moiety is Scaffold Y, and the second scaffold moiety is Scaffold X; or (b) each of the first scaffold moiety and the second scaffold moiety is Scaffold X.

In some aspects, the antigen is linked to a first scaffold moiety on the exterior surface of the EV, e.g., exosome, and the adjuvant is linked to a second scaffold moiety in the luminal surface of the EV. In certain of these aspects, (a) the first scaffold moiety is Scaffold X, and the second scaffold moiety is Scaffold Y; or (b) each of the first scaffold moiety and the second scaffold moiety is Scaffold X.

In some aspects, the antigen is in the lumen or linked to the luminal surface of the EV, e.g., exosome, and the adjuvant is in the lumen or linked to the luminal surface of the EV, e.g., exosome.

In some aspects, the antigen is linked to a first scaffold moiety on the exterior surface of the EV, e.g., exosome, and the adjuvant is linked to a second scaffold moiety on the exterior surface of the EV, e.g., exosome. In some of such aspects, the first scaffold and the second scaffold moiety are Scaffold X.

In some aspects, the antigen is linked to a first scaffold moiety on the exterior surface of the EV, e.g., exosome, and the adjuvant is in the lumen of the EV, e.g., exosome. In certain of these aspects, the first scaffold is Scaffold X.

In some aspects, the antigen is in the lumen of the EV, e.g., exosome, and the adjuvant is linked to a first scaffold moiety on the exterior surface of the EV, e.g., exosome. In some of these aspects, the first scaffold is Scaffold X.

In some aspects, the antigen is linked to a first scaffold moiety on the surface of the EV, e.g., exosome, and the adjuvant is linked to the first scaffold moiety on the luminal surface of the EV, e.g., exosome. In certain aspects, the antigen is linked to a first scaffold moiety on the luminal surface of the EV, e.g., exosome and the adjuvant is linked to the first scaffold moiety on the exterior surface of the EV, e.g., exosome. In some of these aspects, the first scaffold moiety is Scaffold X.

In some aspects, (i) the antigen is linked to the first scaffold moiety by a linker, (ii) the antigen is linked to the second scaffold moiety by a linker, (iii) the adjuvant is linked to the first scaffold moiety by a linker, (iv) the adjuvant is linked to the second moiety by a linker, or (v) combinations thereof. In certain aspects, the linker is a polypeptide. In other aspects, the linker is a non-polypeptide moiety. In some aspects, the linker comprises a maleimide moiety. In some aspects, the linker comprises a cholesterol moiety.

In some aspects, the first scaffold moiety or the second scaffold moiety is PTGFRN protein. In certain aspects, the first scaffold moiety or the second scaffold moiety comprises an amino acid sequence as set forth in SEQ ID NO: 33. In further aspects, the first scaffold moiety or the second scaffold moiety comprises an amino acid sequence at least 50%, at least 60%, at least 70%, at least 80%, at least 85%, at least 90%, at least 95%, at least 96%, at least 97%, at least 98%, at least 99%, or about 100% identical to SEQ ID NO: 1.

In some aspects, the first scaffold moiety or the second scaffold moiety is BASP1 protein. In some aspects, the first scaffold moiety or the second scaffold moiety comprises a peptide of (M)(G)(π)(X)(Φ/π)(π)(+)(+) or (G)(n)(X)(Φ/π)(π)(+)(+), wherein each parenthetical position represents an amino acid, and wherein π is any amino acid selected from the group consisting of Pro, Gly, Ala, and Ser, X is any amino acid, 1 is any amino acid selected from the group consisting of Val, Ile, Leu, Phe, Trp, Tyr, and Met, and (+) is any amino acid selected from the group consisting of Lys, Arg, and His; and wherein position five is not (+) and position six is neither (+) nor (Asp or Glu). In certain aspects, the first scaffold moiety or the second scaffold moiety comprises an amino acid sequence set forth in any one of SEQ ID NO: 50-155. In further aspects, the first scaffold moiety or the second scaffold moiety comprises an amino acid sequence at least 50%, at least 60%, at least 70%, at least 80%, at least 85%, at least 90%, at least 95%, at least 96%, at least 97%, at least 98%, at least 99%, or about 100% identical to SEQ ID NO: 3.

Also provided herein is an EV, e.g., exosome, comprising (i) an antigen and (ii) an adjuvant, wherein: (a) the antigen is linked to a first Scaffold Y on the luminal surface, and the adjuvant is linked to a second Scaffold Y on the luminal surface of the EV, e.g., exosome; (b) the antigen is linked to a Scaffold Y on the luminal surface, and the adjuvant is in the lumen of the EV, e.g., exosome; (c) the antigen is in the lumen of the EV, e.g., exosome, and the adjuvant is linked to a Scaffold Y on the luminal surface of the EV, e.g., exosome; (d) the antigen is linked to a Scaffold Y on the luminal surface of the EV, e.g., exosome, and the adjuvant is linked to a Scaffold X on the exterior surface of the EV, e.g., exosome; (e) the antigen is in the lumen of the EV, e.g., exosome, and the adjuvant is linked to a Scaffold X on the exterior surface of the EV, e.g., exosome; (f) the antigen is linked to a Scaffold Y on the luminal surface of the EV, e.g., exosome, and the adjuvant is linked to a Scaffold X on the luminal surface of the EV, e.g., exosome; (g) the antigen is in the lumen of the EV, e.g., exosome, and the adjuvant is linked to a Scaffold X on the luminal surface of the EV, e.g., exosome; (h) the antigen is linked to a Scaffold X on the luminal surface of the EV, e.g., exosome, and the adjuvant is linked to the Scaffold X on the exterior surface of the EV, e.g., exosome; (i) the antigen is linked to a first Scaffold X on the exterior surface of the EV, e.g., exosome, and the adjuvant is linked to a second Scaffold X on the exterior surface of the EV, e.g., exosome; (j) the antigen is linked to a Scaffold X on the exterior surface of the EV, e.g., exosome, and the adjuvant is linked to a Scaffold Y on the luminal surface of the EV, e.g., exosome; (k) the antigen is linked to a Scaffold X on the exterior surface of the EV, e.g., exosome, and the adjuvant is in the lumen of the EV, e.g., exosome; (1) the antigen is linked to a Scaffold X on the exterior surface of the EV, e.g., exosome, and the adjuvant is linked to the Scaffold X on the luminal surface of the EV, e.g., exosome; (m) the antigen is linked to a first Scaffold X on the luminal surface of the EV, e.g., exosome, and the adjuvant is linked to a second Scaffold X in on the luminal surface of the EV, e.g., exosome; (n) the antigen is linked to a Scaffold X on the luminal surface of the EV, e.g., exosome, and the adjuvant is linked to a Scaffold Y on the luminal surface of the EV, e.g., exosome; (o) the antigen is linked to a Scaffold X on the luminal surface of the EV, e.g., exosome, and the adjuvant is in the lumen of the EV, e.g., exosome; (p) the antigen is linked to a first Scaffold X on the exterior surface of the EV, e.g., exosome, and the adjuvant is linked to a second Scaffold X on the luminal surface of the EV, e.g., exosome; (q) the antigen is linked to a first Scaffold X on the luminal surface of the EV, e.g., exosome, and the adjuvant is linked to a second Scaffold X on the exterior surface of the EV, e.g., exosome; (r) the antigen is in the lumen of the EV, e.g., exosome, and the adjuvant is on the luminal surface of the EV, e.g., exosome; (s) the antigen is linked directly to the luminal surface of the EV, and the adjuvant is linked directly to the luminal surface of the EV; (t) the antigen is linked directly to the luminal surface of the EV, and the adjuvant is in the lumen of the EV; (u) the antigen is linked directly to the luminal surface of the EV, and the adjuvant is linked to a Scaffold Y on the luminal surface of the EV; (v) the antigen is linked directly to the luminal surface of the EV, and the adjuvant is linked to a Scaffold X on the luminal surface of the EV; (w) the antigen is linked directly to the luminal surface of the EV, and the adjuvant is linked directly to the exterior surface of the EV; (x) the antigen is linked directly to the luminal surface of the EV, and the adjuvant is linked to a Scaffold X on the exterior surface of the EV; (y) the antigen is linked to a Scaffold Y on the luminal surface of the EV, and the adjuvant is linked directly to the luminal surface of the EV; (z) the antigen is linked to a Scaffold Y on the luminal surface of the EV, and the adjuvant is linked directly to the exterior surface of the EV; (aa) the antigen is linked to a Scaffold X on the luminal surface of the EV, and the adjuvant is linked directly to the luminal surface of the EV; (bb) the antigen is linked to a Scaffold X on the luminal surface of the EV, and the adjuvant is linked directly to the exterior surface of the EV; (cc) the antigen is in the lumen of the EV, and the adjuvant is linked directly to the luminal surface of the EV; or (dd) the antigen is in the lumen of the EV, and the adjuvant is linked directly to the exterior of the EV.

In some aspects, an EV, e.g., exosome disclosed herein further comprises an immune modulator. In some aspects, the immune modulator is directly linked to the luminal surface or the exterior surface of the EV. In certain aspects, the immune modulator is linked to a Scaffold X on the exterior surface of the EV, e.g., exosome or on the luminal surface of the EV, e.g., exosome. In some aspects, the immune modulator is linked to a Scaffold Y on the luminal surface of the EV, e.g., exosome. In further aspects, the immune modulator is on the luminal surface of the EV, e.g., exosome.

In some aspects, an EV comprises an antigen, adjuvant, and immune modulator, wherein: (i) the antigen is linked directly to the luminal surface by a linker, (ii) the adjuvant is linked directly to the luminal surface by a linker, (iii) the immune modulator is linked directly to the luminal surface by a linker, (iv) the antigen is linked directly to the exterior surface by a linker, (v) the adjuvant is linked directly to the exterior surface by a linker, (vi) the immune modulator is linked directly to the exterior surface by a linker, or (vii) combinations thereof. In some aspects, an EV comprises an antigen, adjuvant, and immune modulator, wherein: (i) the antigen is linked to a Scaffold X by a linker, (ii) the adjuvant is linked to a Scaffold X by a linker, (iii) the immune modulator is linked to a Scaffold X by a linker, (iv) the antigen is linked to a Scaffold Y by a linker, (v) the adjuvant is linked to a Scaffold Y by a linker, (vi) the immune modulator is linked to a Scaffold Y by a linker, or (vii) combinations thereof. In some aspects, the immune modulator is in the lumen of the EV.

In some aspects, the linker is a polypeptide. In certain aspects, the linker is a non-polypeptide moiety. In some aspects, the linker comprises a maleimide moiety. In some aspects, the linker comprises a cholesterol moiety.

In some aspects, an immune modulator comprises an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, an immune modulator comprises an activator for a positive co-stimulatory molecule or an activator for a binding partner of a positive co-stimulatory molecule. In certain aspects, the positive co-stimulatory molecule is a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2). In further aspects, the positive co-stimulatory molecule is a CD28-superfamily co-stimulatory molecule (e.g., ICOS or CD28). In some aspects, the activator for a positive co-stimulatory molecule is ICOSL, CD80, or CD86.

In some aspects, an immune modulator comprises a cytokine or a binding partner of a cytokine. In certain aspects, the cytokine comprises IL-2, IL-4, IL-7, IL-10, IL-12, IL-15, IL-21, IFN-γ, IL-1α, IL-1β, IL-1ra, IL-18, IL-33, IL-36α, IL-36β, IL-36γ, IL-36ra, IL-37, IL-38, IL-3, IL-5, IL-6, IL-11, IL-13, IL-23, granulocyte-macrophage colony stimulating factor (GM-CSF), granulocyte-colony stimulating factor (G-CSF), leukemia inhibitory factor (LIF), stem cell factor (SCF), thrombopoietin (TPO), macrophage-colony stimulating factor (M-CSF), erythropoietin (EPO), Flt-3, IFN-α, IFN-β, IFN-γ, IL-19, IL-20, IL-22, IL-24, TNF-α, TNF-β, BAFF, APRIL, lymphotoxin beta (TNF-γ), IL-17A, IL-17B, IL-17C, IL-17D, IL-17E, IL-17F, IL-25, TSLP, IL-35, IL-27, TGF-β, or combinations thereof.

In some aspects, an immune modulator comprises a protein that supports intracellular interactions required for germinal center responses. In certain aspects, the protein that supports intracellular interactions required for germinal center responses comprises a signaling lymphocyte activation molecule (SLAM) family member, a SLAM-associated protein (SAP), ICOS-ICOSL, CD40-40L, CD28/B7, PD-1/L1, IL-4/IL4R, IL21/IL21R, TLR4, TLR7, TLR8, TLR9, CD180, CD22, or combinations thereof. In some aspects, the SLAM family member comprises SLAM family member 1, CD48, CD229 (Ly9), Ly108, 2B4, CD84, NTB-A, CRACC, BLAME, CD2F-10, or combinations thereof.

Also provided herein is an isolated EV, e.g., exosome, comprising (i) an antigen and (ii) an immune modulator, wherein: (a) the antigen is linked to a first Scaffold Y on the luminal surface of the EV, and the immune modulator is linked to a second Scaffold Y on the luminal surface of the EV; (b) the antigen is linked to a Scaffold Y on the luminal surface of the EV, and the immune modulator is in the lumen of the EV; (c) the antigen is in the lumen of the EV, and the immune modulator is linked to a Scaffold Y on the luminal surface of the EV; (d) the antigen is linked to a Scaffold Y on the luminal surface of the EV, and the immune modulator is linked to a Scaffold X on the exterior surface the EV; (e) the antigen is in the lumen of the EV, and the immune modulator is linked to a Scaffold X on the exterior surface of the EV; (f) the antigen is linked to a Scaffold Y on the luminal surface of the EV, and the immune modulator is linked to a Scaffold X on the luminal surface of the EV; (g) the antigen is in the lumen of the EV, and the immune modulator is linked to a Scaffold X on the luminal surface of the EV; (h) the antigen is linked to a Scaffold X on the luminal surface of the EV, and the immune modulator is linked to the Scaffold X on the exterior surface of the EV; (i) the antigen is linked to a first Scaffold X on the exterior surface of the EV, and the immune modulator is linked to a second Scaffold X on the exterior surface of the EV; (j) the antigen is linked to a Scaffold X on the exterior surface of the EV, and the immune modulator is linked to a Scaffold Y on the luminal surface of the EV; (k) the antigen is linked to a Scaffold X on the exterior surface of the EV, and the immune modulator is in the lumen of the EV; (l) the antigen is linked to a Scaffold X on the exterior surface of the EV, and the immune modulator is linked to the Scaffold X on the luminal surface of the EV; (m) the antigen is linked to a first Scaffold X on the luminal surface of the EV, and the immune modulator is linked to a second Scaffold X on the luminal surface of the EV; (n) the antigen is linked to a Scaffold X on the luminal surface of the EV, and the immune modulator is linked to a Scaffold Y on the luminal surface of the EV; (o) the antigen is linked to a Scaffold X on the luminal surface of the EV, and the immune modulator is in the lumen of the EV; (p) the antigen is linked to a first Scaffold X on the exterior surface of the EV, and the immune modulator is linked to a second Scaffold X on the luminal surface of the EV; (q) the antigen is linked to a first Scaffold X on the luminal surface of the EV, and the immune modulator is linked to a second Scaffold X on the exterior surface of the EV; (r) the antigen is in the lumen of the EV, and the immune modulator is in the lumen of the EV; (s) the antigen is linked directly to the luminal surface of the EV, and the immune modulator is linked directly to the luminal surface of the EV; (t) the antigen is linked directly to the luminal surface of the EV, and the immune modulator is in the lumen of the EV; (u) the antigen is linked directly to the luminal surface of the EV, and the immune modulator is linked to a Scaffold Y on the luminal surface of the EV; (v) the antigen is linked directly to the luminal surface of the EV, and the immune modulator is linked to a Scaffold X on the luminal surface of the EV; (w) the antigen is linked directly to the luminal surface of the EV, and the immune modulator is linked directly to the exterior of the EV; (x) the antigen is linked directly to the luminal surface of the EV, and the immune modulator is linked to a Scaffold X on the exterior of the EV; (y) the antigen is linked to a Scaffold Y on the luminal surface of the EV, and the immune modulator is linked directly to the luminal surface of the EV; (z) the antigen is linked to a Scaffold Y on the luminal surface of the EV, and the immune modulator is linked directly to the exterior of the EV; (aa) the antigen is linked to a Scaffold X on the luminal surface of the EV, and the immune modulator is linked directly to the luminal surface of the EV; (bb) the antigen is linked to a Scaffold X on the luminal surface of the EV, and the immune modulator is linked directly to the exterior of the EV; (cc) the antigen is in the lumen of the EV, and the immune modulator is linked directly to the luminal surface of the EV; or (dd) the antigen is in the lumen of the EV, and the immune modulator is linked directly to the exterior of the EV.

In some aspects, an EV, e.g., exosome comprising (i) an antigen and (ii) an immune modulatory further comprises an adjuvant (e.g., those described herein). In some of these aspects, the adjuvant is linked to a Scaffold X on the exterior surface of the EV, e.g., exosome or on the luminal surface of the EV, e.g., exosome. In some of these aspects, the adjuvant is linked to a Scaffold Y on the luminal surface of the EV, e.g., exosome. In further aspects, the adjuvant is in the lumen of the EV, e.g., exosome. In some aspects, the adjuvant is directly linked to the luminal surface or the exterior surface of the EV.

In some aspects, an antigen is a tumor antigen. In some aspects, the tumor antigen comprises alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, TNF-related apoptosis-inducing ligand, Brachyury, (e.g., expressed antigen in melanoma (PRAME)), Wilms tumor 1 (WT1), CD19, CD22, or any combination thereof.

In some aspects, an antigen is derived from a bacterium, a virus, fungus, protozoa, or any combination thereof. In certain aspects, the antigen is derived from an oncogenic virus. In some aspects, the antigen is derived from a Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV (e.g., HIV-1, HIV-2), corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and Burrelia mayonii (e.g., Lyme disease), herpes simplex virus 2 (HSV2), *Klebsiella* sp., *Pseudomonas aeruginosa, Enterococcus* sp., *Proteus* sp., *Enterobacter* sp., *Actinobacter* sp., coagulase-negative staphylococci (CoNS), *Mycoplasma* sp., Adenovirus, Adeno-associated virus (AAV), or combinations thereof.

In some aspects, an adjuvant is a Stimulator of Interferon Genes (STING) agonist, a toll-like receptor (TLR) agonist, an inflammatory mediator, RIG-I agonists, alpha-gal-cer (NKT agonist), heat shock proteins (e.g., HSP65 and HSP70), C-type lectin agonists (e.g., beta glucan (Dectin 1), chitin, and curdlan), or any combination thereof.

In some aspects, an adjuvant is a STING agonist. In certain aspects, the STING agonist comprises a cyclic dinucleotide STING agonist or a non-cyclic dinucleotide STING agonist.

In some aspects, an adjuvant is a TLR agonist. In certain aspects, the TLR agonist comprises a TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), or any combination thereof.

In some aspects, an EV disclosed herein is an exosome.

In some aspects, an EV (e.g., exosome) disclosed herein further comprises a targeting moiety. In certain aspects, the targeting moiety specifically binds to a marker for a dendritic cell. In certain aspects, the marker is present only on the dendritic cell. In some aspects, the dendritic cell comprises a plasmacytoid dendritic cell (pDC), a myeloid/conventional dendritic cell 1 (cDC1), a myeloid/conventional dendritic cell 2 (cDC2), inflammatory monocyte derived dendritic cells, Langerhans cells, dermal dendritic cells, lysozyme-expressing dendritic cells (LysoDCs), Kupffer cells, or any combination thereof. In certain aspects, the dendritic cell is cDC1. In further aspects, the marker comprises a C-type lectin domain family 9 member A (Clec9a) protein, a dendritic cell-specific intercellular adhesion molecule-3-grabbing non-integrin (DC-SIGN), CD207, CD40, Clec6, dendritic cell immunoreceptor (DCIR), DEC-205, lectin-like oxidized low-density lipoprotein receptor-1 (LOX-1), MARCO, Clec12a, Clec10a, DC-asialoglycoprotein receptor (DC-ASGPR), DC immunoreceptor 2 (DCIR2), Dectin-1, macrophage mannose receptor (MMR), BDCA-1 (CD303, Clec4c), Dectin-2, Bst-2 (CD317), Langerin, CD206, CD11b, CD11c, CD123, CD304, XCR1, AXL, Siglec 6, CD209, SIRPA, CX3CR1, GPR182, CD14, CD16, CD32, CD34, CD38, CD10, or any combination thereof. In certain aspects, the marker is Clec9a protein.

In some aspects, the targeting moiety specifically binds to a marker for a T cell. In certain aspects, the marker comprises a CD3 molecule.

In some aspects, the targeting moiety is linked directly to the exterior surface of the EV. In some aspects, the targeting moiety is linked to a Scaffold X on the exterior surface of the EV. In some aspects, the targeting moiety is linked directly to the exterior surface of the EV by a linker. In some aspects, the targeting moiety is linked to the Scaffold X by a linker. In certain aspects, the linker is a polypeptide. In some aspects, the linker is a non-polypeptide moiety. In some aspects, the linker comprises a maleimide moiety. In some aspects, the linker comprises a cholesterol moiety.

In some aspects, the Scaffold Y of an EV (e.g., exosome) described herein comprises an N terminus domain (ND) and an effector domain (ED), wherein the ND and/or the ED are associated with the luminal surface of the EV. In some aspects, the ND is associated with the luminal surface of the exosome via myristoylation. In some aspects, the ED is associated with the luminal surface of the exosome by an ionic interaction. In some aspects, the ED comprises (i) a basic amino acid or (ii) two or more basic amino acids in sequence, wherein the basic amino acid is selected from the group consisting of Lys, Arg, His, and any combination thereof. In some aspects, the basic amino acid is (Lys)n, wherein n is an integer between 1 and 10. In some aspects, the ED comprises Lys (K), KK, KKK, KKKK (SEQ ID NO: 205), KKKKK (SEQ ID NO: 206), Arg (R), RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof.

In some aspects, the ND comprises the amino acid sequence as set forth in G:X2:X3:X4:X5:X6, wherein G represents Gly; wherein ":" represents a peptide bond, wherein each of the X2 to the X6 is independently an amino acid, and wherein the X6 comprises a basic amino acid. In some aspects,
(i) the X2 is selected from the group consisting of Pro, Gly, Ala, and Ser;
(ii) the X4 is selected from the group consisting of Pro, Gly, Ala, Ser, Val, Ile, Leu, Phe, Trp, Tyr, Gln and Met;
(iii) the X5 is selected from the group consisting of Pro, Gly, Ala, and Ser;
(iv) the X6 is selected from the group consisting of Lys, Arg, and His; or
(v) any combination of (i)-(iv).

In some aspects, the ND comprises the amino acid sequence of G:X2:X3:X4:X5:X6, wherein
(i) G represents Gly;
(ii) ":" represents a peptide bond;
(iii) the X2 is an amino acid selected from the group consisting of Pro, Gly, Ala, and Ser;
(iv) the X3 is an amino acid;
(v) the X4 is an amino acid selected from the group consisting of Pro, Gly, Ala, Ser, Val, Ile, Leu, Phe, Trp, Tyr, Gln and Met;
(vi) the X5 is an amino acid selected from the group consisting of Pro, Gly, Ala, and Ser; and
(vii) the X6 is an amino acid selected from the group consisting of Lys, Arg, and His.

In some aspects, the X3 is selected from the group consisting of Asn, Gln, Ser, Thr, Asp, Glu, Lys, His, and Arg.

In some aspects, the ND and the ED are joined by a linker. In some aspects, the linker comprises one or more amino acids. In some aspects, the ND comprises an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), (v) GGKLSK (SEQ ID NO: 215), or (vi) any combination thereof. In some aspects, the ND comprises an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof. In some aspects, the ND comprises the amino acid sequence GGKLSKK (SEQ ID NO: 211).

In some aspects, the Scaffold Y is at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 120, at least about 130, at least about 140, at least about 150, at least about 160, at least about 170, at least about 180, at least about 190, or at least about 200 amino acids in length. In some aspects, the Scaffold Y comprises (i) GGKLSKKKKGYNVN (SEQ ID NO: 246), (ii) GAKL-SKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKL-SKKKKGYSGG (SEQ ID NO: 250), (vi) GGKL-SKKKKGSGGS (SEQ ID NO: 251), (vii) GGKL-SKKKKSGGSG (SEQ ID NO: 252), (viii) GGKLSKKKSGGSGG (SEQ ID NO: 253), (ix) GGKL-SKKSGGSGGS (SEQ ID NO: 254), (x) GGKL-SKSGGSGGSV (SEQ ID NO: 255), or (xi) GAKK-SKKRFSFKKS (SEQ ID NO: 256). In certain aspects, the Scaffold Y consists of (i) GGKLSKKKKGYNVN (SEQ ID NO: 246), (ii) GAKLSKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKL-SKKKKGYSGG (SEQ ID NO: 250), (vi) GGKL-SKKKKGSGGS (SEQ ID NO: 251), (vii) GGKL-SKKKKSGGSG (SEQ ID NO: 252), (viii) GGKLSKKKSGGSGG (SEQ ID NO: 253), (ix) GGKL-SKKSGGSGGS (SEQ ID NO: 254), (x) GGKL-SKSGGSGGSV (SEQ ID NO: 255), or (xi) GAKK-SKKRFSFKKS (SEQ ID NO: 256).

In some aspects, the Scaffold Y does not comprise Met at the N terminus. In some aspects, the Scaffold Y comprises a myristoylated amino acid residue at the N terminus of the scaffold protein. In some aspects, the amino acid residue at the N terminus of the Scaffold Y is Gly. In some aspects, the amino acid residue at the N terminus of the Scaffold Y is synthetic. In some aspects, the amino acid residue at the N terminus of the Scaffold Y is a glycine analog.

Provided herein is a pharmaceutical composition comprising an EV, e.g., exosome, described herein and a pharmaceutically acceptable carrier.

Provided herein is a cell that produces an EV, e.g., exosome, of the present disclosure. Present disclosure further provides a cell comprising one or more vectors, wherein the vectors comprises a nucleic acid sequence encoding: (i) an antigen (e.g., those described herein), (ii) adjuvant (e.g., those described herein), (iii) immune modulator, (iv) targeting moiety (e.g., those described herein), or (v) combinations thereof.

Provided herein is a kit comprising an EV, e.g., exosome, described herein and instructions for use. Also provided herein is an EV-drug conjugate comprising any of the EVs (e.g., exosomes) described herein.

Provided herein is a method of making EVs, e.g., exosomes, comprising culturing a cell disclosed herein under a suitable condition and obtaining the EV, e.g., exosome.

Provided herein is a method of inducing an immune response in a subject in need thereof comprising administering an EV, e.g., exosome, of the present disclosure to the subject.

Provided herein is a method of preventing or treating a disease in a subject in need thereof, comprising administering an EV, e.g., exosome, described herein, wherein the disease is associated with the antigen. In certain aspects, the disease is a cancer. In some aspects, the cancer comprises bladder cancer, cervical cancer, renal cell cancer, testicular cancer, colorectal cancer, lung cancer, head and neck cancer, ovarian, lymphoma, liver cancer, glioblastoma, melanoma, myeloma, leukemia, pancreatic cancer, or combinations thereof. In further aspects, the disease is an infection.

In some aspects, an EV, e.g., exosome, is administered parenterally, orally, intravenously, intramuscularly, intratumorally, intranasally, subcutaneously, or intraperitoneally.

In some aspects, methods disclosed herein (e.g., of inducing an immune response or of preventing or treating a disease) comprises administering an additional therapeutic agent.

Provided herein is a method of inhibiting or reducing metastasis of cancer in a subject in need thereof, comprising administering to the subject an EV, e.g., exosome, of the present disclosure.

BRIEF DESCRIPTION OF FIGURES

FIG. 5A shows the CD8 T cell response. FIG. 5B shows the CD4 T cell response. The control animals received one of the following: (i) soluble OVA protein alone ("OVA"); (ii) CL656 in combination with soluble OVA protein ("OVA+CL656"); (iii) EV, e.g., exosome expressing only OVA-Scaffold Y fusion protein ("Py-OVA"); (iv) CL656 in combination with an EV, e.g., exosome, expressing only OVA-Scaffold Y fusion protein ("Py-OVA+CL656"). Data are shown both individually and as mean±S.D. "*" indicates p<0.05 by one way ANOVA.

FIG. 6 provides a schematic of the experimental design for assessing the efficacy of Clec9a exosomes in a vaccination model.

FIG. 7A shows superior effector memory, in particular, CD8 T-cell response following administration of a standard vaccine (AddaVax) subcutaneously (SQ), or engineered exosomes subcutaneously (SQ), intranasally (IN) or intravenously (IV). FIG. 7B shows induction of tissue resident memory, in particular, T-cell response in lung (line of defense) following intra-nasal vaccination with a standard vaccine or an engineered exosome.

FIG. 8 is a schematic representation of an engineered EV, e.g., an exosome, comprising an adjuvant (cyclic purine dinucleotides, e.g., CDN) and the EBV BZLF1 antigen attached to the luminal surface of the EV.

FIG. 11A show the uptake of anti-Clec9a expressing exosomes by different dendritic cell populations after administration into mice. The dendritic cell populations shown include the following: (i) conventional DC 1 ("cDC1"), (ii) conventional DC 2 ("cDC2"), and (iii) plasmacytoid DC ("pDC"). Control animals received either PBS alone or an exosome expressing Scaffold X protein alone ("PrX EVs"). **** p<0.0001. FIG. 11B provide a comparison of STING activity in mouse dendritic cells after stimulation with one of the following at three different doses (0.4 nM, 1 nM, or 4 nM): (i) soluble STING agonist ("free STING"), (ii) EVs (e.g., exosomes) expressing Scaffold X protein alone (i.e., no anti-Clec9a antibody fragment) and loaded with the STING agonist ("PrX-STING"), (iii) exosome expressing anti-Clec9a antibody fragment linked to Scaffold X protein ("aClec9a-STING"); and (iv) EVs (e.g., exosomes) expressing a non-relevant antibody and loaded with the STING agonist ("Isotype-STING"). STING activity is shown by the amount of IL-12 produced by the DCs.

FIG. 12A provides a bar graph showing the average of the results. *, p=0.0013; , p=0.0074; ns, not significant compared to OVA+ADDAVAX™ group by one-way ANOVA. FIG. 12B provides a flow cytometry plot of representative samples from the different treatment groups. The percentages provided in the upper right quadrant in each of the flow plots represents the % OVA-specific CD8+ TEM cell response observed. The different treatment groups are indicated in the upper left quadrant in each of the flow plots.

FIG. 13C provides a flow cytometry plot of representative samples of the data shown in FIGS. 13A and 13B. The top row corresponds to CD8+ T cells. The bottom row corresponds to CD4+ T cells.

FIGS. 14A, 14B, 14C, 14D, 14E, 14F, 14G, 14H, 14I, 14J, 14K, 14L, 14M, and 14N show the anti-tumor immune response in mice that received one of the following: (i) exosome expressing OVA-Scaffold Y and loaded with the STING agonist CL656 via intranasal administration ("exoVACC (IN)"), (ii) exosome expressing OVA-Scaffold Y and loaded with the STING agonist CL656 via subcutaneous administration ("exoVACC (SQ)"), (iii) soluble OVA+ soluble poly I:C via intranasal administration ("OVA+poly I:C (IN)"), and (iv) soluble OVA+soluble poly I:C via subcutaneous administration ("OVA+poly I:C (SC)"). Untreated animals were used as controls. FIG. 14A provides a schematic of the experimental design. FIGS. 14B and 14N provide the survival data from two independent experiments. FIGS. 14C and 14I (untreated), 14D and 14J (OVA+ poly I:C (SC)), 14E and 14L (exoVACC (SQ)), 14F and 14K (OVA+poly I:C (IN)), and 14G and 14M (exoVACC (IN)) provide the tumor volume data from two independent experiments. The percentages shown in FIGS. 14E and 14G represent the number of animals (of the total group) that were completely protected. FIG. 14H shows the rate of tumor growth in each of the different treatment groups. In FIG. 14H, *, p=0.028; ns, not significant compared to untreated control by one-way ANOVA.

FIG. 15A provides a schematic of the experimental design. FIGS. 15B, 15C, and 15D show the frequency of OVA-specific CD4+ T cells (left bar in each of the treatment groups) and OVA-specific CD8+ T cells (right bar in each of the treatment groups) in the spleen, lung, and mesenteric lymph nodes, respectively, as measured by IFN-γ ELISPOT. FIGS. 15E and 15F show the frequency of OVA-specific effector memory CD8+ T cells in the lung and spleen, respectively, as measured by flow cytometry.

FIGS. 16A, 16B, and 16C show the ability of surface-engineered EVs (e.g., exosomes) comprising a Scaffold X and loaded with STING agonist to induce an antigen-specific immune response. FIG. 16A provides a schematic of the experimental design. As shown, CD4 peptide (Itgb1) and/or CD8 peptide (Lama4) were linked to the Scaffold X of the EVs (e.g., exosomes). FIGS. 16B and 16C show the frequency of Itgb1-specific CD4+ T cells and Lama4-specific CD8+ T cells, respectively, in the spleen of animals from the different treatment groups, as measured by IFN-γ ELISPOT.

FIGS. 17A, 17B, and 17C show the ability of a surface-engineered EV (e.g., exosome) comprising a Scaffold X and loaded with CpG adjuvant to induce an antigen-specific immune response. FIG. 17A provides a schematic of the experimental design. As shown, either (i) CD8 peptide (Lama4) alone (Group 2) or (ii) both CD8 peptide and CD4 peptide (Itgb1) (Group 3) were linked to Scaffold X using maleimide chemistry. Control EVs expressed only Scaffold X (i.e., no peptide and no CpG adjuvant) (Group 1). FIGS. 17B and 17C show the frequency of Itgb1-specific CD4+ T cells and Lama4-specific CD8+ T cells, respectively, in the spleen of animals from the different treatment groups, as measured by IFN-γ ELISPOT.

In FIGS. 18A, 18B, 18C, 18D, 18E, and 18F, 293 SF cells were transfected with plasmids encoding one of the following full-length proteins: (i) HPV16 E6, (ii) HPV16 E7, (iii) HPV16 E6/E7, (iv) HPV18 E6, (v) HPV18 E7, and (vi) HPV18 E6/E7. In FIGS. 18G, 18H, 18I, 18J, 18K, and 18L, a split protein expression strategy was used. The 293 SF cells were transfected with one of the following plasmids: (i) pUC57-Kan-AAVS1HR-CAGGS-PTGFRN-FLAG-coHPV16nE6 ("pCB-2014"), (ii) pUC57-Kan-AAVS1HR-CAGGS-PTGFRN-FLAG-coHPV16cE6 ("pCB-2015"), (iii) pUC57-Kan-AAVS1HR-CAGGS-coHPV16nE6-FLAG-PTGFRN ("pCB-2016"), (iv) pUC57-Kan-AAVS1HR-CAGGS-coHPV16cE6-FLAG-PTGFRN ("pCB-2017"), (v) pUC57-Kan-AAVS1HR-CAGGS-PrY-FLAG-coHPV16nE6 ("pCB-2018"), and (vi) pUC57-Kan-AAVS1HR-CAGGS-PrY-FLAG-coHPV16cE6 ("pCB-2019"). Detailed description of the plasmids can be found in Example 23 (see also Table 11).

FIGS. 19A, 19B, and 19C show the ability of a surface-engineered EV (e.g., exosome) loaded with STING agonist and expressing (i) an anti-Clec9A targeting moiety linked to Scaffold X and (ii) OVA linked to Scaffold Y. FIG. 19A provides a schematic of the experimental design. FIGS. 19B and 19C show the number of OVA-specific CD8+ effector memory T cells observed in the spleen of animals from the different treatment groups shown in FIG. 19A. FIG. 19B shows the results at one-week post a single EV administration. FIG. 19C shows the results at one-week post a second dose of EV administration.

FIG. 20A provides a schematic of the experimental design. As shown, the animals received one of the following: (i) soluble OVA alone (Group 1), (ii) soluble OVA in combination with free STING agonist (Group 2), (iii) EV (e.g., exosome) expressing OVA-Scaffold Y alone ("PyOVA") (Group 3), (iv) PyOVA in combination with free STING agonist (Group 4), (v) engineered-exosome expressing OVA-Scaffold Y and loaded with the STING agonist CL656 ("Py-OVA exoVACC") (Group 5), and (vi) soluble OVA in combination with alum. FIG. 20B provides a comparison of the amount of OVA-specific IgG1 antibodies in the serum. FIG. 20C provides a comparison of the amount of OVA-specific IgA antibodies in the serum.

FIG. 22 provides a schematic representation showing the conjugation of an LPA1 antagonist (AM152) to exosomes, to yield a population of exosomes containing a plurality of LPA1 antagonist molecules on their surface.

FIG. 28 shows that after protection of the carboxylic acid group, it is possible to use the same reagents used to derivatize the carboxylic acid group to derivatize AM152 at its carbamate group. The resulting product would be subsequently deprotected to free the carboxylic acid group.

DETAILED DESCRIPTION OF DISCLOSURE

Figure 1A:
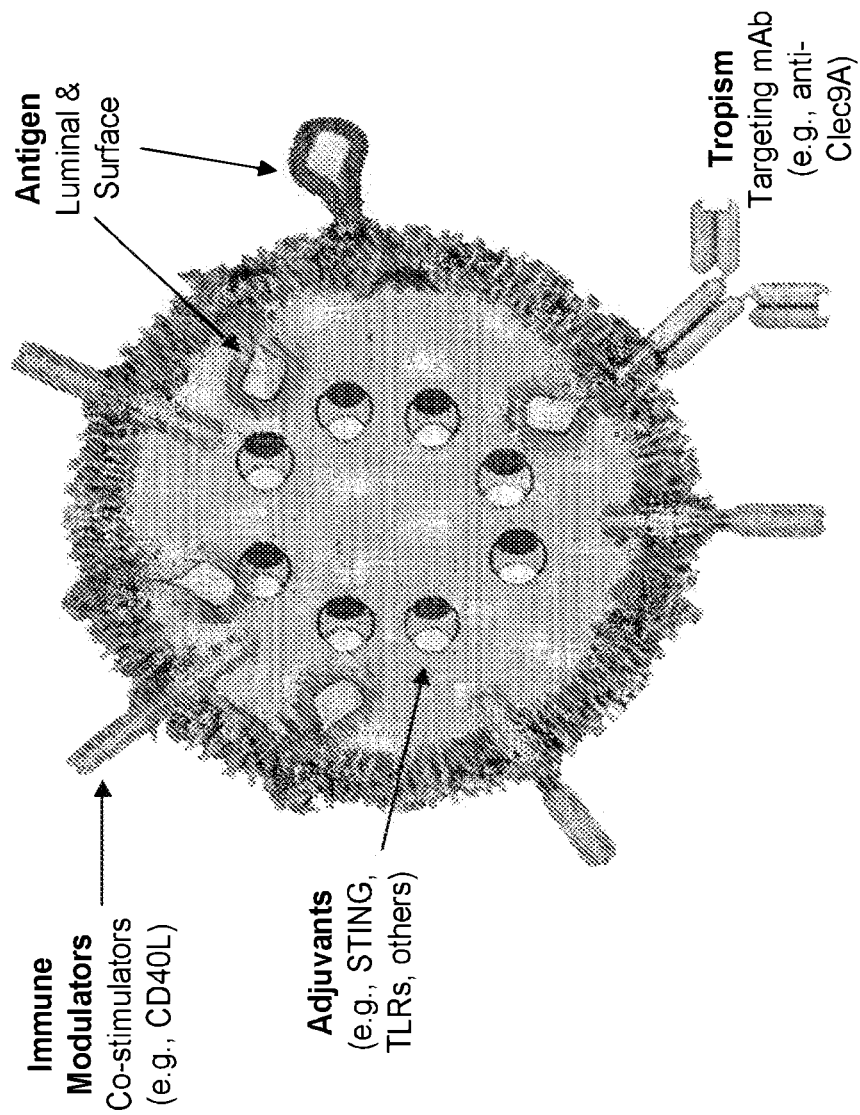
FIG. 1A shows an exemplary EV comprising one or more antigens, one or more adjuvants, one or more molecules for targeting moiety, or any combination thereof.

The present disclosure is directed to an engineered EV, e.g., exosome, that delivers antigens and adjuvants simultaneously to the same antigen presenting cells. The EV platform allows luminal expression of antigens and surface expression of immune co-stimulatory molecules designed to create a modular vaccination system. Various adjuvants can be incorporated into the EVs, e.g., exosomes, to enhance the immune response against a broad array of antigens. The engineered EVs can comprise one or more payloads and can improve at least one property (e.g., such as those disclosed herein) of the EV, and uses thereof. In some aspects, the one or more payloads comprise an antigen, an adjuvant, and/or an immune modulator. In certain aspects, the EV (e.g., exosome) comprises one or more additional moieties (e.g., targeting moiety). In some aspects, the one or more payloads (e.g., antigen, adjuvant, and/or the immune modulator) and/or the one or more additional moieties (e.g., targeting moiety) can be attached (or linked) to one or more scaffold moieties on the surface of EVs, e.g., exosomes, or on the luminal surface of EVs, e.g., exosomes. Therefore, the EVs of the present disclosure allow a platform delivery vehicle for a vaccine (i.e., exoVACC™), wherein the antigen on the EV and/or the In some aspects, the one or more payloads (e.g., antigen, adjuvant, and/or the immune modulator can be combined in a particular way) and/or replaced with a different antigen and/the one or an adjuvant or immune modulator. more additional moieties (e.g., targeting moiety) can be attached (or linked) directly to the exterior surface and/or luminal surface of EVs (e.g., exosomes). Non-limiting examples of the various aspects are shown in the present disclosure.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "extracellular vesicle" or "EV" refers to a cell-derived vesicle comprising a membrane that encloses an internal space. Extracellular vesicles comprise all membrane-bound vesicles (e.g., exosomes, nanovesicles) that have a smaller diameter than the cell from which they are derived. In some aspects, extracellular vesicles range in diameter from 20 nm to 1000 nm, and can comprise various macromolecular payload either within the internal space (i.e., lumen), displayed on the external surface of the extracellular vesicle, and/or spanning the membrane. In some aspects, the payload can comprise nucleic acids, proteins, carbohydrates, lipids, small molecules, and/or combinations thereof. In certain aspects, an extracellular vehicle comprises a scaffold moiety. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, the extracellular vesicles are produced by cells that express one or more transgene products.

As used herein, the term "exosome" refers to an extracellular vesicle with a diameter between 20-300 nm (e.g., between 40-200 nm). Exosomes comprise a membrane that encloses an internal space (i.e., lumen), and, in some aspects, can be generated from a cell (e.g., producer cell) by direct plasma membrane budding or by fusion of the late endosome or multi-vesicular body with the plasma membrane. In certain aspects, an exosome comprises a scaffold moiety. As described infra, exosome can be derived from a producer cell, and isolated from the producer cell based on its size, density, biochemical parameters, or a combination thereof. In some aspects, the EVs, e.g., exosomes, of the present disclosure are produced by cells that express one or more transgene products.

As used herein, the term "nanovesicle" refers to an extracellular vesicle with a diameter between 20-250 nm (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some aspects, production of nanovesicles can result in the destruction of the producer cell. In some aspects, population of nanovesicles described herein are substantially free of vesicles that are derived from cells by way of direct budding from the plasma membrane or fusion of the late endosome with the plasma membrane. In certain aspects, a nanovesicle comprises a scaffold moiety. Nanovesicles, once derived from a producer cell, can be isolated from the producer cell based on its size, density, biochemical parameters, or a combination thereof.

As used herein the term "surface-engineered EVs, e.g., exosomes" (e.g., Scaffold X-engineered EVs, e.g., exosomes) refers to an EV, e.g., exosome, with the membrane or the surface of the EV, e.g., exosome, modified in its composition so that the surface of the engineered EV, e.g., exosome, is different from that of the EV, e.g., exosome, prior to the modification or of the naturally occurring EV, e.g., exosome. The engineering can be on the surface of the EV, e.g., exosome, or in the membrane of the EV, e.g., exosome, so that the surface of the EV, e.g., exosome, is changed. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV, e.g., exosome, comprises an exogenous protein (i.e., a protein that the EV, e.g., exosome, does not naturally express) or a fragment or variant thereof that can be exposed to the surface of the EV, e.g., exosome, or can be an anchoring point (attachment) for a moiety exposed on the surface of the EV, e.g., exosome. In other aspects, a surface-engineered EV, e.g., exosome, comprises a higher expression (e.g., higher number) of a natural exosome protein (e.g., Scaffold X) or a fragment or variant thereof that can be exposed to the surface of the EV, e.g., exosome, or can be an anchoring point (attachment) for a moiety exposed on the surface of the EV, e.g., exosome.

As used herein the term "lumen-engineered exosome" (e.g., Scaffold Y-engineered exosome) refers to an EV, e.g., exosome, with the membrane or the lumen of the EV, e.g., exosome, modified in its composition so that the lumen of the engineered EV, e.g., exosome, is different from that of the EV, e.g., exosome, prior to the modification or of the naturally occurring EV, e.g., exosome. The engineering can be directly in the lumen or in the membrane of the EV, e.g., exosome so that the lumen of the EV, e.g., exosome is changed. For example, the membrane is modified in its composition of a protein, a lipid, a small molecule, a carbohydrate, etc. so that the lumen of the EV, e.g., exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises an exogenous protein (i.e., a protein that the EV, e.g., exosome does not naturally express) or a fragment or variant thereof that can be exposed in the lumen of the EV, e.g., exosome or can be an anchoring point (attachment) for a moiety exposed on the inner layer of the EV, e.g., exosome. In other aspects, a lumen-engineered EV, e.g., exosome, comprises a higher expression of a natural exosome protein (e.g., Scaffold X or Scaffold Y) or a fragment or variant thereof that can be exposed to the lumen of the exosome or can be an anchoring point (attachment) for a moiety exposed in the lumen of the exosome.

The term "modified," when used in the context of EVs, e.g., exosomes described herein, refers to an alteration or engineering of an EV, e.g., exosome and/or its producer cell, such that the modified EV, e.g., exosome is different from a naturally-occurring EV, e.g., exosome. In some aspects, a modified EV, e.g., exosome described herein comprises a membrane that differs in composition of a protein, a lipid, a small molecular, a carbohydrate, etc. compared to the membrane of a naturally-occurring EV, e.g., exosome (e.g., membrane comprises higher density or number of natural exosome proteins and/or membrane comprises proteins that are not naturally found in exosomes (e.g., antigen, adjuvant, and/or immune modulator). In certain aspects, such modifications to the membrane changes the exterior surface of the EV, e.g., exosome (e.g., surface-engineered EVs, e.g., exosomes described herein). In certain aspects, such modifications to the membrane changes the lumen of the EV, e.g., exosome (e.g., lumen-engineered EVs, e.g., exosomes described herein).

As used herein, the term "scaffold moiety" refers to a molecule that can be used to anchor a payload or any other compound of interest (e.g., antigen, adjuvant, and/or immune modulator) to the EV, e.g., exosome either on the luminal surface or on the exterior surface of the EV, e.g., exosome. In certain aspects, a scaffold moiety comprises a synthetic molecule. In some aspects, a scaffold moiety comprises a non-polypeptide moiety. In other aspects, a scaffold moiety comprises a lipid, carbohydrate, or protein that naturally exists in the EV, e.g., exosome. In some aspects, a scaffold moiety comprises a lipid, carbohydrate, or protein that does not naturally exist in the EV, e.g., exosome. In certain aspects, a scaffold moiety is Scaffold X. In some aspects, a scaffold moiety is Scaffold Y. In further aspects, a scaffold moiety comprises both Scaffold X and Scaffold Y. Non-limiting examples of other scaffold moieties that can be used with the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); CD9, CD63, CD81, PDGFR, GPI anchor proteins, lactadherin, LAMP2, and LAMP2B.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome). In some aspects, a Scaffold X can anchor a moiety (e.g., antigen, adjuvant, and/or immune modulator) to the external surface or the luminal surface of the exosome.

As used herein, the term "Scaffold Y" refers to exosome proteins that were newly identified within the lumen of exosomes. See, e.g., International Appl. No. PCT/US2018/061679, which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some aspects, a Scaffold Y protein can be a whole protein or a fragment thereof (e.g., functional fragment, e.g., the smallest fragment that is capable of anchoring a moiety to the luminal surface of the exosome). In some aspects, a Scaffold Y can anchor a moiety (e.g., antigen, adjuvant, and/or immune modulator) to the luminal surface of the EV, e.g., exosome.

As used herein, the term "fragment" of a protein (e.g., therapeutic protein, Scaffold X, or Scaffold Y) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface or on the exterior surface of the EV, e.g., exosome. Similarly, in certain aspects, a functional fragment of a Scaffold Y protein retains the ability to anchor a moiety on the luminal surface of the EV, e.g., exosome. Whether a fragment is a functional fragment can be assessed by any art known methods to determine the protein content of EVs, e.g., exosomes including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein. In some aspects, a functional fragment of a Scaffold Y protein retains at least about 50%, at least about 60%, at least about 70%, at least about 80%, at least about 90% or at least about 100% of the ability, e.g., an ability to anchor another molecule, of the naturally occurring Scaffold Y protein.

As used herein, the term "variant" of a molecule (e.g., functional molecule, antigen, Scaffold X and/or Scaffold Y) refers to a molecule that shares certain structural and functional identities with another molecule upon comparison by a method known in the art. For example, a variant of a protein can include a substitution, insertion, deletion, frameshift or rearrangement in another protein.

In some aspects, a variant of a Scaffold X comprises a variant having at least about 70% identity to the full-length, mature PTGFRN, BSG, IGSF2, IGSF3, IGSF8, ITGB1, ITGA4, SLC3A2, or ATP transporter proteins or a fragment (e.g., functional fragment) of the PTGFRN, BSG, IGSF2, IGSF3, IGSF8, ITGB1, ITGA4, SLC3A2, or ATP transporter proteins. In some aspects, variants or variants of fragments of PTGFRN share at least about 70%, at least about 80%, at least about 85%, at least about 90%, at least about 95%, at least about 96%, at least about 97%, at least about 98%, or at least about 99% sequence identity with PTGFRN according to SEQ ID NO: 1 or with a functional fragment thereof. In some aspects, variants or variants of fragments of BSG share at least about 70%, at least about 80%, at least about 85%, at least about 90%, at least about 95%, at least about 96%, at least about 97%, at least about 98%, or at least about 99% sequence identity with BSG according to SEQ ID NO: 9 or with a functional fragment thereof. In some aspects, variants or variants of fragments of IGSF2 share at least about 70%, at least about 80%, at least about 85%, at least about 90%, at least about 95%, at least about 96%, at least about 97%, at least about 98%, or at least about 99% sequence identity with IGSF2 according to SEQ ID NO: 34 or with a functional fragment thereof. In some aspects, variants or variants of fragments of IGSF3 share at least about 70%, at least about 80%, at least about 85%, at least about 90%, at least about 95%, at least about 96%, at least about 97%, at least about 98%, or at least about 99% sequence identity with IGSF3 according to SEQ ID NO: 20 or with a functional fragment thereof. In some aspects, variants or variants of fragments of IGSF8 share at least about 70%, at least about 80%, at least about 85%, at least about 90%, at least about 95%, at least about 96%, at least about 97%, at least about 98%, or at least about 99% sequence identity with IGSF8 according to SEQ ID NO: 14 or with a functional fragment thereof. In some aspects, variants or variants of fragments of ITGB1 share at least about 70%, at least about 80%, at least about 85%, at least about 90%, at least about 95%, at least about 96%, at least about 97%, at least about 98%, or at least about 99% sequence identity with ITGB1 according to SEQ ID NO: 21 or with a functional fragment thereof. In some aspects, variants or variants of fragments of ITGA4 share at least about 70%, at least about 80%, at least about 85%, at least about 90%, at least about 95%, at least about 96%, at least about 97%, at least about 98%, or at least about 99% sequence identity with ITGA4 according to SEQ ID NO: 22 or with a functional fragment thereof. In some aspects, variants or variants of fragments of SLC3A2 share at least about 70%, at least about 80%, at least about 85%, at least about 90%, at least about 95%, at least about 96%, at least about 97%, at least about 98%, or at least about 99% sequence identity with SLC3A2 according to SEQ ID NO: 23 or with a functional fragment thereof. In some aspects, variants or variants of fragments of ATP1A1 share at least about 70%, at least about 80%, at least about 85%, at least about 90%, at least about 95%, at least about 96%, at least about 97%, at least about 98%, or at least about 99% sequence identity with ATP1A1 according to SEQ ID NO: 24 or with a functional fragment thereof. In some aspects, variants or variants of fragments of ATP1A2 share at least about 70%, at least about 80%, at least about 85%, at least about 90%, at least about 95%, at least about 96%, at least about 97%, at least about 98%, or at least about 99% sequence identity with ATP1A2 according to SEQ ID NO: 25 or with a functional fragment thereof. In some aspects, variants or variants of fragments of ATP1A3 share at least about 70%, at least about 80%, at least about 85%, at least about 90%, at least about 95%, at least about 96%, at least about 97%, at least about 98%, or at least about 99% sequence identity with ATP1A3 according to SEQ ID NO: 26 or with a functional fragment thereof. In some aspects, variants or variants of fragments of ATP1A4 share at least about 70%, at least about 80%, at least about 85%, at least about 90%, at least about 95%, at least about 96%, at least about 97%, at least about 98%, or at least about 99% sequence identity with ATP1A4 according to SEQ ID NO: 27 or with a functional fragment thereof. In some aspects, variants or variants of fragments of ATP1B3 share at least about 70%, at least about 80%, at least about 85%, at least about 90%, at least about 95%, at least about 96%, at least about 97%, at least about 98%, or at least about 99% sequence identity with ATP1B3 according to SEQ ID NO: 28 or with a functional fragment thereof. In some aspects, variants or variants of fragments of ATP2B1 share at least about 70%, at least about 80%, at least about 85%, at least about 90%, at least about 95%, at least about 96%, at least about 97%, at least about 98%, or at least about 99% sequence identity with ATP2B1 according to SEQ ID NO: 29 or with a functional fragment thereof. In some aspects, variants or variants of fragments of ATP2B2 share at least about 70%, at least about 80%, at least about 85%, at least about 90%, at least about 95%, at least about 96%, at least about 97%, at least about 98%, or at least about 99% sequence identity with ATP2B2 according to SEQ ID NO: 30 or with a functional fragment thereof. In some aspects, variants or variants of fragments of ATP2B3 share at least about 70%, at least about 80%, at least about 85%, at least about 90%, at least about 95%, at least about 96%, at least about 97%, at least about 98%, or at least about 99% sequence identity with ATP2B3 according to SEQ ID NO: 31 or with a functional fragment thereof. In some aspects, variants or variants of fragments of ATP2B4 share at least about 70%, at least about 80%, at least about 85%, at least about 90%, at least about 95%, at least about 96%, at least about 97%, at least about 98%, or at least about 99% sequence identity with ATP2B4 according to SEQ ID NO: 32 or with a functional fragment thereof. In some aspects, the variant or variant of a fragment of Scaffold X protein disclosed herein retains the ability to be specifically targeted to EVs, e.g., exosomes. In some aspects, the Scaffold X includes one or more mutations, for example, conservative amino acid substitutions.

In some aspects, a variant of a Scaffold Y comprises a variant having at least about 70% identity to MARCKS, MARCKSL1, BASP1 or a fragment of MARCKS, MARCKSL1, or BASP1. In some aspects, variants or variants of fragments of MARCKS share at least about 70%, at least about 80%, at least about 85%, at least about 90%, at least about 95%, at least about 96%, at least about 97%, at least about 98%, or at least about 99% sequence identity with MARCKS according to SEQ ID NO: 47 or with a functional fragment thereof. In some aspects, variants or variants of fragments of MARCKSL1 share at least about 70%, at least about 80%, at least about 85%, at least about 90%, at least about 95%, at least about 96%, at least about 97%, at least about 98%, or at least about 99% sequence identity with MARCKSL1 according to SEQ ID NO: 48 or with a functional fragment thereof. In some aspects, variants or variants of fragments of BASP1 share at least about 70%, at least about 80%, at least about 85%, at least about 90%, at least about 95%, at least about 96%, at least about 97%, at least about 98%, or at least about 99% sequence identity with BASP1 according to SEQ ID NO: 49 or with a functional fragment thereof. In some aspects, the variant or variant of a fragment of Scaffold Y protein retains the ability to be specifically targeted to the luminal surface of EVs, e.g., exosomes. In some aspects, the Scaffold Y includes one or more mutations, e.g., conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at worldwideweb.tcoffee.org, and alternatively available, e.g., from the EBI. It will also be appreciated that the final alignment used to calculate percent sequence identity can be curated either automatically or manually.

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X and/or Scaffold Y is modified at any convenient location.

As used herein the term "linked to," "fused," or "conjugated to" are used interchangeably and refer to a covalent or non-covalent bond formed between a first moiety and a second moiety, e.g., Scaffold X and an antigen (or adjuvant or immune modulator), respectively, e.g., a scaffold moiety expressed in or on the extracellular vesicle and an antigen, e.g., Scaffold X (e.g., a PTGFRN protein), respectively, in the luminal surface of or on the external surface of the extracellular vesicle. In some aspects, a payload disclosed herein (e.g., antigen, adjuvant, and/or immune modulator) and/or a targeting moiety can be directly linked to the exterior surface and/or the luminal surface of an EV (e.g., exosome). As used herein, the term "directly linked,"

"directly fused," or "directly conjugated to" refer to the process of linking (fusing or conjugating) a moiety (e.g., a payload and/or targeting moiety) to the surface of an EV (e.g., exosome) without the use of a scaffold moiety disclosed herein.

As used herein, the term "fusion protein" refers to two or more proteins that are linked or conjugated to each other. For instance, in some aspects, a fusion protein that can be expressed in an EV (e.g., exosome) disclosed herein comprises (i) a payload (e.g., antigen, adjuvant, and/or immune modulator) and (ii) a scaffold moiety (e.g., Scaffold X and/or Scaffold Y). In some aspects, a fusion protein that can be expressed in an EV (e.g., exosome) useful for the present disclosure comprises (i) a targeting moiety and (ii) a scaffold moiety (e.g., Scaffold X and/or Scaffold Y). As described herein, in some aspects, EVs (e.g., exosomes) of the present disclosure can express multiple fusion proteins, wherein a first fusion protein comprises (i) a payload (e.g., antigen, adjuvant, and/or immune modulator) and (ii) a scaffold moiety (e.g., Scaffold X and/or Scaffold Y), and wherein a second fusion protein comprises (i) a targeting moiety and (ii) a scaffold moiety (e.g., Scaffold X and/or Scaffold Y).

The term "encapsulated", or grammatically different forms of the term (e.g., encapsulation, or encapsulating) refers to a status or process of having a first moiety (e.g., antigen, adjuvant, or immune modulator) inside a second moiety (e.g., an EV, e.g., exosome) without chemically or physically linking the two moieties. In some aspects, the term "encapsulated" can be used interchangeably with the terms "in the lumen of" and "loaded". Non-limiting examples of encapsulating (or loading) a first moiety (e.g., payload, e.g., antigen, adjuvant, or immune modulator) into a second moiety (e.g., EVs, e.g., exosomes) are disclosed elsewhere herein.

As used herein, the term "producer cell" refers to a cell used for generating an EV, e.g., exosome. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In certain aspects, a producer cell is not an antigen-presenting cell. In some aspects, a producer cell is not a dendritic cell, a B cell, a mast cell, a macrophage, a neutrophil, Kupffer-Browicz cell, cell derived from any of these cells, or any combination thereof. In some aspects, a producer cell is not a naturally-existing antigen-presenting cell (i.e., has been modified). In some aspects, a producer cell is not a naturally-existing dendritic cell, a B cell, a mast cell, a macrophage, a neutrophil, Kupffer-Browicz cell, cell derived from any of these cells, or any combination thereof. Additional disclosures relating to such producer cells are provided elsewhere in the present disclosure. In some aspects, the EVs, e.g., exosomes useful in the present disclosure do not carry an antigen on MHC class I or class II molecule (i.e., antigen is not presented on MHC class I or class II molecule) exposed on the surface of the EV, e.g., exosome, but instead can carry an antigen in the lumen of the EV, e.g., exosome, or on the surface of the EV, e.g., exosome, by attachment to Scaffold X and/or Scaffold Y.

As used herein, an "MHC class I molecule" refers to a protein product of a wild-type or variant HLA class I gene encoding an MHC class I molecule. Accordingly, "HLA class I molecule" and "MHC class I molecule" are used interchangeably herein.

MHC class I molecules are one of two primary classes of major histocompatibility complex (MHC) molecules (the other being MHC class II) and are found on the cell surface of all nucleated cells in the bodies of jawed vertebrates. They also occur on platelets, but not on red blood cells. Their function is to display peptide fragments of proteins from within the cell to cytotoxic T cells; this will trigger an immediate response from the immune system against a particular non-self antigen displayed with the help of an MHC class I protein. Because MHC class I molecules present peptides derived from cytosolic proteins, the pathway of MHC class I presentation is often called cytosolic or endogenous pathway.

In humans, the HLAs corresponding to MHC class I are HLA-A, HLA-B, and HLA-C. The MHC Class I molecule comprises two protein chains: the alpha chain and the β2-microglobulin (β2m) chain. Human β2m is encoded by the B2M gene. Class I MHC molecules bind peptides generated mainly from degradation of cytosolic proteins by the proteasome. The MHC I:peptide complex is then inserted via endoplasmic reticulum into the external plasma membrane of the cell. The epitope peptide is bound on extracellular parts of the class I MHC molecule. Thus, the function of the class I MHC is to display intracellular proteins to cytotoxic T cells (CTLs). However, class I MHC can also present peptides generated from exogenous proteins, in a process known as cross-presentation.

A normal cell will display peptides from normal cellular protein turnover on its class I MHC, and CTLs will not be activated in response to them due to central and peripheral tolerance mechanisms. When a cell expresses foreign proteins, such as after viral infection, a fraction of the class I MHC will display these peptides on the cell surface. Consequently, CTLs specific for the MHC:peptide complex will recognize and kill presenting cells. Alternatively, class I MHC itself can serve as an inhibitory ligand for natural killer cells (NKs). Reduction in the normal levels of surface class I MHC, a mechanism employed by some viruses and certain tumors to evade CTL responses, activates NK cell killing.

As used herein, an "MHC class II molecule" refers to a protein product of a wild-type or variant HLA class II gene encoding an MHC class II molecule. Accordingly, "HLA class II molecule" and "MHC class II molecule" are used interchangeably herein.

MHC class II molecules are a class of major histocompatibility complex (MHC) molecules normally found only on professional antigen-presenting cells such as dendritic cells, mononuclear phagocytes, some endothelial cells, thymic epithelial cells, and B cells. These cells are important in initiating immune responses. The antigens presented by class II peptides are derived from extracellular proteins (not cytosolic as in MHC class I).

Like MHC class I molecules, class II molecules are also heterodimers, but in this case consist of two homogenous peptides, an a and (3 chain, both of which are encoded in the MEW. The subdesignation α1, α2, etc. refers to separate domains within the HLA gene; each domain is usually encoded by a different exon within the gene, and some genes have further domains that encode leader sequences, transmembrane sequences, etc. These molecules have both extracellular regions as well as a transmembrane sequence and a cytoplasmic tail. The α1 and β1 regions of the chains come together to make a membrane-distal peptide-binding domain, while the α2 and β2 regions, the remaining extracellular parts of the chains, form a membrane-proximal immunoglobulin-like domain. The antigen binding groove, where the antigen or peptide binds, is made up of two α-helixes walls and β-sheet. Because the antigen-binding groove of MEW class II molecules is open at both ends while the corresponding groove on class I molecules is closed at each end, the antigens presented by MEW class II molecules are longer, generally between 15 and 24 amino acid residues long. Loading of a MHC class II molecule occurs by phagocytosis; extracellular proteins are endocytosed, digested in lysosomes, and the resulting epitopic peptide fragments are loaded onto MEW class II molecules prior to their migration to the cell surface. In humans, the MEW class II protein complex is encoded by the human leukocyte antigen gene complex (HLA). HLAs corresponding to MEW class II are HLA-DP, HLA-DM, HLA-DOA, HLA-DOB, HLA-DQ, and HLA-DR. Mutations in the HLA gene complex can lead to bare lymphocyte syndrome (BLS), which is a type of MEW class II deficiency.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In other aspects, an isolated EV composition has an amount and/or concentration of desired EVs at or above an acceptable amount and/or concentration. In other aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "immune modulator" refers to an agent (i.e., payload) that acts on a target (e.g., a target cell) that is contacted with the extracellular vesicle, and regulates the immune system. Non-limiting examples of immune modulator that can be introduced into an EV (e.g., exosome) and/or a producer cell include agents such as, modulators of checkpoint inhibitors, ligands of checkpoint inhibitors, cytokines, derivatives thereof, or any combination thereof. The immune modulator can also include an agonist, an antagonist, an antibody, an antigen-binding fragment, a polynucleotide, such as siRNA, antisense oligonucleotide, a phosphorodiamidate morpholino oligomer (PMO), a peptide-conjugated phosphorodiamidate morpholino oligomer (PPMO), miRNA, lncRNA, mRNA DNA, or a small molecule.

As used herein, the term a "bio-distribution modifying agent," which refers to an agent (i.e., payload) that can modify the distribution of extracellular vesicles (e.g., exosomes, nanovesicles) in vivo or in vitro (e.g., in a mixed culture of cells of different varieties). In some aspects, the term "targeting moiety" can be used interchangeably with the term bio-distribution modifying agent. In some aspects, the targeting moiety alters the tropism of the EV (e.g., exosome) ("tropism moiety"). As used herein, the term "tropism moiety" refers to a targeting moiety that when expressed on an EV (e.g., exosome) alters and/or enhances the natural movement of the EV. For example, in some aspects, a tropism moiety can promote the EV to be taken up by a particular cell, tissue, or organ. Non-limiting examples of tropism moieties that can be used with the present disclosure include those that can bind to a marker expressed specifically on a dendritic cell (e.g., Clec9A or DEC205) or T cells (e.g., CD3). Unless indicated otherwise, the term "targeting moiety," as used herein, encompasses tropism moieties. The bio-distribution agent can be a biological molecule, such as a protein, a peptide, a lipid, or a carbohydrate, or a synthetic molecule. For example, the bio-distribution modifying agent can be an affinity ligand (e.g., antibody, VHH domain, phage display peptide, fibronectin domain, camelid, VNAR), a synthetic polymer (e.g., PEG), a natural ligand/molecule (e.g., CD40L, albumin, CD47, CD24, CD55, CD59), a recombinant protein (e.g., XTEN), but not limited thereto.

In certain aspects, the bio-distribution modifying agent, and/or targeting moiety, is displayed on the surface of EVs (e.g., exosomes). The bio-distribution modifying agent can be displayed on the EV surface by being fused to a scaffold protein (e.g., Scaffold X) (e.g., as a genetically encoded fusion molecule). In some aspects, the bio-distribution modifying agent can be displayed on the EV surface by chemical reaction attaching the bio-distribution modifying agent to an EV surface molecule. A non-limiting example is PEGylation. In some aspects, EVs disclosed herein (e.g., exosomes) can further comprise a bio-distribution modifying agent, in addition to an antigen, adjuvant, or immune modulator. Non-limiting examples of bio-distribution modifying agent or targeting moiety that can be used with the present disclosure include a C-type lectin domain family 9 member A (Clec9a) protein, a dendritic cell-specific intercellular adhesion molecule-3-grabbing non-integrin (DC-SIGN), CD207, CD40, Clec6, dendritic cell immunoreceptor (DCIR), DEC-205, lectin-like oxidized low-density lipoprotein receptor-1 (LOX-1), MARCO, Clec12a, DC-asialoglycoprotein receptor (DC-ASGPR), DC immunoreceptor 2 (DCIR2), Dectin-1, macrophage mannose receptor (MMR), BDCA-1 (CD303, Clec4c), Dectin-2, Bst-2 (CD317), CD3, or any combination thereof. In certain aspects, the targeting moiety is Clec9a protein. In some aspects, the targeting moiety is a CD3 molecule.

As used herein, the term "C-type lectin domain family 9 member A" (Clec9a) protein refers to a group V C-type lectin-like receptor (CTLR) that functions as an activation receptor and is expressed on myeloid lineage cells (e.g., DCs). Huysamen et al., *J Biol Chem* 283(24):16693-701 (2008); U.S. Pat. No. 9,988,431 B2, each of which is herein incorporated by reference in its entirety. Synonyms of Clec9a are known and include CD370, DNGR-1, 5B5, HEEE9341, and C-type lectin domain containing 9A. In some aspects, Clec9a protein is expressed on human cDC1 cells. In some aspects, Clec9a protein is expressed on mouse cDC1 and pDC cells. Unless indicated otherwise, Clec9a, as used herein, can refer to Clec9a from one or more species (e.g., humans, non-human primates, dogs, cats, guinea pigs, rabbits, rats, mice, horses, cattle, and bears).

As used herein, the term "CD3" or "cluster of differentiation 3" refers to the protein complex associated with the T cell receptor (TCR). The CD3 molecule is made up of four distinct chains (CD3γ, CD3δ, and two CD3ε chains). These chains associate with the T-cell receptor (TCR) and the ζ-chain to generate an activation signal in T lymphocytes. The TCR, ζ-chain, and CD3 molecules together constitute the TCR complex. CD3 molecules are expressed on all T cells, including both CD4+ T cells and CD8+ T cells. Unless indicated otherwise, CD3, as used herein, can refer to CD3 from one or more species (e.g., humans, non-human primates, dogs, cats, guinea pigs, rabbits, rats, mice, horses, cattle, and bears).

As used herein, the term "payload" refers to an agent that acts on a target (e.g., a target cell) that is contacted with the EV (e.g., exosome). In some aspects, unless indicated otherwise, the term payload can be used interchangeably with the term "biologically active molecules." Non-limiting examples of payload that can be included on the EV, e.g., exosome, are an antigen, an adjuvant, and/or an immune modulator. Payloads that can be introduced into an EV, e.g., exosome, and/or a producer cell include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), a peptide-conjugated phosphorodiamidate morpholino oligomer (PPMO), or combinations thereof), amino acids (e.g., amino acids comprising a detectable moiety or a toxin or that disrupt translation), polypeptides (e.g., enzymes), lipids, carbohydrates, and small molecules (e.g., small molecule drugs and toxins). In certain aspects, a payload comprises an antigen. As used herein, the term "antigen" refers to any agent that when introduced into a subject elicits an immune response (cellular or humoral) to itself.

As used herein, the term "affinity ligand" refers to a molecule that can selectively and preferentially bind to a specific marker, e.g., expressed on a target cell. Non-limiting examples of affinity ligands that can be used with the present disclosure include an antibody, phage display peptide, fibronectin domain, camelid, VNAR, VHH domain, and combinations thereof. As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibody includes bispecific antibodies and multispecific antibodies so long as they exhibit the desired biological activity or function.

The terms "individual," "subject," "host," and "patient," are used interchangeably herein and refer to any mammalian subject for whom diagnosis, treatment, or therapy is desired, particularly humans. The compositions and methods described herein are applicable to both human therapy and veterinary applications. In some aspects, the subject is a mammal, and in other aspects, the subject is a human. As used herein, a "mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substantially free" means that the sample comprising EVs, e.g., exosomes, comprise less than about 10% of macromolecules by mass/volume (m/v) percentage concentration. Some fractions can contain less than about 0.001%, less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in exosomes, including but is not limited to CD9, CD63, CD81, PDGFR, GPI anchor proteins, lactadherin LAMP2, and LAMP2B, a fragment thereof, or a peptide that binds thereto.

"Administering," as used herein, means to give a composition comprising an EV, e.g., exosome, disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. EVs, e.g., exosomes can be administered as part of a pharmaceutical composition comprising at least one excipient.

An "immune response," as used herein, refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4+ cell, a CD8+ T cell, or a Treg cell, or activation or inhibition of any other cell of the immune system, e.g., NK cell. Accordingly an immune response can comprise a humoral immune response (e.g., mediated by B-cells), cellular immune response (e.g., mediated by T cells), or both humoral and cellular immune responses. In some aspects, an immune response is an "inhibitory" immune response. An "inhibitory" immune response is an immune response that blocks or diminishes the effects of a stimulus (e.g., antigen). In certain aspects, the inhibitory immune response comprises the production of inhibitory antibodies against the stimulus. In some aspects, an immune response is a "stimulatory" immune response. A "stimulatory" immune response is an immune response that results in the generation of effectors cells (e.g., cytotoxic T lymphocytes) that can destroy and clear a target antigen (e.g., tumor antigen or viruses).

As used herein, the term "cellular immune response" can be used interchangeably with the term "cell-mediated immune response" and refers to an immune response that does not predominantly involve antibodies. Instead, a cellular immune response involves the activation of different immune cells (e.g., phagocytes and antigen-specific cytotoxic T-lymphocytes) that produce various effector molecules (e.g., cytokines, perforin, granzymes) upon activation (e.g., via antigen stimulation). As used herein, the term "humoral immune response" refers to an immune response predominantly mediated by macromolecules found in extracellular fluids, such as secreted antibodies, complement proteins, and certain antimicrobial peptides. The term "antibody-mediated immune response" refers to an aspect of a humoral immune response that is mediated by antibodies.

As used herein, the term "immune cells" refers to any cells of the immune system that are involved in mediating an immune response. Non-limiting examples of immune cells include a T lymphocyte, B lymphocyte, natural killer (NK) cell, macrophage, eosinophil, mast cell, dendritic cell, neutrophil, or combination thereof. In some aspects, an immune cell expresses CD3. In certain aspects, the CD3-expressing immune cells are T cells (e.g., CD4+ T cells or CD8+ T cells). In some aspects, an immune cell that can be targeted with a targeting moiety disclosed herein (e.g., anti-CD3) comprises a naïve CD4+ T cell. In some aspects, an immune cell comprises a memory CD4+ T cell. In some aspects, an immune cell comprises an effector CD4+ T cell. In some aspects, an immune cell comprises a naïve CD8+ T cell. In some aspects, an immune cell comprises a memory CD8+ T cell. In some aspects, an immune cell comprises an effector CD8+ T cell. In some aspects, an immune cell is a dendritic cell. In certain aspects, a dendritic cell comprises a plasmacytoid dendritic cell (pDC), a conventional dendritic cell 1 (cDC1), a conventional dendritic cell 2 (cDC2), inflammatory monocyte derived dendritic cells, Langerhans cells, dermal dendritic cells, lysozyme-expressing dendritic cells (LysoDCs), Kupffer cells, or any combination thereof. Accordingly, in certain aspects, an immune cell that an EV disclosed herein (e.g., exosomes) can specifically target includes a conventional dendritic cell 1 (cDC1) and/or plasmacytoid dendritic cells (pDC).

As used herein, the term "T cell" or "T-cell" refers to a type of lymphocyte that matures in the thymus. T cells play an important role in cell-mediated immunity and are distinguished from other lymphocytes, such as B cells, by the presence of a T-cell receptor on the cell surface. T-cells include all types of immune cells expressing CD3, including T-helper cells (CD4+ cells), cytotoxic T-cells (CD8+ cells), natural killer T-cells, T-regulatory cells (Treg), and gamma-delta T cells.

A "naïve" T cell refers to a mature T cell that remains immunologically undifferentiated (i.e., not activated). Following positive and negative selection in the thymus, T cells emerge as either CD4+ or CD8+ naïve T cells. In their naïve state, T cells express L-selectin (CD62L+), IL-7 receptor-α (IL-7R-α), and CD132, but they do not express CD25, CD44, CD69, or CD45RO. As used herein, "immature" can also refers to a T cell which exhibits a phenotype characteristic of either a naïve T cell or an immature T cell, such as a TSCM cell or a TCM cell. For example, an immature T cell can express one or more of L-selectin (CD62L+), IL-7Rα, CD132, CCR7, CD45RA, CD45RO, CD27, CD28, CD95, CXCR3, and LFA-1. Naïve or immature T cells can be contrasted with terminal differentiated effector T cells, such as TEM cells and TEFF cells.

As used herein, the term "effector" T cells or "TEFF" cells refers to a T cell that can mediate the removal of a pathogen or cell without requiring further differentiation. Thus, effector T cells are distinguished from naive T cells and memory T cells, and these cells often have to differentiate and proliferate before becoming effector cells.

As used herein, the term "memory" T cells refer to a subset of T cells that have previously encountered and responded to their cognate antigen. In some aspects, the term is synonymous with "antigen-experienced" T cells. In some aspects, memory T cells can be effector memory T cells or central memory T cells. In some aspects, the memory T cells are tissue-resident memory T cells. As used herein, the term "tissue-resident memory T cells" or "TRM cells" refers to a lineage of T cells that occupies tissues (e.g., skin, lung, gastrointestinal tract) without recirculating. TRM cells are transcriptionally, phenotypically and functionally distinct from central memory and effector memory T cells which recirculate between blood, the T cell zones of secondary lymphoid organs, lymph and nonlymphoid tissues. One of the roles of TRM cells is to provide immune protection against infection in extralymphoid tissues.

As used herein, the term "dendritic cells" or "DCs" refers to a class of bone-marrow-derived immune cells that are capable of processing extracellular and intracellular proteins and to present antigens in the context of MHC molecules to prime naïve T cells. In some aspects, dendritic cells can be divided into further subtypes, such as conventional dendritic cell 1 (cDC1), conventional dendritic cell 2 (cDC2), plasmacytoid dendritic cell (pDC), inflammatory monocyte derived dendritic cells, Langerhans cells, dermal dendritic cells, lysozyme-expressing dendritic cells (LysoDCs), Kupffer cells, and combinations thereof. In certain aspects, the different DC subsets can be distinguished based on their phenotypic expression. For example, in some aspects, human cDC1 cells are CD1c$^-$ and CD141$^+$. In some aspects, human cDC2 cells are CD1c$^+$ and CD141$^-$. In some aspects, human pDC cells are CD123$^+$. In some aspects, mouse cDC1 cells are XCR1$^+$, Clec9a$^+$, and Sirpa$^-$. In some aspects, mouse cDC2 cells are CD8$^+$, CD11b$^+$, Sirpa$^+$, XCR1$^-$, and CD1c,b$^+$. In some aspects, mouse pDC cells are CD137$^+$, XCR1$^-$, and Sirpa$^-$. Other phenotypic markers for distinguishing the different DC subsets are known in the art. See, e.g., Collin et al., *Immunology* 154(1): 3-20 (2018). In some aspects, the different DC subsets can be distinguished based on their functional properties. For example, in certain aspects, pDCs produce large amounts of IFN-α, while cDC1s and cDC2s produce inflammatory cytokines, such as IL-12, IL-6, and TNF-α. Other methods of distinguishing the different DC subsets are known in the art. See, e.g., U.S. Pat. Nos. 8,426,565 B2 and 9,988,431, each of which is herein incorporated by reference in its entirety.

The term "immunoconjugate," as used herein, refers to a compound comprising a binding molecule (e.g., an antibody) and one or more moieties, e.g., therapeutic or diagnostic moieties, chemically conjugated to the binding molecule. In general, an immunoconjugate is defined by a generic formula: A-(L-M)n, wherein A is a binding molecule (e.g., an antibody), L is an optional linker, and M is a heterologous moiety which can be for example a therapeutic agent, a detectable label, etc., and n is an integer. In some aspects, multiple heterologous moieties can be chemically conjugated to the different attachment points in the same binding molecule (e.g., an antibody). In other aspects, multiple heterologous moieties can be concatenated and attached to an attachment point in the binding molecule (e.g., an antibody). In some aspects, multiple heterologous moieties (being the same or different) can be conjugated to the binding molecule (e.g., an antibody).

Immunoconjugates can also be defined by the generic formula in reverse order. In some aspects, the immunoconjugate is an "antibody-Drug Conjugate" ("ADC"). In the context of the present disclosure, the term "immunoconjugate" is not limited to chemically or enzymatically conjugates molecules. The term "immunoconjugate" as used in the present disclosure also includes genetic fusions. In some aspects of the present disclosure, the biologically active molecule is an immunoconjugate. The terms "antibody-drug conjugate" and "ADC" are used interchangeably and refer to an antibody linked, e.g., covalently, to a therapeutic agent (sometimes referred to herein as agent, drug, or active pharmaceutical ingredient) or agents. In some aspects of the present disclosure, the biologically active molecule (i.e., a payload) is an antibody-drug conjugate.

"Treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

"Prevent" or "preventing," as used herein, refers to decreasing or reducing the occurrence or severity of a particular outcome. In some aspects, preventing an outcome is achieved through prophylactic treatment.

II. Extracellular Vesicles, e.g., Exosomes

Disclosed herein are EVs, e.g., exosomes, capable of regulating the immune system of a subject. The EVs, e.g., exosomes, useful in the present disclosure have been engineered to produce multiple agents (i.e., payloads) together (e.g., an antigen and an adjuvant in a single EV, e.g., exosome; an antigen and an immune modulator in a single EV, e.g., exosome; and an antigen, an adjuvant, and an immune modulator in a single EV, e.g., exosome; instead of a single agent, e.g., an antigen alone, an adjuvant alone, or an immune modulator alone). In some aspects, an EV, e.g., exosome, comprises (i) an antigen and (ii) an adjuvant. In other aspects, an EV, e.g., exosome, comprises (i) an antigen and (ii) an immune modulator. In some aspects, an EV (e.g., exosome) comprises (i) an antigen, (ii) an adjuvant, and (iii) an immune modulator. In certain aspects, an EV (e.g., exosome) disclosed herein can also comprise additional moieties, such as a targeting moiety. In some aspects, an antigen is not expressed or presented on major histocompatibility complex I and/or II molecules. In other aspects, while an antigen in the EV, e.g., exosome, is not expressed or presented as part of the MHC class I or II complex, the EV, e.g., exosome, can still contain MHC class I/II molecules on the surface of the EV, e.g., exosome. Accordingly, in certain aspects, EVs, e.g., exosomes, disclosed herein do not directly interact with T-cell receptors (TCRs) of T cells to induce an immune response against the antigen. Similarly, in certain aspects, EVs, e.g., exosomes, of the present disclosure do not transfer the antigen directly to the surface of the target cell (e.g., dendritic cell) through cross-dressing. "Cross-dressing" is a mechanism commonly used by EVs, e.g., exosomes, derived from dendritic cells (DEX) to induce T cell activation. See Pitt, J. M., et al., J Clin Invest 126(4): 1224-32 (2016). In other aspects, the EVs, e.g., exosomes, of the present disclosure are engulfed by antigen presenting cells and can be expressed on the surface of the antigen presenting cells as MHC class I and/or MHC class II complex.

As will be apparent to those skilled in the art, EVs (e.g., exosomes) disclosed herein do not need to comprise an antigen and can instead comprise multiple other payloads disclosed herein. For example, in some aspects, an EV (e.g., exosome) can comprise multiple different adjuvants. In some aspects, an EV (e.g., exosome) can comprise multiple different immune modulators. In some aspects, an EV (e.g., exosome) can comprise one or more adjuvants in combination with one or more immune modulators. Such antigen-less EVs (e.g., exosomes) can be useful in inducing and/or increasing an innate immune response. Non-limiting examples of therapeutic settings where such antigen-less EVs could be useful include: to treat bacterial and/or viral infections, such as *Pseudomonas aeruginosa* for ventilator-associated pneumonia, influenza and RSV, SARS/MERs, *Toxoplasma*, sepsis, yellow fever, and staph *aureus* for surgical site infection. In certain aspects, such antigen-less EVs (e.g., exosomes) can be used in combination with one or more additional therapeutic agents. In some aspects, the one or more additional therapeutic agents comprise an antigen, wherein the antigen is not expressed in an EV (e.g., exosome) (e.g., soluble form of the antigen) . . . . Unless indicated otherwise, the relevant disclosures provided herein are equally applicable regardless of whether an EV (e.g., exosome) comprises an antigen or not.

As described supra, EVs, e.g., exosomes, described herein are extracellular vesicles with a diameter between about 20-300 nm. In certain aspects, an EV, e.g., exosome, of the present disclosure has a diameter between about 20-290 nm, between about 20-280 nm, between about 20-270 nm, between about 20-260 nm, between about 20-250 nm, between about 20-240 nm, between about 20-230 nm, between about 20-220 nm, between about 20-210 nm, between about 20-200 nm, between about 20-190 nm, between about 20-180 nm, between about 20-170 nm, between about 20-160 nm, between about 20-150 nm, between about 20-140 nm, between about 20-130 nm, between about 20-120 nm, between about 20-110 nm, between about 20-100 nm, between about 20-90 nm, between about 20-80 nm, between about 20-70 nm, between about 20-60 nm, between about 20-50 nm, between about 20-40 nm, between about 20-30 nm, between about 30-300 nm, between about 30-290 nm, between about 30-280 nm, between about 30-270 nm, between about 30-260 nm, between about 30-250 nm, between about 30-240 nm, between about 30-230 nm, between about 30-220 nm, between about 30-210 nm, between about 30-200 nm, between about 30-190 nm, between about 30-180 nm, between about 30-170 nm, between about 30-160 nm, between about 30-150 nm, between about 30-140 nm, between about 30-130 nm, between about 30-120 nm, between about 30-110 nm, between about 30-100 nm, between about 30-90 nm, between about 30-80 nm, between about 30-70 nm, between about 30-60 nm, between about 30-50 nm, between about 30-40 nm, between about 40-300 nm, between about 40-290 nm, between about 40-280 nm, between about 40-270 nm, between about 40-260 nm, between about 40-250 nm, between about 40-240 nm, between about 40-230 nm, between about 40-220 nm, between about 40-210 nm, between about 40-200 nm, between about 40-190 nm, between about 40-180 nm, between about 40-170 nm, between about 40-160 nm, between about 40-150 nm, between about 40-140 nm, between about 40-130 nm, between about 40-120 nm, between about 40-110 nm, between about 40-100 nm, between about 40-90 nm, between about 40-80 nm, between about 40-70 nm, between about 40-60 nm, between about 40-50 nm, between about 50-300 nm, between about 50-290 nm, between about 50-280 nm, between about 50-270 nm, between about 50-260 nm, between about 50-250 nm, between about 50-240 nm, between about 50-230 nm, between about 50-220 nm, between about 50-210 nm, between about 50-200 nm, between about 50-190 nm, between about 50-180 nm, between about 50-170 nm, between about 50-160 nm, between about 50-150 nm, between about 50-140 nm, between about 50-130 nm, between about 50-120 nm, between about 50-110 nm, between about 50-100 nm, between about 50-90 nm, between about 50-80 nm, between about 50-70 nm, between about 50-60 nm, between about 60-300 nm, between about 60-290 nm, between about 60-280 nm, between about 60-270 nm, between about 60-260 nm, between about 60-250 nm, between about 60-240 nm, between about 60-230 nm, between about 60-220 nm, between about 60-210 nm, between about 60-200 nm, between about 60-190 nm, between about 60-180 nm, between about 60-170 nm, between about 60-160 nm, between about 60-150 nm, between about 60-140 nm, between about 60-130 nm, between about 60-120 nm, between about 60-110 nm, between about 60-100 nm, between about 60-90 nm, between about 60-80 nm, between about 60-70 nm, between about 70-300 nm, between about 70-290 nm, between about 70-280 nm, between about 70-270 nm, between about 70-260 nm, between about 70-250 nm, between about 70-240 nm, between about 70-230 nm, between about 70-220 nm, between about 70-210 nm, between about 70-200 nm, between about 70-190 nm, between about 70-180 nm, between about 70-170 nm, between about 70-160 nm, between about 70-150 nm, between about 70-140 nm, between about 70-130 nm, between about 70-120 nm, between about 70-110 nm, between about 70-100 nm, between about 70-90 nm, between about 70-80 nm, between about 80-300 nm, between about 80-290 nm, between about 80-280 nm, between about 80-270 nm, between about 80-260 nm, between about 80-250 nm, between about 80-240 nm, between about 80-230 nm, between about 80-220 nm, between about 80-210 nm, between about 80-200 nm, between about 80-190 nm, between about 80-180 nm, between about 80-170 nm, between about 80-160 nm, between about 80-150 nm, between about 80-140 nm, between about 80-130 nm, between about 80-120 nm, between about 80-110 nm, between about 80-100 nm, between about 80-90 nm, between about 90-300 nm, between about 90-290 nm, between about 90-280 nm, between about 90-270 nm, between about 90-260 nm, between about 90-250 nm, between about 90-240 nm, between about 90-230 nm, between about 90-220 nm, between about 90-210 nm, between about 90-200 nm, between about 90-190 nm, between about 90-180 nm, between about 90-170 nm, between about 90-160 nm, between about 90-150 nm, between about 90-140 nm, between about 90-130 nm, between about 90-120 nm, between about 90-110 nm, between about 90-100 nm, between about 100-300 nm, between about 110-290 nm, between about 120-280 nm, between about 130-270 nm, between about 140-260 nm, between about 150-250 nm, between about 160-240 nm, between about 170-230 nm, between about 180-220 nm, or between about 190-210 nm. The size of the EV, e.g., exosome, described herein can be measured according to methods described, infra.

In some aspects, an EV, e.g., exosome, of the present disclosure comprises a bi-lipid membrane ("EV, e.g., exosome, membrane"), comprising an interior surface and an exterior surface. In certain aspects, the interior surface faces the inner core (i.e., lumen) of the EV, e.g., exosome. In certain aspects, the exterior surface can be in contact with the endosome, the multivesicular bodies, or the membrane/cytoplasm of a producer cell or a target cell In some aspects, the EV, e.g., exosome, membrane comprises lipids and fatty acids. In some aspects, the EV, e.g., exosome, membrane comprises phospholipids, glycolipids, fatty acids, sphingolipids, phosphoglycerides, sterols, cholesterols, and phosphatidylserines.

In some aspects, the EV, e.g., exosome, membrane comprises an inner leaflet and an outer leaflet. The composition of the inner and outer leaflet can be determined by transbilayer distribution assays known in the art, see, e.g., Kuypers et al., *Biohim Biophys Acta* 1985 819:170. In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, the EV, e.g., exosome, membrane comprises one or more polysaccharide, such as glycan.

In some aspects, the EV, e.g., exosome, membrane further comprises one or more scaffold moieties, which are capable of anchoring, e.g., an antigen and/or an adjuvant and/or an immune modulator, to the EV, e.g., exosome, (e.g., either on the luminal surface or on the exterior surface). In certain aspects, scaffold moieties are polypeptides ("exosome proteins"). In other aspects, scaffold moieties are non-polypeptide moieties. In some aspects, exosome proteins include various membrane proteins, such as transmembrane proteins, integral proteins and peripheral proteins, enriched on the exosome membranes. They can include various CD proteins, transporters, integrins, lectins, and cadherins. In certain aspects, a scaffold moiety (e.g., exosome protein) comprises Scaffold X. In other aspects, a scaffold moiety (e.g., exosome protein) comprises Scaffold Y. In further aspects, a scaffold moiety (e.g., exosome protein) comprises both a Scaffold X and a Scaffold Y.

In some aspects, an EV, e.g., exosome, disclosed herein is capable of delivering a payload (e.g., an antigen, an adjuvant, and/or an immune modulator) to a target. The payload is an agent that acts on a target (e.g., a target cell) that is contacted with the EV. Contacting can occur in vitro or in a subject. Non-limiting examples of payloads that can be introduced into an EV include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), or a peptide-conjugated phosphorodiamidate morpholino oligomer (PPMO)), amino acids (e.g., amino acids comprising a detectable moiety or a toxin that disrupt translation), polypeptides (e.g., enzymes), lipids, carbohydrates, and small molecules (e.g., small molecule drugs and toxins).

As demonstrated herein (see, e.g., Example 16), in some aspects, EVs (e.g., exosomes) of the present disclosure are capable of inducing effector and memory T cells. In certain aspects, the memory T cells are tissue-resident memory T cells. Such EVs (e.g., exosomes) could be particularly useful as vaccines for certain infectious diseases. For example, most of the currently available influenza vaccines are inactivated and largely focused on generating neutralizing antibodies against certain influenza surface antigens (e.g., hemagglutinin (HA) and neuraminidase (NA). See Wang et al., *Science* 367(6480): 1-12 (Feb. 21, 2020), which is herein incorporated by reference in its entirety). However, such antigens undergo constant mutations, requiring the vaccines to be updated annually. Even with the annual updates, there have been years in which influenza vaccines were ineffective because of mismatched HA and/or NA antigenicity between the vaccine viral strains and strains in circulation. Broad immunity can be evoked by natural viral infections or live vector-engineered and attenuated vaccines, as these all induce tissue (lung) resident memory T cells apart from the humoral immunity. However, a delicate balance must be struck between safety and immunogenicity of these "replicating" vaccines and are often suitable for only some individuals. EVs (e.g., exosomes) of the present disclosure do not share such limitations. Accordingly, in some aspects, EVs (e.g., exosomes) disclosed herein (e.g., comprising one or more influenza antigens in combination with a payload disclosed herein, e.g., STING agonist) could be useful as an "universal" vaccine against a particular pathogen (e.g., different influenza subtypes).

In some aspects, EVs (e.g., exosomes) disclosed herein are inherently capable of inducing the activation of a signaling pathway involved in an immune response. In certain aspects, the signaling pathway involved in an immune response comprises toll-like receptors (TLRs), retinoid acid-inducible gene I (RIG-I)-like receptors (RLRs), stimulator of interferon genes (STING) pathway, or combinations thereof. In some aspects, the activation of such signaling pathway can result in the production of a type I interferon. For example, in certain aspects, the bi-lipid membrane of an EV (e.g., exosome) disclosed herein comprises one or more lipids that share one of the following features: (i) unsaturated lipid tail, (ii) dihydroimidazole linker, (iii) cyclic amine head groups, and (iv) combinations thereof. Lipids with such features have been shown to activate the TLR/RLR-independent STING pathway. See Miao et al., *Nature Biotechnology* 37:1174-1185 (October 2019), which is herein incorporated by reference in its entirety.

II.A Antigen

In some aspects, the payload is an antigen, which is capable of inducing an immune response in a subject. In some aspects, an EV (e.g., exosome) disclosed herein comprises a single antigen. In some aspects, an EV (e.g., exosome) disclosed herein comprises multiple antigens. In certain aspects, each of the multiple antigens is different. In some aspects, an EV (e.g., exosome) disclosed herein comprises at least 2, 3, 4, 5, 6, 7, 8, 9, 10 or more different antigens. As disclosed herein, an antigen can be linked to a surface of an EV (e.g., exosome) using a scaffold moiety (e.g., Scaffold X and/or Scaffold Y). In certain aspects, an antigen can be directly linked (i.e., without the use of a scaffold moiety) to a surface of an EV (e.g., exosome). In some aspects, an antigen can be in the lumen of the EV (e.g., exosome).

In some aspects, an EV (e.g., exosome) comprises the one or more antigens in combination with one or more additional payloads described herein (e.g., adjuvant and/or immune modulator). In some aspects, an EV (e.g., exosome) can comprise one or more additional moieties (e.g., targeting moiety). For instance, in certain aspects, an EV (e.g., exosome) disclosed herein can comprise (i) one or more additional antigens, (ii) one or more additional payloads (e.g., adjuvant and/or immune modulator), and (iii) one or more targeting moieties.

In some aspects, the antigen comprises a tumor antigen. Non-limiting examples of tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen (CTA), MART-1 gp100, TNF-related apoptosis-inducing ligand, Brachyury (preferentially expressed antigen in melanoma (PRAME)), Wilms tumor 1 (WT1), CD19, CD22, or combinations thereof.

In some aspects, the antigen is a universal tumor antigen. As used herein, the term "universal tumor antigen" refers to an immunogenic molecule, such as a protein, that is, generally, expressed at a higher level in tumor cells than in non-tumor cells and also is expressed in tumors of different origins. In some aspects, the universal tumor antigen is expressed in more than about 30%, about 40%, about 50%, about 60%, about 70%, about 80%, about 90% or more of cancers (e.g., human cancers). In some aspects, the universal tumor antigen can be expressed in non-tumor cells (e.g., normal cells) but at lower levels than it is expressed in tumor cells. In certain aspects, the expression level of the universal tumor antigen is greater than about 1-fold, about 2-fold, about 3-fold, about 4-fold, about 5-fold, about 6-fold, about 7-fold, about 8-fold, about 9-fold, about 10-fold or more on tumor cells compared to non-tumor cells. In certain aspects, the universal tumor antigen is not expressed in normal cells and only expressed in tumor cells. Non-limiting examples of universal tumor antigens that can be used with the present disclosure include endothelial lining antigens in tumor vasculature, survivin, tumor protein D52 (TPD52), androgen receptor epitopes, ephrin type-A receptor 2 (EphA2), human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

In further aspects, an antigen can comprise a neoantigen. As used herein, the term "neoantigen" refers to antigens encoded by tumor-specific mutated genes.

In some aspects, the antigen is derived from a bacterium, a virus, fungus, protozoa, or any combination thereof. In some aspects, the antigen is derived from an oncogenic virus (also referred to herein as cancer associated viruses (CAVs)). In further aspects, the antigen is derived from a group comprising: a Human Gamma herpes virus 4 (i.e., Epstein Barr virus (EBV)), influenza A virus, influenza B virus, cytomegalovirus, *Staphylococcus aureus*, *Mycobacterium tuberculosis*, *Chlamydia trachomatis*, HIV (e.g., HIV-2), corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B virus (HBV), Hepatitis C virus (HCV), human T-lymphotropic virus (HTLV1), human herpes virus 8 (HHV8), Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and Burrelia mayonii (e.g., Lyme disease), herpes simplex virus 2 (HSV-2), *Klebsiella* sp., *Pseudomonas aeruginosa, Enterococcus* sp., *Proteus* sp., *Enterobacter* sp., *Actinobacter* sp., coagulase-negative staphylococci (CoNS), *Mycoplasma* sp., Adenovirus, Adeno-associated virus (AAV), or combinations thereof.

Figure 7A:
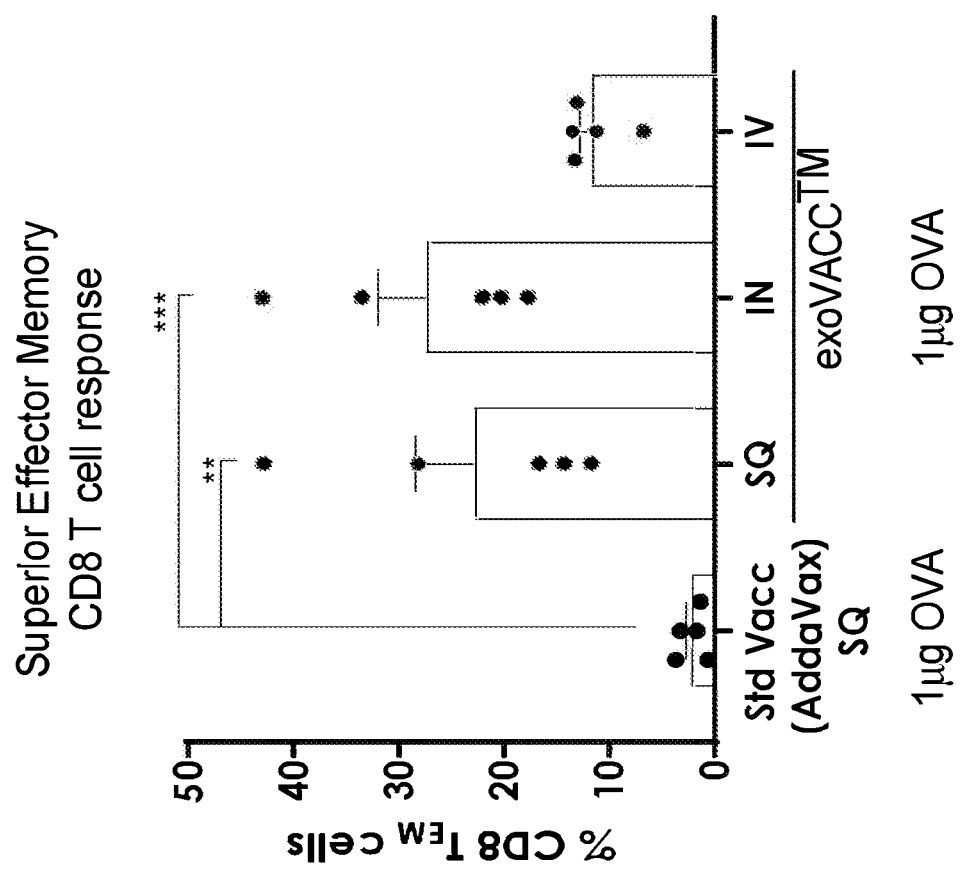
FIGS. 7A and 7B show that an engineered EV, e.g., an exosome, induces superior CD8 T-cell response as compared to standard vaccine formulations.
Figure 7B:
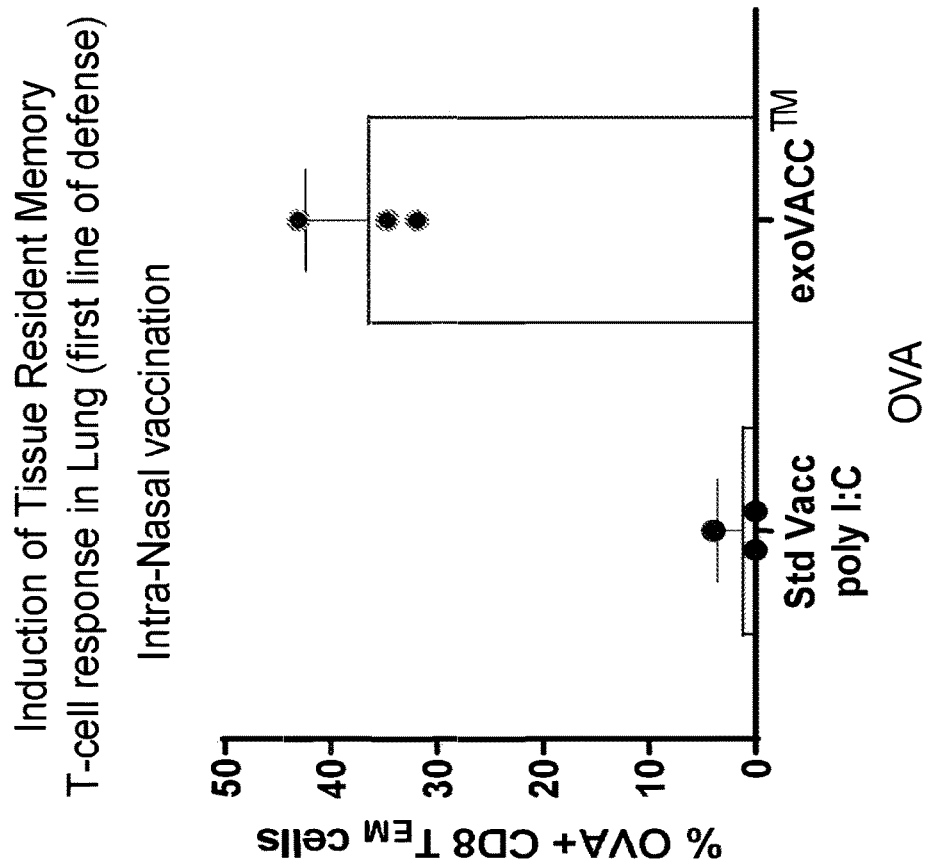

In some aspects, the antigen derived from EBV is BZLF1. BZLF1 (also known as Zta or EB1) is an immediate-early viral gene of EBV, which induces cancers and infects primarily the B-cells of 95% of the human population. This gene (along with others) produces the expression of other EBV genes in other stages of disease progression, and is involved in converting the virus from the latent to the lytic form. ZEBRA (BamHI Z Epstein-Barr virus replication activator, also known as Zta and BZLF1)) is an early lytic protein of EBV encoded by BZLF1. See Hartlage et al. (2015) Cancer Immunol. Res. 3(7): 787-94, and Rist et al. (2015) J. Virology 70:703-12, both of which are incorporated herein by reference in their entireties. EV, e.g., exosomes, disclosed herein comprising an EBV antigen, e.g., BZLF1, can be used, e.g., to treat post-transplant lymphoproliferative disorder (PTLD). Such EV can be administered to EBV negative patients receiving EBV positive transplants. BZLF1 is a dominant T cell antigen associated with durable remission in PTLD patients. The EV, e.g., exosomes, disclosed herein comprising BZLF1 can elicit a potent CD8 T-cell mediated immunity of BZLF1. Accordingly, mucosal immunity and tissue resident memory cells (see FIGS. 7A and 7B) can protect the patient from developing PTLDF. Non-limiting exemplary antigens include, but are not limited to, the antigens disclosed in U.S. Pat. No. 8,617,564 B2, which is herein incorporated by reference in its entirety.

In some aspects, the antigen is derived from *Mycobacterium tuberculosis* to induce cellular and/or humoral immune response. In some aspects, the antigen comprises one or more epitopes of *Mycobacterium tuberculosis* (TB antigen). Various antigens are associated with *Mycobacterium tuberculosis* infection, including ESAT-6, TB10.4, CFP10, Rv2031 (hspX), Rv2654c (TB7.7), and Rv1038c (EsxJ). See, e.g., Lindestam et al., J. Immunol. 188(10):5020-31 (2012), which is incorporated herein in its entirety. In some aspects, the antigen useful for the present disclosure comprises one or more epitopes of ESAT6. In some aspects, the antigen useful for the present disclosure comprises one or more epitopes of TB10.4. In some aspects, the antigen useful for the present disclosure comprises one or more epitopes of CFP10. In some aspects, the antigen useful for the present disclosure comprises one or more epitopes of Rv2031 (hspX). In some aspects, the antigen useful for the present disclosure comprises one or more epitopes of Rv2654c (TB7.7). In some aspects, the antigen useful for the present disclosure comprises one or more epitopes of Rv1038c (EsxJ). In some aspects, the antigen useful for the present disclosure comprises an epitope selected from the group consisting of ESAT6, TB10.4 (ESAT-6-like protein EsxH; cfp7), CFP10, Rv2031 (hspX), Rv2654c (TB7.7), Rv1038c (EsxJ), and any combination thereof.

In some aspects, the TB antigen comprises a particular epitope of a TB antigen, e.g., a particular epitope of ESAT6 or TB10.4. In some aspects, the ESAT6 antigen comprises an epitope having at least three amino acids, at least four amino acids, at least five amino acids, at least six amino acids, at least seven amino acids, at least eight amino acids, at least nine amino acids, at least ten amino acids, at least eleven amino acids, at least twelve amino acids, at least thirteen amino acids, at least fourteen amino acids, at least fifteen amino acids of the amino acid sequence as set forth in MTEQQWNFAGIEAAASAIQGNVTSIHSLDE-GKQSLTKLAAAWGGSGSEAYQGVQQKW-DATATELNNALQNL ARTISEAGQAMAS-TEGNVTGMFA (SEQ ID NO: 370). In some aspects, wherein the TB10.4 antigen comprises an epitope having at least three amino acids, at least four amino acids, at least five amino acids, at least six amino acids, at least seven amino acids, at least eight amino acids, at least nine amino acids, at least ten amino acids, at least eleven amino acids, at least twelve amino acids, at least thirteen amino acids, at least fourteen amino acids, at least fifteen amino acids of the amino acid sequence as set forth in (SEQ ID NO: 371)
MSQIMYNYPAMLGHAGDMAGYAGTLQSLGAEIAVEQAALQSAWQGDTGITY

QAWQAQWNQAMEDLVRAYHAMSSTHEANTMAMMARDTAEAAKWGG

In some aspects, an antigen comprises a self-antigen. As used herein, the term "self-antigen" refers to an antigen that is expressed by a host cell or tissue. Under normal healthy state, such antigens are recognized by the body as self and do not elicit an immune response. However, under certain diseased conditions, a body's own immune system can recognize self-antigens as foreign and mount an immune response against them, resulting in autoimmunity. In certain aspects, EVs, e.g., exosomes, of the present disclosure can comprise a self-antigen (i.e., the self (germline) protein to which T cell responses have been induced and resulted in autoimmunity). Such EVs, e.g., exosomes, can be used to target the autoreactive T cells and suppress their activity. Non-limiting examples of self-antigens (including the associated disease or disorder) include: (i) beta-cell proteins, insulin, islet antigen 2 (IA-2), glutamic acid decarboxylase (GAD65), and zinc transporter 8 (ZNT8) (type I diabetes), (ii) myelin oligodendrocyte glycoprotein (MOG), myelin basic protein (MBP), proteolipid protein (PLP), and myelin-associated glycoprotein (MAG) (multiple sclerosis), (iii) citrullinated antigens and synovial proteins (rheumatoid arthritis), (iv) aquaporin-4 (AQP4) (neuromyelitis optica), (v) nicotinic acetylcholine receptors (nAChRs) (myasthenia gravis), (vi) desmoglein-1 (DSG1) and desoglein-2 (DSG2) (pemphigus vulgaris), (v) thyrotropin receptor (Graves' disease), (vi) type IV collagen (Goodpasture syndrome), (vii) thyroglobulin, thyroid peroxidase, and thyroid-stimulating hormone receptor (TSHR) (Hashimoto's thyroiditis), or (viii) combinations thereof.

II.B Adjuvants

As described supra, EVs, e.g., exosomes, of the present disclosure can comprise an adjuvant (e.g., in combination with an antigen and/or other payloads disclosed herein). In some aspects, an EV (e.g., exosome) disclosed herein comprises multiple adjuvants. In certain aspects, each of the multiple adjuvants is different. In some aspects, an EV (e.g., exosome) disclosed herein comprises at least 2, 3, 4, 5, 6, 7, 8, 9, 10 or more different adjuvants. As disclosed herein, an adjuvant can be linked to a surface of an EV (e.g., exosome) using a scaffold moiety (e.g., Scaffold X and/or Scaffold Y). In certain aspects, an adjuvant can be directly linked (i.e., without the use of a scaffold moiety) to a surface of an EV (e.g., exosome). In some aspects, an adjuvant can be in the lumen of the EV (e.g., exosome).

In some aspects, an EV (e.g., exosome) comprises the one or more adjuvants in combination with one or more additional payloads (e.g., antigen, and/or immune modulator). In some aspects, an EV (e.g., exosome) can comprise one or more additional moieties (e.g., targeting moieties). For instance, in certain aspects, an EV (e.g., exosome) disclosed herein can comprise (i) one or more additional adjuvants, (ii) one or more additional payloads (e.g., antigen and/or immune modulator), and (iii) one or more targeting moieties.

As used herein, the term "adjuvant" refers to any substance that enhances the therapeutic effect of the payload (e.g., increasing an immune response to the antigen). Accordingly, EVs, e.g., exosomes, described herein comprising an adjuvant are capable of increasing an immune response, e.g., to an antigen, by at least about 5%, at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more or more, compared to a reference (e.g., corresponding EV without the adjuvant or a non-EV delivery vehicle comprising an antigen alone or in combination with the adjuvant). In some aspects, incorporating an adjuvant disclosed herein to an EV (e.g., exosome) can increase an immune response, e.g., to an antigen, by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV comprising the antigen alone or a non-EV delivery vehicle comprising an antigen alone or in combination with the adjuvant).

Non-limiting examples of adjuvants that can be used with the present disclosure include: Stimulator of Interferon Genes (STING) agonist, a toll-like receptor (TLR) agonist, an inflammatory mediator, RIG-I agonists, alpha-gal-cer (NKT agonist), heat shock proteins (e.g., HSP65 and HSP70), C-type lectin agonists (e.g., beta glucan (Dectin 1), chitin, and curdlan), and combinations thereof.

In some aspects, incorporating an adjuvant (e.g., such as those disclosed herein) to an EV (e.g., exosome) can broaden an immune response induced by the EV. As used herein, to "broaden an immune response" refers to enhancing the diversity of an immune response. In some aspects, the diversity of an immune response can be enhanced through epitope spreading (i.e., inducing and/or increasing an immune response (cellular and/or humoral immune response) against a greater number/variety of epitopes on an antigen). In some aspects, the diversity of an immune response can be enhanced through the production of different and/or multiple antibody isotypes (e.g., IgG, IgA, IgD, IgM, and/or IgE).

In some aspects, an adjuvant (e.g., such as those disclosed herein) can also help regulate the type of immune response induced by the EV (e.g., exosome). For example, in some aspects, incorporating an adjuvant to an EV (e.g., exosome) can help drive an immune response towards a more Th1 phenotype. As used herein, a "Th1" immune response is generally characterized by the production of IFN-γ, which can activate the bactericidal activities of innate cells (e.g., macrophages), help induce B cells to make opsonizing (marking for phagocytosis) and complement-fixing antibodies, and/or lead to cell-mediated immunity (i.e., not mediated by antibodies). In general, Th1 responses are more effective against intracellular pathogens (viruses and bacteria that are inside host cells) and/or cancers.

In some aspects, incorporating an adjuvant to an EV (e.g., exosome) can help drive an immune response towards a more Th2 phenotype. As used herein, a "Th2" immune response can be characterized by the release of certain cytokines, such as IL-5 (induces eosinophils in the clearance of parasites) and IL-4 (facilitates B cell isotype switching). In general, Th2 responses are more effective against extracellular bacteria, parasites including helminths and toxins.

In some aspects, incorporating an adjuvant to an EV (e.g., exosome) can help drive an immune response towards a more Th17 phenotype. As used herein, a "Th17" immune response is mediated by Th17 cells. As used herein, "Th17 cells" refer to a subset of CD4+ T cells characterized by the production of pro-inflammatory cytokines, such as IL-17A, IL-17F, IL-21, IL-22, and granulocyte-macrophage colony-stimulating factor (GM-CSF). Th17 cells are generally thought to play an important role in host defense against infection, by recruiting neutrophils and macrophages to infected tissues.

In some aspects, incorporating an adjuvant to an EV (e.g., exosome) can help drive an immune response towards a more cellular immune response (e.g., T-cell mediated). In some aspects, incorporating an adjuvant to an EV (e.g., exosome) can help drive an immune response towards a more humoral immune response (e.g., antibody-mediated).

In some aspects, an adjuvant induces the activation of a cytosolic pattern recognition receptor. Non-limiting examples of cytosolic pattern recognition receptor includes: stimulator of interferon genes (STING), retinoic acid-inducible gene I (RIG-1), Melanoma Differentiation-Associated protein 5 (MDA5), Nucleotide-binding oligomerization domain, Leucine rich Repeat and Pyrin domain containing (NLRP), inflammasomes, or combinations thereof. In certain aspects, an adjuvant is a STING agonist. Stimulator of Interferon Genes (STING) is a cytosolic sensor of cyclic dinucleotides that is typically produced by bacteria. Upon activation, it leads to the production of type I interferons (e.g., IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin)) and initiates an immune response. In certain aspects, the STING agonist comprises a cyclic dinucleotide STING agonist or a non-cyclic dinucleotide STING agonist. As described herein, in some aspects, the STING agonist is loaded in the lumen of the EV (e.g., exosome). In some aspects, such EVs (e.g., exosomes) are referred to herein as "exoSTING." Non-limiting examples of exoSTING are provided in International Publication No. WO 2019183578A1, which is herein incorporated by reference in its entirety. Further disclosures of useful STING agonists are also provided throughout the present disclosure.

Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, are known to stimulate or enhance an immune or inflammation response in a patient. The CDNs can have 2'2', 2'3', 2'5', 3'3', or 3'5' bonds linking the cyclic dinucleotides, or any combination thereof.

Cyclic purine dinucleotides can be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides can be modified analogues. Any suitable modification known in the art can be used, including, but not limited to, phosphorothioate, biphosphorothioate, fluorinate, and difluorinate modifications.

Non cyclic dinucleotide agonists can also be used, such as 5,6-Dimethylxanthenone-4-acetic acid (DMXAA), or any other non-cyclic dinucleotide agonist known in the art.

Non-limiting examples of STING agonists that can be used with the present disclosure include: DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, and combinations thereof. Non-limiting examples of the STING agonists can be found at U.S. Pat. No. 9,695,212, WO 2014/189805 A1, WO 2014/179335 A1, WO 2018/100558 A1, U.S. Pat. No. 10,011,630 B2, WO 2017/027646 A1, WO 2017/161349 A1, and WO 2016/096174 A1, each of which is incorporated by reference in its entirety.

In some aspects, the STING agonist useful for the present disclosure comprises a compound having the following formula:

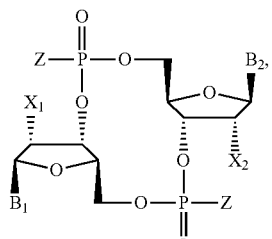

Formula 1

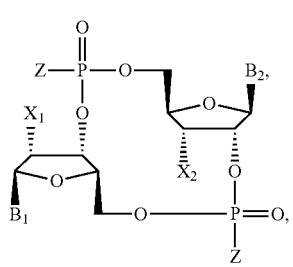

Formula 2

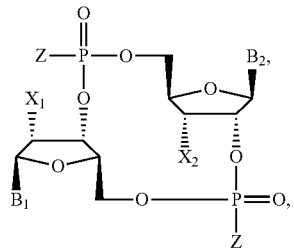

Formula 3 wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

$B_1$ and $B_2$ are bases chosen from:

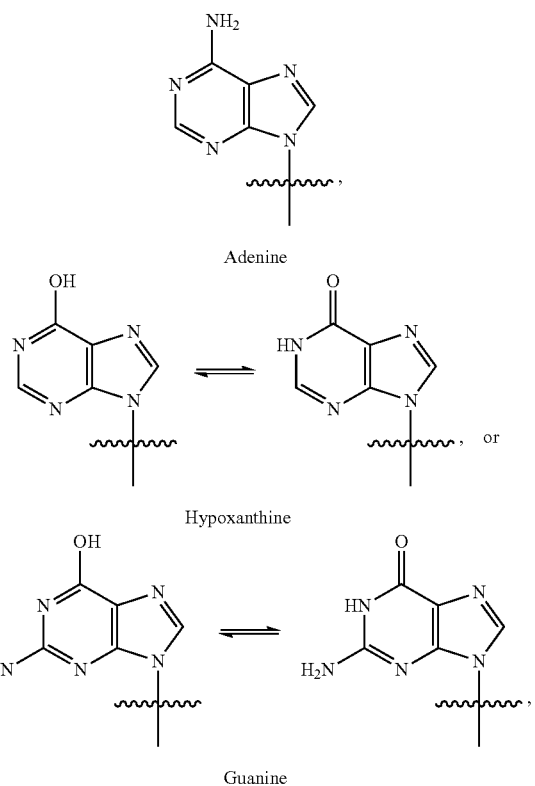

With proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH.

See WO 2016/096174, the content of which is incorporated herein by reference in its entirety.

In some aspects, the STING agonist useful for the present disclosure comprises:

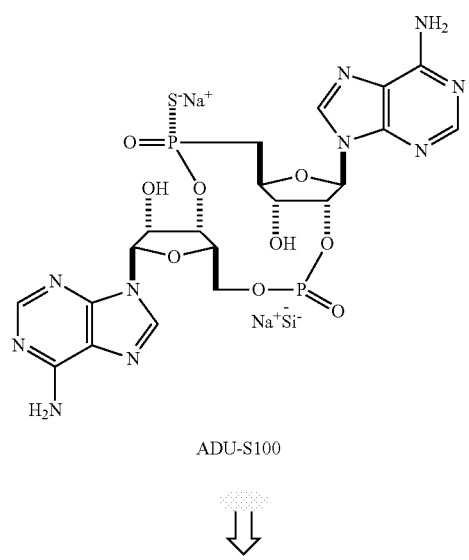
ADU-S100
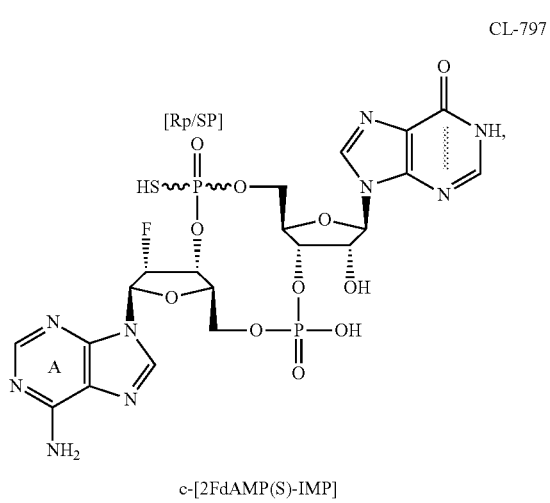
c-[2FdAMP(S)-IMP]
CL-797
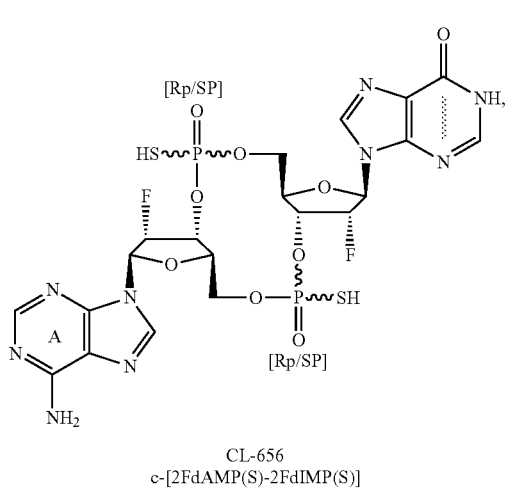
CL-656
c-[2FdAMP(S)-2FdIMP(S)]
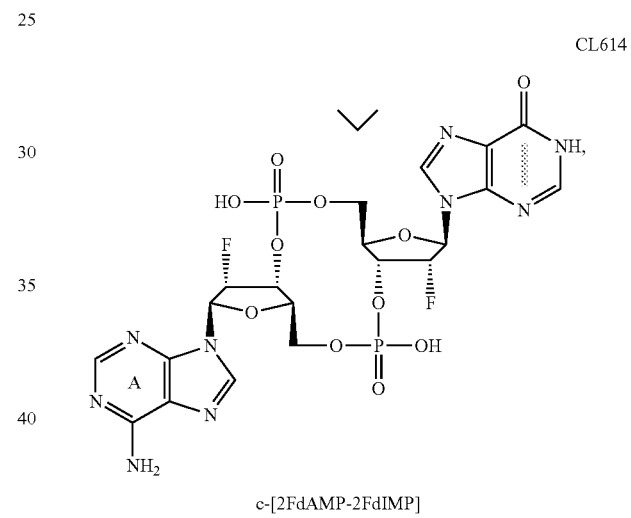
c-[2FdAMP-2FdIMP]
CL614
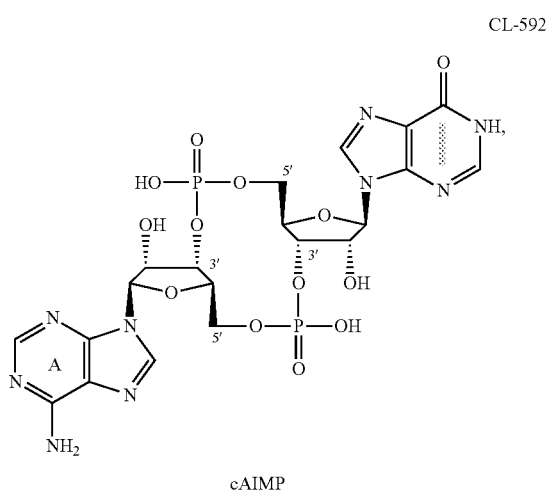
cAIMP
CL-592
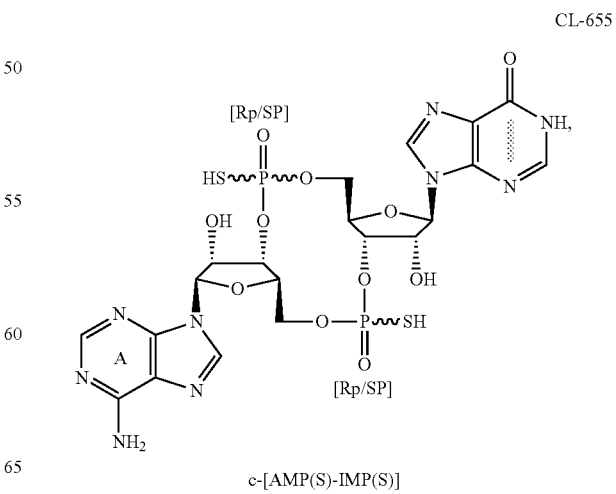
c-[AMP(S)-IMP(S)]
CL-655

-continued
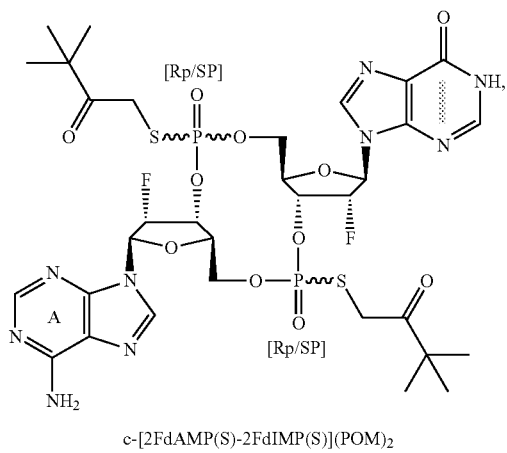
c-[2FdAMP(S)-2FdIMP(S)](POM)$_2$
and
a pharmaceutically acceptable salt thereof. See WO 2016/096174 A1, which is incorporated herein by reference in its entirety.
In other aspects, the STING agonist useful for the present disclosure comprises a compound having the following formula:
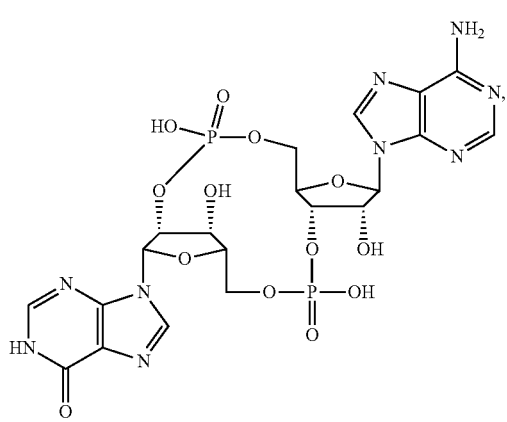
(3',2')c-AIMP
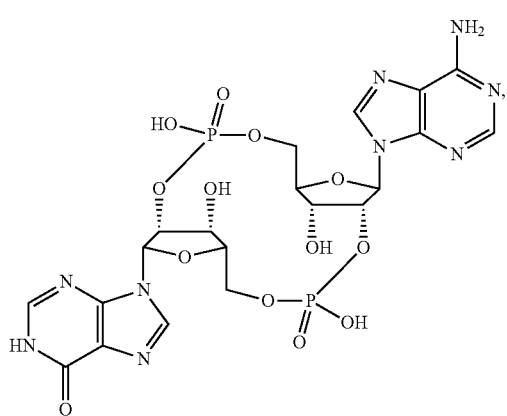
(2',2')c-AIMP
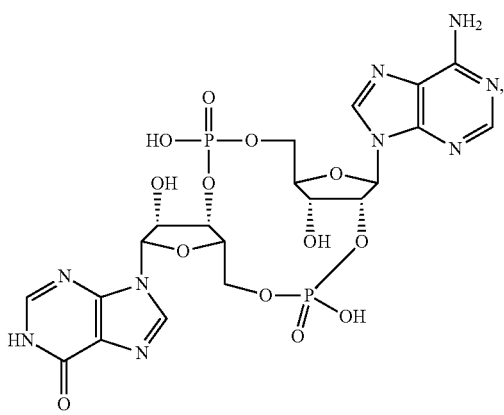
(2',3')c-AIMP
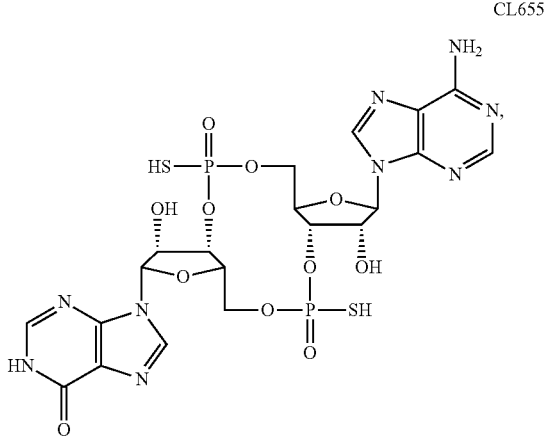
c-AIMP(S)
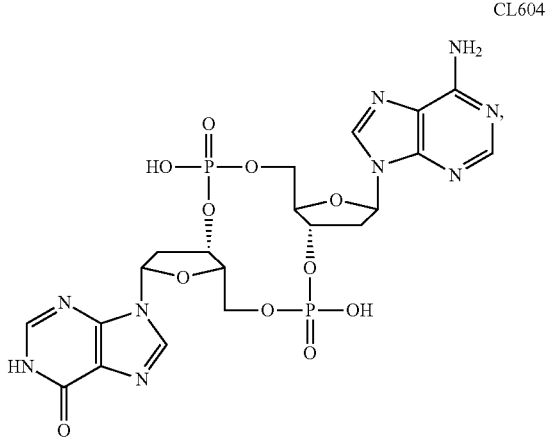
c-(dAMP-dIMP)

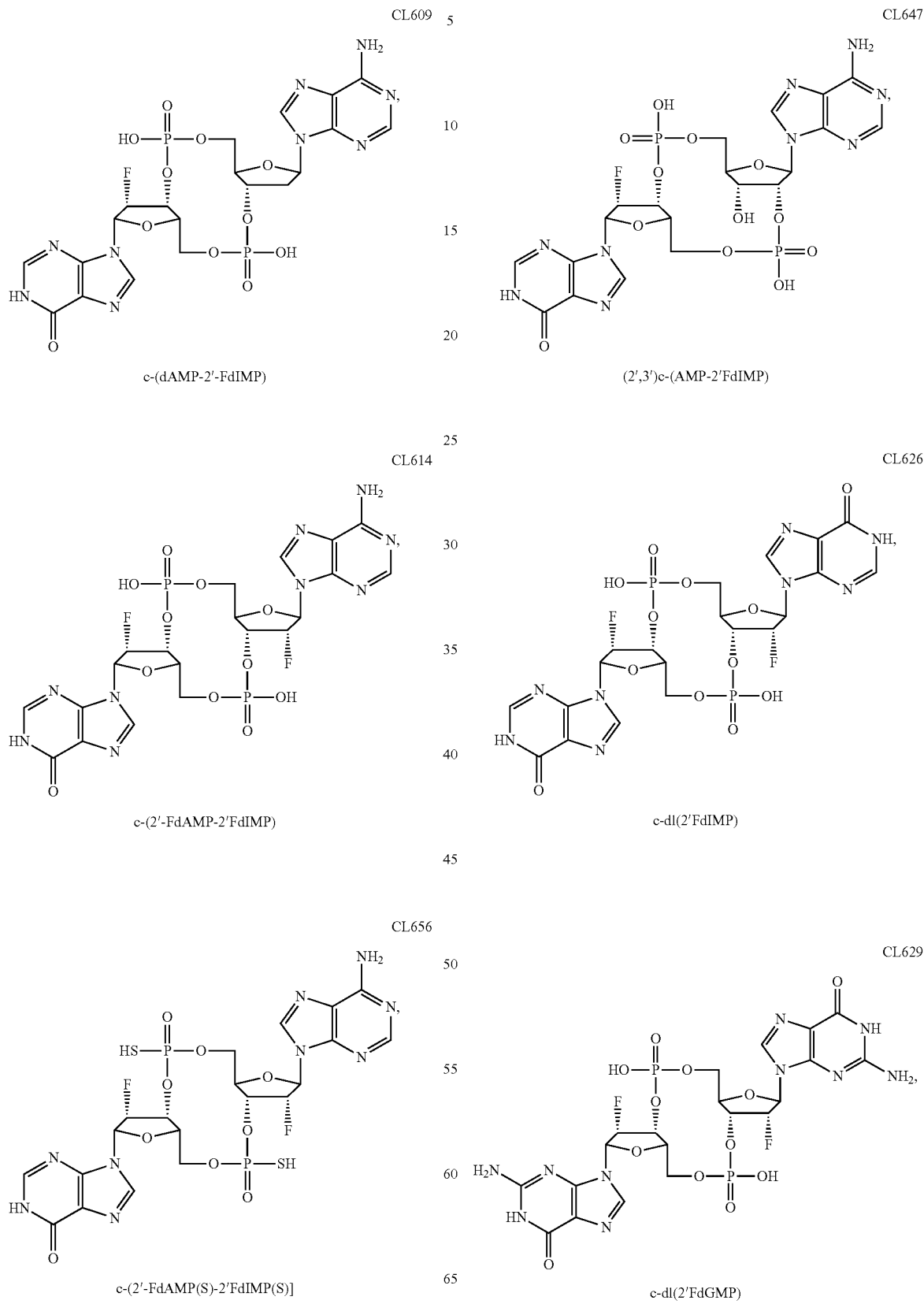

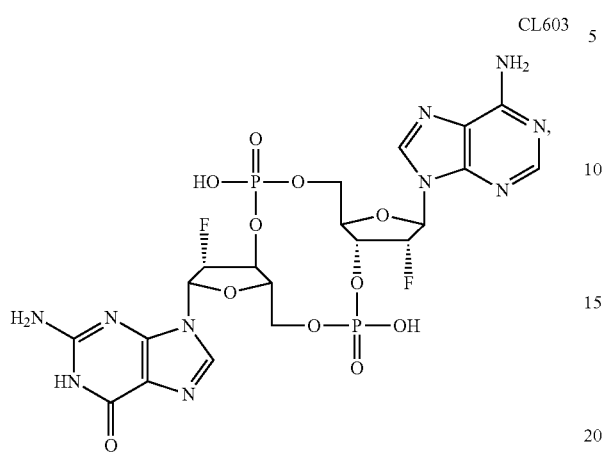

c-(2'FdGMP-2'FdAMP)

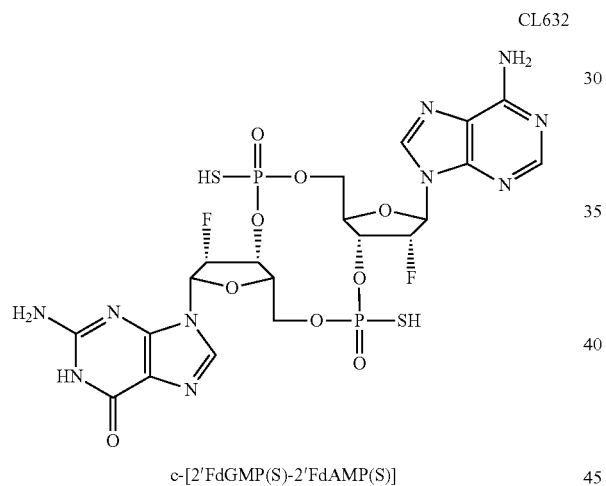

c-[2'FdGMP(S)-2'FdAMP(S)]

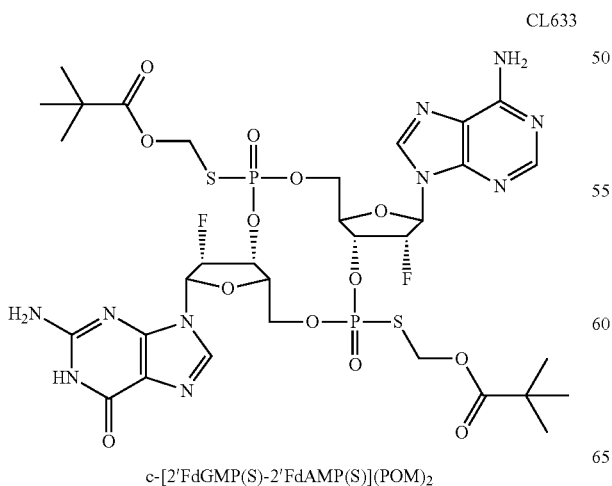

c-[2'FdGMP(S)-2'FdAMP(S)](POM)₂

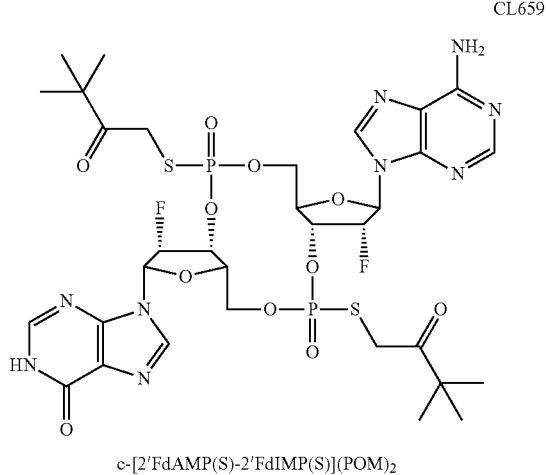

c-[2'FdAMP(S)-2'FdIMP(S)](POM)₂ or any pharmaceutically acceptable salts thereof.

In some aspects, the STING agonist useful for the present disclosure comprises a compound having the following formula:

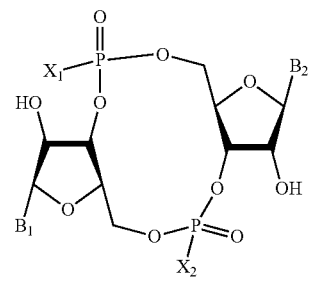

wherein each symbol is defined in WO 2014/093936, the content of which is incorporated herein by reference in its entirety.

In some aspects, the STING agonist useful for the present disclosure comprises a compound having the following formula:

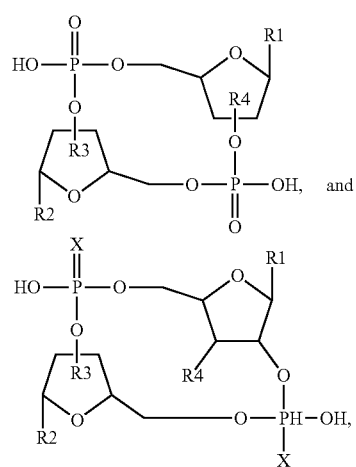

wherein each symbol is defined in WO 2014/189805, the content of which is incorporated herein by reference in its entirety.

In some aspects, the STING agonist useful for the present disclosure comprises a compound having the following formula:

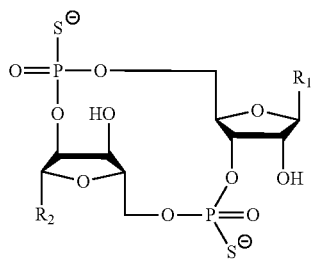

wherein each symbol is defined in WO 2015/077354, the content of which is incorporated herein by reference in its entirety. See also Cell reports 11, 1018-1030 (2015), which is incorporated herein by reference in its entirety.

In some aspects, the STING agonist useful for the present disclosure comprises c-di-AMP, c-di-GMP, c-di-IMP, c-AMP-GMP, c-AMP-IMP, and c-GMP-IMP, described in WO 2013/185052 and Sci. Transl. Med. 283,283ra52 (2015), which are incorporated herein by reference in their entireties.

In some aspects, the STING agonist useful for the present disclosure comprises a compound having the following formula:

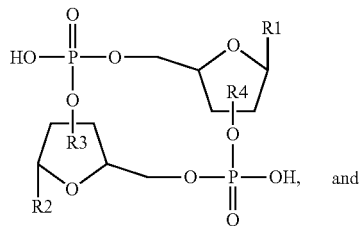

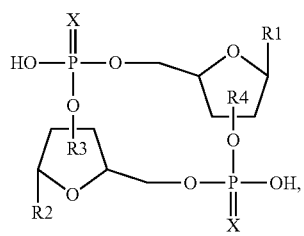

wherein each symbol is defined in WO 2014/189806, the content of which is incorporated herein by reference in its entirety.

In some aspects, the STING agonist useful for the present disclosure comprises a compound having the following formula:

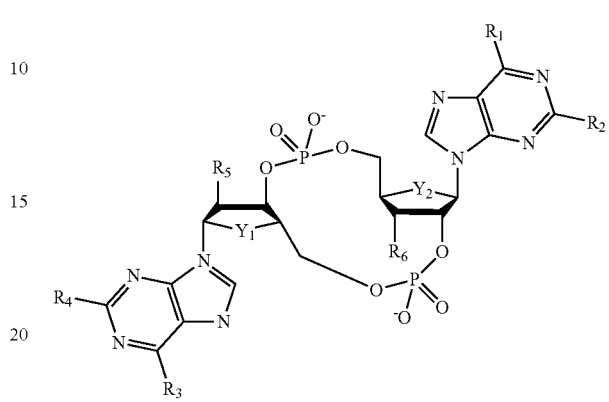

wherein each symbol is defined in WO 2015/185565, the content of which is incorporated herein by reference in its entirety.

In some aspects, the STING agonist useful for the present disclosure comprises a compound having the following formula:

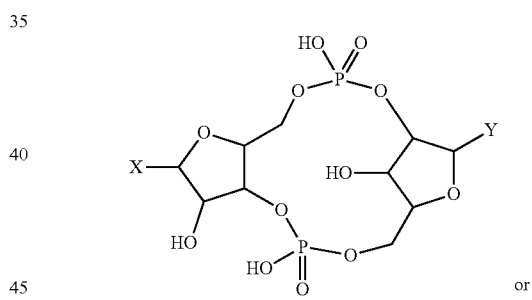

or

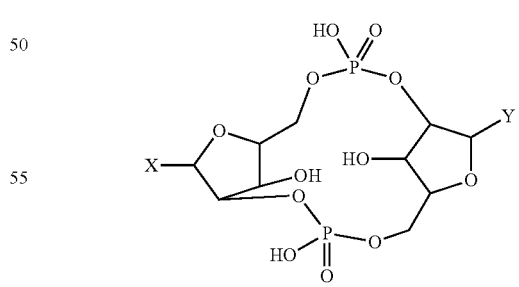

wherein each symbol is defined in WO 2014/179760, the content of which is incorporated herein by reference in its entirety.

In some aspects, the STING agonist useful for the present disclosure comprises a compound having the following formula:

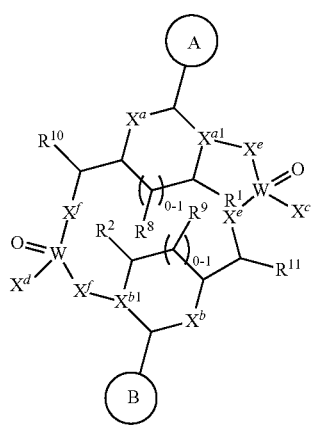
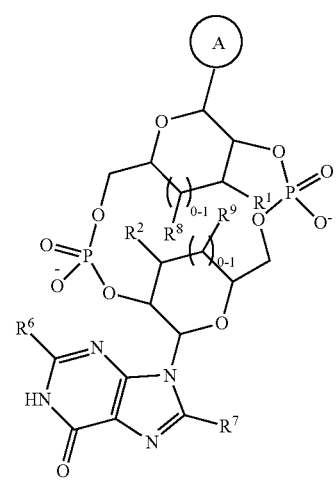
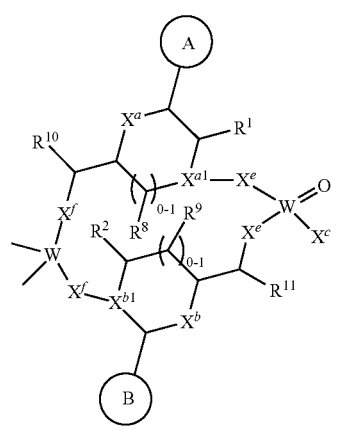
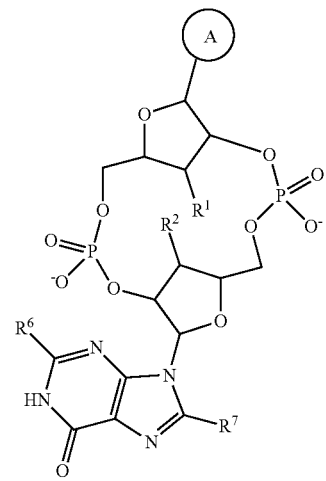
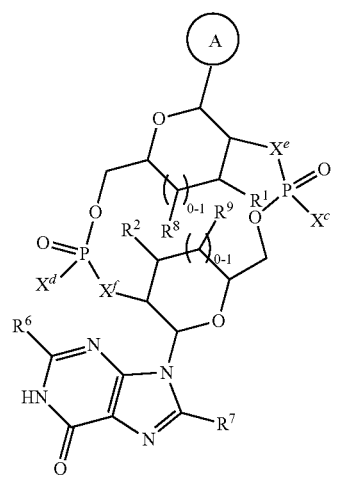
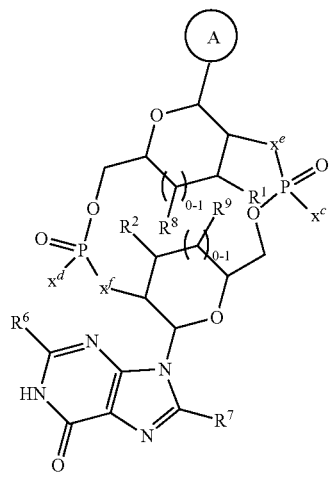

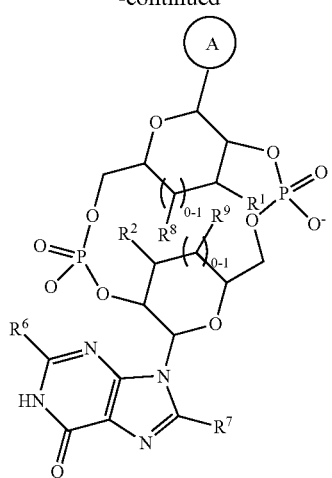

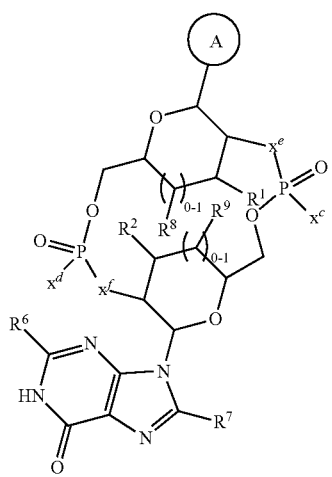

wherein each symbol is defined in WO 2014/179335, the content of which is incorporated herein by reference in its entirety.

In some aspects, the STING agonist useful for the present disclosure comprises a compound having the following formula:

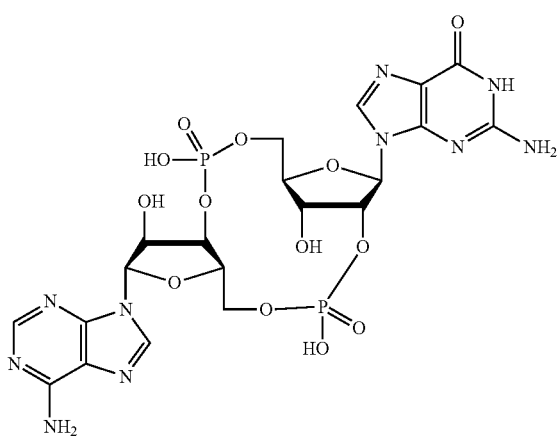

described in WO 2015/017652, the content of which is incorporated herein by reference in its entirety.

In some aspects, the STING agonist useful for the present disclosure comprises a compound having the following formula:

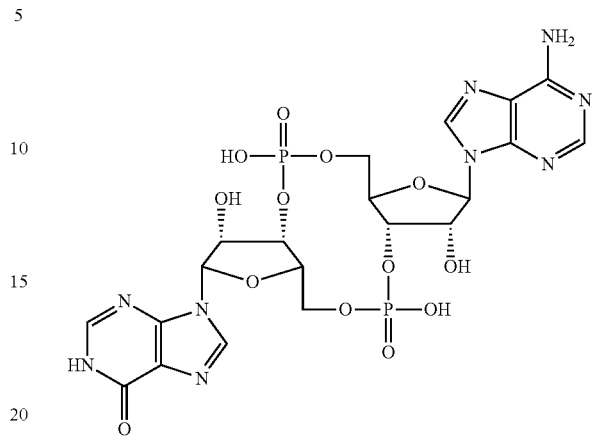

described in WO 2016/096577, the content of which is incorporated herein by reference in its entirety.

In some aspects, the STING agonist useful for the present disclosure comprises a compound having the following formula:

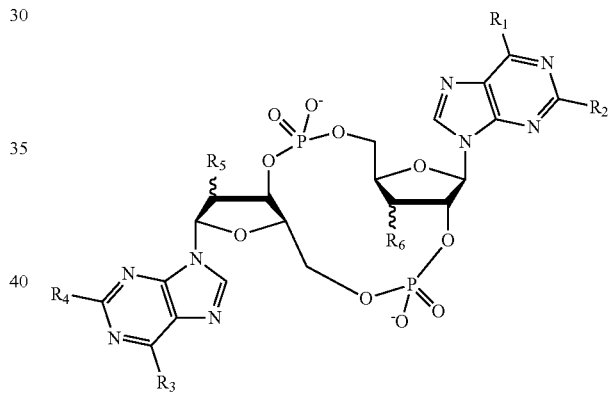

wherein each symbol is defined in WO 2016/120305, the content of which is incorporated herein by reference in its entirety.

In some aspects, the STING agonist useful for the present disclosure comprises a compound having the following formula:

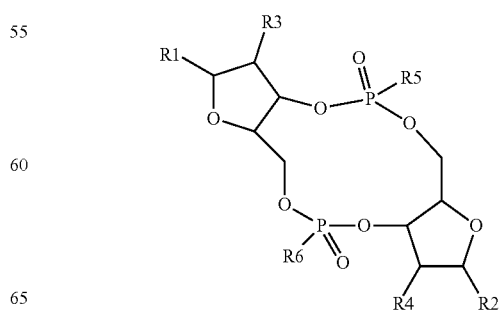

wherein each symbol is defined in WO 2016/145102, the content of which is incorporated herein by reference in its entirety.

In some aspects, the STING agonist useful for the present disclosure comprises a compound having the following formula:

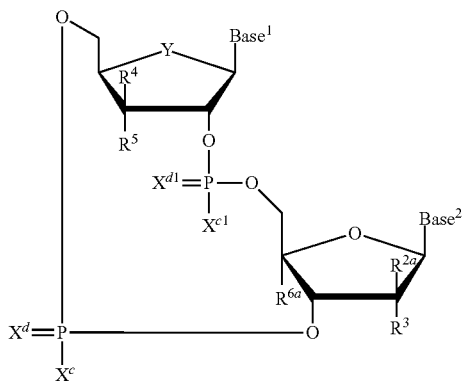

wherein each symbol is defined in WO 2017/027646, the content of which is incorporated herein by reference in its entirety.

In some aspects, the STING agonist useful for the present disclosure comprises a compound having the following formula:

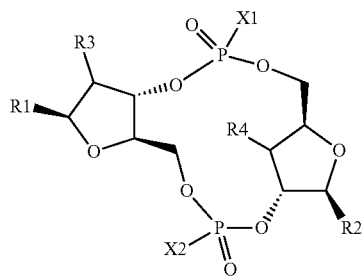

wherein each symbol is defined in WO 2017/075477, the content of which is incorporated herein by reference in its entirety.

In some aspects, the STING agonist useful for the present disclosure comprises a compound having the following formula:

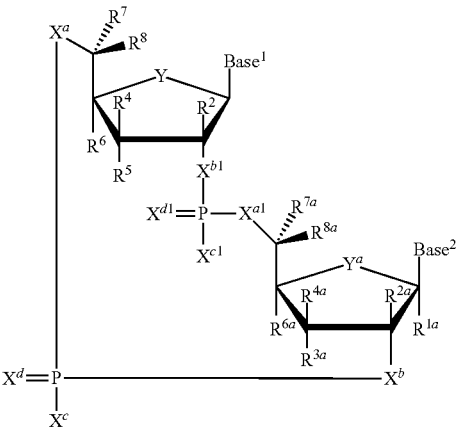

wherein each symbol is defined in WO 2017/027645, the content of which is incorporated herein by reference in its entirety.

In some aspects, the STING agonist useful for the present disclosure comprises a compound having the following formula:

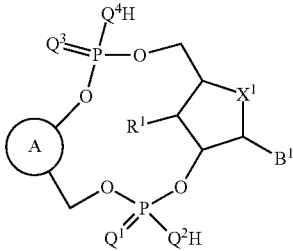

wherein each symbol is defined in WO 2018/100558, the content of which is incorporated herein by reference in its entirety.

In some aspects, the STING agonist useful for the present disclosure comprises a compound having the following formula:

(I-N)

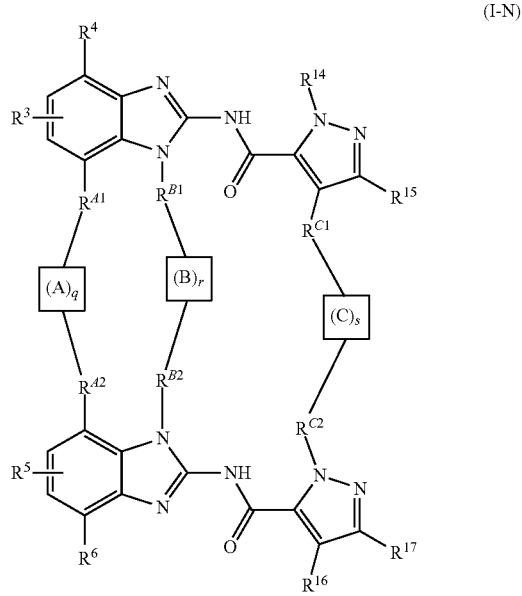

wherein each symbol is defined in WO 2017/175147, the content of which is incorporated herein by reference in its entirety.

In some aspects, the STING agonist useful for the present disclosure comprises a compound having the following formula:

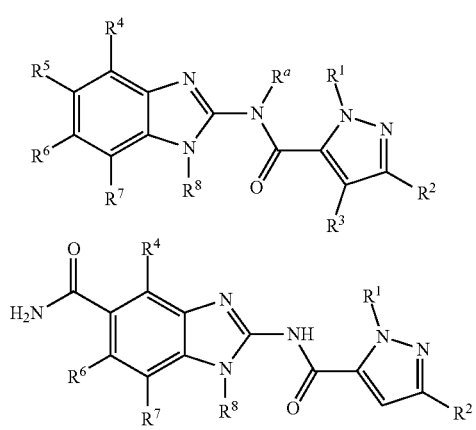

wherein each symbol is defined in WO 2017/175156, the content of which is incorporated herein by reference in its entirety.

In some aspects, the STING agonist useful for the present disclosure is CL606, CL611, CL602, CL655, CL604, CL609, CL614, CL656, CL647, CL626, CL629, CL603, CL632, CL633, CL659, or a pharmaceutically acceptable salt thereof. In some aspects, the STING agonist useful for the present disclosure is CL606 or a pharmaceutically acceptable salt thereof. In some aspects, the STING agonist useful for the present disclosure is CL611 or a pharmaceutically acceptable salt thereof. In some aspects, the STING agonist useful for the present disclosure is CL602 or a pharmaceutically acceptable salt thereof. In some aspects, the STING agonist useful for the present disclosure is CL655 or a pharmaceutically acceptable salt thereof. In some aspects, the STING agonist useful for the present disclosure is CL604 or a pharmaceutically acceptable salt thereof. In some aspects, the STING agonist useful for the present disclosure is CL609 or a pharmaceutically acceptable salt thereof. In some aspects, the STING agonist useful for the present disclosure is CL614 or a pharmaceutically acceptable salt thereof. In some aspects, the STING agonist useful for the present disclosure is CL656 or a pharmaceutically acceptable salt thereof. In some aspects, the STING agonist useful for the present disclosure is CL647 or a pharmaceutically acceptable salt thereof. In some aspects, the STING agonist useful for the present disclosure is CL626 or a pharmaceutically acceptable salt thereof. In some aspects, the STING agonist useful for the present disclosure is CL629 or a pharmaceutically acceptable salt thereof. In some aspects, the STING agonist useful for the present disclosure is CL603 or a pharmaceutically acceptable salt thereof. In some aspects, the STING agonist useful for the present disclosure is CL632 or a pharmaceutically acceptable salt thereof. In some aspects, the STING agonist useful for the present disclosure is CL633 or a pharmaceutically acceptable salt thereof. In some aspects, the STING agonist useful for the present disclosure is CL659 or a pharmaceutically acceptable salt thereof.

In some aspects, the EV, e.g., exosome, comprises a cyclic dinucleotide STING agonist and/or a non-cyclic dinucleotide STING agonist. In some aspects, when several cyclic dinucleotide STING agonist are present on an EV, e.g., exosome, disclosed herein, such STING agonists can be the same or they can be different. In some aspects, when several non-cyclic dinucleotide STING agonist are present, such STING agonists can be the same or they can be different. In some aspects, an EV, e.g., exosome, composition of the present disclosure can comprise two or more populations of EVs, e.g., exosomes, wherein each population of EVs, e.g., exosomes, comprises a different STING agonist or combination thereof.

The STING agonists can also be modified to increase encapsulation (i.e., loading) of the agonist in an extracellular vesicle or EV (e.g., either unbound in the lumen). In some aspects, the STING agonists are linked to a scaffold moiety, e.g., Scaffold Y. In certain aspects, the modification allows better expression of the STING agonist on the exterior surface of the EV, e.g., exosome, (e.g., linked to a scaffold moiety disclosed herein, e.g., Scaffold X). This modification can include the addition of a lipid binding tag by treating the agonist with a chemical or enzyme, or by physically or chemically altering the polarity or charge of the STING agonist. The STING agonist can be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications can be practiced. The modification can increase encapsulation (i.e., loading) of the agonist in the EV (e.g., exosome) by between about 2-fold and about 10,000 fold, between about 10-fold and about 1,000 fold, or between about 100-fold and about 500-fold compared to encapsulation (i.e., loading) of an unmodified agonist. The modification can increase encapsulation (i.e., loading) of the agonist in the EV by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about, 2000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to encapsulation (i.e., loading) of an unmodified agonist.

In some aspects, STING agonists can be modified to allow for better expression of the agonists on the surface of the EV (e.g., exterior and/or luminal surface of the EV, e.g., exosome, (e.g., linked to a scaffold moiety disclosed herein, e.g., Scaffold X and/or Scaffold Y)). Any of the modifications described above can be used. The modification can increase expression of the agonist in the EV, e.g., on the surface and/or luminal surface of the exosome, by about between 2-fold and 10,000-fold, about between 10-fold and 1,000-fold, or about between 100-fold and 500-fold compared to corresponding expression of an unmodified agonist. The modification can increase expression of the agonist on the exterior surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist. The modification can increase expression of the agonist on the luminal surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist.

The concentration of the STING agonist associated with the EV (e.g., exosome) can be about 0.01 µM to about 1000 µM. The concentration of the associated STING agonist can be between about 0.01-0.05 µM, between about 0.05-0.1 µM, between about 0.1-0.5 µM, between about 0.5-1 µM, between about 1-5 µM, between about 5-10 µM, between about 10-15 µM, between about 15-20 µM, between about 20-25 µM, between about 25-30 µM, between about 30-35 µM, between about 35-40 µM, between about 45-50 µM, between about 55-60 µM, between about 65-70 µM, between about 70-75 µM, between about 75-80 µM, between about 80-85 µM, between about 85-90 µM, between about 90-95 µM, between about 95-100 µM, between about 100-150 µM, between about 150-200 µM, between about 200-250 µM, between about 250-300 µM, between about 300-350 µM, between about 250-400 µM, between about 400-450 µM, between about 450-500 µM, between about 500-550 µM, between about 550-600 µM, between about 600-650 µM, between about 650-700 µM, between about 700-750 µM, between about 750-800 µM, between about 800-850 µM, between about 805-900 µM, between about 900-950 µM, or between about 950-1000 µM. The concentration of the associated STING agonist can be equal to or greater than about 0.01 µM, about 0.1 µM, about 0.5 µM, about 1 µM, about 5 µM, about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM, about 95 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 950 µM, or about 1,000 µM.

In some aspects, an adjuvant is a TLR agonist. Non-limiting examples of TLR agonists include: TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), and combinations thereof. Non-limiting examples of TLR agonists can be found at WO2008115319A2, US20130202707A1, US20120219615A1, US20100029585A1, WO2009030996A1, WO2009088401A2, and WO2011044246A1, each of which are incorporated by reference in its entirety.

In some aspects, an adjuvant is an inflammatory mediator.

In some aspects, an antigen is expressed on the exterior surface or in the lumen (e.g., on the luminal surface) of the EV, e.g., exosome. In some aspects, an adjuvant is expressed on the exterior surface or in the luminal surface of the EVs, e.g., exosomes, directly connected to the lipid bilayer. In such aspects, the antigen and/or the adjuvant can be linked to a scaffold moiety (e.g., Scaffold X and/or Scaffold Y).

In some aspects, an EVs, e.g., exosomes, described herein comprises a first scaffold moiety. In certain aspects, the antigen is linked to the first scaffold moiety. In other aspects, the adjuvant is linked to the first scaffold moiety. In further aspects, both the antigen and the adjuvant are linked to the first scaffold moiety. In some aspects, an EVs, e.g., exosomes, further comprises a second scaffold moiety. In certain aspects, the antigen is linked to the first scaffold moiety, and the adjuvant is linked to the second scaffold moiety. In some aspects, the first scaffold moiety and the second scaffold moiety are the same (e.g., both Scaffold X or both Scaffold Y). In other aspects, the first scaffold moiety and the second scaffold moiety are different (e.g., first scaffold moiety is Scaffold X and the second scaffold moiety is Scaffold Y; or first scaffold moiety is Scaffold Y and the second scaffold moiety is Scaffold X).

Non-limiting examples of Scaffold X include: prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B). In certain aspects, Scaffold X is a whole protein. In other aspects, Scaffold X is a protein fragment (e.g., functional fragment).

In other aspects, the scaffold moiety useful for the present disclose, a first scaffold moiety, a second scaffold moiety, and/or a third scaffold moiety, includes a conventional exosome protein, including, but not limiting, tetraspanin molecules (e.g., CD63, CD81, CD9 and others), lysosome-associated membrane protein 2 (LAMP2 and LAMP2B), platelet-derived growth factor receptor (PDGFR), GPI anchor proteins, lactadherin and fragments thereof, peptides that have affinity to any of these proteins or fragments thereof, or any combination thereof.

Non-limiting examples of Scaffold Y include: the myristoylated alanine rich Protein Kinase C substrate (MARCKS) protein; myristoylated alanine rich Protein Kinase C substrate like 1 (MARCKSL1) protein; and brain acid soluble protein 1 (BASP1) protein. In some aspects, Scaffold Y is a whole protein. In certain aspects, Scaffold Y is a protein fragment (e.g., functional fragment).

In some aspects, the antigen is linked to a first scaffold moiety on the luminal surface of the EVs, e.g., exosomes, and the adjuvant is in the lumen of the EV, e.g., exosome. As used herein, when a molecule (e.g., antigen or adjuvant) is described as "in the lumen" of the e.g. EV, e.g., exosome, it means that the molecule is not linked to a scaffold moiety described herein. In some aspects, the antigen is in the lumen of the EV, e.g., exosome, and the adjuvant is linked to a first scaffold moiety on the luminal surface of the EV, e.g., exosome. In such aspects, the first scaffold moiety can be Scaffold X or Scaffold Y.

In some aspects, the antigen is linked to a first scaffold moiety on the luminal surface of the EV, e.g., exosome, and the adjuvant is linked to a second scaffold moiety on the exterior surface of the EV, e.g., exosome. In some aspects, the adjuvant is linked to a first scaffold moiety on the luminal surface of the EV, e.g., exosome, and the antigen is linked to a second scaffold moiety on the exterior surface of the EV, e.g., exosome. In these aspects, the first scaffold moiety can be Scaffold Y, and the second scaffold moiety can be Scaffold X. In other aspects, each of the first scaffold moiety and the second scaffold moiety can be Scaffold X.

In some aspects, the antigen is linked to a first scaffold moiety on the exterior surface of the EVs, e.g., exosomes, and the adjuvant is linked to a second scaffold moiety on the luminal surface of the EV, e.g., exosome. In other aspects, the adjuvant is linked to a first scaffold moiety on the exterior surface of the EVs, e.g., exosomes, and the antigen is linked to a second scaffold moiety on the luminal surface of the EV, e.g., exosome. In such aspects, the first scaffold moiety is Scaffold X, and the second scaffold moiety is Scaffold Y; or each of the first scaffold moiety and the second scaffold moiety is Scaffold X.

In some aspects, the antigen is in the lumen of the EVs, e.g., exosomes, and the adjuvant is in the lumen of the EV, e.g., exosome.

In some aspects, the antigen is linked to a first scaffold moiety on the exterior surface of the EVs, e.g., exosomes, and the adjuvant is linked to a second scaffold moiety on the exterior surface of the EV, e.g., exosome. In other aspects, the adjuvant is linked to a first scaffold moiety on the exterior surface of the EVs, e.g., exosomes, and the antigen is linked to a second scaffold moiety on the exterior surface of the EV, e.g., exosome. In some aspects, the first scaffold moiety and the second scaffold moiety are Scaffold X.

In some aspects, the antigen is linked to a first scaffold moiety on the exterior surface of the EVs, e.g., exosomes, and the adjuvant is in the lumen of the EV, e.g., exosome. In some aspects, the antigen is in the lumen of the EVs, e.g., exosomes, and the adjuvant is linked to a first scaffold moiety on the exterior surface of the EV, e.g., exosome. In such aspects, the first scaffold moiety can be Scaffold X.

In some aspects, the antigen is linked to a first scaffold moiety on the exterior surface of the EV, e.g., exosome, and the adjuvant is linked to the first scaffold moiety on the luminal surface of the EV, e.g., exosome. In other aspects, the antigen is linked to a first scaffold moiety on the luminal surface of the EV, e.g., exosome, and the adjuvant is linked to the first scaffold moiety on the exterior surface of the EV, e.g., exosome. In these aspects, the first scaffold moiety can be Scaffold X.

Non-limiting examples of specific aspects, include EVs, e.g., exosomes comprising (i) an antigen and (ii) an adjuvant, wherein:
(a) the antigen is linked to a first Scaffold Y on the luminal surface of the EV, e.g., exosome, and the adjuvant is linked to a second Scaffold Y on the luminal surface of the EV, e.g., exosome;
(b) the antigen is linked to a Scaffold Y on the luminal surface of the EV, e.g., exosome, and the adjuvant is in the lumen of the EV, e.g., exosome, not linked to any scaffold moiety;
(c) the antigen is in the lumen of the EV, e.g., exosome, not linked to any scaffold moiety, and the adjuvant is linked to a Scaffold Y on the luminal surface of the EV, e.g., exosome;
(d) the antigen is linked to a Scaffold Y on the luminal surface of the EV, e.g., exosome, and the adjuvant is linked to a Scaffold X on the exterior surface of the EV, e.g., exosome;
(e) the antigen is in the lumen of the EV, e.g., exosome, not linked to any scaffold moiety, and the adjuvant is linked to a Scaffold X on the exterior surface of the EV, e.g., exosome;
(f) the antigen is linked to a Scaffold Y on the luminal surface of the EV, e.g., exosome, and the adjuvant is linked to a Scaffold X on the luminal surface of the EV, e.g., exosome;
(g) the antigen is in the lumen of the EV, e.g., exosome, not linked to any scaffold moiety, and the adjuvant is linked to a Scaffold X on the luminal surface of the EV, e.g., exosome;
(h) the antigen is linked to a Scaffold X on the luminal surface of the EV, e.g., exosome, and the adjuvant is linked to the Scaffold X on the exterior surface of the EV, e.g., exosome;
(i) the antigen is linked to a first Scaffold X on the exterior surface of the EV, e.g., exosome, and the adjuvant is linked to a second Scaffold X on the exterior surface of the EV, e.g., exosome;
(j) the antigen is linked to a Scaffold X on the exterior surface of the EV, e.g., exosome, and the adjuvant is linked to a Scaffold Y on the luminal surface of the EV, e.g., exosome;
(k) the antigen is linked to a Scaffold X on the exterior surface of the EV, e.g., exosome, and the adjuvant is in the lumen of the EV, e.g., exosome, not linked to any scaffold moiety;
(l) the antigen is linked to a Scaffold X on the exterior surface of the EV, e.g., exosome, and the adjuvant is linked to the Scaffold X on the luminal surface of the EV, e.g., exosome;
(m) the antigen is linked to a first Scaffold X on the luminal surface of the EV, e.g., exosome, and the adjuvant is linked to a second Scaffold X on the luminal surface of the EV, e.g., exosome;
(n) the antigen is linked to a Scaffold X on the luminal surface of the EV, e.g., exosome, and the adjuvant is linked to a Scaffold Y on the luminal surface of the EV, e.g., exosome;
(o) the antigen is linked to a Scaffold X on the luminal surface of the EV, e.g., exosome, and the adjuvant is in the lumen of the EV, e.g., exosome, not linked to any scaffold moiety;
(p) the antigen is linked to a first Scaffold X on the exterior surface of the EV, e.g., exosome, and the adjuvant is linked to a second Scaffold X on the luminal surface of the EV, e.g., exosome;
(q) the antigen is linked to a first Scaffold X on the luminal surface of the EV, e.g., exosome, and the adjuvant is linked to a second Scaffold X on the exterior surface of the EV, e.g., exosome;
(r) the antigen is in the lumen of the EV, e.g., exosome, not linked to any scaffold moiety, and the adjuvant is in the lumen of the EV, e.g., exosome, not linked to any scaffold moiety;
(s) the antigen is linked directly to the luminal surface of the EV, e.g., exosome, and the adjuvant is linked directly to the luminal surface of the EV, e.g., exosome;

(t) the antigen is linked directly to the luminal surface of the EV, e.g., exosome, and the adjuvant is in the lumen of the EV, e.g., exosome;

(u) the antigen is linked directly to the luminal surface of the EV, e.g., exosome, and the adjuvant is linked to a Scaffold Y on the luminal surface of the EV, e.g., exosome;

(v) the antigen is linked directly to the luminal surface of the EV, e.g., exosome, and the adjuvant is linked to a Scaffold X on the luminal surface of the EV, e.g., exosome;

(w) the antigen is linked directly to the luminal surface of the EV, e.g., exosome, and the adjuvant is linked directly to the exterior of the EV, e.g., exosome;

(x) the antigen is linked directly to the luminal surface of the EV, e.g., exosome, and the adjuvant is linked to a Scaffold X on the exterior of the EV, e.g., exosome;

(y) the antigen is linked to a Scaffold Y on the luminal surface of the EV, e.g., exosome, and the adjuvant is linked directly to the luminal surface of the EV, e.g., exosome;

(z) the antigen is linked to a Scaffold Y on the luminal surface of the EV, e.g., exosome, and the adjuvant is linked directly to the exterior of the EV, e.g., exosome;

(aa) the antigen is linked to a Scaffold X on the luminal surface of the EV, e.g., exosome, and the adjuvant is linked directly to the luminal surface of the EV, e.g., exosome;

(bb) the antigen is linked to a Scaffold X on the luminal surface of the EV, e.g., exosome, and the adjuvant is linked directly to the exterior of the EV, e.g., exosome;

(cc) the antigen is in the lumen of the EV, e.g., exosome, and the adjuvant is linked directly to the luminal surface of the EV, e.g., exosome; or (dd) the antigen is in the lumen of the EV, e.g., exosome, and the adjuvant is linked directly to the exterior of the EV, e.g., exosome.

In some aspects, an EV, e.g., exosome of the present disclosure comprises (i) an antigen and (ii) an adjuvant, wherein the antigen is linked to a first Scaffold Y on the luminal surface of the EV, e.g., exosome, and the adjuvant is linked to a second Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold Y on the luminal surface of the EV, e.g., exosome, and the adjuvant is in the lumen of the EV, e.g., exosome, not linked to any scaffold moiety. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold Y on the luminal surface of the EV, e.g., exosome, and the adjuvant is linked to a Scaffold X on the exterior surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold X on the exterior surface of the EV, e.g., exosome. In some aspects, an EV, e.g., exosome of the present disclosure comprises (i) an antigen and (ii) an adjuvant, wherein the antigen is linked to a Scaffold Y on the luminal surface of the, e.g., exosome, and the adjuvant is linked to a Scaffold X on the luminal surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is linked to a Scaffold X on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is linked to the Scaffold X on the exterior surface of the EV, e.g., exosome. In some aspects, an EV, e.g., exosome, of the present disclosure comprises (i) an antigen and (ii) an adjuvant, wherein the antigen is linked to a first Scaffold X on the exterior surface of the EV, e.g., exosome, and the adjuvant is linked to a second Scaffold X on the exterior surface of the EV, e.g., exosome. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is in the lumen of the EV, e.g., exosome, not linked to any scaffold moiety. In some aspects, an EV, e.g., exosome of the present disclosure comprises (i) an antigen and (ii) an adjuvant, wherein the antigen is linked to a Scaffold X on the exterior surface of the EV, e.g., exosome, and the adjuvant is linked to the Scaffold X on the luminal surface of the EV, e.g., exosome. In some aspects, an EV, e.g., exosome of the present disclosure comprises (i) an antigen and (ii) an adjuvant, wherein the antigen is linked to a first Scaffold X on the luminal surface of the EV, e.g., exosome, and the adjuvant is linked to a second Scaffold X on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is linked to a Scaffold Y on the luminal surface of the EV, e.g., exosome. In some aspects, an EV, e.g., exosome of the present disclosure comprises (i) an antigen and (ii) an adjuvant, wherein the antigen is linked to a Scaffold X on the luminal surface of the EV, e.g., exosome, and the adjuvant is in the lumen of the EV, e.g., exosome not linked to any scaffold moiety. In some aspects, an EV, e.g., exosome of the present disclosure comprises (i) an antigen and (ii) an adjuvant, wherein the antigen is linked to a first Scaffold X on the exterior surface of the EV, e.g., exosome, and the adjuvant is linked to a second Scaffold X on the luminal surface of the EV, e.g., exosome. In some aspects, an EV, e.g., exosome of the present disclosure comprises (i) an antigen and (ii) an adjuvant, wherein the antigen is linked to a first Scaffold X on the luminal surface of the EV, e.g., exosome, and the adjuvant is linked to a second Scaffold X on the exterior surface of the EV, e.g., exosome. In some aspects, an EV, e.g., exosome of the present disclosure comprises (i) an antigen and (ii) an adjuvant, wherein the antigen is in the lumen of the EV, e.g., exosome, not linked to any scaffold moiety, and the adjuvant is in the lumen of the EV, e.g., exosome, not linked to any scaffold moiety. In some aspects, an EV, e.g., exosome, comprises (i) an antigen and (ii) an adjuvant, wherein the antigen is linked directly to the luminal surface of the EV, and the adjuvant is linked directly to the luminal surface of the EV. In some aspects, an EV, e.g., exosome, comprises (i) an antigen and (ii) an adjuvant, wherein the antigen is linked directly to the luminal surface of the EV, and the adjuvant is in the lumen of the EV. In some aspects, an EV, e.g., exosome, comprises (i) an antigen and (ii) an adjuvant, wherein the antigen is linked directly to the luminal surface of the EV, and the adjuvant is linked to a Scaffold Y on the luminal surface of the EV. In some aspects, an EV, e.g., exosome, comprises (i) an antigen and (ii) an adjuvant, wherein the antigen is linked directly to the luminal surface of the EV, and the adjuvant is linked to a Scaffold X on the luminal surface of the EV. In some aspects, an EV, e.g., exosome, comprises (i) an antigen and (ii) an adjuvant, wherein the antigen is linked directly to the luminal surface of the EV, and the adjuvant is linked directly to the exterior of the EV. In some aspects, an EV, e.g., exosome, comprises (i) an antigen and (ii) an adjuvant, wherein the antigen is linked directly to the luminal surface of the EV, and the adjuvant is linked to a Scaffold X on the exterior of the EV. In some aspects, an EV, e.g., exosome, comprises (i) an antigen and (ii) an adjuvant, wherein the antigen is linked to a Scaffold Y on the luminal surface of the EV, and the adjuvant is linked directly to the luminal surface of the EV. In some aspects, an EV, e.g., exosome, comprises (i) an antigen and (ii) an adjuvant, wherein the antigen is linked to a Scaffold Y on the luminal surface of the EV, and the adjuvant is linked directly to the exterior of the EV. In some aspects, an EV, e.g., exosome, comprises (i) an antigen and (ii) an adjuvant, wherein the antigen is linked to a Scaffold X on the luminal surface of the EV, and the adjuvant is linked directly to the luminal surface of the EV. In some aspects, an EV, e.g., exosome, comprises (i) an antigen and (ii) an adjuvant, wherein the antigen is linked to a Scaffold X on the luminal surface of the EV, and the adjuvant is linked directly to the exterior of the EV. In some aspects, an EV, e.g., exosome, comprises (i) an antigen and (ii) an adjuvant, wherein the antigen is in the lumen of the EV, and the adjuvant is linked directly to the luminal surface of the EV. In some aspects, an EV, e.g., exosome, comprises (i) an antigen and (ii) an adjuvant, wherein the antigen is in the lumen of the EV, and the adjuvant is linked directly to the exterior of the EV.

In some aspects, an adjuvant and/or antigen can be modified to increase encapsulation (i.e., loading) in an EV, e.g., exosome. This modification can include the addition of a lipid binding tag by treating the agonist (i.e., adjuvant and/or antigen) with a chemical or enzyme, or by physically or chemically altering the polarity or charge of the adjuvant and/or antigen. The adjuvant and/or antigen can be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications can be practiced. The modification can increase encapsulation (i.e., loading) of the adjuvant and/or antigen in the EV, e.g., exosome by between about 2-fold and about 10,000-fold, between about 10-fold and 1,000-fold, or between about 100-fold and about 500-fold compared to encapsulation (i.e., loading) of an unmodified agonist (i.e., adjuvant and/or antigen). The modification can increase encapsulation (i.e., loading) of the adjuvant and/or antigen in the EV, e.g., exosome by at least about 2-fold, about 5-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold, about 700-fold, about 800-fold, about 900-fold, about 1,000-fold, about 2,000-fold, about 3,000-fold, about 4,000-fold, about 5,000-fold, about 6,000-fold, about 7,000-fold, about 8,000-fold, about 9,000-fold, or about 10,000-fold compared to encapsulation (i.e., loading) of an unmodified adjuvant and/or antigen.

In some aspects, an adjuvant and/or antigen can be modified to allow for better expression on the surface of the EV (e.g., exterior and/or luminal surface of the EV, e.g., linked to a scaffold moiety disclosed herein, e.g., Scaffold X and/or Scaffold Y). Any of the modifications described above can be used. The modification can increase expression of the agonist in the EV, e.g., on the surface and/or luminal surface of the exosome, by about between 2-fold and 10,000-fold, about between 10-fold and 1,000-fold, or about between 100-fold and 500-fold compared to corresponding expression of an unmodified agonist. The modification can increase expression of the agonist on the exterior surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist. The modification can increase expression of the agonist on the luminal surface of the EV, e.g., exosome, by at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, or at least about 10,000-fold compared to expression of an unmodified agonist.

In some aspects, the EV, e.g., exosome, is further modified to display an additional protein (or fragment thereof) that can help direct EV uptake (e.g., targeting moiety), activate, or block cellular pathways to enhance the combinatorial effects associated with the EV (e.g., effect of a payload loaded into an exosome, e.g., STING agonist). In certain aspects, the EV, e.g., exosome, disclosed herein further comprises a targeting moiety that can modify the distribution of the EVs in vivo or in vitro. In some aspects, the targeting moiety can be a biological molecule, such as a protein, a peptide, a lipid, or a synthetic molecule.

In some aspects, a targeting moiety of the present disclosure specifically binds to a marker for a dendritic cell. In certain aspects, the marker is expressed only on dendritic cells. In some aspects, dendritic cells comprise a progenitor (Pre) dendritic cells, inflammatory mono dendritic cells, plasmacytoid dendritic cell (pDC), a myeloid/conventional dendritic cell 1 (cDC1), a myeloid/conventional dendritic cell 2 (cDC2), inflammatory monocyte derived dendritic cells, Langerhans cells, dermal dendritic cells, lysozyme-expressing dendritic cells (LysoDCs), Kupffer cells, non-classical monocytes, or any combination thereof. Markers that are expressed on these dendritic cells are known in the art. See, e.g., Collin et al., *Immunology* 154(1):3-20 (2018). In some aspects, the targeting moiety is a protein, wherein the protein is an antibody or a fragment thereof that can specifically bind to a marker selected from DEC205, CLEC9A, CLEC6, DCIR, DC-SIGN, LOX-1, MARCO, Clec12a, Clec10a, DC-asialoglycoprotein receptor (DC-ASGPR), DC immunoreceptor 2 (DCIR2), Dectin-1, macrophage mannose receptor (MMR), BDCA-2 (CD303, Clec4c), Dectin-2, Bst-2 (CD317), Langerin, CD206, CD11b, CD11c, CD123, CD304, XCR1, AXL, Siglec 6, CD209, SIRPA, CX3CR1, GPR182, CD14, CD16, CD32, CD34, CD38, CD10, or any combination thereof. In some aspects, a marker useful for the present disclosure comprises a C-type lectin like domain. In certain aspects, a marker is Clec9a and the dendritic cell is cDC1.

In some aspects, a targeting moiety disclosed herein can bind to both human and mouse Clec9a, including any variants thereof. In some aspects, a targeting moiety of the present disclosure can bind to Clec9a from other species, including but not limited to chimpanzee, rhesus monkey, dog, cow, horse, or rat. Sequences for such Clec9a protein are known in the art. See, e.g., U.S. Pat. No. 8,426,565 B2, which is herein incorporated by reference in its entirety.

In some aspects, a targeting moiety of the present disclosure specifically binds to a marker for a T cell. In certain aspects, the T cell is a CD4+ T cell. In some aspects, the T cell is a CD8+ T cell.

In some aspects, a targeting moiety disclosed herein binds to human CD3 protein or a fragment thereof. Sequences for human CD3 protein are known in the art.

In some aspects, a targeting moiety disclosed herein can bind to both human and mouse CD3, including any variants thereof. In some aspects, a targeting moiety of the present disclosure can bind to CD3 from other species, including but not limited to chimpanzee, rhesus monkey, dog, cow, horse, or rat. Sequences for such CD3 protein are also known in the art.

In some aspects, a targeting moiety disclosed herein can allow for greater uptake of an EV (e.g., exosome) by a cell expressing a marker specific for the targeting moiety (e.g., CD3: CD4+ T cell and/or CD8+ T cell; Clec9a: dendritic cells). In some aspects, the uptake of an EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV without the targeting moiety or a non-EV delivery vehicle). In some aspects, a reference comprises an EV (e.g., exosome) that does not express a targeting moiety disclosed herein.

In some aspects, the increased uptake of an EV (e.g., exosome) disclosed herein can allow for greater immune response. Accordingly, in certain aspects, an EV (e.g., exosome) expressing a targeting moiety disclosed herein can increase an immune response (e.g., against a tumor antigen loaded onto the exosome) by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV without the targeting moiety or a non-EV delivery vehicle). In some aspects, a reference comprises an EV (e.g., exosome) that does not express a targeting moiety disclosed herein. In certain aspects, an immune response is mediated by T cells (e.g., CD8+ T cells or CD4+ T cells) and/or B cells.

As described supra, a targeting moiety disclosed herein can comprise a peptide, an antibody or an antigen binding fragment thereof, a chemical compound, or any combination thereof.

In some aspects, the targeting moiety is a peptide that can specifically bind to Clec9a. See, e.g., Yan et al., *Oncotarget* 7(26): 40437-40450 (2016). For example, in certain aspects, the peptide comprises a soluble fragment of Clec9a. A non-limiting example of such a peptide is described in U.S. Pat. No. 9,988,431 B2, which is herein incorporated by reference in its entirety. In certain aspects, the peptide comprises a ligand (natural or synthetic) of Clec9a, such as those described in Ahrens et al., *Immunity* 36(4): 635-45 (2012); and Zhang et al., *Immunity* 36(4): 646-57 (2012). A non-limiting example of a peptide comprising a Clec9a ligand is described in International Publ. No. WO 2013/053008 A2, which is herein incorporated by reference in its entirety.

In some aspects, the targeting moiety is a peptide that can specifically bind to CD3. For example, in certain aspects, the peptide comprises a soluble fragment of CD3. In certain aspects, the peptide comprises a ligand (natural or synthetic) of CD3.

In some aspects, the targeting moiety is an antibody or an antigen binding fragment thereof. In certain aspects, a targeting moiety is a single-chain Fv antibody fragment. In certain aspects, a targeting moiety is a single-chain F(ab) antibody fragment. In certain aspects, a targeting moiety is a nanobody. In certain aspects, a targeting moiety is a monobody.

In some aspects, an EV (e.g., exosome) disclosed herein comprises one or more (e.g., 2, 3, 4, 5, or more) targeting moieties. In certain aspects, the one or more targeting moieties are expressed in combination with other exogenous biologically active molecules disclosed herein (e.g., therapeutic molecule, adjuvant, or immune modulator). In some aspects, the one or more targeting moieties can be expressed on the exterior surface of the EV, e.g., exosome. Accordingly, in certain aspects, the one or more targeting moieties are linked to a scaffold moiety (e.g., Scaffold X) on the exterior surface of the EV, e.g., exosome. When the one or more targeting moieties are expressed in combination with other exogenous biologically active molecules (e.g., therapeutic molecule, adjuvant, or immune modulator), the other exogenous biologically active molecules can be expressed on the surface (e.g., exterior surface or luminal surface) or in the lumen of the EV, e.g., exosome.

The producer cell can be modified to comprise an additional exogenous sequence encoding for the additional protein or fragment thereof. Alternatively, the additional protein or fragment thereof can be covalently linked or conjugated to the EV, e.g., exosome, via any appropriate linking chemistry known in the art. Non-limiting examples of appropriate linking chemistry include amine-reactive groups, carboxyl-reactive groups, sulfhydryl-reactive groups, aldehyde-reactive groups, photoreactive groups, ClickIT chemistry, biotin-streptavidin or other avidin conjugation, or any combination thereof.

II.C Immune Modulator

In some aspects, an EV, e.g., exosome, of the present disclosure can comprise an immune modulator (e.g., along with an antigen and/or other payloads disclosed herein). In some aspects, an EV (e.g., exosome) disclosed herein comprises multiple immune modulators. In certain aspects, each of the multiple immune modulators is different. In some aspects, an EV (e.g., exosome) disclosed herein comprises at least 2, 3, 4, 5, 6, 7, 8, 9, 10 or more different immune modulators.

In certain aspects, an EV (e.g., exosome) comprises the one or more immune modulators in combination with one or more additional payloads (e.g., antigen and/or adjuvants). In some aspects, an EV (e.g., exosome) can comprise one or more additional moieties (e.g., targeting moieties). For instance, in certain aspects, an EV (e.g., exosome) disclosed described herein can comprise (i) one or more immune modulators, (ii) one or more additional payloads (e.g., antigen and/or adjuvant), and (iii) one or more targeting moieties.

In some aspects, an immune modulator can be expressed on the surface (e.g., exterior surface or luminal surface) or in the lumen of the EV, e.g., exosome. Accordingly, in certain aspects, the immune modulator is linked to a scaffold moiety (e.g., Scaffold X) on the exterior surface of the EV, e.g., exosome or on the luminal surface of the EV, e.g., exosome. In other aspects, the immune modulator is linked to a scaffold moiety (e.g., Scaffold Y) on the luminal surface of the EV, e.g., exosome. In further aspects, the immune modulator is in the lumen of the exosome (i.e., not linked to either Scaffold X or Scaffold Y). In some aspects, an immune modulator can be directly linked (i.e., without the use of a scaffold moiety) to the exterior surface and/or luminal surface of an EV (e.g., exosome).

Non-limiting examples of such aspects, include EVs, e.g., exosomes, comprising (i) an antigen and (ii) an immune modulator, wherein:
(a) the antigen is linked to a first Scaffold Y on the luminal surface of the EV, e.g., exosome, and the immune modulator is linked to a second Scaffold Y on the luminal surface of the EV, e.g., exosome;
(b) the antigen is linked to a Scaffold Y on the luminal surface of the EV, e.g., exosome, and the immune modulator is in the lumen of the EV, e.g., exosome, not linked to any scaffold moiety;
(c) the antigen is in the lumen of the EV, e.g., exosome, not linked to any scaffold moiety, and the immune modulator is linked to a Scaffold Y on the luminal surface of the EV, e.g., exosome;
(d) the antigen is linked to a Scaffold Y on the luminal surface of the EV, e.g., exosome, and the immune modulator is linked to a Scaffold X on the exterior surface the EV, e.g., exosome;
(e) the antigen is linked to a Scaffold X on the luminal surface of the EV, e.g., exosome, and the immune modulator is linked to a Scaffold Y on the luminal surface of the EV, e.g., exosome;
(f) the antigen is linked to a Scaffold X on the luminal surface of the EV, e.g., exosome, and the immune modulator is linked to a Scaffold Y on the luminal surface of the EV, e.g., exosome; or
(g) the antigen is linked to a Scaffold X on the exterior surface of the EV, e.g., exosome, and the immune modulator is linked to a Scaffold Y on the luminal surface of the EV, e.g., exosome.

Non-limiting examples of specific aspects, include EVs, e.g., exosomes, comprising (i) an antigen and (ii) an immune modulator, wherein:
(a) the antigen is linked to a first Scaffold Y on the luminal surface of the EV, e.g., exosome, and the immune modulator is linked to a second Scaffold Y on the luminal surface of the EV, e.g., exosome;
(b) the antigen is linked to a Scaffold Y on the luminal surface of the EV, e.g., exosome, and the immune modulator is in the lumen of the EV, e.g., exosome, not linked to any scaffold moiety;
(c) the antigen is in the lumen of the EV, e.g., exosome, not linked to any scaffold moiety, and the immune modulator is linked to a Scaffold Y on the luminal surface of the EV, e.g., exosome;
(d) the antigen is linked to a Scaffold Y on the luminal surface of the EV, e.g., exosome, and the immune modulator is linked to a Scaffold X on the exterior surface of the EV, e.g., exosome;
(e) the antigen is in the lumen of the EV, e.g., exosome, not linked to any scaffold moiety, and the immune modulator is linked to a Scaffold X on the exterior surface of the EV, e.g., exosome;
(f) the antigen is linked to a Scaffold Y on the luminal surface of the EV, e.g., exosome, and the immune modulator is linked to a Scaffold X on the luminal surface of the EV, e.g., exosome;
(g) the antigen is in the lumen of the EV, e.g., exosome, not linked to any scaffold moiety, and the immune modulator is linked to a Scaffold X on the luminal surface of the EV, e.g., exosome;
(h) the antigen is linked to a Scaffold X on the luminal surface of the EV, e.g., exosome, and the immune modulator is linked to the Scaffold X on the exterior surface of the EV, e.g., exosome;
(i) the antigen is linked to a first Scaffold X on the exterior surface of the EV, e.g., exosome, and the immune modulator is linked to a second Scaffold X on the exterior surface of the EV, e.g., exosome;
(j) the antigen is linked to a Scaffold X on the exterior surface of the EV, e.g., exosome, and the immune modulator is linked to a Scaffold Y on the luminal surface of the EV, e.g., exosome;
(k) the antigen is linked to a Scaffold X on the exterior surface of the EV, e.g., exosome, and the immune modulator is in the lumen of the EV, e.g., exosome, not linked to any scaffold moiety;
(l) the antigen is linked to a Scaffold X on the exterior surface of the EV, e.g., exosome, and the immune modulator is linked to the Scaffold X on the luminal surface of the EV, e.g., exosome;
(m) the antigen is linked to a first Scaffold X on the luminal surface of the EV, e.g., exosome, and the immune modulator is linked to a second Scaffold X on the luminal surface of the EV, e.g., exosome;

(n) the antigen is linked to a Scaffold X on the luminal surface of the EV, e.g., exosome, and the immune modulator is linked to a Scaffold Y on the luminal surface of the EV, e.g., exosome;
(o) the antigen is linked to a Scaffold X on the luminal surface of the EV, e.g., exosome, and the immune modulator is in the lumen of the EV, e.g., exosome, not linked to any scaffold moiety;
(p) the antigen is linked to a first Scaffold X on the exterior surface of the EV, e.g., exosome, and the immune modulator is linked to a second Scaffold X on the luminal surface of the EV, e.g., exosome;
(q) the antigen is linked to a first Scaffold X on the luminal surface of the EV, e.g., exosome, and the immune modulator is linked to a second Scaffold X on the exterior surface of the EV, e.g., exosome;
(r) the antigen is in the lumen of the EV, e.g., exosome, not linked to any scaffold moiety, and the immune modulator is in the lumen of the EV, e.g., exosome, not linked to any scaffold moiety;
(s) the antigen is linked directly to the luminal surface of the EV, e.g., exosome, and the immune modulator is linked directly to the luminal surface of the EV, e.g., exosome;
(t) the antigen is linked directly to the luminal surface of the EV, e.g., exosome, and the immune modulator is in the lumen of the EV, e.g., exosome;
(u) the antigen is linked directly to the luminal surface of the EV, e.g., exosome, and the immune modulator is linked to a Scaffold Y on the luminal surface of the EV, e.g., exosome;
(v) the antigen is linked directly to the luminal surface of the EV, e.g., exosome, and the immune modulator is linked to a Scaffold X on the luminal surface of the EV, e.g., exosome;
(w) the antigen is linked directly to the luminal surface of the EV, e.g., exosome, and the immune modulator is linked directly to the exterior of the EV, e.g., exosome;
(x) the antigen is linked directly to the luminal surface of the EV, e.g., exosome, and the immune modulator is linked to a Scaffold X on the exterior of the EV, e.g., exosome;
(y) the antigen is linked to a Scaffold Y on the luminal surface of the EV, e.g., exosome, and the immune modulator is linked directly to the luminal surface of the EV, e.g., exosome;
(z) the antigen is linked to a Scaffold Y on the luminal surface of the EV, e.g., exosome, and the immune modulator is linked directly to the exterior of the EV, e.g., exosome;
(aa) the antigen is linked to a Scaffold X on the luminal surface of the EV, e.g., exosome, and the immune modulator is linked directly to the luminal surface of the EV, e.g., exosome;
(bb) the antigen is linked to a Scaffold X on the luminal surface of the EV, e.g., exosome, and the immune modulator is linked directly to the exterior of the EV, e.g., exosome;
(cc) the antigen is in the lumen of the EV, e.g., exosome, and the immune modulator is linked directly to the luminal surface of the EV, e.g., exosome; or
(dd) the antigen is in the lumen of the EV, e.g., exosome, and the immune modulator is linked directly to the exterior of the EV, e.g., exosome.

In some aspects, an EV, e.g., exosome, of the present disclosure comprises (i) an antigen and (ii) an immune modulator, wherein the antigen is linked to a first Scaffold Y on the luminal surface of the EV, e.g., exosome, and the immune modulator is linked to a second Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is linked to a Scaffold X on the exterior surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold X on the exterior surface of the EV, e.g., exosome. In some aspects, an EV, e.g., exosome, of the present disclosure comprises (i) an antigen and (ii) an immune modulator, wherein the antigen is linked to a Scaffold Y on the luminal surface of the EV, e.g., exosome, and the immune modulator is linked to a Scaffold X on the luminal surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is linked to a Scaffold X on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is linked to the Scaffold X on the exterior surface of the EV, e.g., exosome. In some aspects, an EV, e.g., exosome, of the present disclosure comprises (i) an antigen and (ii) an immune modulator, wherein the antigen is linked to a first Scaffold X on the exterior surface of the EV, e.g., exosome, and the immune modulator is linked to a second Scaffold X on the exterior surface of the EV, e.g., exosome. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is linked to a Scaffold X on the exterior surface of the EV, e.g., exosome, and the immune modulator is linked to the Scaffold X on the luminal surface of the EV, e.g., exosome. In some aspects, an EV, e.g., exosome, of the present disclosure comprises (i) an antigen and (ii) an immune modulator, wherein the antigen is linked to a first Scaffold X on the luminal surface of the EV, e.g., exosome, and the immune modulator is linked to a second Scaffold X on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is linked to a Scaffold Y on the luminal surface of the EV, e.g., exosome. In some aspects, an EV, e.g., exosome, of the present disclosure comprises (i) an antigen and (ii) an immune modulator, wherein the antigen is linked to a Scaffold X on the luminal surface of the EV, e.g., exosome, and the immune modulator is in the lumen of the EV, e.g., exosome, not linked to any scaffold moiety. In some aspects, an EV, e.g., exosome, of the present disclosure comprises (i) an antigen and (ii) an immune modulator, wherein the antigen is linked to a first Scaffold X on the exterior surface of the EV, e.g., exosome, and the immune modulator is linked to a second Scaffold X on the luminal surface of the EV, e.g., exosome. In some aspects, an EV, e.g., exosome, of the present disclosure comprises (i) an antigen and (ii) an immune modulator, wherein the antigen is linked to a first Scaffold X on the luminal surface of the EV, e.g., exosome, and the immune modulator is linked to a second Scaffold X on the exterior surface of the EV, e.g., exosome. In some aspects, an EV, e.g., exosome, of the present disclosure comprises (i) an antigen and (ii) an immune modulator, wherein the antigen is in the lumen of the EV, e.g., exosome, not linked to any scaffold moiety, and the immune modulator is in the lumen of the EV, e.g., exosome, not linked to any scaffold moiety. In some aspects, an EV, e.g., exosome, comprises (i) an antigen and (ii) an immune modulator, wherein the antigen is linked directly to the luminal surface of the EV, and the immune modulator is linked directly to the luminal surface of the EV. In some aspects, an EV, e.g., exosome, comprises (i) an antigen and (ii) an immune modulator, wherein the antigen is linked directly to the luminal surface of the EV, and the immune modulator is in the lumen of the EV. In some aspects, an EV, e.g., exosome, comprises (i) an antigen and (ii) an immune modulator, wherein the antigen is linked directly to the luminal surface of the EV, and the immune modulator is linked to a Scaffold Y on the luminal surface of the EV. In some aspects, an EV, e.g., exosome, comprises (i) an antigen and (ii) an immune modulator, wherein the antigen is linked directly to the luminal surface of the EV, and the immune modulator is linked to a Scaffold X on the luminal surface of the EV. In some aspects, an EV, e.g., exosome, comprises (i) an antigen and (ii) an immune modulator, wherein the antigen is linked directly to the luminal surface of the EV, and the immune modulator is linked directly to the exterior of the EV. In some aspects, an EV, e.g., exosome, comprises (i) an antigen and (ii) an immune modulator, wherein the antigen is linked directly to the luminal surface of the EV, and the immune modulator is linked to a Scaffold X on the exterior of the EV. In some aspects, an EV, e.g., exosome, comprises (i) an antigen and (ii) an immune modulator, wherein the antigen is linked to a Scaffold Y on the luminal surface of the EV, and the immune modulator is linked directly to the luminal surface of the EV. In some aspects, an EV, e.g., exosome, comprises (i) an antigen and (ii) an immune modulator, wherein the antigen is linked to a Scaffold Y on the luminal surface of the EV, and the immune modulator is linked directly to the exterior of the EV. In some aspects, an EV, e.g., exosome, comprises (i) an antigen and (ii) an immune modulator, wherein the antigen is linked to a Scaffold X on the luminal surface of the EV, and the immune modulator is linked directly to the luminal surface of the EV. In some aspects, an EV, e.g., exosome, comprises (i) an antigen and (ii) an immune modulator, wherein the antigen is linked to a Scaffold X on the luminal surface of the EV, and the immune modulator is linked directly to the exterior of the EV. In some aspects, an EV, e.g., exosome, comprises (i) an antigen and (ii) an immune modulator, wherein antigen is in the lumen of the EV, and the immune modulator is linked directly to the luminal surface of the EV. In some aspects, an EV, e.g., exosome, comprises (i) an antigen and (ii) an immune modulator, wherein antigen is in the lumen of the EV, and the immune modulator is linked directly to the exterior of the EV.

Non-limiting examples of specific aspects, include EVs, e.g., exosomes, comprising (i) an antigen, (ii) an adjuvant, and (iii) an immune modulator, wherein:

(a) the antigen is linked to a first Scaffold Y on the luminal surface of the EV, e.g., exosome, the adjuvant is linked to a second Scaffold Y on the luminal surface of the EV, e.g., exosome, and the immune modulator is (a1) in the lumen of the EV, e.g., exosome, not linked to any scaffold moiety, or (a2) linked to a third scaffold moiety, e.g., a Scaffold X on the exterior surface of the exosome or in the lumen of the exosome or a Scaffold Y on the luminal surface of the EV, e.g., exosome;

(b) the antigen is linked to a Scaffold Y on the luminal surface of the EV, e.g., exosome, the adjuvant is in the lumen of the EV, e.g., exosome, not linked to any scaffold moiety, and the immune modulator is (b1) in the lumen of the EV, e.g., exosome, not linked to any scaffold moiety, or (b2) linked to a scaffold moiety, e.g., a Scaffold X on the exterior surface of the exosome or on the luminal surface of the exosome or a Scaffold Y on the luminal surface of the EV, e.g., exosome;

(c) the antigen is in the lumen of the EV, e.g., exosome, not linked to any scaffold moiety, the adjuvant is linked to a Scaffold Y on the luminal surface of the EV, e.g., exosome, and the immune modulator is (c1) in the lumen of the EV, e.g., exosome, not linked to any scaffold moiety, or (c2) linked to a scaffold moiety, e.g., a Scaffold X on the exterior surface of the exosome or on the luminal surface of the exosome or a Scaffold Y on the luminal surface of the EV, e.g., exosome;

(d) the antigen is linked to a Scaffold Y on the luminal surface of the EV, e.g., exosome, the adjuvant is linked to a Scaffold X on the exterior surface of the EV, e.g., exosome, and the immune modulator is (di) in the lumen of the EV, e.g., exosome, not linked to any scaffold moiety, or (d2) linked to a third scaffold moiety, e.g., a Scaffold X on the exterior surface of the exosome or on the luminal surface of the exosome or a Scaffold Y on the luminal surface of the EV, e.g., exosome;

(e) the antigen is in the lumen of the EV, e.g., exosome, not linked to any scaffold moiety, the adjuvant is linked to a Scaffold X on the exterior surface of the EV, e.g., exosome, and the immune modulator is (el) in the lumen of the EV, e.g., exosome, not linked to any scaffold moiety, or (e2) linked to a scaffold moiety, e.g., a Scaffold X on the surface of the exosome or on the luminal surface of the exosome or a Scaffold Y on the luminal surface of the EV, e.g., exosome;

(f) the antigen is linked to a Scaffold Y on the luminal surface of the EV, e.g., exosome, the adjuvant is linked to a Scaffold X on the luminal surface of the EV, e.g., exosome, and the immune modulator is (f1) in the lumen of the EV, e.g., exosome, not linked to any scaffold moiety, or (f2) linked to a third scaffold moiety, e.g., a Scaffold X on the exterior surface of the exosome or on the luminal surface of the exosome or a Scaffold Y on the luminal surface of the EV, e.g., exosome;

(g) the antigen is in the lumen of the EV, e.g., exosome, not linked to any scaffold moiety, the adjuvant is linked to a Scaffold X on the luminal surface of the EV, e.g., exosome, and the immune modulator is (g1) in the lumen of the EV, e.g., exosome, not linked to any scaffold moiety, or (g2) linked to a scaffold moiety, e.g., a Scaffold X on the exterior surface of the exosome or on the luminal surface of the exosome or a Scaffold Y on the luminal surface of the EV, e.g., exosome;

(h) the antigen is linked to a Scaffold X on the luminal surface of the EV, e.g., exosome, the adjuvant is linked to the Scaffold X on the exterior surface of the EV, e.g., exosome, and the immune modulator is (h1) in the lumen of the EV, e.g., exosome, not linked to any scaffold moiety, or (h2) linked to a scaffold moiety, e.g., a Scaffold X on the exterior surface of the exosome or on the luminal surface of the exosome or a Scaffold Y on the luminal surface of the EV, e.g., exosome;

(i) the antigen is linked to a first Scaffold X on the exterior surface of the EV, e.g., exosome, the adjuvant is linked to a second Scaffold X on the exterior surface of the EV, e.g., exosome, and the immune modulator is (i1) in the lumen of the EV, e.g., exosome, not linked to any scaffold moiety, or (i2) linked to a third scaffold moiety, e.g., a Scaffold X on the exterior surface of the exosome or on the luminal surface of the exosome or a Scaffold Y on the luminal surface of the EV, e.g., exosome;

(j) the antigen is linked to a Scaffold X on the exterior surface of the EV, e.g., exosome, the adjuvant is linked to a Scaffold Y on the luminal surface of the EV, e.g., exosome, and the immune modulator is (j1) in the lumen of the EV, e.g., exosome, not linked to any scaffold moiety, or (j2) linked to a third scaffold moiety, e.g., a Scaffold X on the exterior surface of the exosome or on the luminal surface of the exosome or a Scaffold Y on the luminal surface of the EV, e.g., exosome;

(k) the antigen is linked to a Scaffold X on the exterior surface of the EV, e.g., exosome, the adjuvant is in the lumen of the EV, e.g., exosome, not linked to any scaffold moiety, and the immune modulator is (k1) in the lumen of the EV, e.g., exosome, not linked to any scaffold moiety, or (k2) linked to a scaffold moiety, e.g., a Scaffold X on the exterior surface of the exosome or on the luminal surface of the exosome or a Scaffold Y on the luminal surface of the EV, e.g., exosome;

(l) the antigen is linked to a Scaffold X on the exterior surface of the EV, e.g., exosome, the adjuvant is linked to the Scaffold X on the luminal surface of the EV, e.g., exosome, and the immune modulator is (l1) in the lumen of the EV, e.g., exosome, not linked to any scaffold moiety, or (l2) linked to a scaffold moiety, e.g., a Scaffold X on the exterior surface of the exosome or on the luminal surface of the exosome or a Scaffold Y on the luminal surface of the EV, e.g., exosome;

(m) the antigen is linked to a first Scaffold X on the luminal surface of the EV, e.g., exosome, the adjuvant is linked to a second Scaffold on the luminal surface of the EV, e.g., exosome, and the immune modulator is (m1) in the lumen of the EV, e.g., exosome, not linked to any scaffold moiety, or (m2) linked to a third scaffold moiety, e.g., a Scaffold X on the exterior surface of the exosome or on the luminal surface of the exosome or a Scaffold Y on the luminal surface of the EV, e.g., exosome;

(n) the antigen is linked to a Scaffold X on the luminal surface of the EV, e.g., exosome, the adjuvant is linked to a Scaffold Y on the luminal surface of the EV, e.g., exosome, and the immune modulator is (n1) in the lumen of the EV, e.g., exosome, not linked to any scaffold moiety, or (n2) linked to a third scaffold moiety, e.g., a Scaffold X on the exterior surface of the exosome or on the luminal surface of the exosome or a Scaffold Y on the luminal surface of the EV, e.g., exosome;

(o) the antigen is linked to a Scaffold X on the luminal surface of the EV, e.g., exosome, the adjuvant is in the lumen of the EV, e.g., exosome, not linked to any scaffold moiety, and the immune modulator is (o1) in the lumen of the EV, e.g., exosome, not linked to any scaffold moiety, or (o2) linked to a scaffold moiety, e.g., a Scaffold X on the exterior surface of the exosome or on the luminal surface of the exosome or a Scaffold Y on the luminal surface of the EV, e.g., exosome;

(p) the antigen is linked to a first Scaffold X on the exterior surface of the EV, e.g., exosome, the adjuvant is linked to a second Scaffold X on the luminal surface of the EV, e.g., exosome, and the immune modulator is (p1) in the lumen of the EV, e.g., exosome, not linked to any scaffold moiety, or (p2) linked to a third scaffold moiety, e.g., a Scaffold X on the surface of the exosome or in the lumen of the exosome or a Scaffold Y on the luminal surface of the EV, e.g., exosome;

(q) the antigen is linked to a first Scaffold X on the luminal surface of the EV, e.g., exosome, the adjuvant is linked to a second Scaffold X on the exterior surface of the EV, e.g., exosome, and the immune modulator is (q1) in the lumen of the EV, e.g., exosome, not linked to any scaffold moiety, or (q2) linked to a third scaffold moiety, e.g., a Scaffold X on the exterior surface of the exosome or on the luminal surface of the exosome or a Scaffold Y on the luminal surface of the EV, e.g., exosome; or (r) the antigen is in the lumen of the EV, e.g., exosome, not linked to any scaffold moiety, the adjuvant is in the lumen of the EV, e.g., exosome, not linked to any scaffold moiety, and the immune modulator is (r1) in the lumen of the exosome or (r2) linked to a scaffold moiety, e.g., a Scaffold X on the exterior surface of the exosome or on the luminal surface of the exosome or a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a second Scaffold Y on the luminal surface of the EV, e.g., exosome, and the immune modulator is linked to a third Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is in the lumen of the EV, e.g., exosome, not linked to any scaffold moiety, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is in the lumen of the EV, e.g., exosome, not linked to any scaffold moiety, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold Y on the luminal surface of the EV, e.g., exosome, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a Scaffold X on the exterior surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold Y on the luminal surface of the EV, e.g., exosome, the adjuvant is linked to a first Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold Y on the luminal surface of the EV, e.g., exosome, the adjuvant is linked to a Scaffold X on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a first Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is linked to a Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to the Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a Scaffold Y on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a Scaffold Y on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is in the lumen of the EV, e.g., exosome, not linked to any scaffold moiety, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is in the lumen of the EV, e.g., exosome, not linked to any scaffold moiety, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is in the lumen of the EV, e.g., exosome, not linked to any scaffold moiety, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to the Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to the Scaffold X on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to the Scaffold X on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the exterior surface of the EV, e.g., exosome, the adjuvant is linked to the Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to a Scaffold Y on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a Scaffold Y on the luminal surface of the EV, e.g., exosome, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a Scaffold Y on the luminal surface of the EV, e.g., exosome, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is linked to a first Scaffold Y on the luminal surface of the EV, e.g., exosome, and the immune modulator is linked to a second Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is in the lumen of the EV, e.g., exosome, not linked to any scaffold moiety, and the immune modulator is linked to a second Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is in the lumen of the EV, e.g., exosome, not linked to any scaffold moiety, and the immune modulator is linked to a second Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a Scaffold X on the luminal surface of the EV, e.g., exosome, the adjuvant is in the lumen of the EV, e.g., exosome, not linked to any scaffold moiety, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the exterior surface of the EV, e.g., exosome, the adjuvant is linked to a second Scaffold X on the luminal surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a third Scaffold X on the exterior surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a third Scaffold X on the luminal surface of the EV, e.g., exosome. In some aspects, an exosome of the present disclosure comprises: (i) an antigen, (ii) an adjuvant, and (iii) an immune modulator, wherein the antigen is linked to a first Scaffold X on the luminal surface of the EV, e.g., exosome, the adjuvant is linked to a second Scaffold X on the exterior surface of the EV, e.g., exosome, and the immune modulator is linked to a Scaffold Y on the luminal surface of the EV, e.g., exosome.

In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is in the lumen of the EV, e.g., exosome, not linked to any scaffold moiety. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold X on the exterior surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold X on the luminal surface of the EV, e.g., exosome. In some aspects, an exosome of the present disclosure comprises: (i) an antigen, (ii) an adjuvant, and (iii) an immune modulator, wherein the antigen is in the lumen of the EV, e.g., exosome, not linked to any scaffold moiety, the adjuvant is in the lumen of the EV, e.g., exosome, not linked to any scaffold moiety, and the immune modulator is linked to a Scaffold Y on the luminal surface of the EV, e.g., exosome.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold Y in the lumen of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold X in the lumen of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is linked to a Scaffold X in the exterior surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the luminal surface of the EV, and (a3) the immune modulator is in the lumen of the EV.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the external surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold Y on the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold X on the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked to a Scaffold X on the exterior surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is in the lumen of the EV, and (a3) the immune modulator is linked directly to the luminal surface of the EV.

In some aspects, an EV (e.g., exosome) comprises: (i) an antigen, (ii) an adjuvant, and (iii) an immune modulator, wherein (a1) the antigen is linked directly to the external surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold Y on the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold X on the luminal surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked to a Scaffold X on the exterior surface of the EV, (a2) the adjuvant is linked directly to the luminal surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is in the lumen of the EV, (a2) the adjuvant is linked directly to the luminal surface of the EV, and (a3) the immune modulator is linked directly to the luminal surface of the EV.

In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked directly to the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold Y on the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold X on the luminal surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is linked to a Scaffold X on the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the exterior surface of the EV, and (a3) the immune modulator is in the lumen of the EV.

In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked directly to the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold Y on the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold X on the luminal surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is linked to a Scaffold X on the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked directly to the exterior surface of the EV, (a2) the adjuvant is in the lumen of the EV, and (a3) the immune modulator is linked directly to the exterior surface of the EV.

In some aspects, an EV (e.g., exosome) comprises: (i) an antigen, (ii) an adjuvant, and (iii) an immune modulator, wherein (a1) the antigen is linked directly to the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold Y on the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold X on the luminal surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is linked to a Scaffold X on the exterior surface of the EV, (a2) the adjuvant is linked directly to the exterior surface of the EV, and (a3) the immune modulator is linked directly to the exterior surface of the EV. In some aspects, an EV (e.g., exosome) comprises: (i) an antigen, (ii) an adjuvant, and (iii) an immune modulator, wherein (a1) the antigen is in the lumen of the EV, (a2) the adjuvant is linked directly to the exterior surface of the EV, and (a3) the immune modulator is linked directly to the exterior surface of the EV.

In some aspects, an immune modulator that can be used with the EVs, e.g., exosomes, described herein has anti-tumor activity. In other aspects, an immune modulator useful for the present disclosure has tolerogenic activity. In some aspects, an immune modulator can regulate innate immune response. In certain aspects, an immune modulator regulates innate immune response by targeting natural killer cells. In some aspects, an immune modulator can regulate adaptive immune response. In some aspects, the immune modulator regulates adaptive immune response by targeting cytotoxic T cells. In further aspects, the immune modulator regulates adaptive immune response by targeting B cells. In certain aspects, an immune modulator disclosed herein can modulate the distribution of an exosome to a cytotoxic T cell or a B cell (i.e., bio-distribution modifying agent).

In some aspects, an immune modulator comprises an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, the immune modulator is an inhibitor of cytotoxic T-lymphocyte-associate protein 4 (CTLA-4). In certain aspects, the CTLA-4 inhibitor is a monoclonal antibody of CTLA-4 ("anti-CTLA-4 antibody"). In certain aspects, the inhibitor is a fragment of a monoclonal antibody of CTLA-4. In certain aspects, the antibody fragment is a scFv, (scFv)₂, Fab, Fab', and F(ab')₂, F(ab1)₂, Fv, dAb, or Fd of a monoclonal antibody of CTLA-4. In certain aspects, the inhibitor is a nanobody, a bispecific antibody, or a multi-specific antibody against CTLA-4. In some aspects, the anti-CTLA-4 antibody is ipilimumab. In other aspects, the anti-CTLA-4 antibody is tremelimumab.

In some aspects, the immune modulator is an inhibitor of programmed cell death protein 1 (PD-1). In some aspects, the immune modulator is an inhibitor of programmed death-ligand 1 (PD-L1). In some aspects, the immune modulator is an inhibitor of programmed death-ligand 2 (PD-L2). In certain aspects, the inhibitor of PD-1, PD-L1, or PD-L2 is a monoclonal antibody of PD-1 ("anti-PD-1 antibody"), PD-L1 ("anti-PD-L1 antibody"), or PD-L2 ("anti-PD-L2 antibody"). In some aspects, the inhibitor is a fragment of an anti-PD-1 antibody, anti-PD-L1 antibody, or anti-PD-L2 antibody. In certain aspects, the antibody fragment is a scFv, (scFv)₂, Fab, Fab', and F(ab')₂, F(ab1)₂, Fv, dAb, or Fd of a monoclonal antibody of PD-1, PD-L1, or PD-L2. In certain aspects, the inhibitor is a nanobody, a bispecific antibody, or a multispecific antibody against PD-1, PD-L1, or PD-L2. In some aspects, the anti-PD-1 antibody is nivolumab. In some aspects, the anti-PD-1 antibody is pembrolizumab. In some aspects, the anti-PD-1 antibody is pidilizumab. In some aspects, the anti-PD-L1 antibody is atezolizumab. In other aspects, the anti-PD-L1 antibody is avelumab.

In some aspects, the immune modulator is an inhibitor of lymphocyte-activated gene 3 (LAG3). In certain aspects, the inhibitor of LAG3 is a monoclonal antibody of LAG3 ("anti-LAG3 antibody"). In some aspects, the inhibitor is a fragment of an anti-LAG3 antibody, e.g., scFv, (scFv)₂, Fab, Fab', and F(ab')₂, F(ab1)₂, Fv, dAb, or Fd. In certain aspects, the inhibitor is a nanobody, a bispecific antibody, or a multispecific antibody against LAG3.

In some aspects, the immune modulator is an inhibitor of T-cell immunoglobulin mucin-containing protein 3 (TIM-3). In some aspects, the immune modulator is an inhibitor of B and T lymphocyte attenuator (BTLA). In some aspects, the immune modulator is an inhibitor of T cell immunoreceptor with Ig and ITIM domains (TIGIT). In some aspects, the immune modulator is an inhibitor of V-domain Ig suppressor of T cell activation (VISTA). In some aspects, the immune modulator is an inhibitor of adenosine A2a receptor (A2aR). In some aspects, the immune modulator is an inhibitor of killer cell immunoglobulin like receptor (KIR). In some aspects, the immune modulator is an inhibitor of indoleamine 2,3-dioxygenase (IDO). In some aspects, the immune modulator is an inhibitor of CD20, CD39, or CD73.

In some aspects, the immune modulator comprises an activator for a positive co-stimulatory molecule or an activator for a binding partner of a positive co-stimulatory molecule. In certain aspects, the positive co-stimulatory molecule comprises a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2).

In some aspects, the immune modulator is an activator of TNF Receptor Superfamily Member 4 (OX40). In certain aspects, the activator of OX40 is an agonistic anti-OX40 antibody. In further aspects, the activator of OX40 is a OX40 ligand (OX40L).

In some aspects, the immune modulator is an activator of CD27. In certain aspects, the activator of CD27 is an agonistic anti-CD27 antibody. In other aspects, the activator of CD27 is a CD27 ligand (CD27L).

In some aspects, the immune modulator is an activator of CD40. In certain aspects, the activator of CD40 is an agonistic anti-CD40 antibody. In some aspects, the activator of CD40 is a CD40 ligand (CD40L). In certain aspects, the CD40L is a monomeric CD40L. In other aspects, the CD40L is a trimeric CD40L.

In some aspects, the immune modulator is an activator of glucocorticoid-induced TNFR-related protein (GITR). In certain aspects, the activator of GITR is an agonistic anti-GITR antibody. In other aspects, the activator of GITR is a natural ligand of GITR.

In some aspects, the immune modulator is an activator of 4-1BB. In specific aspects, the activator of 4-1BB is an agonistic anti-4-1BB antibody. In certain aspects, the activator of 4-1BB is a natural ligand of 4-1BB.

In some aspects, the immune modulator is a Fas receptor (Fas). In such aspects, the Fas receptor is displayed on the surface of the EV, e.g., exosome. In some aspects, the immune modulator is Fas ligand (FasL). In certain aspects, the Fas ligand is displayed on the surface of the EV, e.g., exosome. In some aspects, the immune modulator is an anti-Fas antibody or an anti-FasL antibody.

In some aspects, the immune modulator is an activator of a CD28-superfamily co-stimulatory molecule. In certain aspects, the CD28-superfamily co-stimulatory molecule is ICOS or CD28. In certain aspects, the immunomodulating component is ICOSL, CD80, or CD86.

In some aspects, the immune modulator is an activator of inducible T cell co-stimulator (ICOS). In certain aspects, the activator of ICOS is an agonistic anti-ICOS antibody. In other aspects, the activator of ICOS is a ICOS ligand (ICOSL).

In some aspects, the immune modulator is an activator of CD28. In some aspects, the activator of CD28 is an agonistic anti-CD28 antibody. In other aspects, the activator of CD28 is a natural ligand of CD28. In certain aspects, the ligand of CD28 is CD80.

In some aspects, the immune modulator comprises a cytokine or a binding partner of a cytokine. In some aspects, the cytokine is selected from (i) common gamma chain family of cytokines; (ii) IL-1 family of cytokines; (iii) hematopoietic cytokines; (iv) interferons (e.g., type I, type II, or type III); (v) TNF family of cytokines; (vi) IL-17 family of cytokines; (vii) damage-associated molecular patterns (DAMPs); (viii) tolerogenic cytokines; or (ix) combinations thereof. In certain aspects, the cytokine comprises IL-2, IL-4, IL-7, IL-10, IL-12, IL-15, IL-21, IFN-γ, IL-1α, IL-1β, IL-1ra, IL-18, IL-33, IL-36α, IL-36β, IL-36γ, IL-36ra, IL-37, IL-38, IL-3, IL-5, IL-6, IL-11, IL-13, IL-23, granulocyte-macrophage colony stimulating factor (GM-CSF), granulocyte-colony stimulating factor (G-CSF), leukemia inhibitory factor (LIF), stem cell factor (SCF), thrombopoietin (TPO), macrophage-colony stimulating factor (M-CSF), erythropoietien (EPO), Flt-3, IFN-α, IFN-β, IFN-γ, IL-19, IL-20, IL-22, IL-24, TNF-α, TNF-β, BAFF, APRIL, lymphotoxin beta (TNF-γ), IL-17A, IL-17B, IL-17C, IL-17D, IL-17E, IL-17F, IL-25, TSLP, IL-35, IL-27, TGF-β, or combinations thereof.

In some aspects, the immune modulator comprises a chemokine. In certain aspects, chemokine comprises a (i) CC chemokine (e.g., CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28); (ii) CXC chemokine (e.g., CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17); (iii) C chemokine (e.g., XCL1, XCL2); (iv) CX3C chemokine (e.g., CX3CL1); (v) or combinations thereof.

In some aspects, the immune modulator comprises an inhibitor of lysophosphatidic acid (LPA). LPA is a highly potent endogenous lipid mediator that protects and rescues cells from programmed cell death. LPA, through its high affinity LPA-1 receptor, is an important mediator of fibrogenesis.

In some aspects, the LPA-1 inhibitor comprises AM095, which is a potent and orally bioavailable antagonist of LPA-1 with $IC_{50}$ values of 0.73 and 0.98 µM for mouse or recombinant human LPA-1, respectively. In vitro, AM095 has been shown to inhibit LPA-1-induced chemotaxis of both mouse LPA-1/CHO cells and human A2058 melanoma cells with $IC_{50}$ values of 0.78 µM and 0.23 µM. In vivo, AM095 can dose-dependently block LPA-induced histamine release with an $ED_{50}$ value of 8.3 mg/kg in mice. Additionally, AM095 has been revealed to remarkably reduce the BALF collagen and protein with an $ED_{50}$ value of 10 mg/kg in lungs. AM095 has also been shown to decrease both macrophage and lymphocyte infiltration induced by bleomycin in mice. See Swaney et al. (2018) Mol. Can. Res. 16:1601-1613, which is herein incorporated by reference in its entirety.

In some aspects, the LPA-1 inhibitor comprises AM152 (also known as BMS-986020). AM152 is a high-affinity LPA-1 antagonist which inhibits bile acid and phospholipid transporters with $IC_{50}$s of 4.8 µM, 6.2 µM, and 7.5 µM for BSEP, MRP4, and MDR3, respectively. AM152 can be used for the treatment of idiopathic pulmonary fibrosis (IPF). See Kihara et al. (2015) Exp. Cell Res. 333:171-7; Rosen et al. (2017) European Respiratory Journal 50:PA1038; and, Palmer et al. (2018) Chest 154:1061-1069, which are herein incorporated by reference in their entireties. The Phase 2 study of AM152 (described in Palmer 2018) was terminated early due to gall bladder toxicity and early signs of liver toxicity liver transporter (2 specific transporters).

Additional disclosures relating to EVs (e.g., exosomes) comprising an LPA-1 inhibitor are provided elsewhere in the present disclosure (see, e.g., Example 24).

In some aspects, the immune modulator that can be combined with an antigen, e.g., HSV-2 antigen, is IL-21. Non-limiting examples of HSV-2 antigens are disclosed elsewhere herein. In some aspects, the EV, e.g., exosome, of the present disclosure comprises both IL-21 and a HSV-2 antigen in the lumen of the EV. In other aspects, the EV comprises IL-21 on the exterior surface of the EV, optionally linked via a first scaffold moiety (e.g., Scaffold X), and a HSV-2 antigen on the exterior surface of the EV, optionally linked via a second scaffold moiety (e.g., Scaffold X), wherein the first scaffold moiety and the second scaffold moiety are the same or different. In other aspects, the EV comprises IL-21 on the exterior surface of the EV, optionally linked via a scaffold moiety (e.g., Scaffold X), and a HSV-2 antigen on the luminal surface of the EV, optionally linked via the scaffold moiety (e.g., Scaffold X). In other aspects, the EV comprises a HSV-2 antigen on the exterior surface of the EV, optionally linked via a scaffold moiety (e.g., Scaffold X), and IL-21 on the luminal surface of the EV, optionally linked via the scaffold moiety (e.g., Scaffold X). In other aspects, the EV comprises IL-21 on the exterior surface of the EV, optionally linked via a first scaffold moiety (e.g., Scaffold X), and a HSV-2 antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a HSV-2 antigen on the exterior surface of the EV, optionally linked via a first scaffold moiety (e.g., Scaffold X), and IL-21 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-21 on the luminal surface of the EV (e.g., Scaffold X or Scaffold Y), optionally linked via a first scaffold moiety, and a HSV-2 antigen on the luminal surface of the EV (e.g., Scaffold X or Scaffold Y), optionally linked via a second scaffold moiety, wherein the first scaffold moiety and the second scaffold moiety are the same or different.

In some aspect, the immune modulator that can be combined with an antigen, e.g., HSV-2 antigen, is CD40L. Non-limiting examples of HSV-2 antigens are disclosed elsewhere herein. In some aspects, the EV, e.g., exosome, of the present disclosure comprises both CD40L and a HSV-2 antigen in the lumen of the EV. In other aspects, the EV comprises CD40L on the exterior surface of the EV, optionally linked via a first scaffold moiety (e.g., Scaffold X), and a HSV-2 antigen on the exterior surface of the EV, optionally linked via a second scaffold moiety (e.g., Scaffold X), wherein the first scaffold moiety and the second scaffold moiety are the same or different. In other aspects, the EV comprises CD40L on the exterior surface of the EV, optionally linked via a scaffold moiety (e.g., Scaffold X), and a HSV-2 antigen on the luminal surface of the EV, optionally linked via the scaffold moiety (e.g., Scaffold X). In other aspects, the EV comprises a HSV-2 antigen on the exterior surface of the EV, optionally linked via a scaffold moiety (e.g., Scaffold X), and CD40L on the luminal surface of the EV, optionally linked via the scaffold moiety (e.g., Scaffold X). In other aspects, the EV comprises CD40L on the exterior surface of the EV, optionally linked via a first scaffold moiety (e.g., Scaffold X), and a HSV-2 antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a HSV-2 antigen on the exterior surface of the EV, optionally linked via a first scaffold moiety (e.g., Scaffold X), and CD40L on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises CD40L on the luminal surface of the EV (e.g., Scaffold X or Scaffold Y), optionally linked via a first scaffold moiety, and a HSV-2 antigen on the luminal surface of the EV (e.g., Scaffold X or Scaffold Y), optionally linked via a second scaffold moiety, wherein the first scaffold moiety and the second scaffold moiety are the same or different.

In some aspect, an EV (e.g., exosome) comprising a HSV-2 antigen (e.g., disclosed herein) and an immune modulator (e.g., IL-21 or CD40L) can further comprise an adjuvant. Non-limiting examples of adjuvants that can be used with the present disclosure are described elsewhere herein.

In some aspect, an EV (e.g., exosome) comprising a HSV-2 antigen and one or more additional payloads (e.g., an immune modulator and/or adjuvant described above) can enhance an immune response to the HSV-2 antigen compared to a reference. In some aspect, the reference comprises an EV (e.g., exosome) comprising only the HSV-2 antigen. In other aspect, the reference comprises a HSV-2 antigen (alone or in combination with one or more additional payloads (e.g., an adjuvant and/or immune modulator)) that is not linked or present in the EVs disclosed herein (e.g., exosomes). In some aspects, an immune response comprises an innate immune response, a humoral immune response, a cell-mediated immune response, or combinations thereof. In certain aspects, the immune response is enhanced by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more compared to the reference. In some aspects, the immune response is enhanced by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV without the targeting moiety or a non-EV delivery vehicle).

In some aspect, an EV (e.g., exosome) comprising a HSV-2 antigen and one or more additional payloads (e.g., an immune modulator and/or adjuvant described above) can reduce viral shedding when administered to a subject in need thereof. In certain aspect, viral shedding is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads). In some aspect, an EV (e.g., exosome) comprising a HSV-2 antigen and one or more additional payloads (e.g., an immune modulator and/or adjuvant) can increase viral clearance when administered to a subject in need thereof. In certain aspect, viral clearance is increased by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more, compared to a reference (e.g., corresponding EV comprising the antigen alone or a non-EV delivery vehicle comprising the antigen alone or in combination with the one or more additional payloads). In some aspects, viral clearance is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to a reference (e.g., corresponding EV comprising the antigen alone or a non-EV delivery vehicle comprising the antigen alone or in combination with the one or more additional payloads). In further aspect, an EV (e.g., exosome) comprising a HSV-2 antigen and one or more additional payloads (e.g., an immune modulator and/or adjuvant) can reduce HSV-2-mediated lesion formation when administered to a subject in need thereof. In certain aspect, lesion formation is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads).

In some aspect, the reference comprises an EV (e.g., exosome) comprising only the HSV-2 antigen. In other aspect, the reference comprises a HSV-2 antigen (alone or in combination with an adjuvant and/or immune modulator) that is not linked or present in the EVs disclosed herein.

In some aspects, the immune modulator that can be combined with an antigen, e.g., EBV antigen, is IL-21. Non-limiting examples of EBV antigens (e.g., BZLF1) are disclosed elsewhere herein. In some aspects, the EV, e.g., exosome, of the present disclosure comprises both IL-21 and an EBV antigen (e.g., BZLF1) in the lumen of the EV. In other aspects, the EV comprises IL-21 on the exterior surface of the EV, optionally linked via a first scaffold moiety (e.g., Scaffold X), and an EBV antigen (e.g., BZLF1) on the exterior surface of the EV, optionally linked via a second scaffold moiety (e.g., Scaffold X), wherein the first scaffold moiety and the second scaffold moiety are the same or different. In other aspects, the EV comprises IL-21 on the exterior surface of the EV, optionally linked via a scaffold moiety (e.g., Scaffold X), and an EBV antigen (e.g., BZLF1) on the luminal surface of the EV, optionally linked via the scaffold moiety (e.g., Scaffold X). In other aspects, the EV comprises an EBV antigen (e.g., BZLF1) on the exterior surface of the EV, optionally linked via a scaffold moiety (e.g., Scaffold X), and IL-21 on the luminal surface of the EV, optionally linked via the scaffold moiety (e.g., Scaffold X). In other aspects, the EV comprises IL-21 on the exterior surface of the EV, optionally linked via a first scaffold moiety (e.g., Scaffold X), and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different. In other aspects, the EV comprises an EBV antigen (e.g., BZLF1) on the exterior surface of the EV, optionally linked via a first scaffold moiety (e.g., Scaffold X), and IL-21 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-21 on the luminal surface of the EV (e.g., Scaffold X or Scaffold Y), optionally linked via a first scaffold moiety, and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different.

In some aspect, the immune modulator that can be combined with an antigen, e.g., an EBV antigen (e.g., BZLF1), is CD40L. Non-limiting examples of an EBV antigen (e.g., BZLF1) are disclosed elsewhere herein. In some aspects, the EV, e.g., exosome, of the present disclosure comprises both CD40L and an EBV antigen (e.g., BZLF1) in the lumen of the EV. In other aspects, the EV comprises CD40L on the exterior surface of the EV, optionally linked via a first scaffold moiety (e.g., Scaffold X), and an EBV antigen (e.g., BZLF1) on the exterior surface of the EV, optionally linked via a second scaffold moiety (e.g., Scaffold X), wherein the first scaffold moiety and the second scaffold moiety are the same or different. In other aspects, the EV comprises CD40L on the exterior surface of the EV, optionally linked via a scaffold moiety (e.g., Scaffold X), and an EBV antigen (e.g., BZLF1) on the luminal surface of the EV, optionally linked via the scaffold moiety (e.g., Scaffold X). In other aspects, the EV comprises an EBV antigen (e.g., BZLF1) on the exterior surface of the EV, optionally linked via a scaffold moiety (e.g., Scaffold X), and CD40L on the luminal surface of the EV, optionally linked via the scaffold moiety (e.g., Scaffold X). In other aspects, the EV comprises CD40L on the exterior surface of the EV, optionally linked via a first scaffold moiety (e.g., Scaffold X), and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different. In other aspects, the EV comprises an EBV antigen (e.g., BZLF1) on the exterior surface of the EV, optionally linked via a first scaffold moiety (e.g., Scaffold X), and CD40L on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises CD40L on the luminal surface of the EV (e.g., Scaffold X or Scaffold Y), optionally linked via a first scaffold moiety, and an EBV antigen (e.g., BZLF1) on the luminal surface of the EV (e.g., Scaffold X or Scaffold Y), optionally linked via a second scaffold moiety, wherein the first scaffold moiety and the second scaffold moiety are the same or different.

In some aspects, an EV (e.g., exosome) comprising an EBV antigen and an immune modulator (e.g., IL-21 or CD40L) can further comprise one or more additional payloads (e.g., additional antigen, additional immune modulator, and/or adjuvant) and/or one or more targeting moieties disclosed herein. In some aspect, an EV (e.g., exosome) comprising an EBV antigen (e.g., BZLF1) (e.g., disclosed herein) and an immune modulator (e.g., IL-21 or CD40L) can further comprise an adjuvant. Non-limiting examples of adjuvants that can be used with the present disclosure are described elsewhere herein. In some aspects, the EV can further comprise an additional antigen (e.g., a different EBV antigen). In some aspects, the EV can further comprise an additional immune modulator (e.g., different from IL-21 or CD40L) disclosed herein.

In some aspect, an EV (e.g., exosome) comprising an EBV antigen (e.g., BZLF1) and one or more additional payloads (e.g., an immune modulator and/or adjuvant described above) can enhance an immune response to the EBV antigen (e.g., BZLF1) compared to a reference. In some aspects, the reference comprises an EV (e.g., exosome) comprising only the EBV antigen (e.g., BZLF1). In other aspects, the reference comprises an EBV antigen (e.g., BZLF1) (alone or in combination with an adjuvant and/or immune modulator) that is not linked or present in the EVs disclosed herein (e.g., exosomes). In some aspects, an immune response comprises an innate immune response, a humoral immune response, a cell-mediated immune response, or combinations thereof. In certain aspects, the immune response is enhanced by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more compared to the reference. In some aspects, the immune response is enhanced by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, at least about 2,000-fold, at least about 3,000-fold, at least about 4,000-fold, at least about 5,000-fold, at least about 6,000-fold, at least about 7,000-fold, at least about 8,000-fold, at least about 9,000-fold, at least about 10,000-fold or more, compared to the reference.

In some aspects, an EV (e.g., exosome) comprising an EBV antigen (e.g., BZLF1) and one or more additional payloads (e.g., an immune modulator and/or adjuvant described above) can reduce viral shedding when administered to a subject in need thereof. In certain aspect, viral shedding is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads). In some aspects, an EV (e.g., exosome) comprising an EBV antigen (e.g., BZLF1) and one or more additional payloads (e.g., an immune modulator and/or adjuvant) can increase viral clearance when administered to a subject in need thereof. In certain aspect, viral clearance is increased by at least about 5%, at least about 10%, at least about 15%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1,000% or more, compared to a reference (e.g., corresponding EV comprising the antigen alone or a non-EV delivery vehicle comprising the antigen alone or in combination with the one or more additional payloads). In some aspects, an EV (e.g., exosome) comprising an EBV antigen (e.g., BZLF1) and one or more additional payloads (e.g., an immune modulator and/or adjuvant) can reduce EBV-mediated lesion formation when administered to a subject in need thereof. In certain aspect, lesion formation is reduced by at least about 5%, at least about 10%, at least about 15%, at least about 20%, at least about 30%, at least about 40%, at least about 50%, at least about 60%, at least about 70%, at least about 80%, at least about 90%, or at least about 100% compared to a reference (e.g., corresponding EV comprising the antigen alone or a non-EV delivery vehicle comprising the antigen alone or in combination with the one or more additional payloads).

In some aspect, the reference comprises an EV (e.g., exosome) comprising only an EBV antigen (e.g., BZLF1). In other aspect, the reference comprises an EBV antigen (e.g., BZLF1) (alone or in combination with an adjuvant and/or immune modulator) that is not linked or present in the EVs disclosed herein.

In some aspect, the immune modulator that can be combined with an antigen, e.g., TB antigen, is IL-12.

Non-limiting examples of TB antigens are disclosed elsewhere herein. In some aspects, the EV, e.g., exosome, of the present disclosure comprises both IL-12 and a TB antigen in the lumen of the EV. In other aspects, the EV comprises IL-12 on the exterior surface of the EV, optionally linked via a first scaffold moiety (e.g., Scaffold X), and a TB antigen on the exterior surface of the EV, optionally linked via a second scaffold moiety (e.g., Scaffold X), wherein the first scaffold moiety and the second scaffold moiety are the same or different. In other aspects, the EV comprises IL-12 on the exterior surface of the EV, optionally linked via a scaffold moiety (e.g., Scaffold X), and a TB antigen on the luminal surface of the EV, optionally linked via the scaffold moiety (e.g., Scaffold X). In other aspects, the EV comprises a TB antigen on the exterior surface of the EV, optionally linked via a scaffold moiety (e.g., Scaffold X), and IL-12 on the luminal surface of the EV, optionally linked via the scaffold moiety (e.g., Scaffold X). In other aspects, the EV comprises IL-12 on the exterior surface of the EV, optionally linked via a first scaffold moiety (e.g., Scaffold X), and a TB antigen on the luminal surface of the EV (e.g., Scaffold X or Scaffold Y), optionally linked via a second scaffold moiety, wherein the first scaffold moiety and the second scaffold moiety are the same or different. In other aspects, the EV comprises a TB antigen on the exterior surface of the EV, optionally linked via a first scaffold moiety (e.g., Scaffold X), and IL-12 on the luminal surface of the EV, optionally linked via a second scaffold moiety (e.g., Scaffold X or Scaffold Y), wherein the first scaffold moiety and the second scaffold moiety are the same or different. In some aspects, the EV of the present disclosure comprises IL-12 on the luminal surface of the EV (e.g., Scaffold X or Scaffold Y), optionally linked via a first scaffold moiety, and a TB antigen on the luminal surface of the EV (e.g., Scaffold X or Scaffold Y), optionally linked via a second scaffold moiety, wherein the first scaffold moiety and the second scaffold moiety are the same or different.

The EVs comprising IL-12 and a TB antigen can induce an immune response to a subject in need thereof. In some aspects, the immune response is a CD4 T cell response, a CD8 T cell response, or both CD4 and CD8 T cell responses. In some aspects, the immune response is CD4 T-cell immune response with effector function that is specific to the TB antigen, e.g., the ESAT6 antigen. In some aspects, the immune response is CD8 T-cell immune response that is specific to the TB antigen, e.g., TB10.4 antigen.

In some aspects, an EV (e.g., exosome) comprising a TB antigen and an immune modulator (e.g., IL-12) can further comprise one or more additional payloads disclosed herein (e.g., additional antigen, additional immune modulator, and/or adjuvant). For instance, in certain aspects, the EV (e.g., exosome) can further comprise an adjuvant (e.g., such as those disclosed herein). In some aspects, the EV can further comprise an additional antigen (e.g., a different EBV antigen). In some aspects, the EV can further comprise an additional immune modulator (e.g., different from IL-21 or CD40L) disclosed herein.

In some aspects, the immune modulator that can be used with the present disclosure comprises a protein that supports intracellular interactions required for germinal center responses. In certain aspects, such a protein comprises a signaling lymphocyte activation molecule (SLAM) family member or a SLAM-associated protein (SAP). In some aspects, a SLAM family members comprises SLAM, CD48, CD229 (Ly9), Ly108, 2B4, CD84, NTB-A, CRACC, BLAME, CD2F-10, or combinations thereof. Non-limiting examples of other immune modulators that can play a role in germinal center response includes: ICOS-ICOSL, CD40-40L, CD28/B7, PD-1/L1, IL-4/IL4R, IL21/IL21R, TLR4, TLR7, TLR8, TLR9, CD180, CD22, and combinations thereof.

In some aspects, the immune modulator comprises a T-cell receptor (TCR) or a derivative thereof. In certain aspects, the immune modulator is a TCR α-chain or a derivative thereof. In other aspects, the immune modulator is a TCR β-chain or a derivative thereof. In further aspects, the immune modulator is a co-receptor of the T-cell or a derivative thereof.

In some aspects, the immune modulator comprises a chimeric antigen receptor (CAR) or a derivative thereof. In certain aspects, the CAR binds to one or more of the antigens disclosed herein (e.g., tumor antigen, e.g., alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand).

In some aspects, the immune modulator comprises an activator of a T-cell receptor or co-receptor. In certain aspects, the immunomodulating component is an activator of CD3. In certain aspects, the activator is a fragment of a monoclonal antibody of CD3. In certain aspects, the antibody fragment is a scFv, (scFv)$_2$, Fab, Fab', and F(ab')$_2$, F(ab1)$_2$, Fv, dAb, or Fd of a monoclonal antibody against CD3. In certain aspects, the activator is a nanobody, a bispecific antibody, or a multispecific antibody against CD3. In certain aspects, the immunomodulating component is an activator of CD28. In certain aspects, the activator is a fragment of a monoclonal antibody of CD28. In certain aspects, the antibody fragment is a scFv, (scFv)$^2$, Fab, Fab', and F(ab')$^2$, F(ab1)$_2$, Fv, dAb, or Fd of a monoclonal antibody of CD28. In certain aspects, the activator is a nanobody, a bispecific antibody, or a multispecific antibody against CD28.

In some aspects, the immune modulator comprises a tolerance inducing agent. In certain aspects, the tolerance inducing agent comprises a NF-κB inhibitor. Non-limiting examples of NF-κB inhibitors that can be used with the present disclosure includes: IKK complex inhibitors (e.g., TPCA-1, NF-κB Activation Inhibitor VI (BOT-64), BMS 345541, Amlexanox, SC-514 (GK 01140), IMD 0354, IKK-16), IκB degradation inhibitor (e.g., BAY 11-7082, MG-115, MG-132, Lactacystin, Epoxomicin, Parthenolide, Carfilzomib, MLN-4924 (Pevonedistat)), NF-κB nuclear translocation inhibitor (e.g., JSH-23, Rolipram), p65 acetylation inhibitor (e.g., Gallic acid, Anacardic acid), NF-κB-DNA binding inhibitor (e.g., GYY 4137, p-XSC, CV 3988, Prostaglandin E2 (PGE2)), NF-κB transactivation inhibitor (e.g., LY 294002, Wortmannin, Mesalamine), or combinations thereof. See also Gupta, S. C., et al., Biochim Biophys Acta 1799:775-787 (2010), which is herein incorporated by reference in its entirety. In some aspects, an immune modulator that can inhibit NF-κB activity and be used with the EVs (e.g., exosomes) disclosed herein comprises an antisense-oligonucleotide that specifically targets NF-κB. In further aspects, an immune modulator capable of inducing tolerance comprises a COX-2 inhibitor, mTOR inhibitor (e.g., rapamycin and derivatives, e.g., antisense oligonucleotides targeting mTor), prostaglandins, nonsteroidal anti-inflammatory agents (NSAIDS), antileukotriene, aryl hydrocarbon receptor (AhR) ligand, vitamin D, retinoic acid, steroids, Fas receptor/ligand, CD22 ligand, IL-10, IL-35, IL-27, metabolic regulator (e.g., glutamate), glycans (e.g., ES62, LewisX, LNFPIII), peroxisome proliferator-activated receptor (PPAR) agonists, immunoglobulin-like transcript (ILT) family of receptors (e.g., ILT3, ILT4, HLA-G, ILT-2), minocycline, TLR4 agonists, or combinations thereof.

In some aspects, the immune modulator is an agonist. In certain aspects, the agonist is an endogenous agonist, such as a hormone, or a neurotransmitter. In other aspects, the agonist is an exogenous agonist, such as a drug. In some aspects, the agonist is a physical agonist, which can create an agonist response without binding to the receptor. In some aspects, the agonist is a superagonist, which can produce a greater maximal response than the endogenous agonist. In certain aspects, the agonist is a full agonist with full efficacy at the receptor. In other aspects, the agonist is a partial agonist having only partial efficacy at the receptor relative to a full agonist. In some aspects, the agonist is an inverse agonist that can inhibit the constitutive activity of the receptor. In some aspects, the agonist is a co-agonist that works with other co-agonists to produce an effect on the receptor. In certain aspects, the agonist is an irreversible agonist that binds permanently to a receptor through formation of covalent bond. In certain aspects, the agonist is selective agonist for a specific type of receptor In some aspects, the immune modulator is an antagonist. In specific aspects, the antagonist is a competitive antagonist, which reversibly binds to the receptor at the same binding site as the endogenous ligand or agonist without activating the receptor. Competitive antagonist can affect the amount of agonist necessary to achieve a maximal response. In other aspects, the antagonist is a non-competitive antagonist, which binds to an active site of the receptor or an allosteric site of the receptor. Non-competitive antagonist can reduce the magnitude of the maximum response that can be attained by any amount of agonist. In further aspects, the antagonist is an uncompetitive antagonist, which requires receptor activation by an agonist before its binding to a separate allosteric binding site.

In some aspects, the immune modulator comprises an antibody or an antigen-binding fragment. The immunomodulating component can be a full length protein or a fragment thereof. The antibody or antigen-binding fragment can be derived from natural sources, or partly or wholly synthetically produced. In some aspects, the antibody is a monoclonal antibody. In some of these aspects, the monoclonal antibody is an IgG antibody. In certain aspects, the monoclonal antibody is an IgG1, IgG2, IgG3, or IgG4. In some other aspects, the antibody is a polyclonal antibody. In certain aspects, the antigen-binding fragment is selected from Fab, Fab', and F(ab')$_2$, F(ab1)$_2$, Fv, dAb, and Fd fragments. In certain aspects, the antigen-binding fragment is an scFv or (scFv)$_2$ fragment. In certain other aspects, the antibody or antigen-binding fragment is a NANOBODY® (single-domain antibody). In some aspects, the antibody or antigen-binding fragment is a bispecific or multispecific antibody.

In various aspects, the antibody or antigen-binding fragment is fully human. In some aspects, the antibody or antigen-binding fragment is humanized. In some aspects, the antibody or antigen-binding fragment is chimeric. In some of these aspects, the chimeric antibody has non-human V region domains and human C region domains. In some aspects, the antibody or antigen-binding fragment is non-human, such as murine or veterinary.

In certain aspects, the immunomodulating component is a polynucleotide. In some of these aspects, the polynucleotide includes, but is not limited to, an mRNA, a miRNA, an siRNA, an antisense oligonucleotide (e.g., antisense RNA or antisense DNA), a phosphorodiamidate morpholino oligomer (PMO), a peptide-conjugated phosphorodiamidate morpholino oligomer (PPMO), an shRNA, a lncRNA, a dsDNA, and combinations thereof. In some aspects, the polynucleotide is an RNA (e.g., an mRNA, a miRNA, an siRNA, an antisense oligonucleotide (e.g., antisense RNA), an shRNA, or an lncRNA). In some of these aspects, when the polynucleotide is an mRNA, it can be translated into a desired polypeptide. In some aspects, the polynucleotide is a microRNA (miRNA) or pre-miRNA molecule. In some of these aspects, the miRNA is delivered to the cytoplasm of the target cell, such that the miRNA molecule can silence a native mRNA in the target cell. In some aspects, the polynucleotide is a small interfering RNA (siRNA) or a short hairpin RNA (shRNA) capable of interfering with the expression of an oncogene or other dysregulating polypeptides. In some of these aspects, the siRNA is delivered to the cytoplasm of the target cell, such that the siRNA molecule can silence a native mRNA in the target cell. In some aspects, the polynucleotide is an antisense oligonucleotide (e.g., antisense RNA) that is complementary to an mRNA. In some aspects, the polynucleotide is a long non-coding RNA (lncRNA) capable of regulating gene expression and modulating diseases. In some aspects, the polynucleotide is a DNA that can be transcribed into an RNA. In some of these aspects, the transcribed RNA can be translated into a desired polypeptide.

In some aspects, the immunomodulating component is a protein, a peptide, a glycolipid, or a glycoprotein.

In various aspects, the EV (e.g., exosome) composition comprises two or more above mentioned immunomodulating components, including mixtures, fusions, combinations and conjugates, of atoms, molecules, etc. In some aspects, the composition comprises one, two, three, four, five, six, seven, eight, nine, ten, eleven, or twelve different immunomodulating components associated with the membrane or enclosed within the enclosed volume of the extracellular vesicle (e.g., exosome). In certain aspects, the composition comprises a nucleic acid combined with a polypeptide. In certain aspects, the composition comprises two or more polypeptides conjugated to each other. In certain aspects, the composition comprises a protein conjugated to a biologically active molecule. In some of these aspects, the biologically active molecule is a prodrug.

II.D Scaffold X-Engineered EVs, e.g., Exosomes,

In some aspects, EVs, e.g., exosomes, of the present disclosure comprise a membrane modified in its composition. For example, their membrane compositions can be modified by changing the protein, lipid, or glycan content of the membrane.

In some aspects, the surface-engineered EVs, e.g., exosomes, are generated by chemical and/or physical methods, such as PEG-induced fusion and/or ultrasonic fusion. In other aspects, the surface-engineered EVs, e.g., exosomes, are generated by genetic engineering. EVs, e.g., exosomes, produced from a genetically-modified producer cell or a progeny of the genetically-modified cell can contain modified membrane compositions. In some aspects, surface-engineered EVs, e.g., exosomes, have scaffold moiety (e.g., exosome protein, e.g., Scaffold X) at a higher or lower density (e.g., higher number) or include a variant or a fragment of the scaffold moiety.

For example, surface (e.g., Scaffold X)-engineered EVs, can be produced from a cell (e.g., HEK293 cells) transformed with an exogenous sequence encoding a scaffold moiety (e.g., exosome proteins, e.g., Scaffold X) or a variant or a fragment thereof. EVs including scaffold moiety expressed from the exogenous sequence can include modified membrane compositions.

Various modifications or fragments of the scaffold moiety can be used for the aspects, of the present invention. For example, scaffold moiety modified to have enhanced affinity to a binding agent can be used for generating surface-engineered EV that can be purified using the binding agent. Scaffold moieties modified to be more effectively targeted to EVs and/or membranes can be used. Scaffold moieties modified to comprise a minimal fragment required for specific and effective targeting to exosome membranes can be also used.

Scaffold moieties can be engineered to be expressed as a fusion molecule, e.g., fusion molecule of Scaffold X to an antigen, an adjuvant, and/or an immune modulator. For example, the fusion molecule can comprise a scaffold moiety disclosed herein (e.g., Scaffold X, e.g., PTGFRN, BSG, IGSF2, IGSF3, IGSF8, ITGB1, ITGA4, SLC3A2, ATP transporter, or a fragment or a variant thereof) linked to an antigen, an adjuvant, and/or an immune modulator. In case of the fusion molecule, the antigen, adjuvant, and/or immune modulator can be a natural peptide, a recombinant peptide, a synthetic peptide, or any combination thereof.

In some aspects, the surface (e.g., Scaffold X)-engineered EVs described herein demonstrate superior characteristics compared to EVs known in the art. For example, surface (e.g., Scaffold X)-engineered contain modified proteins more highly enriched on their surface than naturally occurring EVs or the EVs produced using conventional exosome proteins. Moreover, the surface (e.g., Scaffold X)-engineered EVs of the present invention can have greater, more specific, or more controlled biological activity compared to naturally occurring EVs or the EVs produced using conventional exosome proteins.

In some aspects, the Scaffold X comprises Prostaglandin F2 receptor negative regulator (the PTGFRN polypeptide). The PTGFRN protein can be also referred to as CD9 partner 1 (CD9P-1), Glu-Trp-Ile EWI motif-containing protein F (EWI-F), Prostaglandin F2-alpha receptor regulatory protein, Prostaglandin F2-alpha receptor-associated protein, or CD315. The full length amino acid sequence of the human PTGFRN protein (Uniprot Accession No. Q9P2B2) is shown at TABLE 7 as SEQ ID NO: 1. The PTGFRN polypeptide contains a signal peptide (amino acids 1 to 25 of SEQ ID NO: 1), the extracellular domain (amino acids 26 to 832 of SEQ ID NO: 1), a transmembrane domain (amino acids 833 to 853 of SEQ ID NO: 1), and a cytoplasmic domain (amino acids 854 to 879 of SEQ ID NO: 1). The mature PTGFRN polypeptide consists of SEQ ID NO: 1 without the signal peptide, i.e., amino acids 26 to 879 of SEQ ID NO: 1. In some aspects, a PTGFRN polypeptide fragment useful for the present disclosure comprises a transmembrane domain of the PTGFRN polypeptide. In other aspects, a PTGFRN polypeptide fragment useful for the present disclosure comprises the transmembrane domain of the PTGFRN polypeptide and (i) at least five, at least 10, at least 15, at least 20, at least 25, at least 30, at least 40, at least 50, at least 70, at least 80, at least 90, at least 100, at least 110, at least 120, at least 130, at least 140, at least 150 amino acids at the N terminus of the transmembrane domain, (ii) at least five, at least 10, at least 15, at least 20, or at least 25 amino acids at the C terminus of the transmembrane domain, or both (i) and (ii).

In some aspects, the fragments of PTGFRN polypeptide lack one or more functional or structural domains, such as IgV.

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 26 to 879 of SEQ ID NO: 1. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 33. In other aspects, the Scaffold X comprises the amino acid sequence of SEQ ID NO: 33, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 33 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 33.

In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 2, 3, 4, 5, 6, or 7. In other aspects, the Scaffold X comprises the amino acid sequence of SEQ ID NO: 2, 3, 4, 5, 6, or 7, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 2, 3, 4, 5, 6, or 7 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 2, 3, 4, 5, 6, or 7.

TABLE 7

Exemplary Scaffold X Protein Sequences

| Protein | Sequence |
| --- | --- |
| The PTGFRN Protein (SEQ ID NO: 1) | MGRLASRPLLLALLSLALCRGRVVRVPTATLVRVVGTELVIPCNVSDYDGPSEQNFDWSF SSLGSSFVELASTWEVGFPAQLYQERLQRGEILLRRTANDAVELHIKNVQPSDQGHYKCS TPSTDATVQGNYEDTVQVKVLADSLHVGPSARPPPSLSLREGEPFELRCTAASASPLHTH LALLWEVHRGPARRSVLALTHEGRFHPGLGYEQRYHSGDVRLDTVGSDAYRLSVSRALSA DQGSYRCIVSEWIAEQGNWQEIQEKAVEVATVVIQPSVLRAAVPKNVSVAEGKELDLTCN ITTDRADDVRPEVTWSFSRMPDSTLPGSRVLARLDRDSLVHSSPHVALSHVDARSYHLLV RDVSKENSGYYYCHVSLWAPGHNRSWHKVAEAVSSPAGVGVTWLEPDYQVYLNASKVPGF ADDPTELACRVVDTKSGEANVRFTVSWYYRMNRRSDNVVTSELLAVMDGDWTLKYGERSK QRAQDGDFIFSKEHTDTFNFRIQRTTEEDRGNYYCVVSAWTKQRNNSWVKSKDVFSKPVN IFWALEDSVLVVKARQPKPFFAAGNTFEMTCKVSSKNIKSPRYSVLIMAEKPVGDLSSPN ETKYIISLDQDSVVKLENWTDASRVDGVVLEKVQEDEFRYRMYQTQVSDAGLYRCMVTAW SPVRGSLWREAATSLSNPIEIDFQTSGPIFNASVHSDTPSVIRGDLIKLFCIITVEGAAL DPDDMAFDVSWFAVHSFGLDKAPVLLSSLDRKGIVTTSRRDWKSDLSLERVSVLEFLLQV HGSEDQDFGNYYCSVTPWVKSPTGSWQKEAEIHSKPVFITVKMDVLNAFKYPLLIGVGLS TVIGLLSCLIGYCSSHWCCKKEVQETRRERRRLMSMEMD |
| The PTGFRN protein Fragment (SEQ ID NO: 33) | GPIFNASVHSDTPSVIRGDLIKLFCIITVEGAALDPDDMAFDVSWFAVHSFGLDKAPVLL SSLDRKGIVTTSRRDWKSDLSLERVSVLEFLLQVHGSEDQDFGNYYCSVTPWVKSPTGSW QKEAEIHSKPVFITVKMDVLNAFKYPLLIGVGLSTVIGLLSCLIGYCSSHWCCKKEVQET RRERRRLMSMEM 687-878 of SEQ ID NO: 1 |
| The BSG protein (SEQ ID NO: 9) | MAAALFVLLG FALLGTHGAS GAAGFVQAPL SQQRWVGGSV ELHCEAVGSP VPEIQWWFEG QGPNDTCSQL WDGARLDRVH IHATYHQHAA STISIDTLVE EDTGTYECRA SNDPDRNHLT RAPRVKWVRA QAVVLVLEPG TVFTTVEDLG SKILLTCSLN DSATEVTGHR WLKGGVVLKE DALPGQKTEF KVDSDDQWGE YSCVFLPEPM GTANIQLHGP PRVKAVKSSE HINEGETAML VCKSESVPPV TDWAWYKITD SEDKALMNGS ESRFFVSSSQ GRSELHIENL NMEADPGQYR CNGTSSKGSD QAIITLRVRS HLAALWPFLG IVAEVLVLVT IIFIYEKRRK PEDVLDDDDA GSAPLKSSGQ HQNDKGKNVR QRNSS |

TABLE 7-continued

Exemplary Scaffold X Protein Sequences

| Protein | Sequence |
|---|---|
| The IGSF8 protein (SEQ ID NO: 14) | MGALRPTLLP PSLPLLLLLM LGMGCWAREV LVPEGPLYRV AGTAVSISCN VTGYEGPAQQ NFEWFLYRPE APDTALGIVS TKDTQFSYAV FKSRVVAGEV QVQRLQGDAV VLKIARLQAQ DAGIYECHTP STDTRYLGSY SGKVELRVLP DVLQVSAAPP GPRGRQAPTS PPRMTVHEGQ ELALGCLART STQKHTHLAV SFGRSVPEAP VGRSTLQEVV GIRSDLAVEA GAPYAERLAA GELRLGKEGT DRYRMVVGGA QAGDAGTYHC TAAEWIQDPD GSWAQIAEKR AVLAHVDVQT LSSQLAVTVG PGERRIGPGE PLELLCNVSG ALPPAGRHAA YSVGWEMAPA GAPGPGRLVA QLDTEGVGSL GPGYEGRHIA MEKVASRTYR LRLEAARPGD AGTYRCLAKA YVRGSGTRLR EAASARSRPL PVHVREEGVV LEAVAWLAGG TVYRGETASL LCNISVRGGP PGLRLAASWW VERPEDGELS SVPAQLVGGV GQDGVAELGV RPGGGPVSVE LVGPRSHRLR LHSLGPEDEG VYHCAPSAWV QHADYSWYQA GSARSGPVTV YPYMHALDTL FVPLLVGTGV ALVTGATVLG TITCCFMKRL RKR |
| The ITGB1 protein (SEQ ID NO: 21) | MNLQPIFWIG LISSVCCVFA QTDENRCLKA NAKSCGECIQ AGPNCGWCTN STFLQEGMPT SARCDDLEAL KKKGCPPDDI ENPRGSKDIK KNKNVTNRSK GTAEKLKPED ITQIQPQQLV LRLRSGEPQT FTLKFKRAED YPIDLYYLMD LSYSMKDDLE NVKSLGTDLM NEMRRITSDF RIGFGSFVEK TVMPYISTTP AKLRNPCTSE QNCTSPFSYK NVLSLTNKGE VFNELVGKQR ISGNLDSPEG GFDAIMQVAV CGSLIGWRNV TRLLVFSTDA GFHFAGDGKL GGIVLPNDGQ CHLENNMYTM SHYYDYPSIA HLVQKLSENN IQTIFAVTEE FQPVYKELKN LIPKSAVGTL SANSSNVIQL IIDAYNSLSS EVILENGKLS EGVTISYKSY CKNGVNGTGE NGRKCSNISI GDEVQFEISI TSNKCPKKDS DSFKIRPLGF TEEVEVILQY ICECECQSEG IPESPKCHEG NGTFECGACR CNEGRVGRHC ECSTDEVNSE DMDAYCRKEN SSEICSNNGE CVCGQCVCRK RDNTNEIYSG ASNGQICNGR GICECGVCKC TDPKFQGQTC EMCQTCLGVC AEHKECVQCR AFNKGEKKDT CTQECSYFNI TKVESRDKLP QPVQPDPVSH CKEKDVDDCW FYFTYSVNGN NEVMVHVVEN PECPTGPDII PIVAGVVAGI VLIGLALLLI WKLLMIIHDR REFAKFEKEK MNAKWDTGEN PIYKSAVTTV VNPKYEGK |
| The ITGA4 protein (SEQ ID NO: 22) | MAWEARREPG PRRAAVRETV MLLLCLGVPT GRPYNVDTES ALLYQGPHNT LFGYSVVLHS HGANRWLLVG APTANWLANA SVINPGAIYR CRIGKNPGQT CEQLQLGSPN GEPCGKTCLE ERDNQWLGVT LSRQPGENGS IVTCGHRWKN IFYIKNENKL PTGGCYGVPP DLRTELSKRI APCYQDYVKK FGENFASCQA GISSFYTKDL IVMGAPGSSY WTGSLFVYNI TTNKYKAFLD KQNQVKFGSY LGYSVGAGHF RSQHTTEVVG GAPQHEQIGK AYIFSIDEKE LNILHEMKGK KLGSYFGASV CAVDLNADGF SDLLVGAPMQ STIREEGRVF VYINSGSGAV MNAMETNLVG SDKYAARFGE SIVNLGDIDN DGFEDVAIGA PQEDDLQGAI YIYNGRADGI SSTFSQRIEG LQISKSLSMF GQSISGQIDA DNNGYVDVAV GAFRSDSAVL LRTRPVVIVD ASLSHPESVN RTKFDCVENG WPSVCIDLTL CFSYKGKEVP GYIVLFYNMS LDVNRKAESP PRFYFSSNGT SDVITGSIQV SSREANCRTH QAFMRKDVRD ILTPIQIEAA YHLGPHVISK RSTEEFPPLQ PILQQKKEKD IMKKTINFAR FCAHENCSAD LQVSAKIGFL KPHENKTYLA VGSMKTLMLN VSLFNAGDDA YETTLHVKLP VGLYFIKILE LEEKQINCEV TDNSGVVQLD CSIGYIYVDH LSRIDISFLL DVSSLSRAEE DLSITVHATC ENEEEMDNLK HSRVTVAIPL KYEVKLTVHG FVNPTSFVYG SNDENEPETC MVEKMNLTPH VINTGNSMAP NVSVEIMVPN SFSPQTDKLF NILDVQTTTG ECHFENYQRV CALEQQKSAM QTLKGIVRFL SKTDKRLLYC IKADPHCLNF LCNFGKMESG KEASVHIQLE GRPSILEMDE TSALKFEIRA TGFPEPNPRV IELNKDENVA HVLLEGLHHQ RPKRYFTIVI ISSSLLLGLI VLLLISYVMW KAGFFKRQYK SILQEENRRD SWSYINSKSN DD |
| The SLC3A2 Protein, where the first Met is processed. (SEQ ID NO: 23) | MELQPPEASI AVVSIPRQLP GSHSEAGVQG LSAGDDSELG SHCVAQTGLE LLASGDPLPS ASQNAEMIET GSDCVTQAGL QLLASSDPPA LASKNAEVTG TMSQDTEVDM KEVELNELEP EKQPMNAASG AAMSLAGAEK NGLVKIKVAE DEAEAAAAAK FTGLSKEELL KVAGSPGWVR TRWALLLLFW LGWLGMLAGA VVIIVRAPRC RELPAQKWWH TGALYRIGDL QAFQGHGAGN LAGLKGRLDY LSSLKVKGLV LGPIHKNQKD DVAQTDLLQI DPNFGSKEDF DSLLQSAKKK SIRVILDLTP NYRGENSWFS TQVDTVATKV KDALEFWLQA GVDGFQVRDI ENLKDASSFL AEWQNITKGF SEDRLLIAGT NSSDLQQILS LLESNKDLLL TSSYLSDSGS TGEHTKSLVT QYLNATGNRW CSWSLSQARL LTSFLPAQLL RLYQLMLFTL PGTPVFSYGD EIGLDAAALP GQPMEAPVML WDESSFPDIP GAVSANMTVK GQSEDPGSLL SLFRRLSDQR SKERSLLHGD FHAFSAGPGL FSYIRHWDQN ERFLVVLNFG DVGLSAGLQA SDLPASASLP AKADLLLSTQ PGREEGSPLE LERLKLEPHE GLLLRFPYAA |

In some aspects, a Scaffold X comprises Basigin (the BSG protein), represented by SEQ ID NO: 9. The BSG protein is also known as 5F7, Collagenase stimulatory factor, Extracellular matrix metalloproteinase inducer (EMMPRIN), Leukocyte activation antigen M6, OK blood group antigen, Tumor cell-derived collagenase stimulatory factor (TCSF), or CD147. The Uniprot number for the human BSG protein is P35613. The signal peptide of the BSG protein is amino acid 1 to 21 of SEQ ID NO: 9. Amino acids 138-323 of SEQ ID NO: 9 is the extracellular domain, amino acids 324 to 344 is the transmembrane domain, and amino acids 345 to 385 of SEQ ID NO: 9 is the cytoplasmic domain.

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 22 to 385 of SEQ ID NO: 9. In some aspects, the fragments of BSG polypeptide lack one or more functional or structural domains, such as IgV, e.g., amino acids 221 to 315 of SEQ ID NO: 9. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 10, 11, or 12. In other aspects, the Scaffold X comprises the amino acid sequence of SEQ ID NO: 10, 11, or 12, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID NO: 10, 11, or 12 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 10, 11, or 12.

In some aspects, a Scaffold X comprises Immunoglobulin superfamily member 8 (IgSF8 or the IGSF8 protein), which is also known as CD81 partner 3, Glu-Trp-Ile EWI motif-containing protein 2 (EWI-2), Keratinocytes-associated transmembrane protein 4 (KCT-4), LIR-D1, Prostaglandin regulatory-like protein (PGRL) or CD316. The full length human IGSF8 protein is accession no. Q969P0 in Uniprot and is shown as SEQ ID NO: 14 herein. The human IGSF8 protein has a signal peptide (amino acids 1 to 27 of SEQ ID NO: 14), an extracellular domain (amino acids 28 to 579 of SEQ ID NO: 14), a transmembrane domain (amino acids 580 to 600 of SEQ ID NO: 14), and a cytoplasmic domain (amino acids 601 to 613 of SEQ ID NO: 14).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 14. In some aspects, the IGSF8 protein lack one or more functional or structural domains, such as IgV. In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 15, 16, 17, or 18. In other aspects, the Scaffold X comprises the amino acid sequence of SEQ ID NO: 15, 16, 17, or 18, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, the Scaffold X comprises the amino acid sequence of SEQ ID 15, 16, 17, or 18 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 15, 16, 17, or 18.

In some aspects, a Scaffold X for the present disclosure comprises Immunoglobulin superfamily member 3 (IgSF3 or the IGSF3 protein), which is also known as Glu-Trp-Ile EWI motif-containing protein 3 (EWI-3), and is shown as the amino acid sequence of SEQ ID NO: 20. The human IGSF3 protein has a signal peptide (amino acids 1 to 19 of SEQ ID NO: 20), an extracellular domain (amino acids 20 to 1124 of SEQ ID NO: 20), a transmembrane domain (amino acids 1125 to 1145 of SEQ ID NO: 20), and a cytoplasmic domain (amino acids 1146 to 1194 of SEQ ID NO: 20).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 20. In some aspects, the IGSF3 protein lack one or more functional or structural domains, such as IgV.

In some aspects, a Scaffold X for the present disclosure comprises Integrin beta-1 (the ITGB1 protein), which is also known as Fibronectin receptor subunit beta, Glycoprotein IIa (GPIIA), VLA-4 subunit beta, or CD29, and is shown as the amino acid sequence of SEQ ID NO: 21. The human ITGB1 protein has a signal peptide (amino acids 1 to 20 of SEQ ID NO: 21), an extracellular domain (amino acids 21 to 728 of SEQ ID NO: 21), a transmembrane domain (amino acids 729 to 751 of SEQ ID NO: 21), and a cytoplasmic domain (amino acids 752 to 798 of SEQ ID NO: 21).

In other aspects, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 21 to 798 of SEQ ID NO: 21. In some aspects, the ITGB1 protein lack one or more functional or structural domains, such as IgV.

In other aspects, the Scaffold X comprises the ITGA4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 22 without the signal peptide (amino acids 1 to 33 of SEQ ID NO: 22). In some aspects, the ITGA4 protein lacks one or more functional or structural domains, such as IgV.

In other aspects, the Scaffold X comprises the SLC3A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 23 without the signal peptide. In some aspects, the SLC3A2 protein lacks one or more functional or structural domains, such as IgV.

In other aspects, the Scaffold X comprises the ATP1A1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 24 without the signal peptide. In some aspects, the ATP1A1 protein lacks one or more functional or structural domains, such as IgV.

In other aspects, the Scaffold X comprises the ATP1A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 25 without the signal peptide. In some aspects, the ATP1A2 protein lacks one or more functional or structural domains, such as IgV.

In other aspects, the Scaffold X comprises the ATP1A3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 26 without the signal peptide. In some aspects, the ATP1A3 protein lacks one or more functional or structural domains, such as IgV.

In other aspects, the Scaffold X comprises the ATP1A4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 27 without the signal peptide. In some aspects, the ATP1A4 protein lacks one or more functional or structural domains, such as IgV.

In other aspects, the Scaffold X comprises the ATP1A5 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 28 without the signal peptide. In some aspects, the ATP1A5 protein lacks one or more functional or structural domains, such as IgV.

In other aspects, the Scaffold X comprises the ATP2B1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 29 without the signal peptide. In some aspects, the ATP2B1 protein lacks one or more functional or structural domains, such as IgV.

In other aspects, the Scaffold X comprises the ATP2B2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 30 without the signal peptide. In some aspects, the ATP2B2 protein lacks one or more functional or structural domains, such as IgV.

In other aspects, the Scaffold X comprises the ATP2B3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 31 without the signal peptide. In some aspects, the ATP2B3 protein lacks one or more functional or structural domains, such as IgV.

In other aspects, the Scaffold X comprises the ATP2B4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 32 without the signal peptide. In some aspects, the ATP2B4 protein lacks one or more functional or structural domains, such as IgV.

In other aspects, the Scaffold X comprises the IGSF2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 34 without the signal peptide. In some aspects, the IGSF2 protein lacks one or more functional or structural domains, such as IgV.

Non-limiting examples of other Scaffold X proteins can be found at U.S. Pat. No. 10,195,290B1, issued Feb. 5, 2019, which is incorporated by reference in its entireties.

In some aspects, the sequence encodes a fragment of the scaffold moiety lacking at least 5, 10, 50, 100, 200, 300, 400, 500, 600, 700, or 800 amino acids from the N-terminus of the native protein. In some aspects, the sequence encodes a fragment of the scaffold moiety lacking at least 5, 10, 50, 100, 200, 300, 400, 500, 600, 700, or 800 amino acids from the C-terminus of the native protein. In some aspects, the sequence encodes a fragment of the scaffold moiety lacking at least 5, 10, 50, 100, 200, 300, 400, 500, 600, 700, or 800 amino acids from both the N-terminus and C-terminus of the native protein. In some aspects, the sequence encodes a fragment of the scaffold moiety lacking one or more functional or structural domains of the native protein.

In some aspects, the scaffold moieties, e.g., Scaffold X, e.g., a PTGFRN protein, are linked to one or more heterologous proteins. The one or more heterologous proteins can be linked to the N-terminus of the scaffold moieties. The one or more heterologous proteins can be linked to the C-terminus of the scaffold moieties. In some aspects, the one or more heterologous proteins are linked to both the N-terminus and the C-terminus of the scaffold moieties. In some aspects, the heterologous protein is a mammalian protein. In some aspects, the heterologous protein is a human protein.

In some aspects, Scaffold X can be used to link any moiety to the luminal surface and on the exterior surface of the EV, e.g., exosome, at the same time. For example, the PTGFRN polypeptide can be used to link one or more payloads disclosed herein (e.g., an antigen, an adjuvant, and/or an immune modulator) inside the lumen (e.g., on the luminal surface) in addition to the exterior surface of the EV, e.g., exosome. Therefore, in certain aspects, Scaffold X can be used for dual purposes, e.g., an antigen on the luminal surface and an adjuvant or immune modulator on the exterior surface of the EV, e.g., exosome, an antigen on the exterior surface of the EV, e.g., exosome, and the adjuvant or immune modulator on the luminal surface, an adjuvant on the luminal surface and an immune modulator on the exterior surface of the EV, e.g., exosome, or an immune modulator on the luminal surface and an adjuvant on the exterior surface of the EV, e.g., exosome.

II.E Scaffold Y-Engineered EVs, e.g., Exosomes

In some aspects, EVs, e.g., exosomes, of the present disclosure comprise an internal space (i.e., lumen) that is different from that of the naturally occurring EVs. For example, the EV can be changed such that the composition in the luminal surface of the EV, e.g., exosome has the protein, lipid, or glycan content different from that of the naturally-occurring exosomes.

In some aspects, engineered EVs, e.g., exosomes, can be produced from a cell transformed with an exogenous sequence encoding a scaffold moiety (e.g., exosome proteins, e.g., Scaffold Y) or a modification or a fragment of the scaffold moiety that changes the composition or content of the luminal surface of the EV, e.g., exosome. Various modifications or fragments of the exosome protein that can be expressed on the luminal surface of the EV, e.g., exosome, can be used for the aspects of the present disclosure.

In some aspects, the exosome proteins that can change the luminal surface of the EVs, e.g., exosomes, include, but are not limited to, the myristoylated alanine rich Protein Kinase C substrate (MARCKS) protein, the myristoylated alanine rich Protein Kinase C substrate like 1 (MARCKSL1) protein, the brain acid soluble protein 1 (BASP1) protein, or any combination thereof.

In some aspects, Scaffold Y comprises the MARCKS protein (Uniprot accession no. P29966). The MARCKS protein is also known as protein kinase C substrate, 80 kDa protein, light chain. The full-length human MARCKS protein is 332 amino acids in length and comprises a calmodulin-binding domain at amino acid residues 152-176. In some aspects, Scaffold Y comprises the MARCKSL1 protein (Uniprot accession no. P49006). The MARCKSL1 protein is also known as MARCKS-like protein 1, and macrophage myristoylated alanine-rich C kinase substrate. The full-length human MARCKSL1 protein is 195 amino acids in length. The MARCKSL1 protein has an effector domain involved in lipid-binding and calmodulin-binding at amino acid residues 87-110. In some aspects, the Scaffold Y comprises the BASP1 protein (Uniprot accession number P80723). The BASP1 protein is also known as 22 kDa neuronal tissue-enriched acidic protein or neuronal axonal membrane protein NAP-22. The full-length human BASP1 protein sequence (isomer 1) is 227 amino acids in length. An isomer produced by an alternative splicing is missing amino acids 88 to 141 from SEQ ID NO: 49 (isomer 1). TABLE 8 provides the full-length sequences for the exemplary Scaffold Y disclosed herein (i.e., the MARCKS, MARCKSL1, and BASP1 proteins).

NO: 47. The mature MARCKSL1 protein contains amino acids 2 to 227 of SEQ ID NO: 48.

In other aspects, Scaffold Y useful for the present disclosure comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 2 to 227 of SEQ ID NO: 49. In other aspects, the Scaffold Y comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to any one of SEQ ID NOs: 50-155. In other aspects, a Scaffold Y useful for the present disclosure comprises the amino acid sequence of SEQ ID NO: 49, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some aspects, a Scaffold Y useful for the present disclosure comprises the amino acid sequence of any one of SEQ ID NOs: 50-155 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NOs: 50-155.

In some aspects, the protein sequence of any of SEQ ID NOs: 47-155 is sufficient to be a Scaffold Y for the present disclosure (e.g., scaffold moiety linked to an antigen and/or an adjuvant and/or an immune modulator).

In certain aspects, a Scaffold Y useful for the present disclosure comprises a peptide with the MGXKLSKKK, where X is alanine or any other amino acid (SEQ ID NO:

TABLE 8

Exemplary Scaffold Y Protein Sequences

| Protein | Sequence |
|---|---|
| The MARCKS protein (SEQ ID NO: 47) | MGAQESKTAA KGEAAAERPG EAAVASSPSK ANGQENGHVK VNGDASPAAA ESGAKEELQA NGSAPAADKE EPAAAGSGAA SPSAAEKGEP AAAAAPEAGA SPVEKEAPAE GEAAEPGSPT AAEGEAASAA SSTSSPKAED GATPSPSNET AAAAAEAGAA SGEQAAAPGE EAAAGEEGAA GGDPQEAKPQ EAAVAPEKPP ASKETKAAEE PSKVEEKKAE EAGASAAACE APSAAGPGAP PEQEAAPAEE PAAAAASSAC AAPSQEAQPE CSPEAPPAEA AE |
| The MARCKSL1 protein (SEQ ID NO: 48) | MGSQSSKAPR GDVTAEEAAG ASPAKANGQE NGHVKSNGDL SPKGEGESPP VNGTDEAAGA TGDAIEPAPP SQGAEAKGEV PPKETPKKKK KFSFKKPFKL SGLSFKRNRK EGGGDSSASS PTEEEQEQGE IGACSDEGTA QEGKAAATPE SQEPQAKGAE ASAASEEEAG PQATEPSTPS GPESGPTPAS AEQNE |
| The BASP1 protein (SEQ ID NO: 49) | MGGKLSKKKK GYNVNDEKAK EKDKKAEGAA TEEEGTPKES EPQAAAEPAE AKEGKEKPDQ DAEGKAEEKE GEKDAAAAKE EAPKAEPEKT EGAAEAKAEP PKAPEQEQAA PGPAAGGEAP KAAEAAAAPA ESAAPAAGEE PSKEEGEPKK TEAPAAPAAQ ETKSDGAPAS DSKPGSSEAA PSSKETPAAT EAPSSTPKAQ GPAASAEEPK PVEAPAANSD QTVTVKE |

The mature BASP1 protein sequence is missing the first Met from SEQ ID NO: 49 and thus contains amino acids 2 to 227 of SEQ ID NO: 49. Similarly, the mature MARCKS and MARCKSL1 proteins also lack the first Met from SEQ ID NOs: 47 and 48, respectively. Accordingly, the mature MARCKS protein contains amino acids 2 to 332 of SEQ ID 163). In some aspects, a Scaffold Y useful for the present disclosure comprises a peptide with the GXKLSKKK (S, where X is alanine or any other amino acid (SEQ ID NO: 372). In some aspects, an EV, e.g., exosome, comprises a peptide with sequence of (M)(G)(π)(ξ)(Φ/π)(S/A/G/N)(+)(+) or (G)(π)(Φ/π)(S/A/G/N)(+)(+), wherein each parenthetical position represents an amino acid, and wherein π is any amino acid selected from the group consisting of (Pro, Gly, Ala, Ser), is any amino acid selected from the group consisting of (Asn, Gln, Ser, Thr, Asp, Glu, Lys, His, Arg), 1 is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). In further aspects, an exosome described herein (e.g., engineered exosome) comprises a peptide with sequence of (M)(G)(π)(X)(Φ/π)(π)(+)(+) or (G)(π)(X)(Φ/π)(π)(+)(+), wherein each parenthetical position represents an amino acid, and wherein 7C is any amino acid selected from the group consisting of (Pro, Gly, Ala, Ser), X is any amino acid, 1 is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). See Aasland et al., FEBS Letters 513 (2002) 141-144 for amino acid nomenclature.

In other aspects, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to any one of SEQ ID NO: 47-155.

Scaffold Y-engineered EVs, e.g., exosomes described herein can be produced from a cell transformed with a sequence set forth in SEQ ID NOs: 47-155.

In some aspects, the Scaffold Y protein useful for the present disclosure comprises an "N-terminus domain" (ND) and an "effector domain" (ED), wherein the ND and/or the ED are associated with the luminal surface of the EV, e.g., an exosome. In some aspects, the Scaffold Y protein useful for the present disclosure comprises an intracellular domain, a transmembrane domain, and an extracellular domain; wherein the intracellular domain comprises an "N-terminus domain" (ND) and an "effector domain" (ED), wherein the ND and/or the ED are associated with the luminal surface of the EV, e.g., an exosome. As used herein the term "associated with" refers to the interaction between a scaffold protein with the luminal surface of the EV, e.g., and exosome, that does not involve covalent linking to a membrane component. For example, the scaffolds useful for the present disclosure can be associated with the luminal surface of the EV, e.g., via a lipid anchor (e.g., myristic acid), and/or a polybasic domain that interacts electrostatically with the negatively charged head of membrane phospholipids. In other aspects, the Scaffold Y protein comprises an N-terminus domain (ND) and an effector domain (ED), wherein the ND is associated with the luminal surface of the EV and the ED are associated with the luminal surface of the EV by an ionic interaction, wherein the ED comprises at least two, at least three, at least four, at least five, at least six, or at least seven contiguous basic amino acids, e.g., lysines (Lys), in sequence.

In other aspects, the Scaffold Y protein comprises an N-terminus domain (ND) and an effector domain (ED), wherein the ND is associated with the luminal surface of the EV, e.g., exosome, and the ED is associated with the luminal surface of the EV by an ionic interaction, wherein the ED comprises at least two, at least three, at least four, at least five, at least six, or at least seven contiguous basic amino acids, e.g., lysines (Lys), in sequence.

In some aspects, the ND is associated with the luminal surface of the EV, e.g., an exosome, via lipidation, e.g., via myristoylation. In some aspects, the ND has Gly at the N terminus. In some aspects, the N-terminal Gly is myristoylated.

In some aspects, the ED is associated with the luminal surface of the EV, e.g., an exosome, by an ionic interaction. In some aspects, the ED is associated with the luminal surface of the EV, e.g., an exosome, by an electrostatic interaction, in particular, an attractive electrostatic interaction.

In some aspects, the ED comprises (i) a basic amino acid (e.g., lysine), or (ii) two or more basic amino acids (e.g., lysine) next to each other in a polypeptide sequence. In some aspects, the basic amino acid is lysine (Lys; K), arginine (Arg, R), or Histidine (His, H). In some aspects, the basic amino acid is (Lys)n, wherein n is an integer between 1 and 10.

In other aspects, the ED comprises at least a lysine and the ND comprises a lysine at the C terminus if the N terminus of the ED is directly linked to lysine at the C terminus of the ND, i.e., the lysine is in the N terminus of the ED and is fused to the lysine in the C terminus of the ND. In other aspects, the ED comprises at least two lysines, at least three lysines, at least four lysines, at least five lysines, at least six lysines, or at least seven lysines when the N terminus of the ED is linked to the C terminus of the ND by a linker, e.g., one or more amino acids.

In some aspects, the ED comprises K, KK, KKK, KKKK (SEQ ID NO: 205), KKKKK (SEQ ID NO: 206), R, RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof. In some aspects, the ED comprises KK, KKK, KKKK (SEQ ID NO: 205), KKKKK (SEQ ID NO: 206), or any combination thereof. In some aspects, the ND comprises the amino acid sequence as set forth in G:X2:X3:X4:X5:X6, wherein G represents Gly; wherein ":" represents a peptide bond; wherein each of the X2 to the X6 independently represents an amino acid; and wherein the X6 represents a basic amino acid. In some aspects, the X6 amino acid is selected is selected from the group consisting of Lys, Arg, and His. In some aspects, the X5 amino acid is selected from the group consisting of Pro, Gly, Ala, and Ser. In some aspects, the X2 amino acid is selected from the group consisting of Pro, Gly, Ala, and Ser. In some aspects, the X4 is selected from the group consisting of Pro, Gly, Ala, Ser, Val, Ile, Leu, Phe, Trp, Tyr, Gln, and Met.

In some aspects, the Scaffold Y protein comprises an N-terminus domain (ND) and an effector domain (ED), wherein the ND comprises the amino acid sequence as set forth in G:X2:X3:X4:X5:X6, wherein G represents Gly; wherein ":" represents a peptide bond; wherein each of the X2 to the X6 is independently an amino acid; wherein the X6 comprises a basic amino acid, and wherein the ED is linked to X6 by a peptide bond and comprises at least one lysine at the N terminus of the ED.

In some aspects, the ND of the Scaffold Y protein comprises the amino acid sequence of G:X2:X3:X4:X5:X6, wherein G represents Gly; ":" represents a peptide bond; the X2 represents an amino acid selected from the group consisting of Pro, Gly, Ala, and Ser; the X3 represents any amino acid; the X4 represents an amino acid selected from the group consisting of Pro, Gly, Ala, Ser, Val, Ile, Leu, Phe, Trp, Tyr, Gln, and Met; the X5 represents an amino acid selected from the group consisting of Pro, Gly, Ala, and Ser; and the X6 represents an amino acid selected from the group consisting of Lys, Arg, and His.

In some aspects, the X3 amino acid is selected from the group consisting of Asn, Gln, Ser, Thr, Asp, Glu, Lys, His, and Arg.

In some aspects, the ND and ED are joined by a linker. In some aspects, the linker comprises one or more amino acids. In some aspects, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. Generally, linkers provide flexibility or prevent/ameliorate steric hindrances. Linkers are not typically cleaved; however, in certain aspects, such cleavage can be desirable. Accordingly, in some aspects, a linker can comprise one or more protease-cleavable sites, which can be located within the sequence of the linker or flanking the linker at either end of the linker sequence. When the ND and ED are joined by a linker, the ED comprise at least two lysines, at least three lysines, at least four lysines, at least five lysines, at least six lysines, or at least seven lysines.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the linker is a glycine/serine linker. In some aspects, the peptide linker is glycine/serine linker according to the formula [(Gly)n-Ser]m where n is any integer from 1 to 100 and m is any integer from 1 to 100. In other aspects, the glycine/serine linker is according to the formula [(Gly)x-Sery]z wherein x in an integer from 1 to 4, y is 0 or 1, and z is an integers from 1 to 50. In some aspects, the peptide linker comprises the sequence Gn, where n can be an integer from 1 to 100. In some aspects, the peptide linker can comprise the sequence (GlyAla)n, wherein n is an integer between 1 and 100. In other aspects, the peptide linker can comprise the sequence (GlyGlySer)n, wherein n is an integer between 1 and 100.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect, the peptide linker can comprise non-naturally occurring polypeptides which are modified forms of naturally occurring polypeptides (e.g., comprising a mutation such as an addition, substitution or deletion).

In other aspects, the peptide linker can comprise non-naturally occurring amino acids. In yet other aspects, the peptide linker can comprise naturally occurring amino acids occurring in a linear sequence that does not occur in nature. In still other aspects, the peptide linker can comprise a naturally occurring polypeptide sequence.

The present disclosure also provides an isolated extracellular vesicle (EV), e.g., an exosome, comprising a biologically active molecule (e.g., an antigen, an adjuvant, and/or an immune modulator) linked to a Scaffold Y protein, wherein the Scaffold Y protein comprises ND-ED, wherein: ND comprises G:X2:X3:X4:X5:X6; wherein: G represents Gly; ":" represents a peptide bond; X2 represents an amino acid selected from the group consisting of Pro, Gly, Ala, and Ser; X3 represents any amino acid; X4 represents an amino acid selected from the group consisting of Pro, Gly, Ala, Ser, Val, Ile, Leu, Phe, Trp, Tyr, Glu, and Met; X5 represents an amino acid selected from the group consisting of Pro, Gly, Ala, and Ser; X6 represents an amino acid selected from the group consisting of Lys, Arg, and His; "—" represents an optional linker; and ED is an effector domain comprising (i) at least two contiguous lysines (Lys), which is linked to the X6 by a peptide bond or one or more amino acids or (ii) at least one lysine, which is directly linked to the X6 by a peptide bond.

In some aspects, the X2 amino acid is selected from the group consisting of Gly and Ala. In some aspects, the X3 amino acid is Lys. In some aspects, the X4 amino acid is Leu or Glu. In some aspects, the X5 amino acid is selected from the group consisting of Ser and Ala. In some aspects, the X6 amino acid is Lys. In some aspects, the X2 amino acid is Gly, Ala, or Ser; the X3 amino acid is Lys or Glu; the X4 amino acid is Leu, Phe, Ser, or Glu; the X5 amino acid is Ser or Ala; and X6 amino acid is Lys. In some aspects, the "-" linker comprises a peptide bond or one or more amino acids.

In some aspects, the ED in the scaffold protein comprises Lys (K), KK, KKK, KKKK (SEQ ID NO: 205), KKKKK (SEQ ID NO: 206), Arg (R), RR, RRR, RRRR (SEQ ID NO: 207); RRRRR (SEQ ID NO: 208), KR, RK, KKR, KRK, RKK, KRR, RRK, (K/R)(K/R)(K/R)(K/R) (SEQ ID NO: 209), (K/R)(K/R)(K/R)(K/R)(K/R) (SEQ ID NO: 210), or any combination thereof.

In some aspects, the Scaffold Y protein comprises an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), or (v) any combination thereof.

In some aspects, the ND in the Scaffold Y protein comprises an amino acid sequence selected from the group consisting of (i) GGKLSK (SEQ ID NO: 215), (ii) GAKLSK (SEQ ID NO: 216), (iii) GGKQSK (SEQ ID NO: 217), (iv) GGKLAK (SEQ ID NO: 218), or (v) any combination thereof and the ED in the scaffold protein comprises K, KK, KKK, KKKG (SEQ ID NO: 219), KKKGY (SEQ ID NO: 220), KKKGYN (SEQ ID NO: 221), KKKGYNV (SEQ ID NO: 222), KKKGYNVN (SEQ ID NO: 223), KKKGYS (SEQ ID NO: 224), KKKGYG (SEQ ID NO: 225), KKKGYGG (SEQ ID NO: 226), KKKGS (SEQ ID NO: 227), KKKGSG (SEQ ID NO: 228), KKKGSGS (SEQ ID NO: 229), KKKS (SEQ ID NO: 230), KKKSG (SEQ ID NO: 231), KKKSGG (SEQ ID NO: 232), KKKSGGS (SEQ ID NO: 233), KKKSGGSG (SEQ ID NO: 234), KKSGGSGG (SEQ ID NO: 235), KKKSGGSGGS (SEQ ID NO: 236), KRFSFKKS (SEQ ID NO: 237).

In some aspects, the polypeptide sequence of a Scaffold Y protein useful for the present disclosure consists of an amino acid sequence selected from the group consisting of (i) GGKLSKK (SEQ ID NO: 211), (ii) GAKLSKK (SEQ ID NO: 212), (iii) GGKQSKK (SEQ ID NO: 213), (iv) GGKLAKK (SEQ ID NO: 214), or (v) any combination thereof.

In some aspects, the Scaffold Y protein comprises an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof.

In some aspects, the polypeptide sequence of a Scaffold Y protein useful for the present disclosure consists of an amino acid sequence selected from the group consisting of (i) GGKLSKKK (SEQ ID NO: 238), (ii) GGKLSKKS (SEQ ID NO: 239), (iii) GAKLSKKK (SEQ ID NO: 240), (iv) GAKLSKKS (SEQ ID NO: 241), (v) GGKQSKKK (SEQ ID NO: 242), (vi) GGKQSKKS (SEQ ID NO: 243), (vii) GGKLAKKK (SEQ ID NO: 244), (viii) GGKLAKKS (SEQ ID NO: 245), and (ix) any combination thereof.

In some aspects, the Scaffold Y protein is at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least 31, at least about 32, at least about 33, at least about 34, at least about 35, at least about 36, at least about 37, at least about 38, at least about 39, at least about 39, at least about 40, at least about 41, at least about 42, at least about 43, at least about 44, at least about 50, at least about 46, at least about 47, at least about 48, at least about 49, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 305, at least about 310, at least about 315, at least about 320, at least about 325, at least about 330, at least about 335, at least about 340, at least about 345, or at least about 350 amino acids in length.

In some aspects, the Scaffold Y protein is between about 5 and about 10, between about 10 and about 20, between about 20 and about 30, between about 30 and about 40, between about 40 and about 50, between about 50 and about 60, between about 60 and about 70, between about 70 and about 80, between about 80 and about 90, between about 90 and about 100, between about 100 and about 110, between about 110 and about 120, between about 120 and about 130, between about 130 and about 140, between about 140 and about 150, between about 150 and about 160, between about 160 and about 170, between about 170 and about 180, between about 180 and about 190, between about 190 and about 200, between about 200 and about 210, between about 210 and about 220, between about 220 and about 230, between about 230 and about 240, between about 240 and about 250, between about 250 and about 260, between about 260 and about 270, between about 270 and about 280, between about 280 and about 290, between about 290 and about 300, between about 300 and about 310, between about 310 and about 320, between about 320 and about 330, between about 330 and about 340, or between about 340 and about 250 amino acids in length.

In some aspects, the Scaffold Y protein comprises (i) GGKLSKKKKGYNVN (SEQ ID NO: 246), (ii) GAKL-SKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKL-SKKKKGYSGG (SEQ ID NO: 250), (vi) GGKL-SKKKKGSGGS (SEQ ID NO: 251), (vii) GGKL-SKKKKSGGSG (SEQ ID NO: 252), (viii) GGKLSKKKSGGSGG (SEQ ID NO: 253), (ix) GGKL-SKKSGGSGGS (SEQ ID NO: 254), (x) GGKL-SKSGGSGGSV (SEQ ID NO: 255), or (xi) GAKK-SKKRFSFKKS (SEQ ID NO: 256).

In some aspects, the polypeptide sequence of a Scaffold Y protein useful for the present disclosure consists of (i) GGKLSKKKKGYNVN (SEQ ID NO: 246), (ii) GAKL-SKKKKGYNVN (SEQ ID NO: 247), (iii) GGKQSKKKKGYNVN (SEQ ID NO: 248), (iv) GGKLAKKKKGYNVN (SEQ ID NO: 249), (v) GGKL-SKKKKGYSGG (SEQ ID NO: 250), (vi) GGKL-SKKKKGSGGS (SEQ ID NO: 251), (vii) GGKL-SKKKKSGGSG (SEQ ID NO: 252), (viii) GGKLSKKKSGGSGG (SEQ ID NO: 253), (ix) GGKL-SKKSGGSGGS (SEQ ID NO: 254), (x) GGKL-SKSGGSGGSV (SEQ ID NO: 255), or (xi) GAKK-SKKRFSFKKS (SEQ ID NO: 256).

Non-limiting examples of the Scaffold Y protein useful for the present disclosure are listed below. In some aspects, the Scaffold Y protein comprises an amino acid sequence set forth in TABLE 9. In some aspects, the Scaffold Y protein consists of an amino acid sequence set forth in TABLE 9.

TABLE 9

| SEQ ID NO: | Scaffold Protein: GX2X3X4X5X6-ED |
|---|---|
| 257 | GGKLSKKKKGYNVNDEKAKEKDKKAEGAA |
| 258 | GGKLSKKKKGYNVNDEKAKEKDKKAEGA |
| 259 | GGKLSKKKKGYNVNDEKAKEKDKKAEG |
| 260 | GGKLSKKKKGYNVNDEKAKEKDKKAE |
| 261 | GGKLSKKKKGYNVNDEKAKEKDKKA |
| 262 | GGKLSKKKKGYNVNDEKAKEKDKK |
| 263 | GGKLSKKKKGYNVNDEKAKEKDK |
| 264 | GGKLSKKKKGYNVNDEKAKEKD |
| 265 | GGKLSKKKKGYNVNDEKAKEK |
| 266 | GGKLSKKKKGYNVNDEKAKE |
| 267 | GGKLSKKKKGYNVNDEKAK |
| 268 | GGKLSKKKKGYNVNDEKA |
| 269 | GGKLSKKKKGYNVNDEK |
| 270 | GGKLSKKKKGYNVNDE |
| 271 | GGKLSKKKKGYNVND |
| 246 | GGKLSKKKKGYNVN |
| 272 | GGKLSKKKKGYNV |
| 273 | GGKLSKKKKGYN |
| 274 | GGKLSKKKKGY |
| 275 | GGKLSKKKKG |
| 276 | GGKLSKKKK |

TABLE 9-continued

| SEQ ID NO: | Scaffold Protein: GX2X3X4X5X6-ED |
|---|---|
| 238 | GGKLSKKK |
| 211 | GGKLSKK |
| 300 | GAKKSKKRFSFKKSFKLSGFSFKKNKKEA |
| 277 | GAKKSKKRFSFKKSFKLSGFSFKKNKKE |
| 278 | GAKKSKKRFSFKKSFKLSGFSFKKNKK |
| 279 | GAKKSKKRFSFKKSFKLSGFSFKKNK |
| 280 | GAKKSKKRFSFKKSFKLSGFSFKKN |
| 281 | GAKKSKKRFSFKKSFKLSGFSFKK |
| 282 | GAKKSKKRFSFKKSFKLSGFSFK |
| 283 | GAKKSKKRFSFKKSFKLSGFSF |
| 284 | GAKKSKKRFSFKKSFKLSGFS |
| 285 | GAKKSKKRFSFKKSFKLSGF |
| 286 | GAKKSKKRFSFKKSFKLSG |
| 287 | GAKKSKKRFSFKKSFKLS |
| 288 | GAKKSKKRFSFKKSFKL |
| 289 | GAKKSKKRFSFKKSFK |
| 290 | GAKKSKKRFSFKKSF |
| 291 | GAKKSKKRFSFKKS |
| 292 | GAKKSKKRFSFKK |
| 293 | GAKKSKKRFSFK |
| 294 | GAKKSKKRFSF |
| 295 | GAKKSKKRFS |
| 296 | GAKKSKKRF |
| 297 | GAKKSKKR |
| 298 | GAKKSKK |
| 301 | GAKKAKKRFSFKKSFKLSGFSFKKNKKEA |
| 348 | GAKKAKKRFSFKKSFKLSGFSFKKNKKE |
| 349 | GAKKAKKRFSFKKSFKLSGFSFKKNKK |
| 350 | GAKKAKKRFSFKKSFKLSGFSFKKNK |
| 351 | GAKKAKKRFSFKKSFKLSGFSFKKN |
| 352 | GAKKAKKRFSFKKSFKLSGFSFKK |
| 353 | GAKKAKKRFSFKKSFKLSGFSFK |
| 354 | GAKKAKKRFSFKKSFKLSGFSF |
| 355 | GAKKAKKRFSFKKSFKLSGFS |
| 356 | GAKKAKKRFSFKKSFKLSGF |
| 357 | GAKKAKKRFSFKKSFKLSG |
| 358 | GAKKAKKRFSFKKSFKLS |
| 359 | GAKKAKKRFSFKKSFKL |
| 360 | GAKKAKKRFSFKKSFK |
| 361 | GAKKAKKRFSFKKSF |
| 362 | GAKKAKKRFSFKKS |
| 363 | GAKKAKKRFSFKK |
| 364 | GAKKAKKRFSFK |
| 365 | GAKKAKKRFSF |
| 366 | GAKKAKKRFS |
| 367 | GAKKAKKRF |
| 368 | GAKKAKKR |
| 369 | GAKKAKK |
| 302 | GAQESKKKKKKRFSFKKSFKLSGFSFKK |
| 303 | GAQESKKKKKKRFSFKKSFKLSGFSFK |
| 304 | GAQESKKKKKKRFSFKKSFKLSGFSF |
| 305 | GAQESKKKKKKRFSFKKSFKLSGFS |
| 306 | GAQESKKKKKKRFSFKKSFKLSGF |
| 307 | GAQESKKKKKKRFSFKKSFKLSG |
| 308 | GAQESKKKKKKRFSFKKSFKLS |
| 309 | GAQESKKKKKKRFSFKKSFKL |
| 310 | GAQESKKKKKKRFSFKKSFK |
| 311 | GAQESKKKKKKRFSFKKSF |
| 312 | GAQESKKKKKKRFSFKKS |
| 313 | GAQESKKKKKKRFSFKK |
| 314 | GAQESKKKKKKRFSFK |
| 315 | GAQESKKKKKKRFSF |
| 316 | GAQESKKKKKKRFS |
| 317 | GAQESKKKKKKRF |
| 318 | GAQESKKKKKKR |
| 319 | GAQESKKKKKK |
| 320 | GAQESKKKKK |
| 321 | GAQESKKKK |
| 322 | GAQESKKK |
| 323 | GAQESKK |
| 324 | GSQSSKKKKKKFSFKKPFKLSGLSFKRNRK |
| 325 | GSQSSKKKKKKFSFKKPFKLSGLSFKRNR |
| 326 | GSQSSKKKKKKFSFKKPFKLSGLSFKRN |
| 327 | GSQSSKKKKKKFSFKKPFKLSGLSFKR |
| 328 | GSQSSKKKKKKFSFKKPFKLSGLSFK |
| 329 | GSQSSKKKKKKFSFKKPFKLSGLSF |
| 330 | GSQSSKKKKKKFSFKKPFKLSGLS |
| 331 | GSQSSKKKKKKFSFKKPFKLSGL |

TABLE 9-continued

| SEQ ID NO: | Scaffold Protein: GX2X3X4X5X6-ED |
|---|---|
| 332 | GSQSSKKKKKKFSFKKPFKLSG |
| 333 | GSQSSKKKKKKFSFKKPFKLS |
| 334 | GSQSSKKKKKKFSFKKPFKL |
| 335 | GSQSSKKKKKKFSFKKPFK |
| 336 | GSQSSKKKKKKFSFKKPF |
| 337 | GSQSSKKKKKKFSFKKP |
| 338 | GSQSSKKKKKKFSFKK |
| 339 | GSQSSKKKKKKFSFK |
| 340 | GSQSSKKKKKKFSF |
| 341 | GSQSSKKKKKKFS |
| 342 | GSQSSKKKKKKF |
| 343 | GSQSSKKKKKK |
| 344 | GSQSSKKKKK |
| 345 | GSQSSKKKK |
| 346 | GSQSSKKK |
| 347 | GSQSSKK |

In some aspects, the Scaffold Y protein useful for the present disclosure does not contain an N-terminal Met. In some aspects, the Scaffold Y protein comprises a lipidated amino acid, e.g., a myristoylated amino acid, at the N-terminus of the scaffold protein, which functions as a lipid anchor. In some aspects, the amino acid residue at the N-terminus of the scaffold protein is Gly. The presence of an N-terminal Gly is an absolute requirement for N-myristoylation. In some aspects, the amino acid residue at the N-terminus of the scaffold protein is synthetic. In some aspects, the amino acid residue at the N-terminus of the scaffold protein is a glycine analog, e.g., allylglycine, butylglycine, or propargylglycine.

In other aspects, the lipid anchor can be any lipid anchor known in the art, e.g., palmitic acid or glycosylphosphatidylinositols. Under unusual circumstances, e.g., by using a culture medium where myristic acid is limiting, some other fatty acids including shorter-chain and unsaturated, can be attached to the N-terminal glycine. For example, in BK channels, myristate has been reported to be attached post-translationally to internal serine/threonine or tyrosine residues via a hydroxyester linkage. Membrane anchors known in the art are presented in the following table:

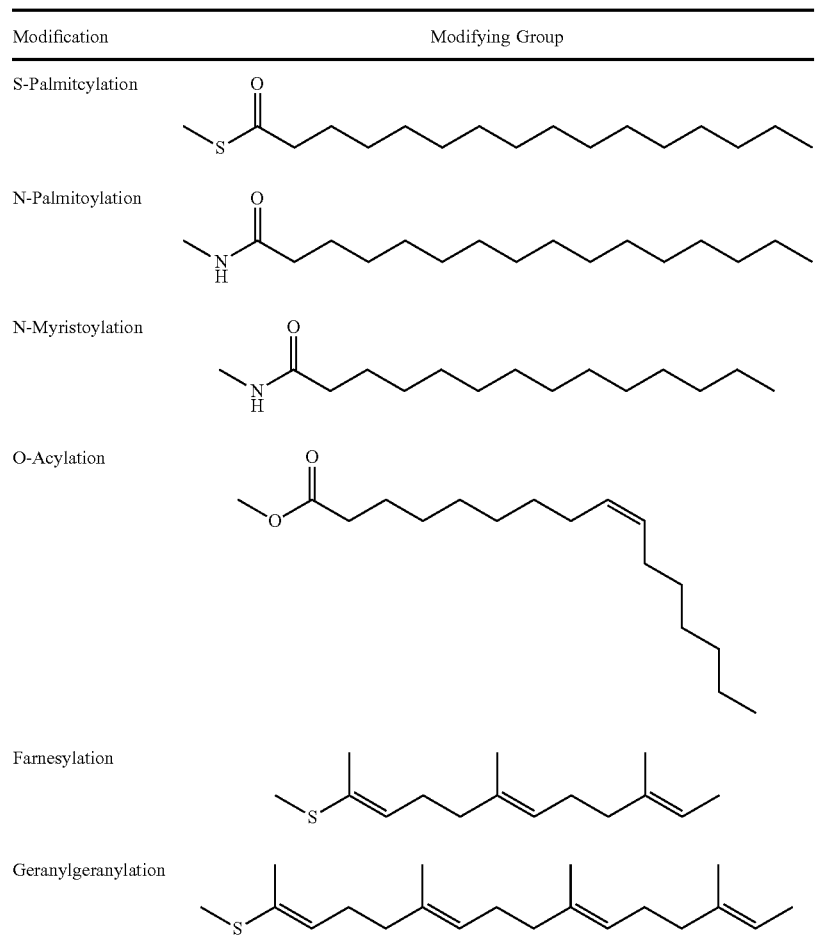

| Modification | Modifying Group |
|---|---|
| S-Palmitoylation | |
| N-Palmitoylation | |
| N-Myristoylation | |
| O-Acylation | |
| Farnesylation | |
| Geranylgeranylation | |

| Modification | Modifying Group |
|---|---|
| Cholesterol | 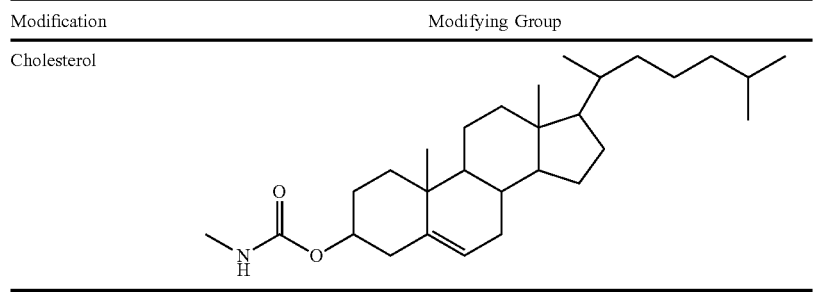 |

II.F Conjugated EVs (e.g., Exosomes)

Unlike antibodies, EVs (e.g., exosomes) can accommodate large numbers of molecules attached to their surface, e.g., on the order of thousands to tens of thousands of molecules per EV (e.g., exosome). EV (e.g., exosome)-drug conjugates thus represent a platform to deliver a high concentration of therapeutic compound to discrete cell types, while at the same time limiting overall systemic exposure to the compound, which in turn reduces off-target toxicity.

Figure 31:
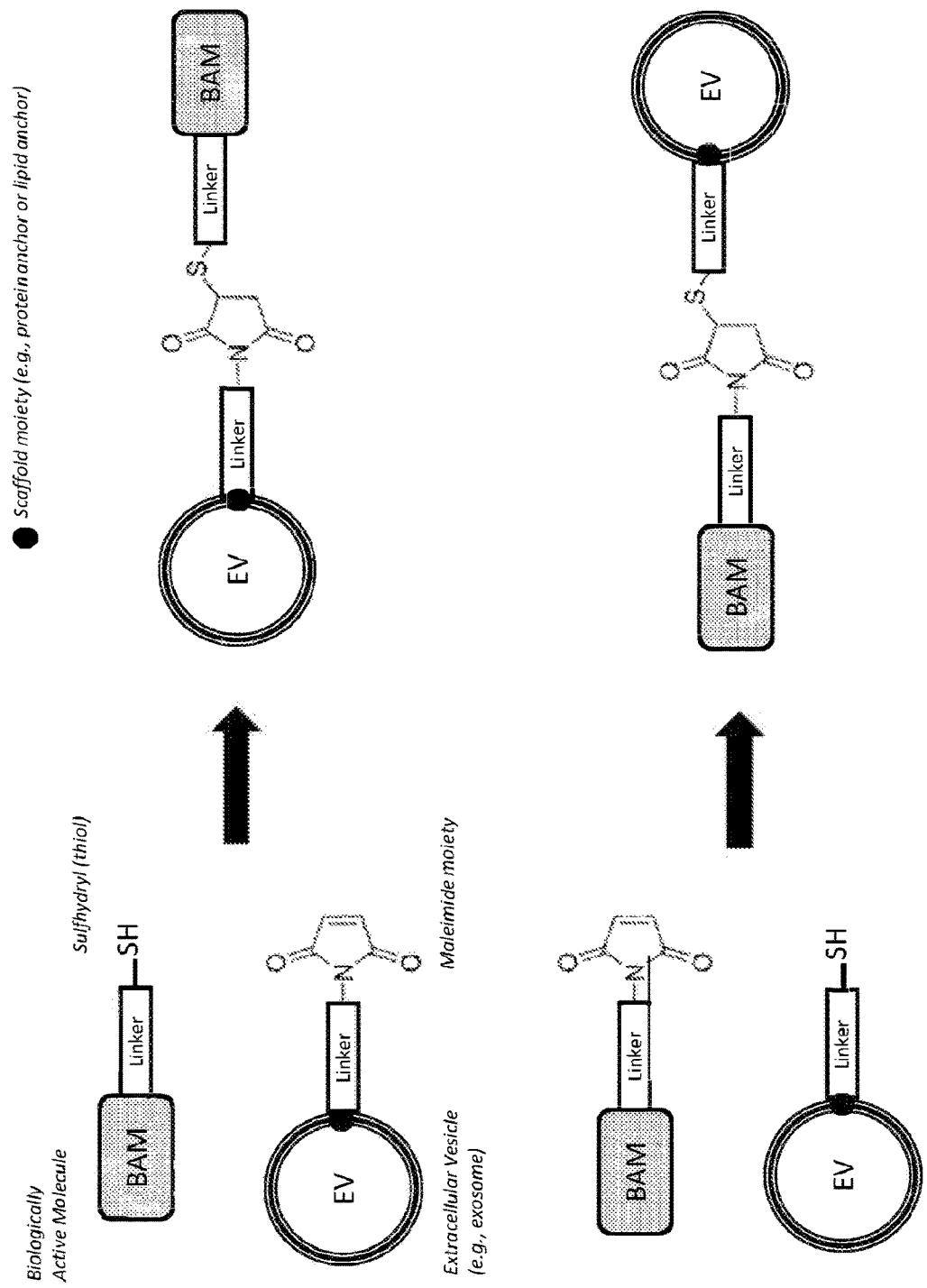
FIG. 31 is a schematic representation showing how maleimide chemistry can be used to chemically link a biologically active molecule (BAM) to an EV (e.g., an exosome), e.g., via a scaffold moiety described herein (e.g., a Scaffold X protein or fragment thereof or a lipid). The linkers depicted in the drawing are optional and when present can comprise a linker (e.g., a cleavable linker) or a combination thereof.

The present disclosure provide EVs, e.g., exosomes, that have been engineered by reacting a first molecular entity comprising a free thiol group with a second molecular entity comprising a maleimide group, wherein the maleimide moiety covalently links the first molecular entity with the second molecular entity via a maleimide moiety as presented in FIG. 31.

Non-limiting examples of biologically active molecules that can attached to an EV (e.g., exosome) via a maleimide moiety include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), morpholino, amino acids (e.g., amino acids comprising a detectable moiety or a toxin that disrupt translation), polypeptides (e.g., enzymes), lipids, carbohydrates, small molecules (e.g., small molecule drugs and toxins), antigens (e.g., vaccine antigens), adjuvants (e.g., vaccine adjuvants), etc.

In some aspects, an EV (e.g., exosome) of the present disclosure can comprise more than one type of biologically active molecule. In some aspects, biologically active molecules can be, e.g., small molecules such as cyclic dinucleotides, toxins such as auristatins (e.g., monoethyl auristatin E, MMAE), antibodies (e.g., naked antibodies or antibody-drug conjugates), STING agonists, tolerizing agents, antisense oligonucleotides, PROTACs, morpholinos, lysophosphatidic acid receptor antagonists (e.g., LPA1 antagonists) or any combinations thereof. In some aspects, an EV (e.g., exosome) of the present disclosure can comprise, e.g., a vaccine antigen and optionally a vaccine adjuvant. In some aspects, an EV (e.g., exosome) of the present disclosure can comprise a therapeutic payload (e.g., a STING or one payload disclosed below) and a targeting moiety and/or a tropism moiety.

Accordingly, in some aspects, the present disclosure provides molecular entities as presented in FIG. 31, wherein an EV (e.g., an exosome) or any molecular component thereof such as a polypeptide (e.g., a Scaffold X protein or fragment thereof), a lipid, a lipoprotein, a glycoprotein, or any variant or derivative of a naturally occurring or non-naturally occurring protein located on an EV (e.g., exosome) can be chemically linked via a maleimide moiety to a biologically active molecule, e.g., a therapeutic payload, a targeting moiety, a tropism moiety, or any combination thereof. As depicted in FIG. 31, in some aspects, an EV (e.g., an exosome) or molecular component thereof comprising a sulfhydryl (thiol) group can react with a maleimide group attached to a biologically active moiety. In other aspects, an EV (e.g., an exosome) or molecular component thereof comprising a maleimide group can react with a sulfhydryl (thiol) group present in a biologically active moiety. In both cases, the final product is a biologically active molecule chemically attached to an EV (e.g., an exosome) via a thioether bond.

II.G Malemide Moiety

As described above, in some aspects, a linker that can be used with the present disclosure can comprise a maleimide moiety (i.e., a "maleimide linker"). Linkers can be introduced into maleimide moieties using techniques known in the art (e.g., chemical conjugation, recombinant techniques, or peptide synthesis). In some aspects, the linkers can be introduced using recombinant techniques. In other aspects, the linkers can be introduced using solid phase peptide synthesis. In certain aspects, a maleimide moiety disclosed herein can contain simultaneously one or more linkers that have been introduced using recombinant techniques and one or more linkers that have been introduced using solid phase peptide synthesis or methods of chemical conjugation known in the art.

Accordingly, in some aspects, an EV (e.g., exosome) disclosed herein can comprise one or more payloads (e.g., antigen, adjuvant, and/or immune modulator), wherein one or more of the payloads are attached to the EV via a maleimide linker. In certain aspects, an EV (e.g., exosome) disclosed herein can further comprise one or more targeting moieties, wherein one or more of the targeting moieties are attached to the EV via a maleimide linker. As described herein, in some aspects, one or more of the payloads and/or one or more of the targeting moieties are linked to an EV (e.g., exosome) via a scaffold moiety (e.g., Scaffold X and/or Scaffold Y). In certain aspects, one or more of the payloads and/or one or more of the targeting moieties are covalently attached to a scaffold moiety via a maleimide moiety. In some aspects, the scaffold moiety comprises Scaffold X and/or Scaffold Y. Non-limiting examples of other scaffold moieties that can be used with the present disclosure include: aminopeptidase N (CD13); Neprilysin (membrane metalloendopeptidase; MME); ectonucleotide pyrophosphatase/phosphodiesterase family member 1 (ENPP1); neuropilin-1 (NRP1); CD9, CD63, CD81, PDGFR, GPI anchor proteins, lactadherin, LAMP2, and LAMP2B, a fragment thereof, and any combination thereof.

As used herein the term "maleimide moiety" or "MM" refers to a bifunctional chemical moiety linking an EV, e.g., exosome, to a linker or a biologically active molecule and comprises the maleimide group:

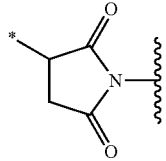 [SMILES: *C1CC(=O)N(*)C1=O]

wherein * indicates the attachment point to any thiol group on the EV, e.g., exosome, (e.g., a free thiol present in a Scaffold X), and the wavy line indicates the attachment site to the rest of the maleimide moiety. In some aspects, * indicates at attachment point to any thiol group on a payload and/or targeting moiety, and the wavy line indicates the attachment site to the rest of the maleimide moiety to the EV, e.g., exosome (e.g., a Scaffold X).

In some aspects, the maleimide moiety attaches to a sulfur atom attached to the EV (e.g., exosome), e.g., a naturally occurring sulfur atom in a thiol group or a sulfur atom introduced via chemical modification or via mutation.

In some aspects, the maleimide moiety has the formula (I):

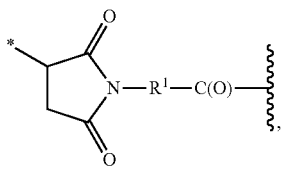

wherein
(i) $R^1$ is selected from the group consisting of —$C_{1-10}$ alkylene-, —$C_{3-8}$ carbocyclo-, —O—($C_{1-8}$ alkylene)-, -arylene-, —$C_{1-10}$ alkylene-arylene-, alkylene-, —$C_{1-10}$ alkylene-($C_{3-8}$ carbocyclo)-, —($C_{3-8}$ carbocyclo)-$C_{1-10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, —($CH_2CH_2O)_r$—, and —($CH_2CH_2O)_r$—$CH_2$—;
(ii) r is an integer, e.g., from 1 to 10;
(iii) * indicates the attachment point to any available reactive sulfur atom, e.g., a sulfur in a thiol group, present on the EV (e.g., exosome); and,
(iv) the wavy line indicates the attachment site of the maleimide moiety to the biologically active molecule (i.e., payload).

In some aspects, $R^1$ is —$C_{1-8}$ alkylene-, —$C_{3-6}$ carbocyclo-, —O—($C_{1-6}$ alkylene)-, -arylene-, —$C_{1-8}$ alkylene-arylene-, -arylene-$C_{1-8}$ alkylene-, —$C_{1-8}$ alkylene-($C_{3-6}$ carbocyclo)-, —($C_{3-6}$ carbocyclo)-$C_{1-8}$ alkylene-, —$C_{3-6}$ heterocyclo-, —$C_{1-8}$ alkylene-($C_{3-6}$ heterocyclo)-, —($C_{3-6}$ heterocyclo)-$C_{1-8}$ alkylene-, -($CH_2CH_2O)_r$—, and —($CH_2CH_2O)_r$—$CH_2$—; where r is an integer, e.g., from 1 to 10.

In some aspects, $R^1$ is —$(CH_2)_s$—, cyclopentyl, cyclohexyl, —O—$(CH_2)_s$—, -phenyl-, —$CH_2$-phenyl-, -phenyl-$CH_2$—, —$CH_2$-cyclopentyl-, -cyclopentyl-$CH_2$—, —$CH_2$-cyclohexyl-, -cyclohexyl-$CH_2$—, —($CH_2CH_2O)_r$—, and —($CH_2CH_2O)_r$—$CH_2$—; where r is an integer, e.g., from 1 to 6.

In some aspects, $R^1$ is —$(CH_2)_s$—, wherein s is, e.g., 4, 5, or 6.

In some aspects, the maleimide moiety has the formula (II), wherein $R^1$ is —$(CH_2)_5$—:

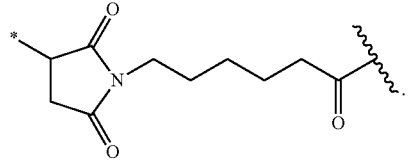

In some aspects, the maleimide moiety has the formula (III), wherein $R^1$ is —($CH_2CH_2O)_r$—$CH_2$—, and wherein r is 2:

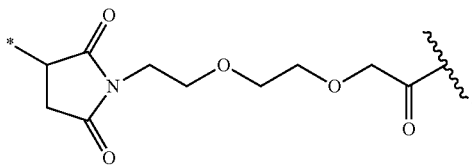

In some aspects, the maleimide moiety is covalently linked to a functional group present on the EV (e.g., exosome), wherein the functional group is a sulfhydryl (thiol) group. In one aspect, the sulfhydryl group is on a protein on the surface of the EV (e.g., exosome), e.g., Scaffold X, or a variant thereof. For example, in some aspects, the sulfhydryl group can be present on a thiol lipid, e.g., cholesterol-SH, DSPE-SH, or derivatives thereof, e.g., cholesterol-PEG-SH or DSPE-PEG-SH.

In some aspects, the maleimide moiety is covalently linked to a functional group present on the EV (e.g., exosome) which has been chemically derivatized to provide a maleimide moiety. For example, in certain aspects, an amine functional group present on the EV (e.g., exosome) (e.g., an amine on the side chain of a lysine or an arginine, or terminal amine group of a protein) can be derivatized with a bifunctional reagent comprising a succinimide moiety and a maleimide moiety.

In some aspects, a carboxyl functional group present on the EV (e.g., exosome) (e.g., a carboxyl on the side chain of a glutamic acid or aspartic acid, or terminal carboxyl group of a protein) can be derivatized with a bifunctional reagent comprising an isocyanate moiety and a maleimide moiety. In yet other aspects, a carbonyl (oxidized carbohydrate) present on the EV (e.g., exosome) can be derivatized with a bifunctional reagent comprising a hydrazine moiety and a maleimide moiety.

In general, the disclosures provided herein can be practiced using any reagent, e.g., a bifunctional or multifunctional reagent, that upon reacting with a molecule present on the surface (external surface or luminal surface) of the EV (e.g., exosome) (e.g., a protein, lipid, sugar) will covalently or non-covalently modify the molecule to yield a modified molecule comprising at least one maleimide moiety. The molecule present on the surface (external surface or luminal surface) of the EV (e.g., exosome) can be naturally occurring, or it can be non-naturally occurring, i.e., it has been modified, e.g., via chemical modification, incubation with a composition comprising the non-naturally occurring molecule, or via mutation (e.g., by introducing one or more cysteine amino acids into a protein via mutation).

Bifunctional reagents comprising a maleimide moiety, reagents in which a number of maleimide-containing units can multimerize, or maleimide-containing reagents that can add a functional moiety (e.g., a PEG) via the maleimide group include, e.g., bifunctional reagents comprising a hydrazine moiety and a maleimide moiety, bifunctional reagents comprising an isocyanate moiety and a maleimide moiety, bifunctional reagents comprising an N-hydroxy succinimidyl ester moiety and a maleimide moiety, bifunctional reagents comprising a succinimide moiety and a maleimide moiety, biotin-maleimide, streptavidin-maleimide, N-4-maleimide butyric acid, N-(4-maleimidebutyloxy) succinimide, N-[5-(3'-maleimide propylamide)-1-carboxypentyl]iminodiacetic acid, maleimide-PEG-succinimidyl esters (e.g., maleimide-$PEG_{12}$-succinimidyl ester, maleimide-$PEG_2$-succinimidyl ester, maleimide-$PEG_{2000}$-succinimidyl ester, maleimide-$PEG_{5000}$-succinimidyl ester, or maleimide-$PEG_n$-succinimidyl ester wherein 1<n<5000), maleimide-PEG-maleimide (e.g., maleimide-$PEG_{12}$-maleimide, maleimide-$PEG_2$-maleimide, maleimide-$PE_{2000}$-maleimide, maleimide-$PEG_{5000}$-maleimide, or maleimide-$PEG_n$-maleimide wherein 1<n<5000), maleimide-OH, maleimide-$PEG_n$-OH wherein 1<n<5000, Maleimide-poly(ethylene glycol)-b-poly(ε-caprolactone), (S)-(−)-N-(1-phenylethyl) maleimide, N-(4-Chlorophenyl)maleimide, N-(1-Pyrenyl) maleimide, methoxypolyethylene glycol maleimide, poly(ethylene glycol) methyl ether maleimide, N-(4,4,5,5,6,6,7,7,8,8,9,9,10,10,11,11,11-Heptadecafluoroundecyl) maleimide, deferoxamine-maleimide (i.e., a chelator-maleimide), maleimide glycidyl ether, bifunctional maleimido DTPA, bifunctional NOTA-maleimide chelators, homobifunctional maleimide crosslinkers (i.e., those which have a maleimide group at each end), bis-maleimidopolyalkylene glycol, DBCO-maleimide, benzotriazole maleimide, alkyne maleimide, maleimide functionalized lipids, maleimide functionalized PEG lipid, and in general any molecule comprising at least one maleimide moiety at least one additional reactive moiety (e.g., maleimide or another reactive group) and one or more optional linkers (e.g., PEG or another polymer such as polyglycerol).

II.H Linkers

As described supra, extracellular vesicles (EVs) of the present disclosure (e.g., exosomes and nanovesicles) can comprises one or more linkers that link a molecule of interest (e.g., antigen, adjuvant, or immune modulator) to the EVs (e.g., to the exterior surface or on the luminal surface). In some aspects, the molecule of interest (i.e., payload) (e.g., antigen, adjuvant, or immune modulator) is linked to the EVs directly or via a scaffold moiety (e.g., Scaffold X or Scaffold Y). For example, in certain aspects, a payload (e.g., an antigen, adjuvant, and/or immune modulator) is linked to the exterior surface of an exosome via Scaffold X. In further aspects, a payload (e.g., an antigen, adjuvant, and/or immune modulator) is linked to the luminal surface of an exosome via Scaffold X or Scaffold Y. In some aspects, a payload (e.g., an antigen, adjuvant, and/or immune modulator) is linked to the luminal surface of an exosome via Scaffold X. In some aspects, a payload (e.g., an antigen, adjuvant, and/or immune modulator) is linked to the luminal surface of an exosome via Scaffold Y. In some aspects, a payload (e.g., an antigen, adjuvant, and/or immune modulator) is linked to the luminal surface of an exosome via Scaffold X and Scaffold Y. In some aspects, a payload (e.g., an antigen, adjuvant, and/or immune modulator) is conjugated to Scaffold X via a linker (e.g., those described herein). In certain aspects, a payload (e.g., an antigen, adjuvant, and/or immune modulator) is conjugated to Scaffold X using more than one linker (i.e., "linker combination"). In some aspects, a payload (e.g., an antigen, adjuvant, and/or immune modulator) is conjugated to Scaffold Y via a linker (e.g., those described herein). In certain aspects, a payload (e.g., an antigen, adjuvant, and/or immune modulator) is conjugated to Scaffold Y using a linker combination. In some aspects, a linker combination comprises at least 2, at least 3, at least 4, at least 5, or at least 6 or more different linkers disclosed herein. In some aspects, linkers in a linker combination can be linked by an ester linkage (e.g., phosphodiester or phosphorothioate ester).

The linker can be any chemical moiety known in the art.

As used herein, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. When multiple linkers are present, each of the linkers can be the same or different. Generally, linkers provide flexibility or prevent/ameliorate steric hindrances. Linkers are not typically cleaved; however in certain aspects, such cleavage can be desirable. Accordingly, in some aspects, a linker can comprise one or more protease-cleavable sites, which can be located within the sequence of the linker or flanking the linker at either end of the linker sequence.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker can comprise at least about 110, at least about 120, at least about 130, at least about 140, at least about 150, at least about 160, at least about 170, at least about 180, at least about 190, or at least about 200 amino acids.

In other aspects, the peptide linker can comprise at least about 200, at least about 300, at least about 400, at least about 500, at least about 600, at least about 700, at least about 800, at least about 900, or at least about 1,000 amino acids. The peptide linker can comprise between 1 and about 5 amino acids, between 1 and about 10 amino acids, between 1 and about 20 amino acids, between about 10 and about 50 amino acids, between about 50 and about 100 amino acids, between about 100 and about 200 amino acids, between about 200 and about 300 amino acids, between about 300 and about 400 amino acids, between about 400 and about 500 amino acids, between about 500 and about 600 amino acids, between about 600 and about 700 amino acids, between about 700 and about 800 amino acids, between about 800 and about 900 amino acids, or between about 900 and about 1000 amino acids.

As described herein, in some aspects, a linker useful for the present disclosure comprises a glycine/serine linker. In some aspects, the peptide linker is glycine/serine linker according to the formula [(Gly)n-Ser]m (SEQ ID NO: 374), where n is any integer from 1 to 100 and m is any integer from 1 to 100. In some aspects, the glycine/serine linker is according to the formula [(Gly)x-Sery]z (SEQ ID NO: 375), wherein x in an integer from 1 to 4, y is 0 or 1, and z is an integers from 1 to 50. In some aspects, the peptide linker comprises the sequence Gn (SEQ ID NO: 376), where n can be an integer from 1 to 100. In some aspects, the peptide linker can comprise the sequence (GlyAla)n (SEQ ID NO: 377), wherein n is an integer between 1 and 100. In some aspects, the peptide linker can comprise the sequence (GlyGlySer)n (SEQ ID NO: 378), wherein n is an integer between 1 and 100. In certain aspects, the peptide linker comprises the sequence GGGG (SEQ ID NO: 197).

In some aspects, the peptide linker comprises the sequence (GGGS)n (SEQ ID NO: 203). In certain aspects, the peptide linker comprises the sequence (GGS)n (GGGGS)n (SEQ ID NO: 204). In such aspects, n can be an integer from 1 to 100. In some aspects, n can be an integer from one to 20, i.e., 1, 2, 3, 4, 5, 6, 7, 8, 9, 10, 11, 12, 13, 14, 15, 16, 17, 18, 19, or 20. In some aspects, n is an integer from 1 to 100.

Examples of linkers that are useful for the present disclosure include, but are not limited to, GGG, SGGSGGS (SEQ ID NO: 198), GGSGGSGGSGGSGGG (SEQ ID NO: 199), GGSGGSGGGGSGGGGS (SEQ ID NO: 200), GGSGGSGGSGGSGGSGGS (SEQ ID NO: 201), or GGGGSGGGGSGGGGS (SEQ ID NO: 202). In some aspects, the linker is a poly-G sequence (GGGG)n (SEQ ID NO: 373), where n can be an integer from 1-100.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect, the peptide linker can comprise non-naturally occurring polypeptides which are modified forms of naturally occurring polypeptides (e.g., comprising a mutation such as an addition, substitution or deletion).

In some aspects, the peptide linker can comprise non-naturally occurring amino acids. In yet other aspects, the peptide linker can comprise naturally occurring amino acids occurring in a linear sequence that does not occur in nature. In still other aspects, the peptide linker can comprise a naturally occurring polypeptide sequence.

In some aspects, the linker comprises a non-peptide linker. In other aspects, the linker consists of a non-peptide linker. In some aspects, the non-peptide linker can be, e.g., maleimido caproyl (MC), maleimido propanoyl (MP), methoxyl polyethyleneglycol (MPEG), succinimidyl 4-(N-maleimidomethyl)-cyclohexane-1-carboxylate (SMCC), m-maleimidobenzoyl-N-hydroxysuccinimide ester (MBS), succinimidyl 4-(p-maleimidophenyl)butyrate (SMPB), N-succinimidyl(4-iodoacetyl)aminobenzonate (SIAB), succinimidyl 6-[3-(2-pyridyldithio)-propionamide]hexanoate (LC-SPDP), 4-succinimidyloxycarbonyl-alpha-methyl-alpha-(2-pyridyldithio)toluene (SMPT), etc. (see, e.g., U.S. Pat. No. 7,375,078, which is herein incorporated by reference in its entirety).

In some aspects, linkers disclosed herein can be introduced into maleimide moieties using techniques known in the art (e.g., chemical conjugation, recombinant techniques, or peptide synthesis). In some aspects, the linkers can be introduced using recombinant techniques. In other aspects, the linkers can be introduced using solid phase peptide synthesis. In certain aspects, a maleimide moiety disclosed herein can contain simultaneously one or more linkers that have been introduced using recombinant techniques and one or more linkers that have been introduced using solid phase peptide synthesis or methods of chemical conjugation known in the art. In some aspects, a linker can comprise a cholesterol moiety. See, e.g., US 2008/0085869 A1, which is herein incorporated by reference in its entirety.

Linkers can be susceptible to cleavage ("cleavable linker") thereby facilitating release of the biologically active molecule (e.g., antigen, adjuvant, or immune modulator). Therefore, in some aspects, a linker that can be used with the present disclosure comprises a cleavable linker. Such cleavable linkers can be susceptible, for example, to acid-induced cleavage, photo-induced cleavage, peptidase-induced cleavage, esterase-induced cleavage, and disulfide bond cleavage, at conditions under which the biologically active molecule remains active. In some aspects, a cleavable linker comprises a spacer. In certain aspects, a spacer comprises PEG.

In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof.

In some aspects, the linker comprises a non-cleavable linker (i.e., resistant or substantially resistant to cleavage).

In some aspects, a linker combination disclosed herein comprises only cleavable linkers. In some aspects, a linker combination disclosed herein comprises only non-cleavable linkers. In some aspects, a linker combination disclosed herein comprises both cleavable and non-cleavable linkers. Additional disclosure relating to cleavable and non-cleavable linkers that can be used with the present disclosure are provided below.

II.H.1 Non-Cleavable Linkers

Non-cleavable linkers are any chemical moiety capable of linking two or more components of a modified biologically active molecule of the present disclosure (e.g., a biologically active molecule and an anchoring moiety; a biologically active molecule and a cleavable linker; an anchoring moiety and a cleavable linker) in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage.

Furthermore, "non-cleavable" refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which a cyclic dinucleotide and/or the antibody does not lose its activity. In some aspects, the biologically active molecule is attached to the linker via another linker, e.g., a self-immolative linker.

In some aspects, a linker combination disclosed herein comprises a non-cleavable linker comprising, e.g., tetraethylene glycol (TEG), hexaethylene glycol (HEG), polyethylene glycol (PEG), succinimide, or any combination thereof. In some aspects, the non-cleavable linker comprises a spacer unit to link the biologically active molecule to the non-cleavable linker.

In some aspects, one or more non-cleavable linkers comprise smaller units (e.g., HEG, TEG, glycerol, C2 to C12 alkyl, and the like) linked together. In some aspects, the linkage is an ester linkage (e.g., phosphodiester or phosphorothioate ester) or other linkage. Examples of non-cleavable linkers that can be used with the present disclosure are known in the art, see, e.g., U.S. Pat. No. 7,569,657 B2; U.S. Pat. No. 8,465,730 B1; U.S. Pat. No. 7,087,229 B2; and U.S. Publ. No. 2014/0193849 A1, each of which is herein incorporated by reference in its entirety.

II.H.2 Cleavable Linkers

As described herein, the one or more linkers (i.e., linker combination) that can be used to link a molecule of interest (e.g., antigen, adjuvant, or immune modulator) to the EVs (e.g., exosomes) can comprise cleavable linkers. The term "cleavable linker" refers to a linker comprising at least one linkage or chemical bond that can be broken or cleaved. As used herein, the term "cleave" refers to the breaking of one or more chemical bonds in a relatively large molecule in a manner that produces two or more relatively smaller molecules. Cleavage can be mediated, e.g., by a nuclease, peptidase, protease, phosphatase, oxidase, or reductase, for example, or by specific physicochemical conditions, e.g., redox environment, pH, presence of reactive oxygen species, or specific wavelengths of light.

In some aspects, the term "cleavable," as used herein, refers, e.g., to rapidly degradable linkers, such as, e.g., phosphodiester and disulfides, while the term "non-cleavable" refers, e.g., to more stable linkages, such as, e.g., nuclease-resistant phosphorothioates.

In some aspects, the cleavable linker comprises a dinucleotide or trinucleotide linker, a disulfide, an imine, a thioketal, a val-cit dipeptide, or any combination thereof.

In some aspects, the cleavable linker comprises valine-alanine-p-aminobenzylcarbamate, valine-citrulline-p-aminobenzylcarbamate, or both.

In some aspects, the cleavable linker comprises redox cleavable linkers, reactive oxygen species (ROS) cleavable linkers, pH dependent cleavable linkers, enzymatic cleavable linkers, protease cleavable linkers, esterase cleavable linkers, phosphatase cleavable linkers, photoactivated cleavable linkers, self-immolative linkers, or combinations thereof. Additional disclosure relating to one or more of these cleavable linkers are provided further below and also known in the art, see, e.g., US 2018/0037639 A1; Trout et al., 79 Proc. Natl. Acad. Sci. USA, 626-629 (1982); Umemoto et al. 43 Int. J. Cancer, 677-684 (1989); Cancer Res. 77(24):7027-7037 (2017); Doronina et al. Nat. Biotechnol. 21:778-784 (2003); U.S. Pat. No. 7,754,681 B2; US 2006/0269480; US 2010/0092496; US 2010/0145036; US 2003/0130189; US 2005/0256030, each of which is herein incorporated by reference in its entirety.

II.H.2.a Redox Cleavable Linkers

In some aspects, the linker combination comprises a redox cleavable linker. In certain aspects, such a linker can comprise a redox cleavable linking group that is cleaved upon reduction or upon oxidation.

In some aspects, the redox cleavable linker contains a disulfide bond, i.e., it is a disulfide cleavable linker. In some aspects, the redox cleavable linker can be reduced, e.g., by intracellular mercaptans, oxidases, reductases, or combinations thereof.

II.H.2.b Reactive Oxygen Species (ROS) Cleavable Linkers

In some aspects, the linker combination can comprise a cleavable linker which can be cleaved by a reactive oxygen species (ROS), such as superoxide (Of) or hydrogen peroxide ($H_2O_2$), generated, e.g., by inflammation processes such as activated neutrophils. In some aspects, the ROS cleavable linker is a thioketal cleavable linker. See, e.g., U.S. Pat. No. 8,354,455B2, which is herein incorporated by reference in its entirety.

II.H.2.c pH Dependent Cleavable Linkers

In some aspects, the linker is an acid labile linker comprising an acid cleavable linking group, which is a linking group that is selectively cleaved under acidic conditions (pH<7).

In some aspects, the acid cleavable linking group is cleaved in an acidic environment, e.g., about 6.0, about 5.5, about 5.0 or less. In some aspects, the pH is about 6.5 or less. In some aspects, the linker is cleaved by an agent such as an enzyme that can act as a general acid, e.g., a peptidase (which can be substrate specific) or a phosphatase. Within cells, certain low pH organelles, such as endosomes and lysosomes, can provide a cleaving environment to the acid cleavable linking group. Although the pH of human serum is 7.4, the average pH in cells is slightly lower, ranging from about 7.1 to 7.3. Endosomes also have an acidic pH, ranging from 5.5 to 6.0, and lysosomes are about 5.0 at an even more acidic pH. Accordingly, pH dependent cleavable linkers are sometimes called endosomically labile linkers in the art.

In some aspects, the acid cleavable group can have the general formula —C=NN—, C (O) O, or —OC (O). In another non-limiting example, when the carbon attached to the ester oxygen (alkoxy group) is attached to an aryl group, a substituted alkyl group, or a tertiary alkyl group such as dimethyl pentyl or t-butyl, for example. Examples of acid cleavable linking groups include, but are not limited to, amine, imine, amino ester, benzoic imine, diortho ester, polyphosphoester, polyphosphazene, acetal, vinyl ether, hydrazone, cis-aconitate, hydrazide, thiocarbamoyl, imizine, azidomethyl-methylmaleic anhydride, thiopropionate, a masked endosomolytic agent, a citraconyl group, or any combination thereof. Disulfide linkages are also susceptible to pH.

In some aspects, the linker comprises a low pH-labile hydrazone bond. Such acid-labile bonds have been extensively used in the field of conjugates, e.g., antibody-drug conjugates. See, for example, Zhou et al, Biomacromolecules 2011, 12, 1460-7; Yuan et al, Acta Biomater. 2008, 4, 1024-37; Zhang et al, Acta Biomater. 2007, 6, 838-50; Yang et al, J. Pharmacol. Exp. Ther. 2007, 321, 462-8; Reddy et al, Cancer Chemother. Pharmacol. 2006, 58, 229-36; Doronina et al, Nature Biotechnol. 2003, 21, 778-84, each of which are hereby incorporated by reference in its entirety.

In some aspects, the linker comprises a low pH-labile bond selected from the following: ketals that are labile in acidic environments (e.g., pH less than 7, greater than about 4) to form a diol and a ketone; acetals that are labile in acidic environments (e.g., pH less than 7, greater than about 4) to form a diol and an aldehyde; imines or iminiums that are labile in acidic environments (e.g., pH less than 7, greater than about 4) to form an amine and an aldehyde or a ketone; silicon-oxygen-carbon linkages that are labile under acidic condition; silicon-nitrogen (silazane) linkages; silicon-carbon linkages (e.g., arylsilanes, vinylsilanes, and allylsilanes); maleamates (amide bonds synthesized from maleic anhydride derivatives and amines); ortho esters; hydrazones; activated carboxylic acid derivatives (e.g., esters, amides) designed to undergo acid catalyzed hydrolysis); or vinyl ethers.

Further examples can be found in U.S. Pat. Nos. 9,790,494 B2 and 8,137,695 B2, the contents of which are incorporated herein by reference in their entireties.

II.H.2.d Enzymatic Cleavable Linkers

In some aspects, the linker combination can comprise a linker cleavable by intracellular or extracellular enzymes, e.g., proteases, esterases, nucleases, amidades. The range of enzymes that can cleave a specific linker in a linker combination depends on the specific bonds and chemical structure of the linker. Accordingly, peptidic linkers can be cleaved, e.g., by peptidades, linkers containing ester linkages can be cleaved, e.g., by esterases; linkers containing amide linkages can be cleaved, e.g., by amidades; etc.

II.H.2.e Esterase Cleavable Linkers

Some linkers are cleaved by esterases ("esterase cleavable linkers"). Only certain esters can be cleaved by esterases and amidases present inside or outside of cells. Esters are formed by the condensation of a carboxylic acid and an alcohol. Simple esters are esters produced with simple alcohols, such as aliphatic alcohols, and small cyclic and small aromatic alcohols. Examples of ester-based cleavable linking groups include, but are not limited to, esters of alkylene, alkenylene and alkynylene groups. The ester cleavable linking group has the general formula —C (O) O— or —OC (O)—.

II.H.2.f Phosphatase Cleavable Linkers

In some aspects, a linker combination can includes a phosphate-based cleavable linking group is cleaved by an agent that degrades or hydrolyzes phosphate groups. An example of an agent that cleaves intracellular phosphate groups is an enzyme such as intracellular phosphatase. Examples of phosphate-based linking groups are —O—P (O) (OR k) —O—, O—P (S) ($OR_k$) —O—, —O—P (S) ($SR_k$) —O—, —S—P (O) ($OR_k$) —O—, —O—P (O) ($OR_k$) —S—, —S—P (O) ($OR_k$) —S—, —O—P (S) ($OR_k$) —S—, —SP (S) ($OR_k$) —O—, —OP (O) ($R_k$) —O—, —OP (S) ($R_k$) —O—, —SP (O) ($R_k$) —O—, —SP (S) ($R_k$) —O—, —SP (O) ($R_k$) —S—, or —OP (S) ($R_k$) —S—.

In some aspects, $R_k$ is any of the following: $NH_2$, $BH_3$, $CH_3$, $C_{1-6}$ alkyl, $C_{6-10}$ aryl, $C_{1-6}$ alkoxy and $C_{6-10}$ aryl-oxy. In some aspects, $C_{1-6}$ alkyl and $C_{6-10}$ aryl are unsubstituted. Further non-limiting examples include —O—P (O) (OH) —O—, —O—P (S) (OH) —O—, —O—P (S) (SH) —O—, —S—P (O) (OH) —O—, —O—P (O) (OH) —S—, —S—P (O) (OH) —S—, —O—P (S) (OH) —S—, —S—P (S) (OH) —O—, —O—P (O) (H) —O—, —O—P (S) (H) —O—, —S —P (O) (H) —O—, —SP (S) (H) —O—, —SP (O) (H) —S—, —OP (S) (H)—S—, or —O—P (O) (OH) —O—.

II.H.2.g Photoactivated Cleavable Linkers

In some aspects, the combination linker comprises a photoactivated cleavable linker, e.g., a nitrobenzyl linker or a linker comprising a nitrobenzyl reactive group.

Conventional vaccines have demonstrated a few challenges. In some aspects, conventional vaccines are not capable of inducing robust T cell response. Moreover, any response generated by conventional vaccines can be limited to tissue specific responses and/or lack antibody diversity. In some aspects, the EVs, e.g., exosomes, comprising an antigen useful for the present disclosure exhibit advantageous properties compared to an antigen (vaccine) alone. In some aspects, the EVs (e.g., exosomes) of the present disclosure is capable of inducing improved T cell directed immune response compared to the antigen alone. In some aspects, the EVs (e.g., exosomes) of the present disclosure is capable of inducing T cell response in peripheral tissues. In some aspects, the EVs (e.g., exosomes) of the present disclosure exhibit enhanced antibody diversity and/or avidity.

Conventional vaccines, e.g., antigens, also face problems of poor uptake by antigen presenting cells, poor immunogenicity, and/or limited complexity. Compared to the conventional antigens, the EVs (e.g., exosomes) of the present disclosure is capable of presenting multiple antigens on an EV (e.g., exosomes) and/or modulating antigen exposure to specific immune cells (e.g., B cells and/or dendritic cells).

Adjuvants for conventional vaccines also have challenges. For example, the potential toxicity of adjuvants limit its route of administration, dose, and combinations of adjuvants. In addition, RNA and/or DNAs are poor adjuvants. The EVs (e.g., exosomes) of the present disclosure overcome these problems. The EVs (e.g., exosomes) of the present disclosure allow selective co-delivery of antigen(s) and adjuvant(s) (and/or other payloads disclosed herein) to antigen presenting cells; this can reduce the adjuvant dose and enables combinations, thereby improving overall safety of the vaccine.

III. Producer Cell for Production of Engineered EVs, e.g., Exosomes

EVs, e.g., exosomes, of the present disclosure can be produced from a cell grown in vitro or a body fluid of a subject. When exosomes are produced from in vitro cell culture, various producer cells, e.g., HEK293 cells, CHO cells, and MSCs, can be used. In certain aspects, a producer cell is not a naturally-existing dendritic cell, macrophage, B cell, mast cell, neutrophil, Kupffer-Browicz cell, cell derived from any of these cells, or any combination thereof (i.e., non-naturally existing producer cell). As used herein, the term "non-naturally existing producer cell" refers to a producer cell (e.g., dendritic cell, macrophage, B cell, mast cell, neutrophil, Kupffer-Browicz cell, cell derived from any of these cells, or any combination thereof) that has been modified, such that the producer cell differs in structure and/or function compared to the naturally-existing counterpart. As described further below, in some aspects, the non-naturally existing producer cell has been modified to express one or more payloads disclosed herein (e.g., antigen, immune modulator, and/or adjuvant. In certain aspects, the non-naturally existing producer cell has been modified to express one or more targeting moieties disclosed herein. In some aspects, the non-naturally existing producer cell has been modified to express one or more scaffold moieties disclosed herein (e.g., Scaffold X and/or Scaffold Y).

The producer cell can be genetically modified to comprise one or more exogenous sequences (e.g., encoding an antigen, adjuvant, immune modulator, and/or targeting moiety) to produce the EVs (e.g., exosomes) described herein. The genetically-modified producer cell can contain the exogenous sequence by transient or stable transformation. The exogenous sequence can be transformed as a plasmid. The exogenous sequences can be stably integrated into a genomic sequence of the producer cell, at a targeted site or in a random site. In some aspects, a stable cell line is generated for production of lumen-engineered EVs (e.g., exosomes).

The exogenous sequences can be inserted into a genomic sequence of the producer cell, located within, upstream (5'-end) or downstream (3'-end) of an endogenous sequence encoding an EV (e.g., exosome) protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present disclosure.

The exogenous sequences can comprise a sequence encoding a scaffold moiety disclosed herein or a fragment or variant thereof. An extra copy of the sequence encoding a scaffold moiety can be introduced to produce an EV (e.g., exosome) described herein (e.g., having a higher density of a scaffold moiety on the surface or on the luminal surface of the EV, e.g., exosome). An exogenous sequence encoding a modification or a fragment of a scaffold moiety can be introduced to produce a lumen-engineered and/or surface-engineered exosome containing the modification or the fragment of the scaffold moiety.

In some aspects, a producer cell can be modified, e.g., transfected, with one or more vectors encoding a scaffold moiety linked to a payload (e.g., an antigen, an adjuvant, and/or an immune modulator) and/or a targeting moiety.

In some aspects, a producer cell disclosed herein is further modified to comprise an additional exogenous sequence. For example, an additional exogenous sequence can be introduced to modulate endogenous gene expression, or produce an EV (e.g., exosome) including a certain polypeptide as a payload (e.g., antigen, adjuvant, and/or immune modulator) and/or targeting moiety. In some aspects, the producer cell is modified to comprise two exogenous sequences, one encoding a scaffold moiety (e.g., Scaffold X and/or Scaffold Y), or a variant or a fragment thereof, and the other encoding a payload and/or targeting moiety. In certain aspects, the producer cell can be further modified to comprise an additional exogenous sequence conferring additional functionalities to EVs (e.g., exosomes) (e.g., adjuvants or immune modulators). In some aspects, the producer cell is modified to comprise two exogenous sequences, one encoding a scaffold moiety disclosed herein, or a variant or a fragment thereof, and the other encoding a protein conferring the additional functionalities to EVs (e.g., exosomes) (e.g., adjuvants or immune modulators). In some aspects, the producer cell is further modified to comprise one, two, three, four, five, six, seven, eight, nine, or ten or more additional exogenous sequences. In certain aspects, the additional exogenous sequences encode any of the payloads (e.g., antigen, adjuvant, and/or immune modulator) and/or targeting moieties disclosed herein.

In some aspects, EVs, e.g., exosomes, of the present disclosure (e.g., surface-engineered and/or lumen-engineered exosomes) can be produced from a cell transformed with a sequence encoding a full-length, mature scaffold moiety disclosed herein or a scaffold moiety linked to a payload (e.g., an antigen, an adjuvant, and/or an immune modulator) and/or targeting moiety. Any of the scaffold moieties described herein can be expressed from a plasmid, an exogenous sequence inserted into the genome, or other exogenous nucleic acid, such as a synthetic messenger RNA (mRNA).

IV. Pharmaceutical Compositions

Provided herein are pharmaceutical compositions comprising an EV, e.g., exosome, of the present disclosure having the desired degree of purity, and a pharmaceutically acceptable carrier or excipient, in a form suitable for administration to a subject. Pharmaceutically acceptable excipients or carriers can be determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some aspects, a pharmaceutical composition comprises one or more therapeutic agents and an exosome described herein. In certain aspects, the EVs, e.g., exosomes, are co-administered with of one or more additional therapeutic agents, in a pharmaceutically acceptable carrier. In some aspects, the pharmaceutical composition comprising the EV, e.g., exosome is administered prior to administration of the additional therapeutic agents. In other aspects, the pharmaceutical composition comprising the EV, e.g., exosome is administered after the administration of the additional therapeutic agents. In further aspects, the pharmaceutical composition comprising the EV, e.g., exosome is administered concurrently with the additional therapeutic agents.

Acceptable carriers, excipients, or stabilizers are nontoxic to recipients (e.g., animals or humans) at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The EVs, e.g., exosomes, can be administered by parenteral, topical, intravenous, oral, subcutaneous, intra-arterial, intradermal, transdermal, rectal, intracranial, intraperitoneal, intranasal, intratumoral, intramuscular route or as inhalants. In certain aspects, the pharmaceutical composition comprising exosomes is administered intravenously, e.g. by injection. The EVs, e.g., exosomes, can optionally be administered in combination with other therapeutic agents that are at least partly effective in treating the disease, disorder or condition for which the EVs, e.g., exosomes, are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the EVs, e.g., exosomes, in an effective amount and in an appropriate solvent with one or a combination of ingredients enumerated herein, as desired. Generally, dispersions are prepared by incorporating the EVs, e.g., exosomes, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The EVs, e.g., exosomes, can be administered in the form of a depot injection or implant preparation which can be formulated in such a manner to permit a sustained or pulsatile release of the EV, e.g., exosomes.

Systemic administration of compositions comprising exosomes can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain aspects, the pharmaceutical composition comprising exosomes is administered intravenously into a subject that would benefit from the pharmaceutical composition. In certain other aspects, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain aspects, the pharmaceutical composition comprising exosomes is administered as a liquid suspension. In certain aspects, the pharmaceutical composition is administered as a formulation that is capable of forming a depot following administration. In certain preferred aspects, the depot slowly releases the EVs, e.g., exosomes, into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the EVs, e.g., exosomes, described herein and optionally a pharmaceutically active or therapeutic agent. The therapeutic agent can be a biological agent, a small molecule agent, or a nucleic acid agent.

Dosage forms are provided that comprise a pharmaceutical composition comprising the EVs, e.g., exosomes, described herein. In some aspects, the dosage form is formulated as a liquid suspension for intravenous injection. In some aspects, the dosage form is formulated as a liquid suspension for intratumoral injection.

In certain aspects, the preparation of exosomes is subjected to radiation, e.g., X rays, gamma rays, beta particles, alpha particles, neutrons, protons, elemental nuclei, UV rays in order to damage residual replication-competent nucleic acids.

In certain aspects, the preparation of exosomes is subjected to gamma irradiation using an irradiation dose of more than 1, 5, 10, 15, 20, 25, 30, 35, 40, 50, 60, 70, 80, 90, 100, or more than 100 kGy.

In certain aspects, the preparation of exosomes is subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

V. Kits

Also provided herein are kits comprising one or more exosomes described herein. In some aspects, provided herein is a pharmaceutical pack or kit comprising one or more containers filled with one or more of the ingredients of the pharmaceutical compositions described herein, such as one or more exosomes provided herein, optional an instruction for use. In some aspects, the kits contain a pharmaceutical composition described herein and any prophylactic or therapeutic agent, such as those described herein.

VI. Methods of Producing EVs, e.g., Exosomes

EVs (e.g., exosomes) of the present disclosure differ from traditional vaccines in that the EVs can be rapidly engineered to express a moiety of interest (e.g., antigen, adjuvant, immune modulator, and/or targeting moiety). As described herein, the moieties of interest (i) can be directly linked to a surface of the EV (e.g., exterior surface and/or luminal surface), (ii) can be linked to a scaffold moiety (e.g., Scaffold X and/or Scaffold Y) and then expressed on a surface of the EV (e.g., exterior surface and/or luminal surface), (iii) can be expressed in the lumen of the EV, or (iv) combinations thereof. Such ability to rapidly engineer EVs (e.g., exosomes) is particularly useful in developing EV (e.g., exosome)-based vaccines. For instance, a single EV (e.g., exosome) engineered to express certain payloads and/ or targeting moieties can be used in treating a wide range of diseases or disorders by simply "plugging" an antigen of interest into the EVs.

Accordingly, in some aspects, the present disclosure is directed to methods of producing such modular or "plug and play" EV (e.g., exosome) vaccines. In certain aspects, a method of producing an EV (e.g., exosome)-based vaccine comprises mixing an engineered EV (e.g., exosome) with an antigen of interest, such that the antigen of interest is expressed in the engineered EV. In some aspects, the engineered EV (e.g., exosome) comprises one or more of the payloads disclosed herein (e.g., antigen, adjuvant, and/or immune modulator). In certain aspects, the engineered EV (e.g., exosome) further comprises one or more scaffold moieties (e.g., Scaffold X and/or Scaffold Y). In some aspects, the engineered EV (e.g., exosome) additionally comprises one or more targeting moieties. In some aspects, the engineered EV (e.g., exosome) can be produced using any of the methods disclosed herein.

In some aspects, the present disclosure is also directed to methods of producing EVs (e.g., exosomes) described herein. In some aspects, the method comprises: obtaining the EV, e.g., exosome, from a producer cell, wherein the producer cell contains two or more components of the EV, e.g., exosome (e.g., (i) antigen and adjuvant, (ii) antigen and immune modulator, (iii) antigen and targeting moiety, (iv) antigen, adjuvant, and targeting moiety, (v) antigen, immune modulator, and targeting moiety, (vi) antigen, adjuvant, and immune modulator, (vii) antigen, adjuvant, immune modulator, and targeting moiety); and optionally isolating the obtained EV, e.g., exosome. In some aspects, the method comprises: modifying a producer cell by introducing two or more components of an EV (e.g., exosome) disclosed herein (e.g., (i) antigen and adjuvant, (ii) antigen and immune modulator, (iii) antigen and targeting moiety, (iv) antigen, adjuvant, and targeting moiety, (v) antigen, immune modulator, (vi) antigen, adjuvant, and immune modulator, (vii) antigen, adjuvant, immune modulator, and targeting moiety); obtaining the EV, e.g., exosome from the modified producer cell; and optionally isolating the obtained EV, e.g., exosome. In further aspects, the method comprises: obtaining an EV (e.g., exosome) from a producer cell; isolating the obtained EV (e.g., exosome); and modifying the isolated EV (e.g., exosome) (e.g., by inserting multiple exogenous biologically active molecules, e.g., antigens, adjuvants, and/or immune modulators, and/or targeting moieties). In certain aspects, the method further comprises formulating the isolated EV (e.g., exosome) into a pharmaceutical composition.

VI.A Methods of Modifying a Producer Cell

As described supra, in some aspects, a method of producing an EV (e.g., exosome) comprises modifying a producer cell with multiple (e.g., two or more) molecule of interest (e.g., exogenous biologically active molecules described herein (e.g., antigen, adjuvant, immune modulator), and/or targeting moiety). In some aspects, a producer cell disclosed herein can be further modified with a scaffold moiety disclosed herein (e.g., Scaffold X or Scaffold Y).

In some aspects, the producer cell can be a mammalian cell line, a plant cell line, an insect cell line, a fungi cell line, or a prokaryotic cell line. In certain aspects, the producer cell is a mammalian cell line. Non-limiting examples of mammalian cell lines include: a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, a mesenchymal stem cell (MSC) cell line, and combinations thereof. In certain aspects, the mammalian cell line comprises HEK-293 cells, BJ human foreskin fibroblast cells, fHDF fibroblast cells, AGE.HN® neuronal precursor cells, CAP® amniocyte cells, adipose mesenchymal stem cells, RPTEC/TERT1 cells, or combinations thereof. In some aspects, the producer cell is a primary cell. In certain aspects, the primary cell can be a primary mammalian cell, a primary plant cell, a primary insect cell, a primary fungi cell, or a primary prokaryotic cell.

In some aspects, the producer cell is not an immune cell, such an antigen presenting cell, a T cell, a B cell, a natural killer cell (NK cell), a macrophage, a T helper cell, or a regulatory T cell (Treg cell). In other aspects, the producer cell is not an antigen presenting cell (e.g., dendritic cells, macrophages, B cells, mast cells, neutrophils, Kupffer-Browicz cell, or a cell derived from any such cells). In some aspects, a producer cell is not a naturally-existing antigen-presenting cell (i.e., has been modified). In some aspects, a producer cell is not a naturally-existing dendritic cell, a B cell, a mast cell, a macrophage, a neutrophil, Kupffer-Browicz cell, cell derived from any of these cells, or any combination thereof.

In some aspects, the one or more moieties (e.g., payload and/or targetin moiety) can be a transgene or mRNA, and introduced into the producer cell by transfection, viral transduction, electroporation, extrusion, sonication, cell fusion, or other methods that are known to the skilled in the art.

In some aspects, the one or more moieties (e.g., payload and/or targetin moiety) is introduced to the producer cell by transfection. In some aspects, the one or more moieties (e.g., payload and/or targetin moiety) can be introduced into suitable producer cells using synthetic macromolecules, such as cationic lipids and polymers (Papapetrou et al., *Gene Therapy* 12: S118-S130 (2005)). In some aspects, the cationic lipids form complexes with the one or more moieties (e.g., payload and/or targetin moiety) through charge interactions. In some of these aspects, the positively charged complexes bind to the negatively charged cell surface and are taken up by the cell by endocytosis. In some other aspects, a cationic polymer can be used to transfect producer cells. In some of these aspects, the cationic polymer is polyethylenimine (PEI). In certain aspects, chemicals such as calcium phosphate, cyclodextrin, or polybrene, can be used to introduce the one or more moieties (e.g., payload and/or targetin moiety) to the producer cells. The one or more moieties (e.g., payload and/or targetin moiety) can also be introduced into a producer cell using a physical method such as particle-mediated transfection, "gene gun", biolistics, or particle bombardment technology (Papapetrou et al., *Gene Therapy* 12: S118-S130 (2005)). A reporter gene such as, for example, beta-galactosidase, chloramphenicol acetyl-transferase, luciferase, or green fluorescent protein can be used to assess the transfection efficiency of the producer cell.

In certain aspects, the one or more moieties (e.g., payload and/or targetin moiety) are introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain aspects, the one or more moieties (e.g., payload and/or targetin moiety) are introduced to the producer cell by electroporation. Electroporation creates transient pores in the cell membrane, allowing for the introduction of various molecules into the cell. In some aspects, DNA and RNA as well as polypeptides and non-polypeptide therapeutic agents can be introduced into the producer cell by electroporation.

In certain aspects, the one or more moieties (e.g., payload and/or targetin moiety) introduced to the producer cell by microinjection. In some aspects, a glass micropipette can be used to inject the one or more moieties (e.g., payload and/or targetin moiety) into the producer cell at the microscopic level.

In certain aspects, the one or more moieties (e.g., payload and/or targetin moiety) are introduced to the producer cell by extrusion.

In certain aspects, the one or more moieties (e.g., payload and/or targetin moiety) are introduced to the producer cell by sonication. In some aspects, the producer cell is exposed to high intensity sound waves, causing transient disruption of the cell membrane allowing loading of the one or more moieties (e.g., payload and/or targetin moiety).

In certain aspects, the one or more moieties (e.g., payload and/or targetin moiety) are introduced to the producer cell by cell fusion. In some aspects, the one or more moieties (e.g., payload and/or targetin moiety) are introduced by electrical cell fusion. In other aspects, polyethylene glycol (PEG) is used to fuse the producer cells. In further aspects, sendai virus is used to fuse the producer cells.

In some aspects, the one or more moieties (e.g., payload and/or targetin moiety) are introduced to the producer cell by hypotonic lysis. In such aspects, the producer cell can be exposed to low ionic strength buffer causing them to burst allowing loading of the one or more moieties (e.g., payload and/or targetin moiety). In other aspects, controlled dialysis against a hypotonic solution can be used to swell the producer cell and to create pores in the producer cell membrane. The producer cell is subsequently exposed to conditions that allow resealing of the membrane.

In some aspects, the one or more moieties (e.g., payload and/or targetin moiety) are introduced to the producer cell by detergent treatment. In certain aspects, producer cell is treated with a mild detergent which transiently compromises the producer cell membrane by creating pores allowing loading of the one or more moieties (e.g., payload and/or targetin moiety). After producer cells are loaded, the detergent is washed away thereby resealing the membrane.

In some aspects, the one or more moieties (e.g., payload and/or targetin moiety) introduced to the producer cell by receptor mediated endocytosis. In certain aspects, producer cells have a surface receptor which upon binding of the one or more moieties (e.g., payload and/or targetin moiety) induces internalization of the receptor and the associated moieties.

In some aspects, the one or more moieties (e.g., payload and/or targetin moiety) are introduced to the producer cell by filtration. In certain aspects, the producer cells and the one or more moieties (e.g., payload and/or targetin moiety) can be forced through a filter of pore size smaller than the producer cell causing transient disruption of the producer cell membrane and allowing the one or more moieties (e.g., payload and/or targetin moiety) to enter the producer cell.

In some aspects, the producer cell is subjected to several freeze thaw cycles, resulting in cell membrane disruption allowing loading of the one or more moieties (e.g., payload and/or targetin moiety).

VI.B Methods of Modifying an EV (e.g., Exosome)

In some aspects, a method of producing an EV (e.g., exosome) comprises modifying the isolated EV (e.g., exosome) by directly introducing one or more moieties (e.g., payload and/or targetin moiety) into the EVs (e.g., exosomes). In certain aspects, the one or more moieties comprise an antigen, adjuvant, immune modulator, targeting moiety, or combinations thereof. In some aspects, the one or more moieties comprise a scaffold moiety disclosed herein (e.g., Scaffold X or Scaffold Y).

In certain aspects, the one or more moieties (e.g., payload and/or targetin moiety) are introduced to the EV (e.g., exosome) by transfection. In some aspects, the one or more moieties (e.g., payload and/or targetin moiety) can be introduced into the EV (e.g., exosome) using synthetic macromolecules such as cationic lipids and polymers (Papapetrou et al., Gene Therapy 12: S118-S130 (2005)). In certain aspects, chemicals such as calcium phosphate, cyclodextrin, or polybrene, can be used to introduce the one or more moieties (e.g., payload and/or targetin moiety) to the EV (e.g., exosome).

In certain aspects, the one or more moieties (e.g., payload and/or targetin moiety) are introduced to the EV (e.g., exosome) by electroporation. In some aspects, EVs (e.g., exosomes) are exposed to an electrical field which causes transient holes in the EV (e.g., exosome) membrane, allowing loading of the one or more moieties (e.g., payload and/or targetin moiety).

In certain aspects, the one or more moieties (e.g., payload and/or targetin moiety) are introduced to the EV (e.g., exosome) by microinjection. In some aspects, a glass micropipette can be used to inject the one or more moieties (e.g., payload and/or targetin moiety) directly into the EV (e.g., exosome) at the microscopic level.

In certain aspects, the one or more moieties (e.g., payload and/or targetin moiety) are introduced to the EV (e.g., exosome) by extrusion.

In certain aspects, the one or more moieties (e.g., payload and/or targetin moiety) are introduced to the EV (e.g., exosome) by sonication. In some aspects, EVs (e.g., exosomes) are exposed to high intensity sound waves, causing transient disruption of the EV (e.g., exosome) membrane allowing loading of the one or more moieties (e.g., payload and/or targetin moiety).

In some aspects, one or more moieties (e.g., payload and/or targetin moiety) can be conjugated to the surface of the EV (e.g., exosome) (i.e., conjugated or linked directly to the exterior surface of the EV or to the luminal surface of the EV). Conjugation can be achieved chemically or enzymatically, by methods known in the art.

In some aspects, the EV (e.g., exosome) comprises one or more moieties (e.g., payload and/or targetin moiety) that are chemically conjugated. Chemical conjugation can be accomplished by covalent bonding of the one or more moieties (e.g., payload and/or targetin moiety) to another molecule, with or without use of a linker. The formation of such conjugates is within the skill of artisans and various techniques are known for accomplishing the conjugation, with the choice of the particular technique being guided by the materials to be conjugated. In certain aspects, polypeptides are conjugated to the EV (e.g., exosome). In some aspects, non-polypeptides, such as lipids, carbohydrates, nucleic acids, and small molecules, are conjugated to the EV (e.g., exosome).

In some aspects, the one or more moieties (e.g., payload and/or targetin moiety) are introduced to the EV (e.g., exosome) by hypotonic lysis. In such aspects, the EVs (e.g., exosomes) can be exposed to low ionic strength buffer causing them to burst allowing loading of the one or more moieties (e.g., payload and/or targetin moiety). In other aspects, controlled dialysis against a hypotonic solution can be used to swell the EV (e.g., exosome) and to create pores in the EV (e.g., exosome) membrane. The EV (e.g., exosome) is subsequently exposed to conditions that allow resealing of the membrane.

In some aspects, the one or more moieties (e.g., payload and/or targetin moiety) are introduced to the EV (e.g., exosome) by detergent treatment. In certain aspects, extracellular vesicles are treated with a mild detergent which transiently compromises the EV (e.g., exosome) membrane by creating pores allowing loading of the one or more moieties (e.g., payload and/or targetin moiety). After EVs (e.g., exosomes) are loaded, the detergent is washed away thereby resealing the membrane.

In some aspects, the one or more moieties (e.g., payload and/or targetin moiety) are introduced to the EV (e.g., exosome) by receptor mediated endocytosis. In certain aspects, EVs (e.g., exosomes) have a surface receptor which upon binding of the one or more moieties (e.g., payload and/or targetin moiety) induces internalization of the receptor and the associated moieties.

In some aspects, the one or more moieties (e.g., payload and/or targetin moiety) are introduced to the EV (e.g., exosome) by mechanical firing. In certain aspects, extracellular vesicles can be bombarded with one or more moieties (e.g., payload and/or targetin moiety) attached to a heavy or charged particle such as gold microcarriers. In some of these aspects, the particle can be mechanically or electrically accelerated such that it traverses the EV (e.g., exosome) membrane.

In some aspects, extracellular vesicles (e.g., exosomes) are subjected to several freeze thaw cycles, resulting in EV (e.g., exosome) membrane disruption allowing loading of the one or more moieties (e.g., payload and/or targetin moiety).

VI.C Methods of Isolating an EV, e.g., Exosome

In some aspects, methods of producing EVs (e.g., exosomes) disclosed herein comprises isolating the EV (e.g., exosome) from the producer cells. In certain aspects, the EVs (e.g., exosomes) released by the producer cell into the cell culture medium. It is contemplated that all known manners of isolation of EVs (e.g., exosomes) are deemed suitable for use herein. For example, physical properties of EVs (e.g., exosomes) can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using EV (e.g., exosome) or producer cell-specific surface markers. For example, specific surface markers can be used in immunoprecipitation, FACS sorting, affinity purification, and magnetic separation with bead-bound ligands.

In some aspects, size exclusion chromatography can be utilized to isolate the EVs (e.g., exosomes). Size exclusion chromatography techniques are known in the art. Exemplary, non-limiting techniques are provided herein. In some aspects, a void volume fraction is isolated and comprises the EVs (e.g., exosomes) of interest. Further, in some aspects, the EVs (e.g., exosomes) can be further isolated after chromatographic separation by centrifugation techniques (of one or more chromatography fractions), as is generally known in the art. In some aspects, for example, density gradient centrifugation can be utilized to further isolate the extracellular vesicles. In certain aspects, it can be desirable to further separate the producer cell-derived EVs (e.g., exosomes) from EVs (e.g., exosomes) of other origin. For example, the producer cell-derived EVs (e.g., exosomes) can be separated from non-producer cell-derived EVs (e.g., exosomes) by immunosorbent capture using an antigen antibody specific for the producer cell.

In some aspects, the isolation of EVs (e.g., exosomes) can involve combinations of methods that include, but are not limited to, differential centrifugation, size-based membrane filtration, immunoprecipitation, FACS sorting, and magnetic separation.

VII. Methods of Treatment

Present disclosure also provides methods of preventing and/or treating a disease or disorder in a subject in need thereof, comprising administering an EV (e.g., exosome) disclosed herein to the subject. In some aspects, a disease or disorder that can be treated with the present methods comprises a cancer, graft-versus-host disease (GvHD), autoimmune disease, infectious diseases, or fibrotic diseases. Other non-limiting examples of diseases or disorders that can be treated with the present disclosure include tolerance, allergy, atopy, pain, addiction, and combinations thereof. Not to be bound by any one theory, in some aspects, an EV (e.g., exosome) disclosed herein can treat and/or prevent these diseases or disorders by inducing neutralizing antibodies that can specifically bind to a molecule associated with the disease or disorder (e.g., addiction: nicotine; pain: CGRP or substance P). For example, an EV (e.g., exosome) favoring a humoral response against a pain-mediating neuropeptide such as substance-P, nerve growth factor, bradykinin, or calcitonin-related gene product (CGRP) can be used in lieu of passive antibody therapy against these targets to treat or prevent pain syndromes. The recent regulatory approval of several preventative passive antibody therapies targeting CGRP for migraine treatment provides strong rationale for the proposed humoral active vaccine approach. By chemically conjugating illicit drugs such as nicotine, cocaine, fentanyl, heroin, methamphetamine and others to proteins or other molecules expressed on EV (e.g., exosome) vaccines it is possible to generate antibody responses against these small molecules. Such anti-drug abuse vaccines can limit brain exposure of the abused substance, thereby reducing its ability to create euphoria and CNS toxicity. Thus, illicit drug conjugated EVs combined with potent TH2 orienting adjuvants can provide a vaccine treatment strategy for drug abuse rehabilitation. In some aspects, the treatment is prophylactic. In other aspects, the EVs (e.g., exosomes) for the present disclosure are used to induce an immune response. In other aspects, the EVs (e.g., exosomes) for the present disclosure are used to vaccinate a subject.

In some aspects, the disease or disorder is a cancer. When administered to a subject with a cancer, in certain aspects, EVs of the present disclosure can up-regulate an immune response and enhance the tumor targeting of the subject's immune system. In some aspects, the cancer being treated is characterized by infiltration of leukocytes (T-cells, B-cells, macrophages, dendritic cells, monocytes) into the tumor microenvironment, or so-called "hot tumors" or "inflammatory tumors". In some aspects, the cancer being treated is characterized by low levels or undetectable levels of leukocyte infiltration into the tumor microenvironment, or so-called "cold tumors" or "non-inflammatory tumors". In some aspects, an EV (e.g., exosome) is administered in an amount and for a time sufficient to convert a "cold tumor" into a "hot tumor", i.e., said administering results in the infiltration of leukocytes (such as T-cells) into the tumor microenvironment. In certain aspects, cancer comprises bladder cancer, cervical cancer, renal cell cancer, testicular cancer, colorectal cancer, lung cancer, head and neck cancer, and ovarian, lymphoma, liver cancer, glioblastoma, melanoma, myeloma, leukemia, pancreatic cancers, or combinations thereof. In other term, "distal tumor" or "distant tumor" refers to a tumor that has spread from the original (or primary) tumor to distant organs or distant tissues, e.g., lymph nodes. In some aspects, the EVs of the disclosure treats a tumor after the metastatic spread.

In some aspects, the disease or disorder is a graft-versus-host disease (GvHD). In some aspects, the disease or disorder that can be treated with the present disclosure is an autoimmune disease. Non-limiting examples of autoimmune diseases include: multiple sclerosis, peripheral neuritis, Sjogren's syndrome, rheumatoid arthritis, alopecia, autoimmune pancreatitis, Behcet's disease, Bullous pemphigoid, Celiac disease, Devic's disease (neuromyelitis optica), Glomerulonephritis, IgA nephropathy, assorted vasculitides, scleroderma, diabetes, arteritis, vitiligo, ulcerative colitis, irritable bowel syndrome, psoriasis, uveitis, systemic lupus erythematosus, Graves' disease, myasthenia gravis, pemphigus vulgaris, anti-glomerular basement membrane disease (Goodpasture syndrome), Hashimoto's thyroiditis, autoimmune hepatitis, and combinations thereof.

In some aspects, the disease or disorder is an infectious disease. In certain aspects, the disease or disorder is an oncogenic virus. In some aspects, infectious diseases that can be treated with the present disclosure includes, but not limited to, Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV (e.g., HIV-2), corona viruses (e.g., COVID-19, MERS-CoV, and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, Merkel cell polyomavirus (MCV), bunyavirus (e.g., hanta virus), arena virus (e.g., LCMV and Lassa virus), flavivirus (e.g., dengue, Zika, Japanese encephalitis, west nile, and yellow fever), enterovirus (e.g., polio), astrovirus (e.g., gastroenteritis), rhabdoviridae (e.g., rabies), *Borrelia burgdorferi* and Burrelia mayonii (e.g., Lyme disease), herpes simplex virus 2 (HSV2), *Klebsiella* sp., *Pseudomonas aeruginosa, Enterococcus* sp., *Proteus* sp., *Enterobacter* sp., *Actinobacter* sp., coagulase-negative staphylococci (CoNS), *Mycoplasma* sp., or combinations thereof.

In some aspects, the disease or disorder includes pain. As used herein, the term "pain" refers to all categories of pain, including, but not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV (e.g., HIV-1, HIV-2) pain, postherpetic pain, non-cardiac chest pain, irritable bowel syndrome and pain associated with bowel disorders and dyspepsia, pain associated with narcotic drug addiction withdrawal, and combinations thereof.

In some aspects, the disease or disorder includes allergy. As used herein, the term "allergy" refers to an acquired potential to develop immunologically mediated adverse reaction to normally innocuous substances ("allergens"). Non-limiting examples of allergies include eczema, allergic rhinitis or coryza, hay fever, conjunctivitis, bronchial or allergic asthma, urticaria (hives), food allergies, atopic dermatitis, drug allergy, angioedema, allergic conjunctivitis, hypersensitivity, and combinations thereof. In certain aspects, an allergy that can be treated with the present disclosure is caused by food allergens (e.g., peanut, milk, egg, shellfish, and tree nut) (i.e., food allergy). In some aspects, an allergy that can be treated with the present disclosure is caused by environmental allergens (e.g., cat dander, ragweed, grass pollen, house dust mite, bee venom, latex, and poison ivy).

EVs (e.g., exosomes) of the present disclosure can be administered to a subject by any useful method and/or route known in the art. In some aspects, the EVs (e.g., exosomes) are administered intravenously to the circulatory system of the subject. In some aspects, the EVs (e.g., exosomes) are infused in suitable liquid and administered into a vein of the subject.

In some aspects, the EVs (e.g., exosomes) are administered intra-arterially to the circulatory system of the subject. In some aspects, the EVs (e.g., exosomes) are infused in suitable liquid and administered into an artery of the subject.

In some aspects, the EVs (e.g., exosomes) are administered to the subject by intrathecal administration. In some aspects, the EVs (e.g., exosomes) are administered via an injection into the spinal canal, or into the subarachnoid space so that it reaches the cerebrospinal fluid (CSF).

In some aspects, the EVs (e.g., exosomes) are administered intratumorally into one or more tumors of the subject.

In some aspects, the EVs (e.g., exosomes) are administered to the subject by intranasal administration. In some aspects, the EVs (e.g., exosomes) can be insufflated through the nose in a form of either topical administration or systemic administration. In certain aspects, the EVs (e.g., exosomes) are administered as nasal spray. In some aspects, intranasal administration can allow for the effective delivery of an EV (e.g., exosome) disclosed herein to the gastrointestinal tissues (see, e.g., Example 20). Such EVs (e.g., exosomes) delivered to the gastrointestinal tissues could be useful in providing protection against various gut-associated pathogens.

In some aspects, the EVs (e.g., exosomes) are administered to the subject by intraperitoneal administration. In some aspects, the EVs (e.g., exosomes) are infused in suitable liquid and injected into the peritoneum of the subject. In some aspects, the intraperitoneal administration results in distribution of the EVs (e.g., exosomes) to the lymphatics. In some aspects, the intraperitoneal administration results in distribution of the EVs (e.g., exosomes) to the thymus, spleen, and/or bone marrow. In some aspects, the intraperitoneal administration results in distribution of the EVs (e.g., exosomes) to one or more lymph nodes. In some aspects, the intraperitoneal administration results in distribution of the EVs (e.g., exosomes) to one or more of the cervical lymph node, the inguinal lymph node, the mediastinal lymph node, or the sternal lymph node. In some aspects, the intraperitoneal administration results in distribution of the EVs (e.g., exosomes) to the pancreas.

In some aspects, the EVs, e.g., exosomes, are administered to the subject by intra-ocular administration (e.g., periocular administration). In some aspects, the EVs, e.g., exosomes, are injected into the periocular tissues. Periocular drug administration includes the routes of subconjunctival, anterior sub-Tenon's, posterior sub-Tenon's, and retrobulbar administration.

Non-limiting examples of other routes of administration that can be used to administer the EVs (e.g., exosomes) disclosed herein include parenteral, topical, oral, subcutaneous, intradermal, transdermal, rectal, intraperitoneal, intramuscular, sublingual, or combinations thereof.

As disclosed herein, in some aspects, EVs (e.g., exosomes) disclosed herein can be administered to a subject in combination with one or more additional therapeutic agents. In certain aspects, the one or more additional therapeutic agents and the EVs (e.g., exosomes) are administered concurrently. In some aspects, the one or more additional therapeutic agents and the EVs (e.g., exosomes) are administered sequentially. In some aspects, the EVs (e.g., exosomes) are administered to the subject prior to administering the one or more additional therapeutic agents. In certain aspects, the EVs (e.g., exosome) are administered to the subject after administering the one or more additional therapeutic agents. As used herein, the term "therapeutic agents" refers to any agents that can be used in treating a disease or disorder disclosed herein (e.g., chemotherapy or immune checkpoint inhibitors (e.g., anti-PD-1 antibody) for treating a cancer). In some aspects, the one or more additional therapeutic agents that can be used in combination with the EVs (e.g., exosomes) of the present disclosure include a payload (e.g., antigen, adjuvant, and/or immune modulator) which is not expressed in an EV (e.g., exosome). For instance, a treatment method disclosed herein can comprise administering to a subject in need thereof (i) an antigen-less EV (e.g., exosome) and (ii) an antigen that is not expressed in an EV (e.g., soluble antigen).

In some aspects, a subject that can be treated with the present disclosure is a human. In some aspects, a subject is a non-human mammal (e.g., non-human primates, dogs, cats, guinea pigs, rabbits, rats, mice, horses, cattle, chickens, birds, and bears). Accordingly, in some aspects, the EVs (e.g., exosomes) disclosed herein can be used to improve the health of an animal (i.e., non-human mammal).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); Crooke, Antisense drug Technology: Principles, Strategies and Applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1: Generation of Engineered-Exosomes

Figure 1B:
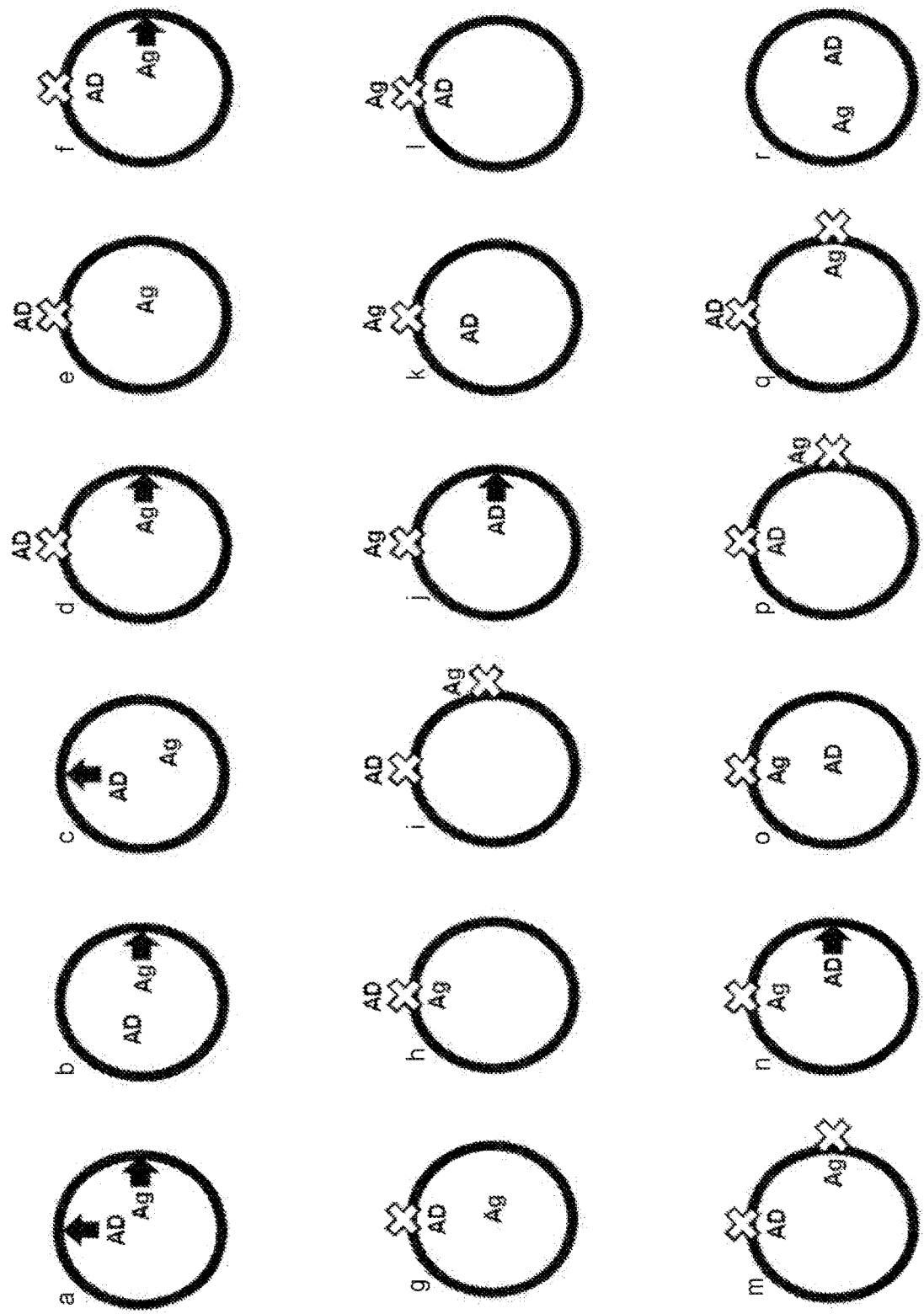
FIG. 1B shows non-limiting examples (a-r) of EVs, e.g., exosomes, comprising an antigen and an adjuvant. "Ag" and "AD" represent antigen and adjuvant, respectively. Arrowheads represent Scaffold Y moiety. "X" represents Scaffold X moiety. As will be apparent from the present disclosure, the EVs (e.g., exosomes) shown in FIG. 1B can comprise multiple antigens, multiple adjuvants, or both multiple antigens and multiple adjuvants. The EVs (e.g., exosomes) can also further comprise one or more additional moieties (e.g., immune modulator and/or targeting moiety). Further description of such EVs (e.g., exosomes) are provided throughout the present disclosure.
Figure 2:
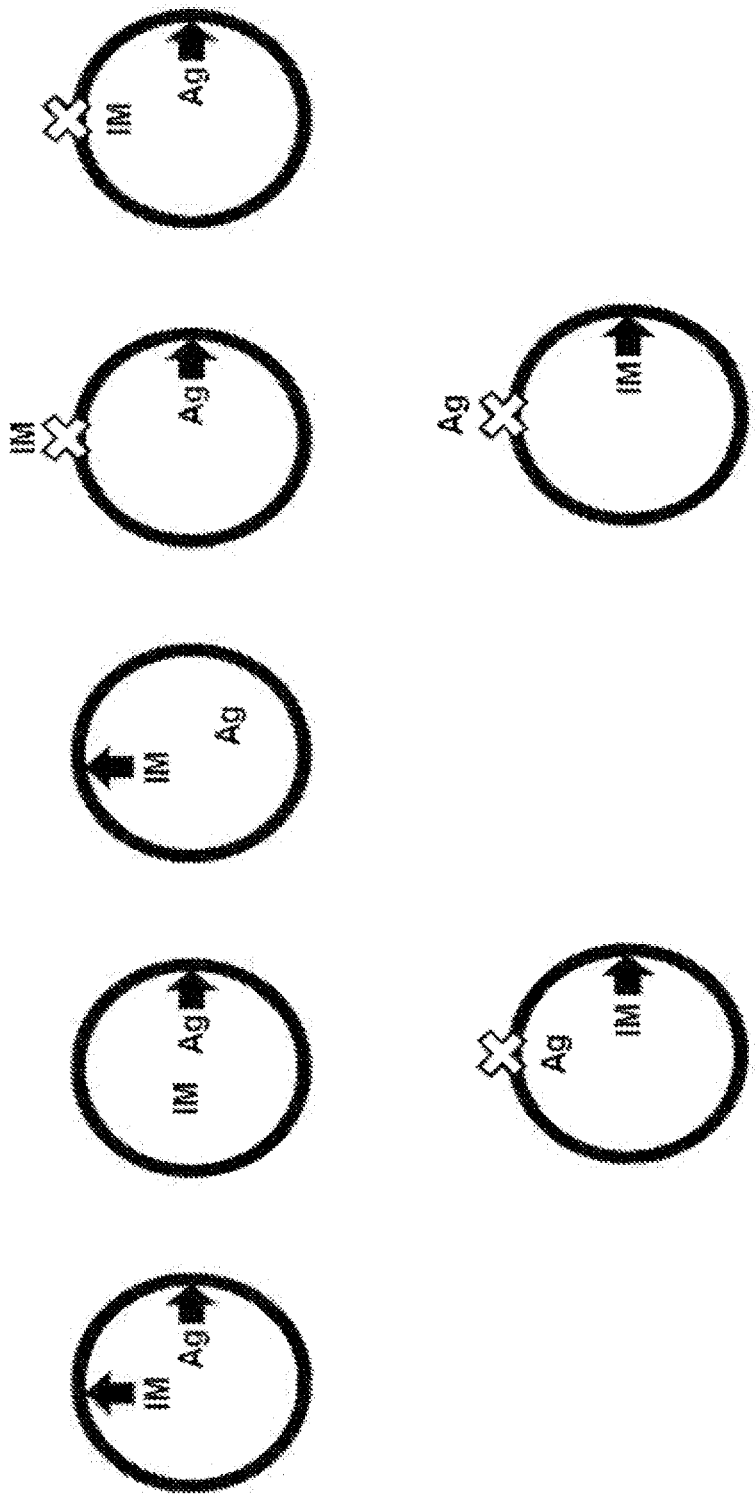
FIG. 2 shows seven selected examples of exosomes comprising an antigen and an immune modulator. "Ag" and "IM" represent antigen and immune modulator, respectively. Arrowheads represent Scaffold Y moiety. "X" represents Scaffold X moiety. As will be apparent from the present disclosure, the EVs (e.g., exosomes) shown in FIG. 2 can comprise multiple antigens, multiple immune modulators, or both multiple antigens and multiple immune modulators. The EVs (e.g., exosomes) can also further comprise one or more additional moieties (e.g., adjuvant and/or targeting moiety). Further description of such EVs (e.g., exosomes) are provided throughout the present disclosure.

To generate exosomes described herein, human embryonic kidney (HEK) cell line (HEK293 SF) was used. The cells were then stably transfected with Scaffold X and/or Scaffold Y linked to an agent of interest (e.g., antigen, adjuvant, or immune modulator). See FIGS. 1A, 1B, and 2. For example, CD40L-expressing exosomes were generated by transfecting HEK293 SF cells with CD40L-GFP PTG-FRN fusion molecules, which were expressed as a monomer (pCB-518 to pCB-526) or as a forced trimer (pCB-607 and pCB-527). An example of a trimeric CD40L-GFP PTGFRN fusion molecule is shown in FIG. 1A. Similarly, to generate chicken ovalbumin (OVA)-expressing exosomes, ovalbumin was stably expressed in HEK293SF cells as a fusion to amino acids 1-10 of BASP1 ("BASP1(1-10)-OVA").

Upon transfection, HEK293 SF cells were grown to high density in chemically defined medium for 7 days. Conditioned cell culture media was collected and centrifuged at 300-800×g for 5 minutes at room temperature to remove cells and large debris. Media supernatant was then supplemented with 1000 U/L BENZONASE® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and any residual media was aspirated from the bottom of the tube. The pellet was resuspended in 200-1000 µL PBS (—Ca —Mg).

To further enrich exosome populations, the pellet was processed via density gradient purification (sucrose or OPTIPREP™).

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 µL) and stored at 4° C.

For OPTIPREP™ gradient, a 3-tier sterile gradient is prepared with equal volumes of 10%, 30%, and 45% OPTIPREP™ in a 12 mL Ultra-Clear (344059) tube for a SW 41 Ti rotor. The pellet was added to the OPTIPREP™ gradient and ultracentrifuged at 200,000×g for 16 hours at 4° C. to separate the exosome fraction. The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 µL) and stored at 4° C. until ready to be used.

Example 2: Efficacy of Engineered-Exosomes to Induce Antigen-Specific T Cell Responses To assess the ability of the exosomes disclosed herein to induce immune response, an engineered-exosome expressing OVA-Scaffold Y and loaded with the STING agonist CL656 ("Py-OVA-exoSTING") was administered to mice either intravenously or intranasally. One week after administration, the frequency of CD8+ T cells reactive to OVA was assessed via both flow cytometry and/or IFN-γ ELISPOT assay by enzymatic dissociation of spleens and blood or lungs and spleens following intravenous or intranasal administration, respectively. Control animals received one of the following: (i) intra-peritoneal injected anti-CD40 antibody in combination with soluble OVA protein (not part of an exosome) aCD40+OVA"); (ii) cAIM(PS)2 Difluor (Rp/Sp) ("CL656"; STING agonist) in combination with soluble OVA protein (not part of an exosome) ("CL656+OVA"); (iii) exosome over-expressing only Scaffold X and loaded with STING agonist in combination with soluble OVA protein (OVA is not part of the exosome) ("Px-exoSTING+OVA"); and (iv) exosome expressing only OVA-Scaffold Y fusion protein ("Py-OVA").

Figure 3B:
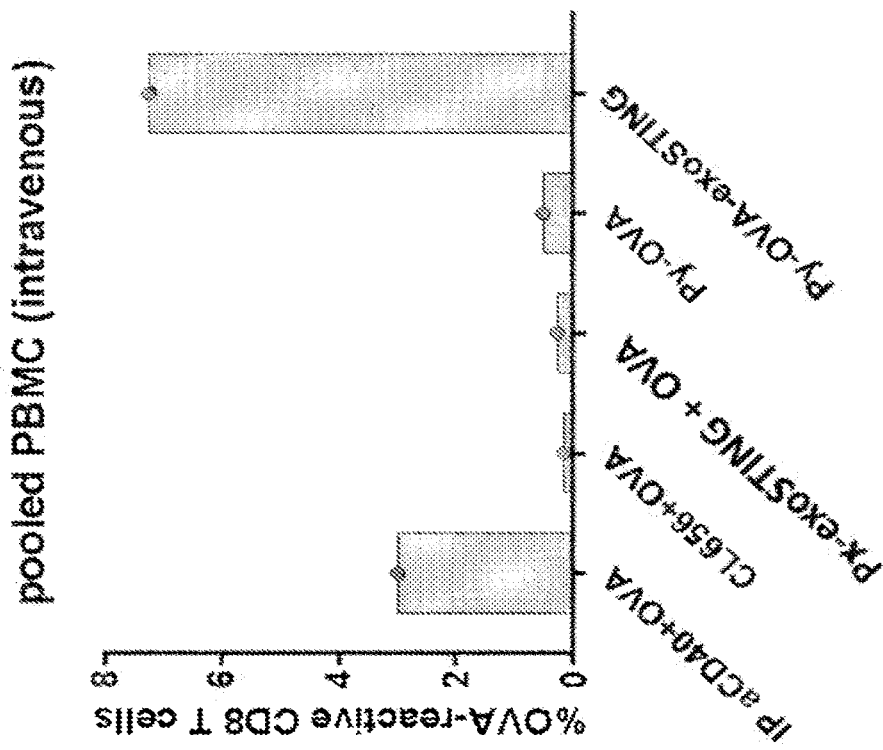
FIGS. 3A and 3B show the ability of an engineered-EV, e.g., exosome, comprising both OVA-Scaffold Y and loaded with STING agonist ("Py-OVA-exoSTING") to induce OVA-specific CD8 T cell immune response after intravenous administration into naïve C57/BL6 mice. The induction of OVA-specific CD8 T cell immune response is shown both in the spleen (FIG. 3A) and in pooled peripheral blood mononuclear cells (PBMCs) (FIG. 3B). The following constructs were used as controls: (i) anti-CD40 antibody in combination with soluble OVA protein (not part of an EV, e.g., exosome) ("IP aCD40+OVA"); (ii) cAIM(PS)2 Difluor (Rp/Sp) ("CL656"; STING agonist) in combination with soluble OVA protein (not part of an EV, e.g., exosome) ("CL656+OVA"); (iii) EV, e.g., exosome overexpressing Scaffold X, loaded with STING agonist in combination with soluble OVA protein (OVA is not part of the EV, e.g., exosome) ("Px-exoSTING+OVA"); and (iv) EV, e.g., exosome, expressing only OVA-Scaffold Y fusion protein ("Py-OVA"). Data are shown both individually and as mean±S.D. "***" indicates p<0.0005 by one-way ANOVA.
Figure 3A:
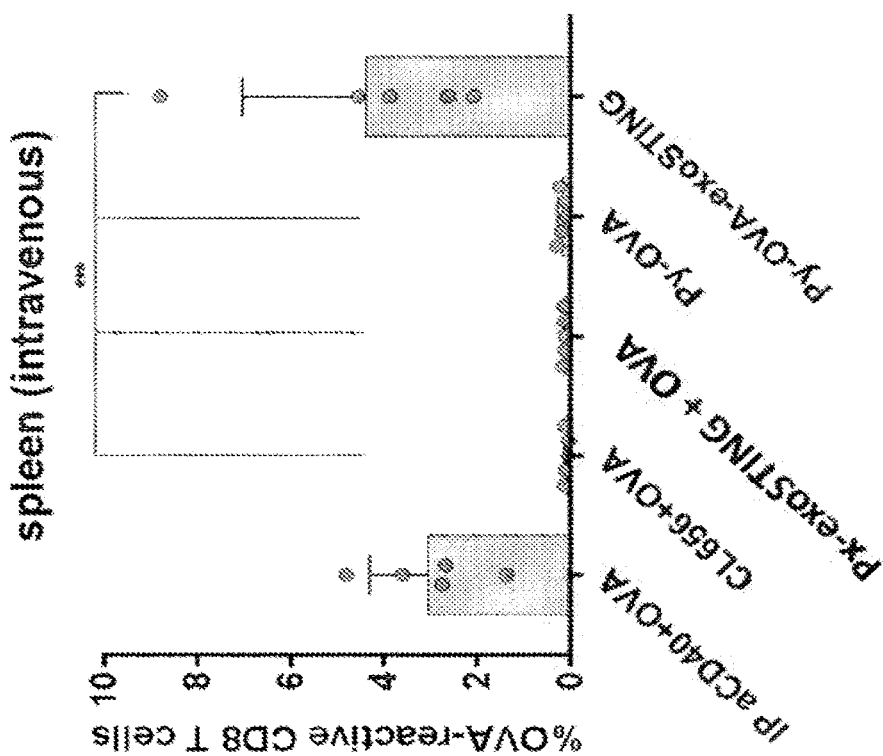
Figure 4B:
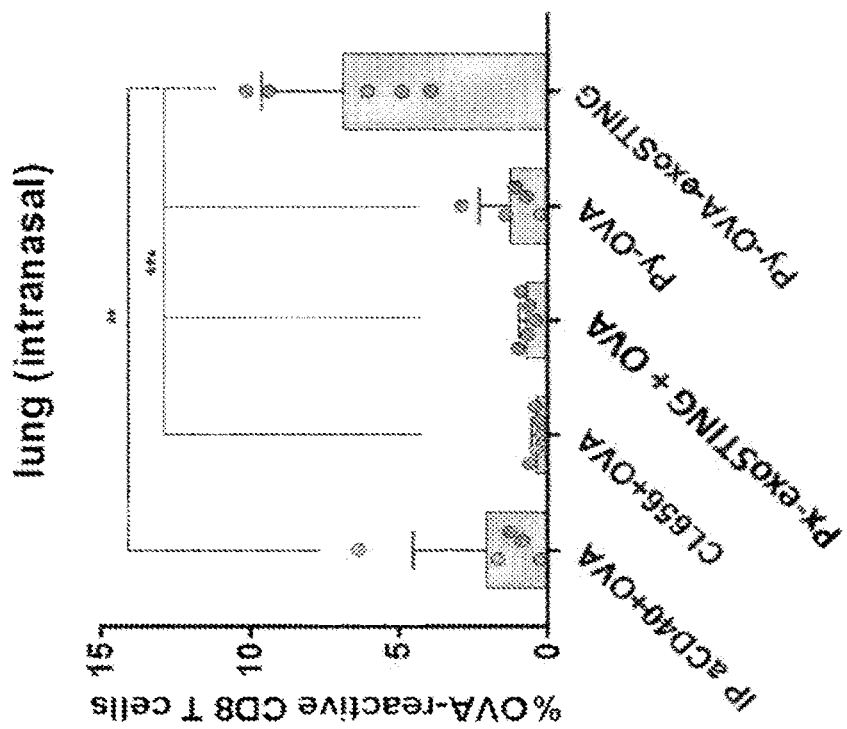
FIGS. 4A and 4B show the ability of an engineered-EV, e.g., exosome comprising both OVA-Scaffold Y and loaded with STING-agonist ("Py-OVA-exoSTING") to induce OVA-specific CD8 T cell immune response after intranasal administration into naïve C57/BL6 mice. The induction of OVA-specific CD8 T cell immune response is shown both in the spleen (FIG. 4A) and in the lung (FIG. 4B). The following constructs were used as controls: (i) anti-CD40 antibody in combination with soluble OVA protein (not part of an EV, e.g., exosome); (ii) cAIM(PS)2 Difluor (Rp/Sp) ("CL656"; STING agonist) in combination with soluble OVA protein ("CL656+OVA"); (iii) EV, e.g., exosome overexpressing Scaffold X, loaded with STING-agonist in combination with soluble OVA protein (OVA is not part of the EV, e.g., exosome) ("Px-exoSTING+OVA"); and (iv) EV, e.g., exosome, expressing only OVA-Scaffold Y fusion protein ("Py-OVA"). Data are shown both individually and as mean±S.D. "" indicates p<0.005 by one way ANOVA. "*" indicates p<0.0005 by one-way ANOVA.
Figure 4A:
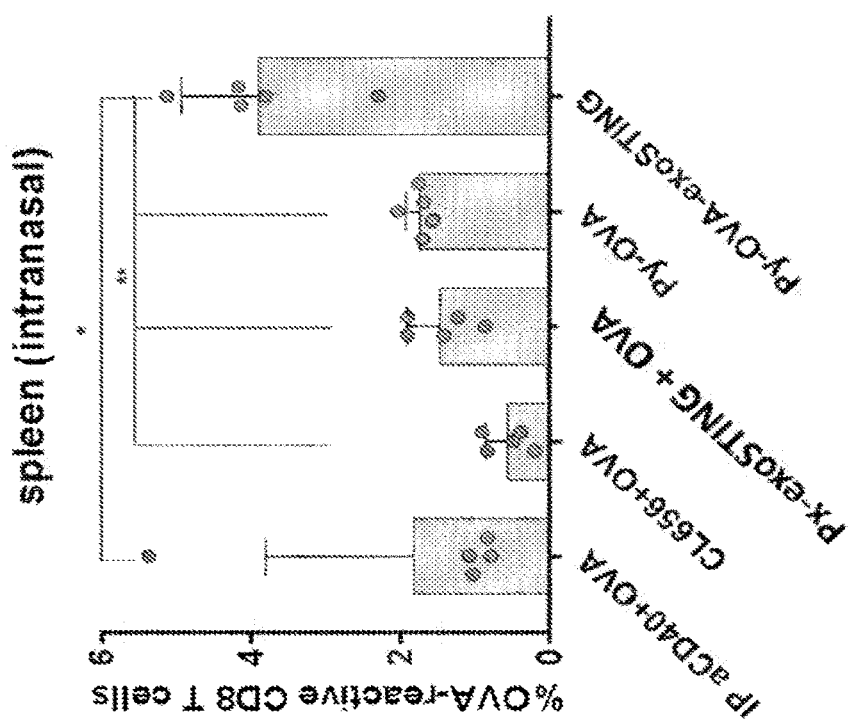
Figure 5B:
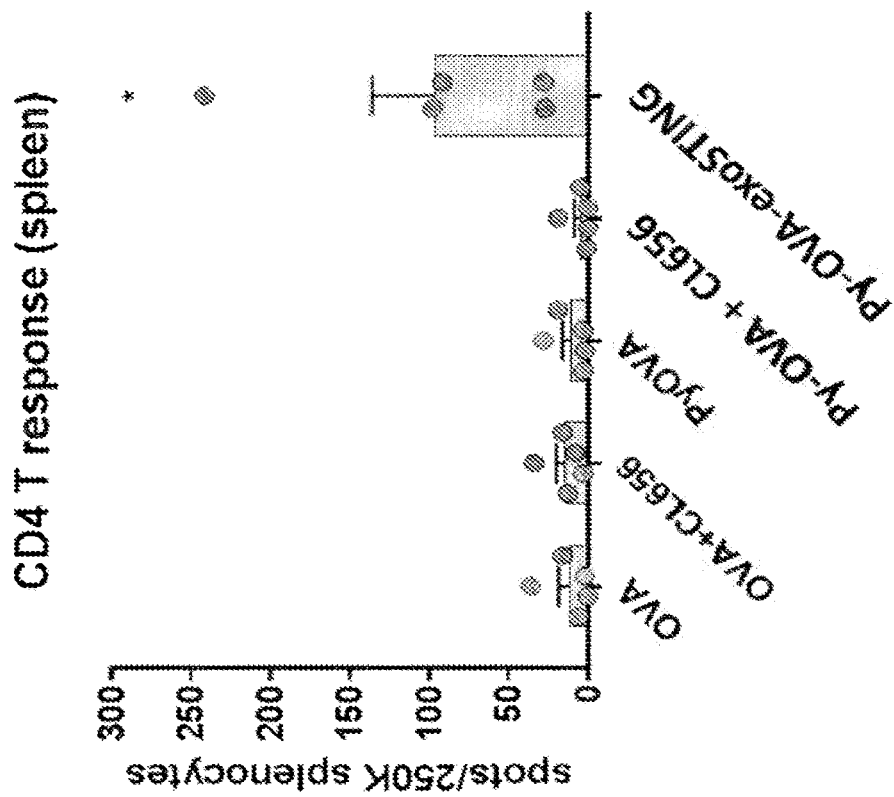
FIGS. 5A and 5B show a comparison of OVA-specific T cell response in the spleen of mice after intranasal administration of an engineered-EV, e.g., exosome comprising both OVA-Scaffold Y and loaded with STING agonist ("Py-OVA-exoSTING"). OVA-specific T cell responses were measured using an IFN-γ ELISPOT analysis one week post administration.
Figure 5A:
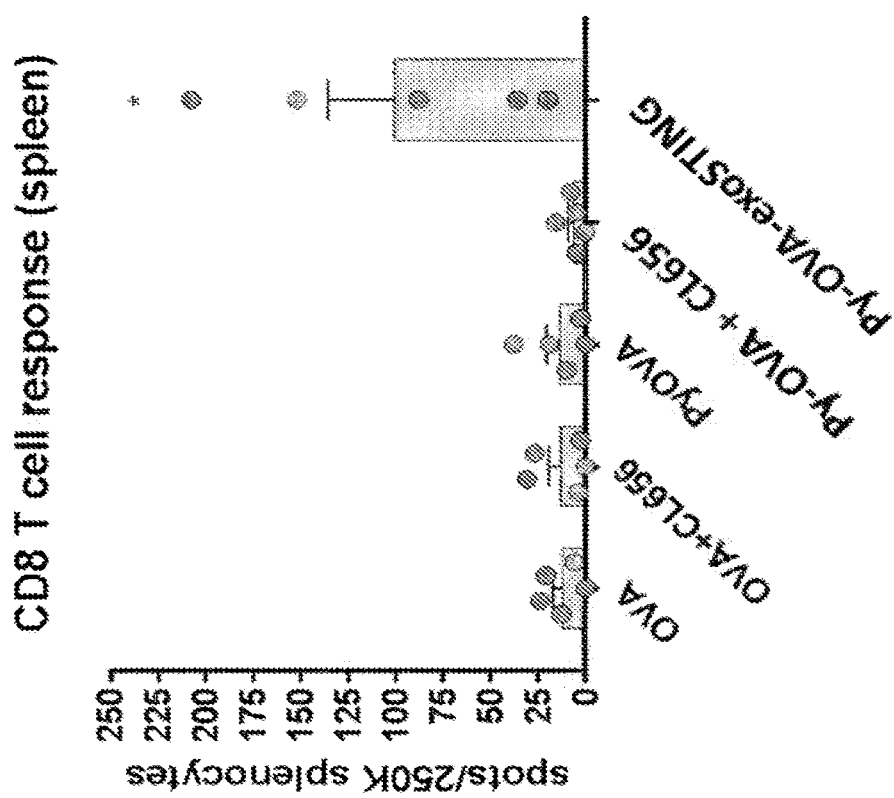

As shown in FIGS. 3A and 3B, among the different treatment groups, animals that received intravenous administration of the Py-OVA-exoSTING exosome had the greatest number of OVA-specific CD8 T cells both in the spleen and in PBMC. Similar results were observed when the different treatment regiments were administered intranasally. (See FIGS. 4A and 4B for flow cytometry analysis and FIGS. 5A and 5B for ELISPOT results). These results demonstrate that the exosomes disclosed herein (i.e., comprising both OVA-Scaffold Y and loaded with a STING agonist) can be used to induce robust immune responses against antigens of interest (e.g., tumor or microbial antigen).

Example 3: Efficacy of Engineered-Exosomes to Induce Immune Tolerance

To assess the tolerogenic potential of exosomes disclosed herein, engineered-exosomes comprising antigens associated with autoimmune diseases (e.g., beta-cell proteins (type I diabetes), myelin oligodendrocyte glycoprotein (MOG, multiple sclerosis), or synovial proteins (rheumatoid arthritis)) will be constructed. As in Example 2, the antigen will be linked to a Scaffold Y protein described herein. Some of the engineered-exosomes will further comprise immune modulators in the NFkB inhibition class such as rapamycin and/or its derivatives. These immune modulators will be expressed in the exosome linked to a Scaffold X protein (e.g., those described herein) or loaded exogenously into exosomes.

The above-engineered exosomes will be administered to an experimental animal model for delayed type hypersensitivity (DTH) or experimental autoimmune encephalomyelitis (EAE). Then, the tolerogenic/regulatory T cell responses to the target antigen will be assessed in the animals using assays, such as flow cytometry and ELISPOT assay.

Example 4: Comparison of Engineered-Exosomes to Other Antigen-Adjuvant Combinations in Inducing Immune Response The ability of the engineered-exosomes disclosed herein (e.g., see Example 2) to induce OVA-specific immune response (both T and B cells) will be compared to other known antigen-adjuvant combinations. Specifically, a direct head-to-head comparison will be conducted against the following antigen-adjuvant combinations: vaccination with soluble OVA (antigen) and Monophosphoryl Lipid A (MPLA), squalene in water emulsions (AddaVax™), saponin based vaccines (Quil-A®), incomplete Freund's adjuvant (IFA), and/or Polyinosinic-polycytidylic acid (poly I:C).

The following endpoints will be analyzed: (i) distribution of T cell subsets induced, i.e. % OVA-reactive CD8 and CD4 T cells one week after a single administration as well as one week after a boost administration (two doses, two weeks a part); (ii) T cell effector analysis: same as above, but examining the types of T cell responses in the CD4 and CD8 compartment. Time points would be identical to above, and the analysis would be intracellular cytokine staining (ICS) by flow; and (iii) humoral responses one week after boost administration (2nd dose): This would be analysis of serum for OVA-specific antibodies and antibody class, by ELISA or Bio-Layer Interferometry (BLI), as well as flow based analysis of B cell reactivity to biotinylated, whole OVA antigen.

Example 5: Dose Response Analysis of Luminal Antigens

A dose response analysis will be conducted to determine the lowest amount of antigen required for the engineered-exosomes disclosed herein to mount an effective immune response. The study will compare a Py-OVA:Py-GFP mixture (i.e., exosome expressing OVA and GFP, both linked to Scaffold Y protein) loaded with equal amounts of CL656, and decreasing amounts of Py-OVA with increasing amounts of Py-GFP. See TABLE 10 (below).

TABLE 10

| Make-up of different exosomes to be tested | | | |
|---|---|---|---|
| Py-OVA ng | Py-GFP ng | CL656 | total exosomes ng |
| 150 | 50 | 100 | 200 |
| 100 | 100 | | |
| 50 | 150 | | |

As described in Example 2, approximately a week after the administration, animals will be sacrificed and antigen-specific immune response will be assessed in various tissues (e.g., spleen, lung, blood) using flow cytometry and/or ELISPOT assay.

Example 6: Effect of Route of Administration on Inducing Immune Response

Data will compare several doses of Py-OVA-exoSTING (see Example 2) following intranasal, intravenous, subcutaneous, intraperitoneal, and intramuscular administration. Endpoint analysis will include splenic and circulating (PBMC) OVA-reactive CD4 and CD8 T cells one week after a single and double (two weeks apart) administration.

Example 7: Induction of Mucosal Homing

To assess the ability of the exosomes disclosed herein to induce immune response within mucosal tissues, Py-OVA-exoSTING (see Example 2) will be administered intranasally to female mice. After one or two doses, female mice will be challenged by induction of intravaginal administration of MPLA and squalene. 5 days after intravaginal challenge, genital tracts will be harvested and assessed for recruitment of OVA-specific CD4 and CD8 T cells.

Example 8: Tissue Resident Memory T Cell Responses Following Intravenous or Intranasal Vaccination To better characterize the ability of the engineered-exosomes disclosed herein to induce circulating and/or tissue-resident memory T cells, Py-OVA-exoSTING will be administered to animals as described in Example 2. One week post administration, the lung (from animals that received intranasal administration) and/or the liver (from animals that received intravenous administration) will be processed and analyzed for circulating and/or tissue-resident memory T cells.

Example 9: Therapeutic Vaccination Against Human Herpes Virus 2 (HSV2)

A mouse model of HSV2 infection, wherein the animals have genital HSV2 infection, will be treated intranasally with one of the following: (i) an exosome expressing HSV2 antigen linked to Scaffold Y and loaded with a STING agonist ("Py-HSV2-exoSTING"), (ii) an exosome expressing OVA antigen linked to Scaffold Y and loaded with a STING agonist ("Py-OVA-exoSTING"), or ACYCLOVIR™. The Py-HSV2-exoSTING construct will express two to three different HSV2 antigens. Endpoints will measure viral shedding and paralysis after 1 or 2 (biweekly) doses of the different treatment regiments.

Example 10: Prophylactic Vaccination Against Human Herpes Virus 2 (HSV2)

Using the exosome constructs described in Example 9, naïve mice will be vaccinated intranasally one or two times (bi-weekly) and intravaginally challenged with HSV2 one week after final administration. Endpoints will include measurements of viral shedding and paralysis through three weeks post challenge.

Example 11: Therapeutic Vaccination Against Mice Bearing EG7-OVA Tumors

Mice will be inoculated with subcutaneous EG7-OVA tumors. When tumors reach 50 mm$^3$, mice will be vaccinated intranasally, intravenously, or subcutaneously with Py-OVA-exoSTING (see Example 2) or appropriate controls. Endpoints will be measurement of tumor growth expressed as tumor growth inhibition (TGI).

Example 12: Vaccination with CD40L-Px:Py-OVA-exoSTING Compared to Py-OVA-exoSTING The ability of Py-OVA-exoSTING (see Example 2) to induce immune response will be directly compared to an exosome expressing (i) CD40L linked to a Scaffold X, (ii) OVA linked to a Scaffold Y, and (iii) loaded with STING agonist ("CD40L-Px:Py-OVA-exoSTING"). The exosomes will be administered to naïve animals and then OVA-specific T cell response will be assessed in various tissues approximately one week after administration, as described in Example 2.

Example 13: Vaccination with Anti-Clec9a EVs (e.g., Exosomes)

The ability of an OVA-expressing EV (e.g., exosome) loaded with STING agonist and expressing anti-Clec9a moiety ("anti-Clec9a EVs") to induce immune response will also be assessed in an animal model. FIG. 6 provides a schematic of a proposed experimental design. Animals will be treated with one of the following: (i) OVA-expressing EVs (e.g., exosomes) loaded with STING agonist and expressing a control isotype antibody; (ii) OVA-expressing EVs (e.g., exosomes) expressing a control isotype antibody alone; (iii) OVA-expressing EVs (e.g., exosomes) loaded with STING agonist and expressing anti-Clec9a targeting moiety; (iv) OVA-expressing EVs (e.g., exosomes) expressing anti-Clec9a targeting moiety but not loaded with STING agonist; and (v) EVs (e.g., exosomes) expressing OVA alone. The different treatment regimens will be administered intranasally. Then, some of the animals will be sacrificed and OVA-specific T cell responses will be assessed in the spleen and lung. Some of the animals will receive a second administration of the EVs (e.g., exosomes) approximately 14 days after the initial administration. OVA-specific T cell responses will be further assessed after the boost.

Example 14: Vaccination with Anti-EBV BZLF1 EVs (e.g. Exosomes)

Figure 8:
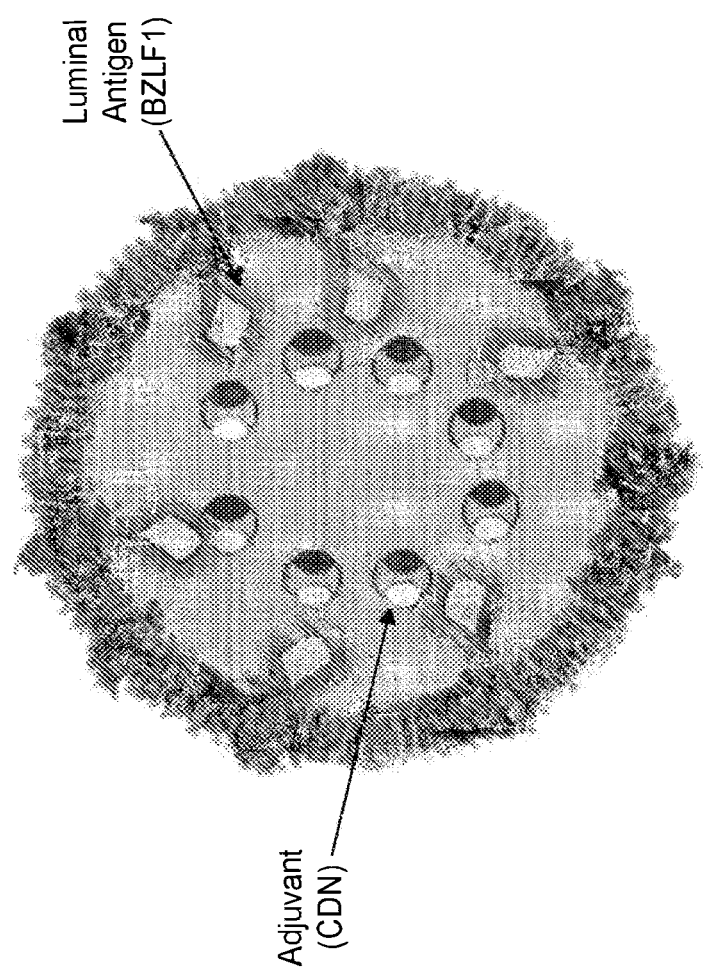
FIG. 8 illustrate the use of EBV BZLF1 as a targeting antigen for post-transplant lymphoproliferative disease in EBV− transplant patients.

The ability of an EV (e.g., exosome) loaded with an Epstein Barr Virus (EBV) BZLF1 antigen to induce an immune response will in assessed in an animal model according to the methods and experimental designs disclosed above (e.g., replacing an antigen disclosed above with BZLF1). FIG. 8 shows an schematic representation of an EV, e.g., an exosome, containing the BZLF1 antigen attached to the luminal surface of the EV membrane.

Example 15: Efficacy of Engineered-Exosomes to Induce Effector and Memory T Cells (Spleen)

To further characterize the T cell response observed after immunization with an exosome disclosed herein (see Example 2), the ability of the exosomes to induce both effector and memory T cells was observed in mice. Briefly, mice were subcutaneously administered with an engineered-exosome expressing OVA-Scaffold Y and loaded with the STING agonist CL656 ("Py-OVA exoVACC"). Control animals received one of the following: (i) soluble OVA ("OVA"), (ii) soluble OVA+CL656 ("OVA+STING"), (iii) exosome expressing only OVA-Scaffold Y fusion protein ("PyOVA"), (iv) exosome expressing only OVA-Scaffold Y fusion protein+soluble CL656 (i.e., the STING agonist is not loaded into the exosomes) ("PyOVA+STING"), and (v) soluble OVA+alum adjuvant ("OVA+Alum").

Two weeks after administration, some of the animals were sacrificed and the frequency of OVA-specific T cells (both CD4+ and CD4+ T cells) in the spleen was assessed using an IFN-γ ELISPOT assay. To induce IFN-γ production, the splenocytes were stimulated in vitro with OVA peptides specific for CD4+ and CD8+ T cells. The remaining animals were boosted (i.e., immunized again) with the same treatment regimen. Then, at day 28 post initial immunization (or day 14 after the boost), the animals were sacrificed and the frequency of OVA-specific T cells (both CD4+ and CD4+ T cells) in the spleen was also assessed using an IFN-γ ELISPOT assay.

Figure 9B:
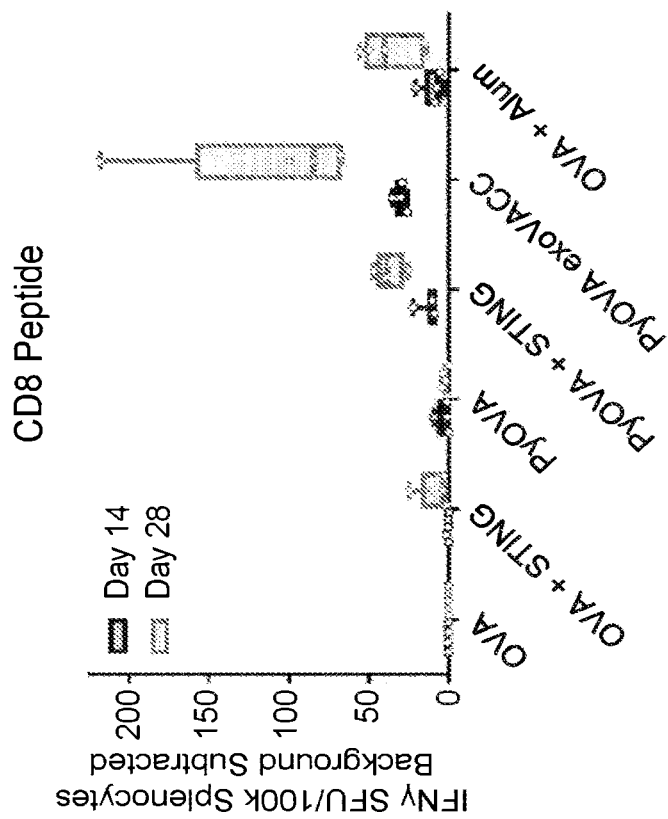
FIGS. 9A and 9B provide a comparison of the number of CD4+(FIG. 9A) and CD8+(FIG. 9B) T cells from wild-type mice immunized with soluble or exosomal OVA with or without STING adjuvant. Wild-type mice were immunized with soluble OVA (Ovalbumin); soluble OVA+CL656 (STING agonist); PyOVA (exosomal luminal expression of OVA fused to BASP1); PyOVA+soluble CL656; PyOVA exoVacc (PyOVA exosomes loaded with CL656); or soluble OVA+alum adjuvant, as indicated (FIGS. 9A and 9B). Antigen-specific cells were identified by IFN-g expression and data expressed as the number of IFN-g positive spot forming units (SFU) per 100,000 splenocytes after subtracting for background (non-antigen-specific activation) (x-axis, FIGS. 9A and 9B). "Day 14" represent the number of CD4+ and CD8+ T cells observed in the animals after a single immunization. "Day 28" represent the number of CD4+ and CD8+ T cells observed in the animals after a boost with a second administration.
Figure 9A:
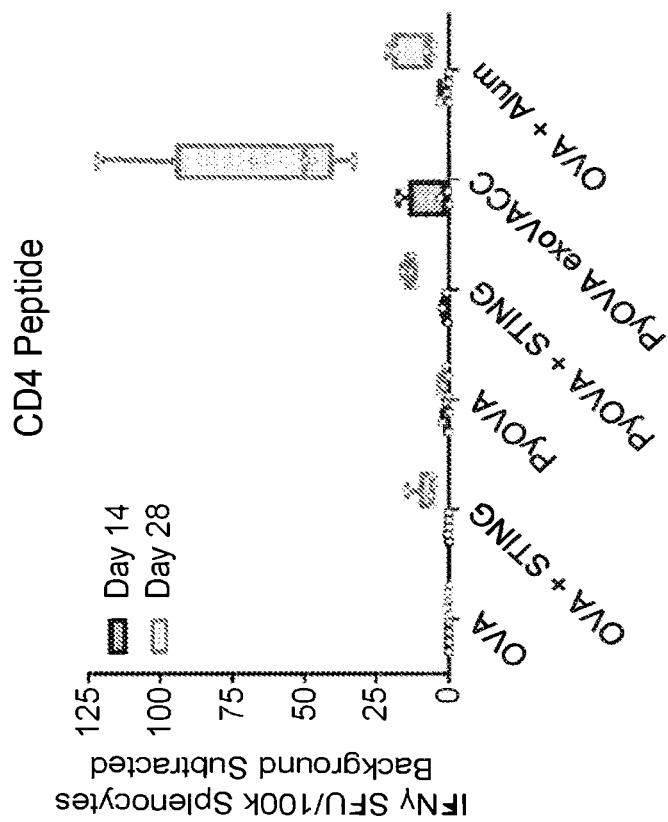

As shown in FIGS. 9A and 9B, after a single subcutaneous administration, animals that received the Py-OVA exoVACC exosome had the greatest number of OVA-specific CD4+ and CD8+ T cells in the spleen. This increase in CD4+ and CD8+ T cell numbers increased further after the boost in animals that received the Py-OVA exoVACC exosome.

The above data are in agreement with the results from Example 2 and further demonstrate that the exosomes disclosed herein (e.g., engineered-exosome expressing OVA-Scaffold Y and loaded with the STING agonist CL656) can be used to induce robust effector and memory T cells against an antigen of interest (e.g., tumor or microbial antigens) even when administered subcutaneously.

Example 16: Efficacy of Engineered-Exosomes to Induce Effector and Memory T Cells (Lung)

To assess whether the results from Example 15 are also observed in other tissues (e.g., mucosal tissues), an engineered-exosome expressing OVA-Scaffold Y and loaded with the STING agonist CL656 ("Py-OVA exoVACC") was administered to mice via intranasal administration. At day 7 post immunization, some of the animals were sacrificed and the frequency of OVA-specific CD8+ T cells was assessed in the lung using flow cytometry. The remaining mice were instead boosted with a second administration of Py-OVA exoVACC. These animals were sacrificed a week later (i.e., day 14 post initial immunization) and the frequency of OVA-specific CD8+ T cells was assessed in the lung using flow cytometry. At both time points, OVA-specific CD8+ T cells were further categorized as effector memory (CD44+ and CD62L-) or resident memory (CD44+, CD62L-, and CD103+) T cells.

Figure 10:
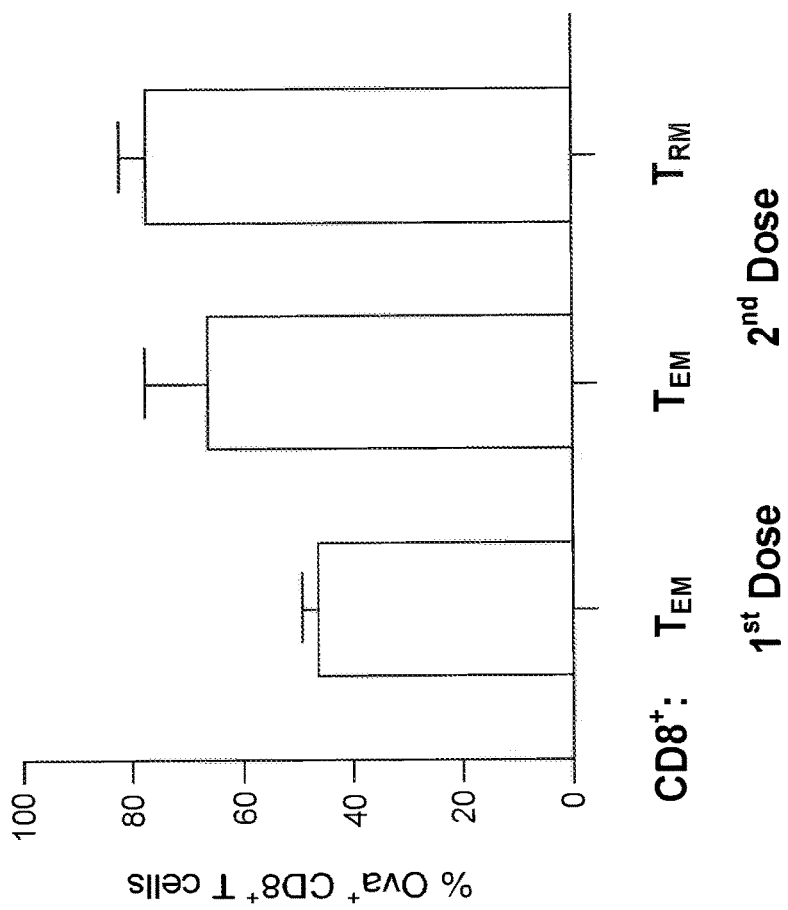
FIG. 10 shows the number of OVA-specific CD8+ T cells in the lung of mice treated with an exosome disclosed herein (e.g., expressing OVA-Scaffold Y and loaded with the STING agonist CL656). "1$^{st}$ Dose" represents the number of effector memory (TEM) CD8+ T cells observed after a single administration of the exosome. "2nd Dose" represents the number of effector memory and/or resident memory ($T_{RM}$) CD8+ T cells observed after a boost with a second administration.

As shown in FIG. 10, after a single intranasal administration of Py-OVA exoVACC, robust OVA-specific effector memory CD8+ T cells were observed in the lungs of the treated animals. After a boost, the number of OVA-specific CD8+ T cells increased further, resulting in robust effector and memory CD8+ T cells.

To assess whether the EVs (e.g., exosomes) disclosed herein can also mount a robust resident memory CD4+ T cells, mice were administered via intranasal administration one of the following: (i) soluble OVA ("OVA"), (ii) exosome expressing only OVA-Scaffold Y fusion protein ("PyOVA"), (iii) exosome expressing OVA-Scaffold Y and loaded with the STING agonist CL656 ("Py-OVA exoVACC"), (iv) soluble OVA+soluble poly I:C ("OVA+poly I:C"), and (v) exosome expressing only OVA-Scaffold Y fusion protein+soluble poly I:C ("PyOVA+poly I:C"). At day 7 post initial immunization, the animals received a second administration of the same treatment. Animals were then sacrificed a week later (i.e., day 14 post initial immunization) and the frequency of OVA-specific CD8+ T cells was assessed in the lung using flow cytometry.

Figures 13A, 13B:
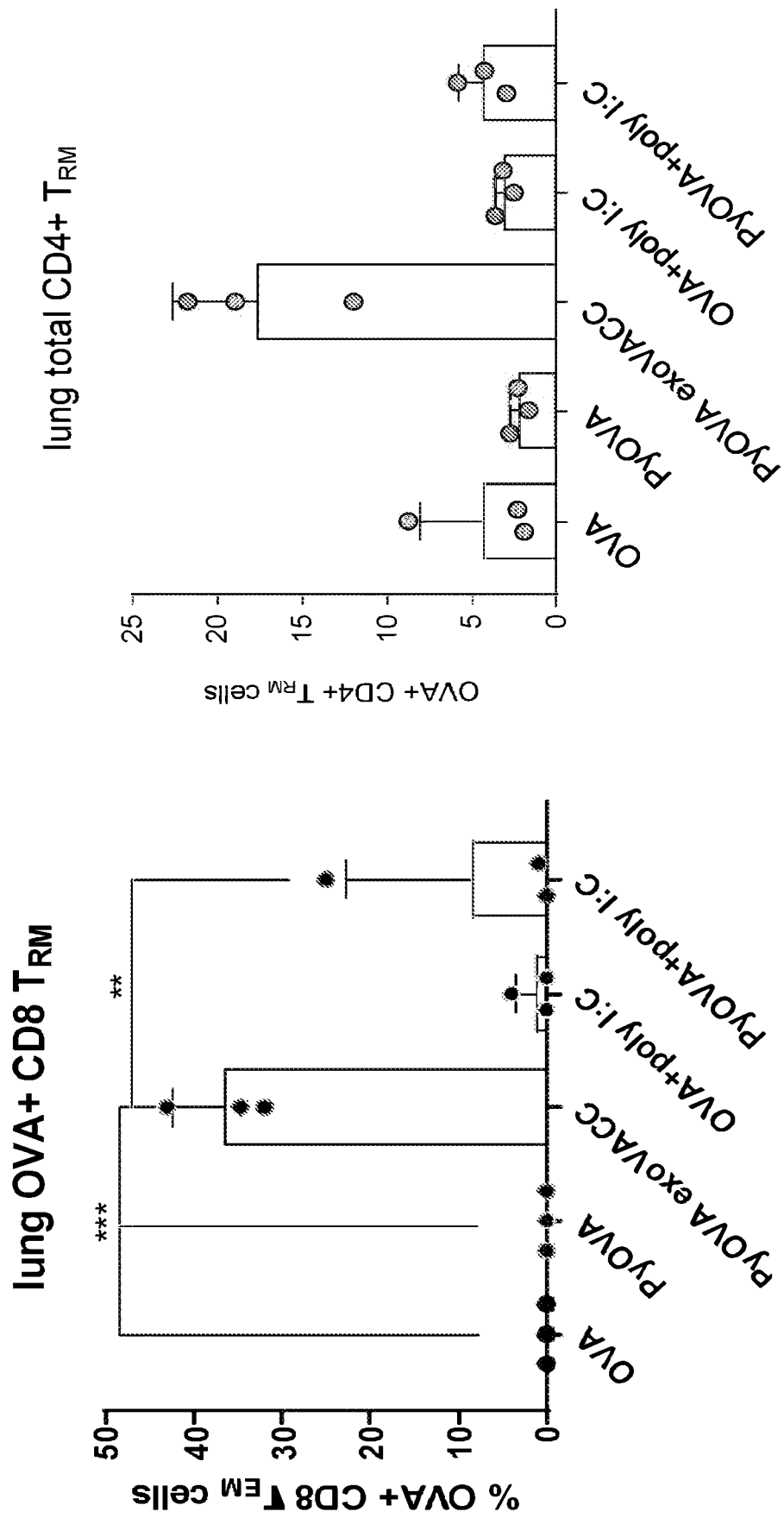
FIGS. 13A, 13B, and 13C show the induction of OVA-specific resident memory ($T_{RM}$) CD8+ T cells (FIG. 13A) and CD4+ T cells (FIG. 13B) in the lungs of mice that received two administrations of an exosome expressing OVA-Scaffold Y and loaded with the STING agonist CL656 ("Py-OVA exoVACC"). Control animals received one of the following: (i) soluble OVA ("OVA"), (ii) exosome expressing only OVA-Scaffold Y fusion protein ("PyOVA"), (iii) soluble OVA+soluble poly I:C ("OVA+poly I:C"), and (iv) exosome expressing only OVA-Scaffold Y fusion protein+ soluble poly I:C ("PyOVA+poly I:C").
Figure 13C:
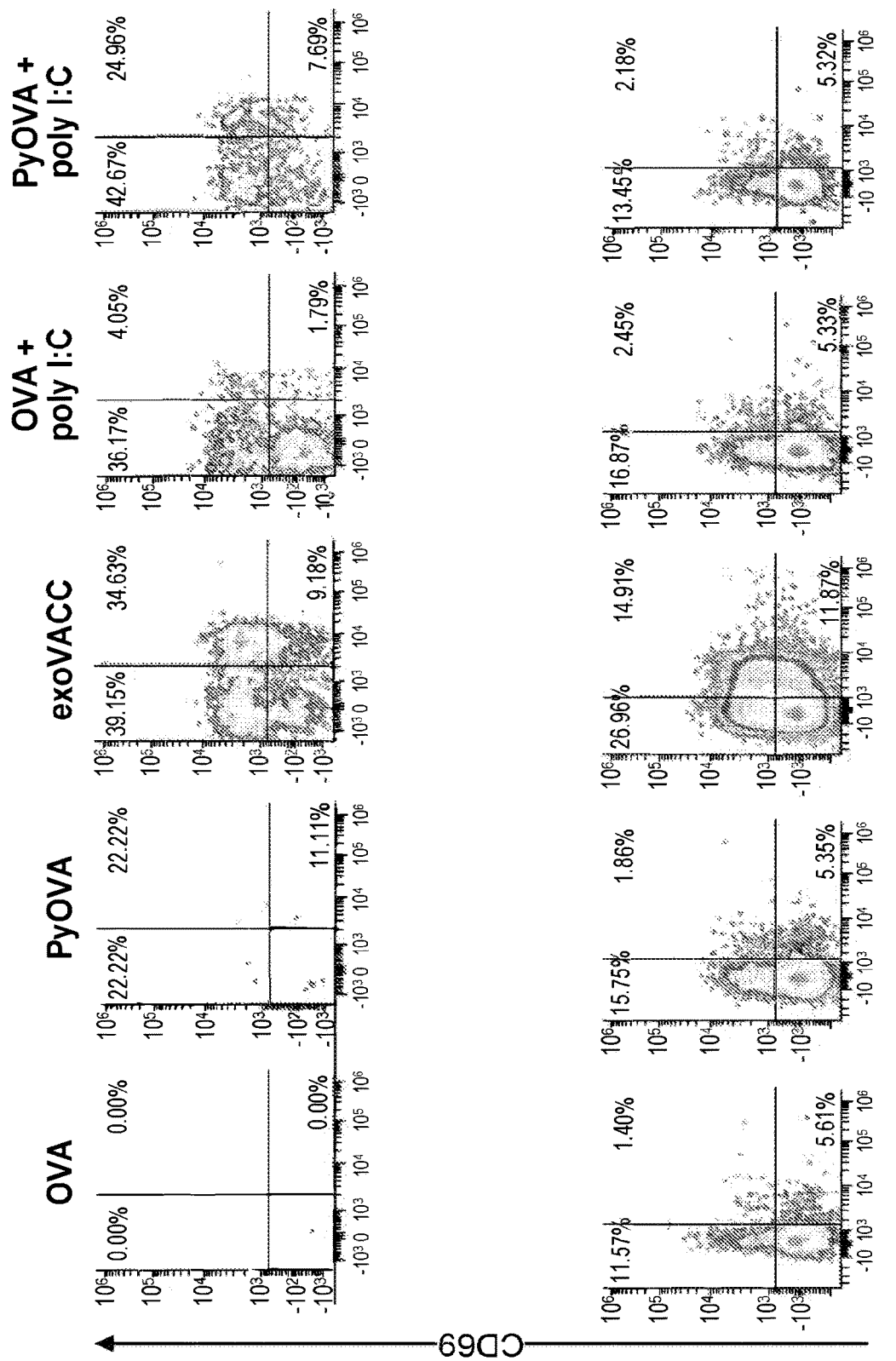

In agreement with the above results, animals that were treated with Py-OVA exoVACC exhibited robust resident memory CD8+ T cells within the lung (FIGS. 13A, 13B, and 13C). Similar results were observed for resident memory CD4+ T cells.

Collectively, the above data further demonstrate the effectiveness of the exosomes disclosed herein (e.g., engineered-exosome expressing OVA-Scaffold Y and loaded with the STING agonist CL656) to induce robust effector and memory T cells (both CD8+ and CD4+), including in mucosal tissues (e.g., lung).

Example 17: Analysis of the Tropism of Anti-Clec9a Expressing EVs (e.g., Exosomes)

Further to Example 13 described above, EVs (e.g., exosomes) were engineered to express an anti-Clec9a antibody fragment linked to a Scaffold X protein on their surface ("anti-Clec9a EV"). As in the earlier Examples, the anti-Clec9a EVs were loaded with the STING agonist CL656.

Figure 11B:
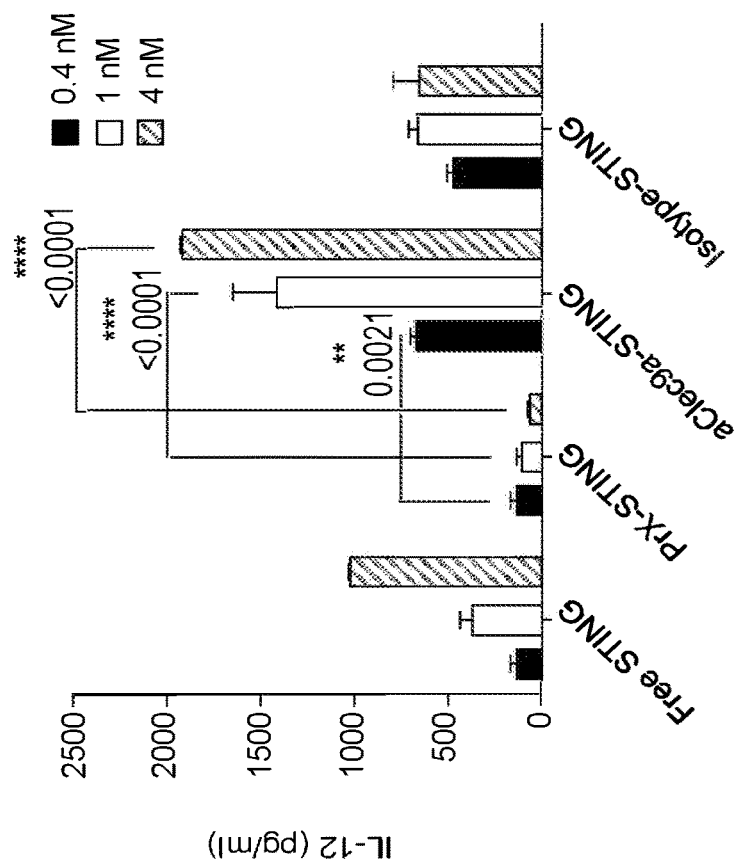
FIGS. 11A and 11B show the effect of expressing anti-Clec9a binding moiety in an EV (e.g., exosome) disclosed herein.
Figure 11A:
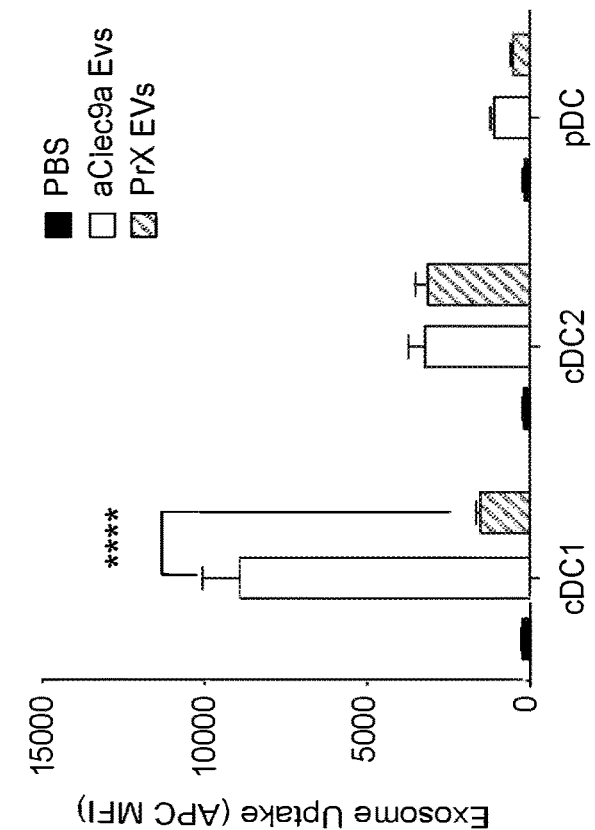

The anti-Clec9a EVs were administered to mice and their cell-specific tropism was assessed. Control animals received either PBS alone ("PBS") or an exosome expressing Scaffold X protein alone ("PrX EVs"). As shown in FIG. 11A, there was a preferential uptake of the anti-Clec9a EVs by the conventional dendritic cell 1 ("cDC1") population within the spleen. Among the other dendritic cells analyzed (i.e., conventional DC 2 ("cDC2") and plasmacyotid DC ("pDC")), there was no noticeable difference in the uptake of the anti-Clec9a EV compared to the control exosome (PrX EVs).

Next, to further assess the effect of the enhanced tropism of the anti-Clec9a EVs to cDC1, splenic dendritic cells (isolated from wild-type mice) were stimulated in vitro with anti-Clec9a EVs, and STING activity within the DCs was assessed. The DCs were stimulated with varying concentrations of the anti-Clec9a EVs (i.e., 0.4 nM, 1 nM, or 4 nM). DCs in the control groups were stimulated with one of the following: (i) soluble STING agonist ("free STING"), (ii) EVs (e.g., exosomes) expressing Scaffold X protein alone (i.e., no anti-Clec9a antibody fragment) and loaded with the STING agonist ("PrX-STING"), and (iii) EVs (e.g., exosomes) expressing a non-relevant antibody and loaded with the STING agonist ("Isotype-STING"). STING activity was assessed by measuring the amount of IL-12 produced by the different DCs. As shown in FIG. 11B, isolated DCs treated with anti-Clec9a EV produced much greater amount of IL-12 compared to the other groups, including DCs treated with PrX-STING.

The above results demonstrate that EVs (e.g., exosomes) expressing anti-Clec9a targeting moieties can preferentially target Clec9a-expressing cells, such as cDC1, and that this enhanced tropism can help increase dendritic cell activation. Such abilities can be useful in the context of vaccination, as described in the present disclosure.

Example 18: Effect of Route of Administration on Inducing Immune Response

Further to Example 6 provided above, the effect of administration route on the ability of the EVs (e.g., exosomes) disclosed herein to induce an immune response was further assessed. Briefly, an engineered-exosome expressing OVA-Scaffold Y and loaded with the STING agonist CL656 ("Py-OVA exoVACC") (1 µg OVA) was administered to mice via one of the following administration routes: (i) intravenous ("IV"), (ii) intranasal ("IN"), and (iii) subcutaneous ("SQ"). As a comparison, some of the mice received a subcutaneous administration of soluble OVA in a commercially available formulation (ADDAVAX™, InvioGen) ("SubQ AV"). At day 7 post immunization, all the animals were sacrificed, splenocytes isolated, and the frequency of OVA-specific effector memory CD8+ T cells (CD44+ and CD62L−) was assessed via flow cytometry.

Figure 12B:
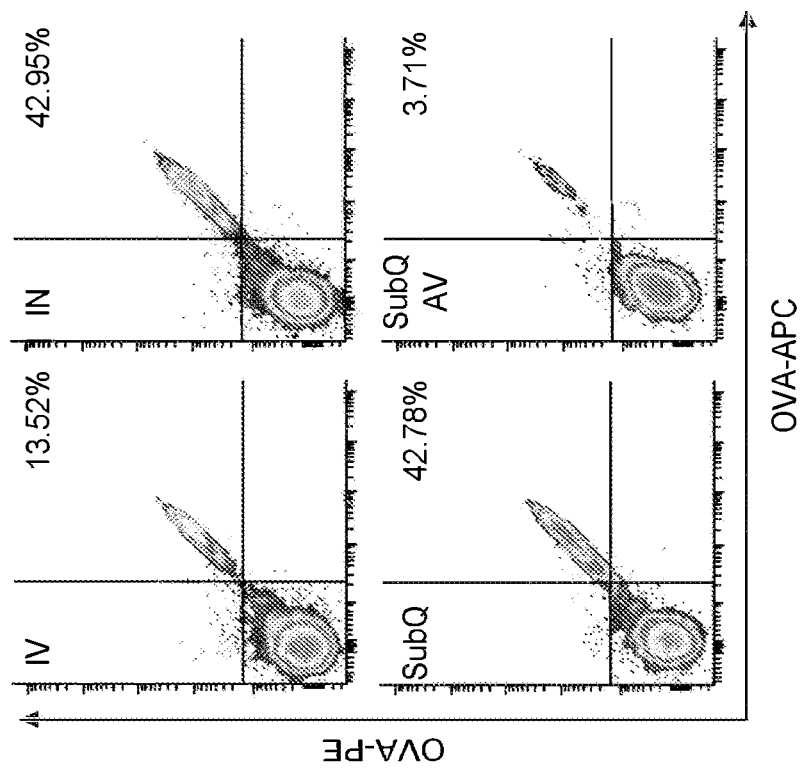
FIGS. 12A and 12B show the effect of administration route on the induction of OVA-specific CD8+ TEM cells by an engineered-exosome expressing OVA-Scaffold Y and loaded with the STING agonist CL656 ("Py-OVA exoVACC"). The administration routes shown include: (i) intravenous ("IV"), (ii) intranasal ("IN"), and (iii) subcutaneous ("SQ"). "SubQ AV" corresponds to animals treated with soluble OVA in a commercially available formulation (ADDAVAX™ InvioGen) ("SubQ AV").
Figure 12A:
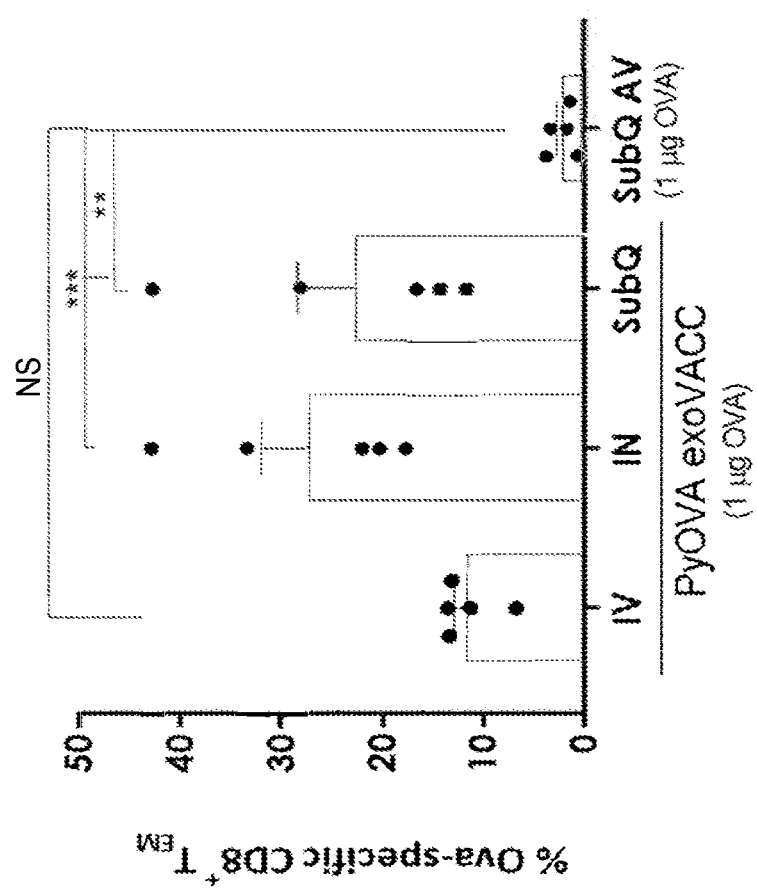

As shown in FIGS. 12A and 12B, regardless of the administration route, Py-OVA exoVACC was able to induce robust OVA-specific effector memory CD8+ T cells in the animals, particularly when compared to OVA delivered using the commercially available formulation. These results further confirm the efficacy of EVs (e.g., exosomes) disclosed herein and demonstrate that the EVs could be used to induce robust immune response regardless of the route of administration.

Example 19: Anti-Tumor Effects of Py-OVA exoVACC EVs (e.g., Exosomes)

Further to Example 11 provided above, the ability of the EVs (e.g., exosomes) disclosed herein to induce an anti-tumor immune response was assessed in a mouse model. Briefly, mice were treated with one of the following: (i) exosome expressing OVA-Scaffold Y and loaded with the STING agonist CL656 ("Py-OVA exoVACC") via intranasal administration ("exoVACC (IN)"), (ii) exosome expressing OVA-Scaffold Y and loaded with the STING agonist CL656 (Py-OVA exoVACC) via subcutaneous administration ("exoVACC (SQ)"), (iii) soluble OVA+soluble poly I:C via intranasal administration ("OVA+poly I:C (IN)"), and (iv) soluble OVA+soluble poly I:C via subcutaneous administration ("OVA+poly I:C (IN)"). See FIG. 14A. Untreated or PBS-only treated animals were used as controls. Then, at day 7 post immunization, EG7-OVA tumor cells were subcutaneously implanted into all the animals. Then, both tumor volume and survival of the animals were monitored over a course of at least 30 days.

Figure 14B:
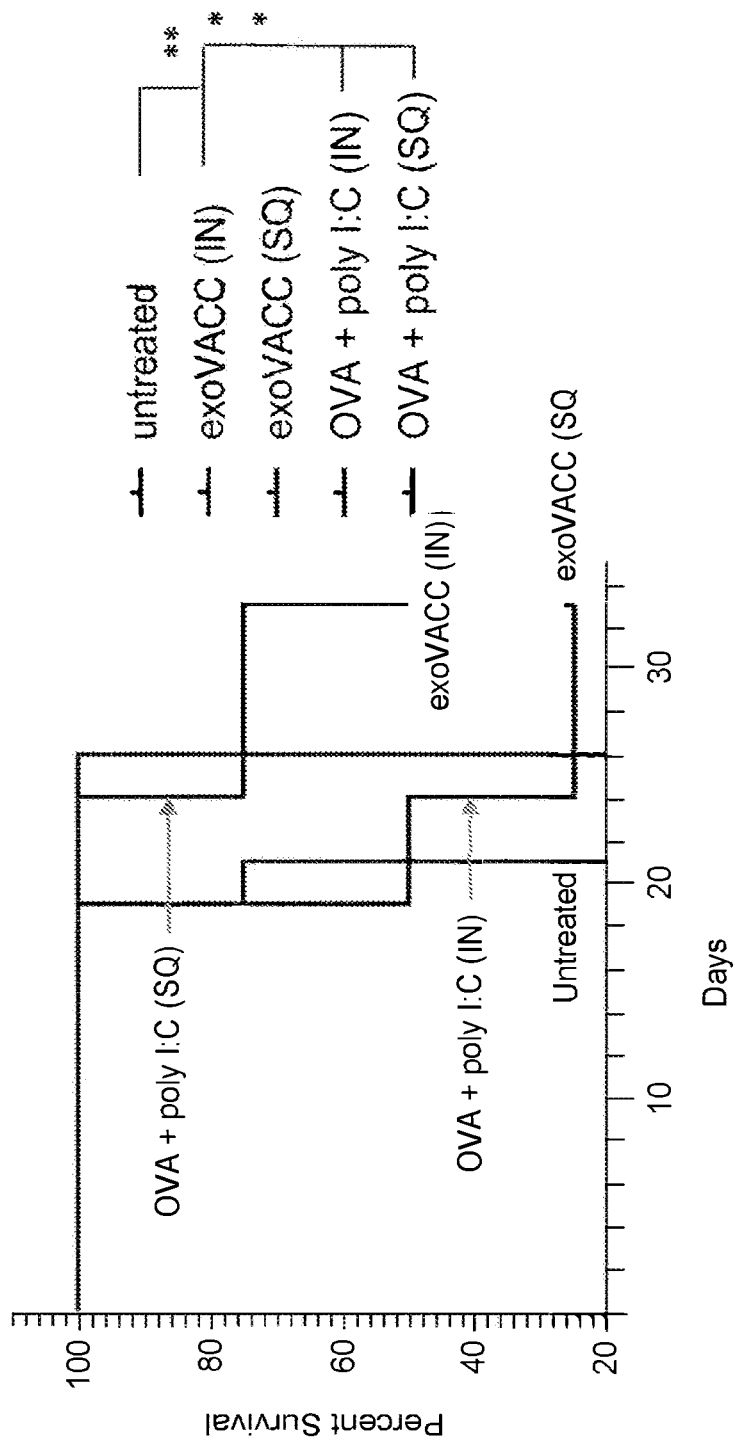
Figure 14H:
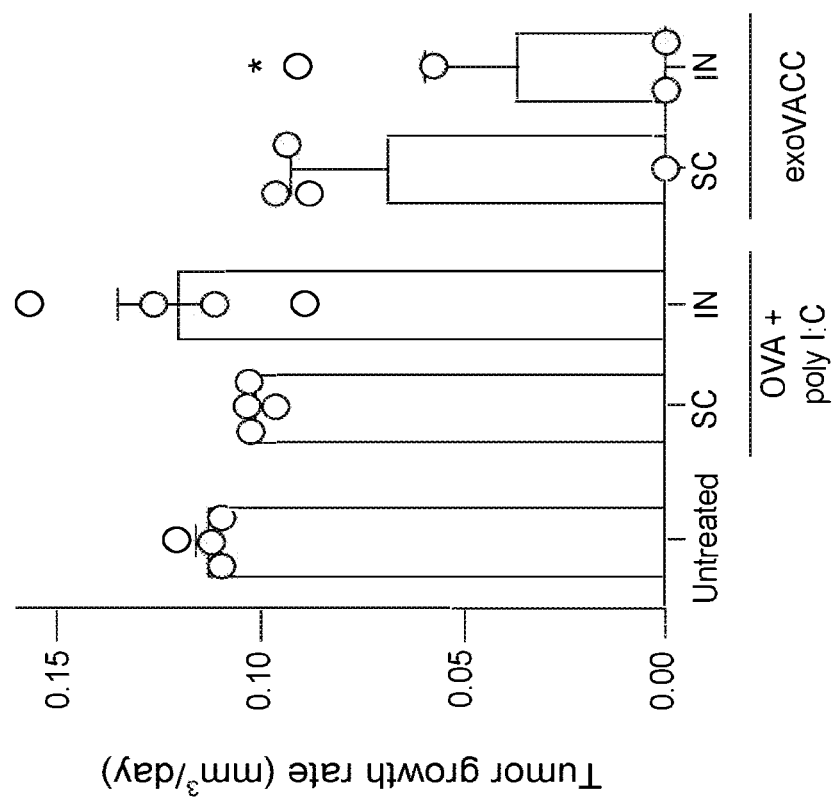
Figures 14I, 14J, 14K:
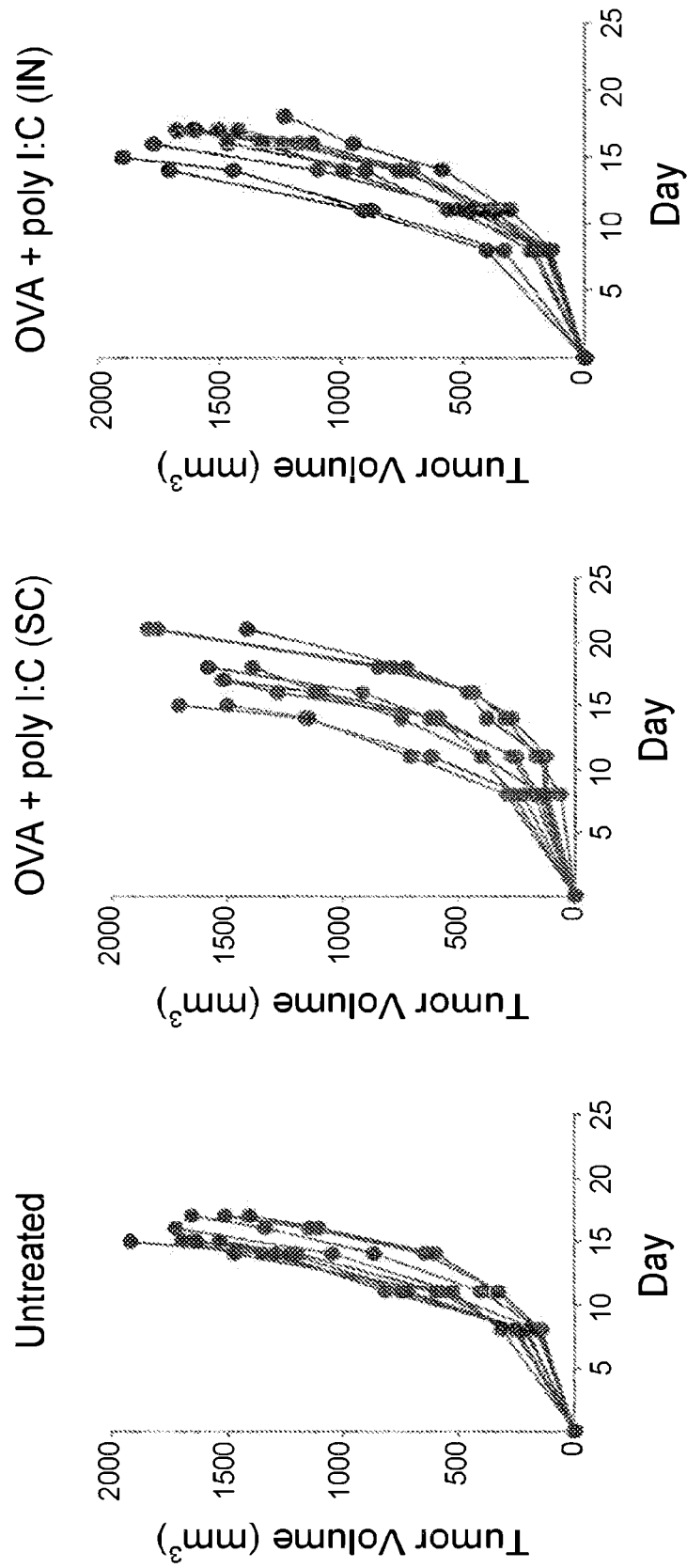
Figure 14M:
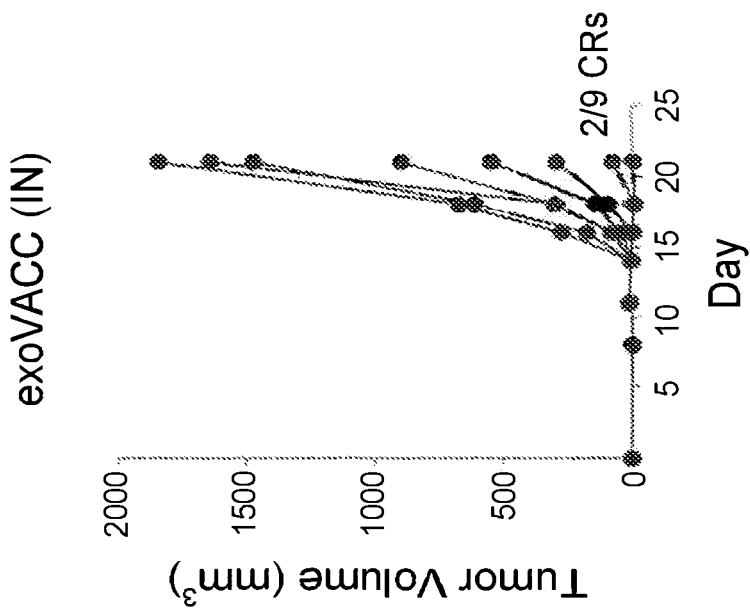
Figure 14L:
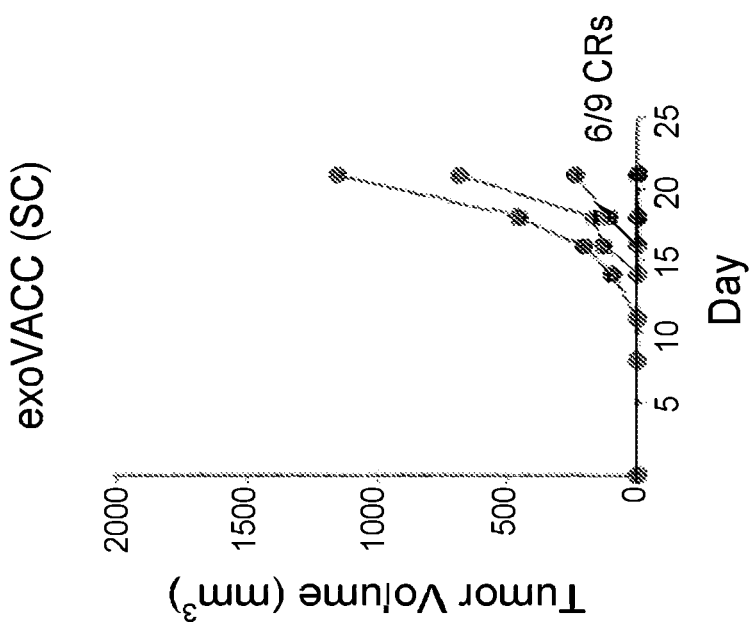
Figure 14N:
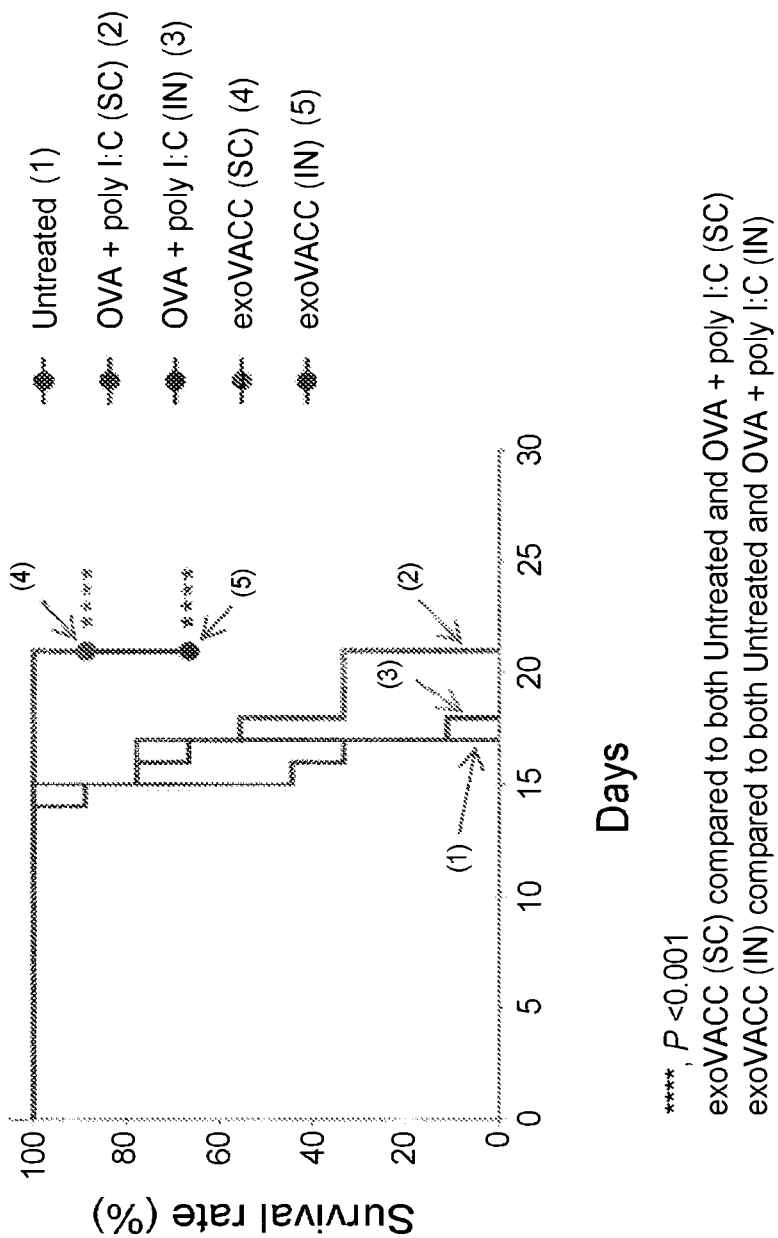

As shown in FIGS. 14B, 14C, 14D, and 14F, animals that were either untreated or treated with OVA+poly I:C (both intranasal and subcutaneous administration) failed to control the tumor and succumbed to the disease by about day 30 post tumor implantation. However, in animals that received an administration of exoVACC, improved anti-tumor immune response was observed. For the exoVACC (SQ) group, 25% of the animals effectively controlled the tumor and survived to the end of the experiment (FIGS. 14B and 14E). For the exoVACC (IN) group, 50% of the animals mounted an effective anti-tumor immune response against the EG7-tumor cells (FIGS. 14B and 14G). As shown in FIG. 14H, the improved anti-tumor immune response correlated with a decrease in the rate of tumor growth. In a separate independent experiment, greater percentage of animals from both the exoVACC (SQ) group and the exoVACC (IN) group controlled tumor growth and survived the entire duration of the experiment (see FIGS. 14L, 14M, and 14N).

The above results demonstrate that the EVs (e.g., exosomes) disclosed herein could be used as a vaccine for the treatment of certain cancers.

Figures 15A, 15B, 15C, 15D:
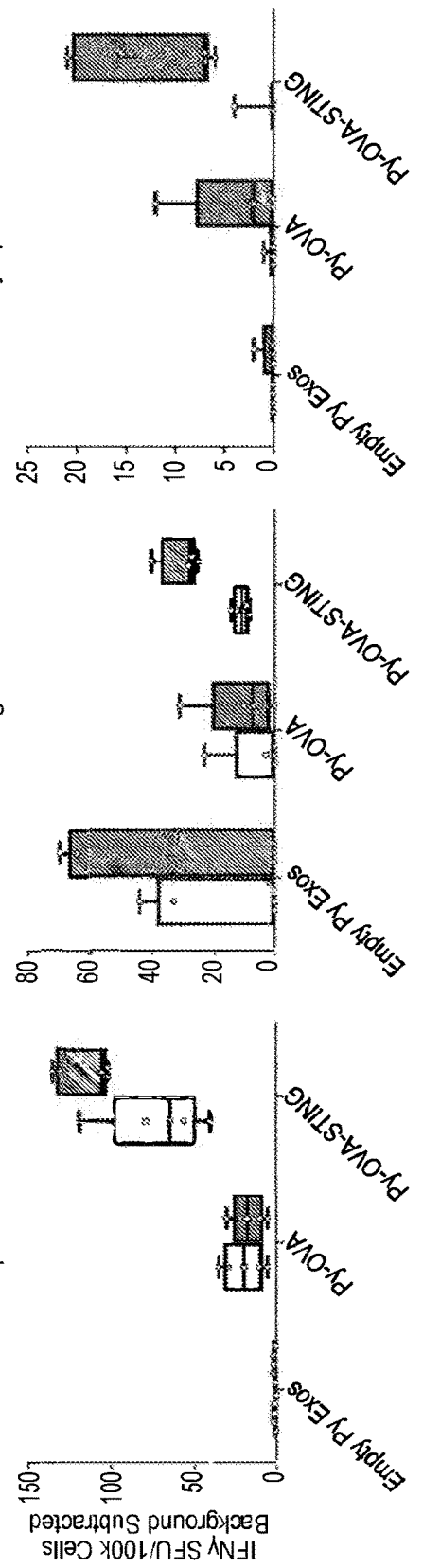
FIGS. 15A, 15B, 15C, 15D, 15E, and 15F show the ability of the engineered EVs (e.g., exosomes) disclosed herein to migrate to mesenteric lymph nodes after intranasal administration.
Figure 15F:
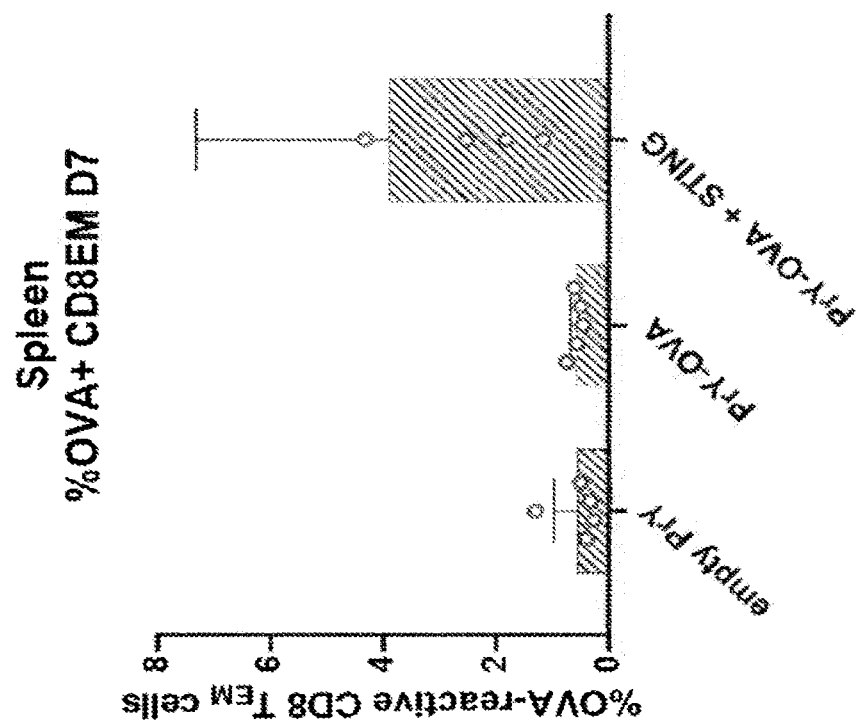
Figure 15E:
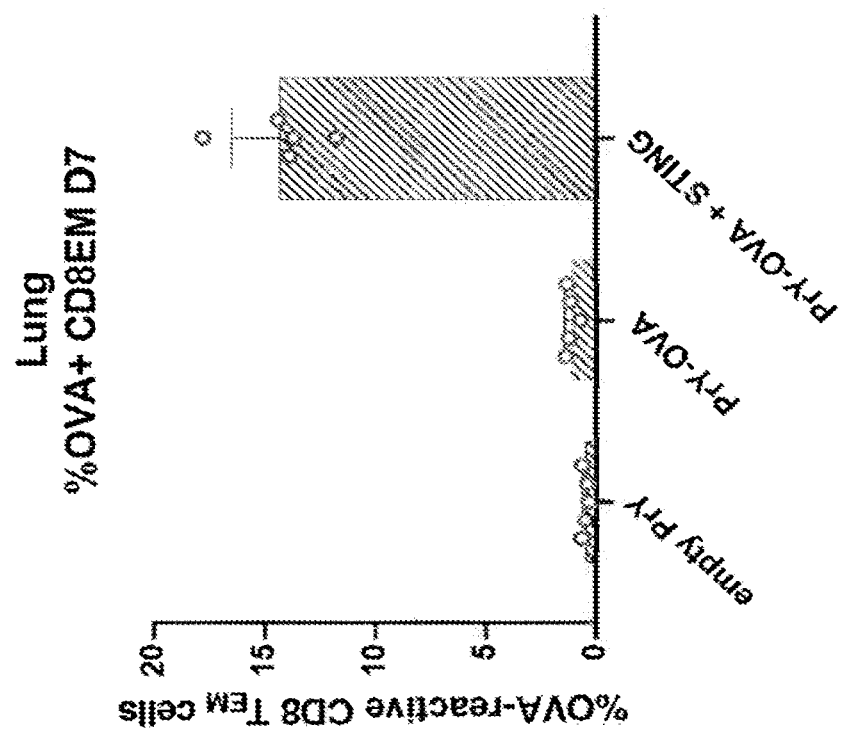

Example 20: Ability of Py-OVA exoVACC EVs (e.g., Exosomes) to Induce Antigen-Specific T Cells in Mesenteric Lymph Nodes after Intranasal Administration To further assess the ability of the EVs (e.g., exosomes) disclosed herein to induce a mucosal immune response, the frequency of antigen-specific T cells in mesenteric lymph nodes (i.e., gut draining lymph nodes) was assessed after intranasal administration of Py-OVA exoVACC (i.e., engineered-exosome expressing OVA-Scaffold Y and loaded with the STING agonist CL656) (see "Group 5" in FIG. 15A). The control animals received one of the following: (i) empty (i.e., no OVA antigen) exosome expressing Scaffold Y alone ("Group 1"); (ii) soluble OVA ("Group 2"); (iii) soluble OVA+soluble STING agonist ("Group 3"); or (iv) exosome expressing only OVA-Scaffold Y fusion protein ("Group 4"). At day 7 post-vaccination, the animals were sacrificed and the frequency of OVA-specific CD8+ T cells was assessed using both IFN-γ ELISPOT and/or flow cytometry.

As shown in FIGS. 15B, 15C, 15E, and 15F (and in agreement with the earlier results—see, e.g., Example 2), animals that received an intranasal administration of the Py-OVA exoVACC had significantly greater number of OVA-specific CD4+ and OVA-specific CD8+ T cells in both the spleen and the lung, compared to the control animals (e.g., Group 1 and Group 4). In the mesenteric lymph nodes, no significant differences were observed for CD4+ T cells among the different treatment groups (see FIG. 15D, left bar in each of the groups). However, a significant increase in the number of OVA-specific CD8+ T cells was observed in the mesenteric lymph nodes of animals treated with Py-OVA exoVACC (see FIG. 15D, right bar in each of the groups). These results confirm that the EVs (e.g., exosomes) disclosed herein (e.g., comprising OVA-Scaffold Y and loaded with STING agonist) can be useful in inducing robust mucosal immune response when administered intranasally.

Example 21: Efficacy of Scaffold X-Engineered EVs (e.g., Exosomes) Comprising Antigen and STING Agonist in Inducing Antigen-Specific T Cell Responses To further assess the ability of the EVs (e.g., exosomes) disclosed herein to induce immune response, engineered EVs (e.g., exosomes) overexpressing Scaffold X ("Scaffold X-engineered EVs") were generated (see, e.g., Example 1). CD8 peptide (Lama4) and/or CD4 peptide (Itgb1) containing maleimide linker were cross-linked to the Scaffold X expressed on the surface of the engineered EVs. The CD8 peptide had the following structure: (maleimide linker)-QKISFFDGFEVGFNFRTLQPNGLLFYYT (SEQ ID NO: 379). The underlined amino acid indicates a mutation. The bolded residues represent the CD8+ T cell epitope. The CD4 peptide had the following structure: (maleimide linker)-WFYFTYSVNGYNEAIVHVVETPD (SEQ ID NO: 380). The underlined amino acid indicates a mutation. The CD4+ T cell epitope was unknown. The Scaffold X-engineered EVs were further loaded with a STING agonist (CL656). The Scaffold X-engineered EVs were then administered to mice as shown in FIG. 16A. Briefly, the animals received one of the following: (i) PBS alone (i.e., no EV) (Group 1); (ii) Scaffold X-engineered EVs expressing the CD8 peptide (Lama4) alone (Group 2); (iii) Scaffold X-engineered EVs expressing the CD4 peptide (Itgb1) alone (Group 3); and (iv) Scaffold X-engineered EVs expressing both the CD4 peptide and the CD8 peptide. The Scaffold X-engineered EVs were administered to the animals via subcutaneous administration at a dose that would result in the animals receiving the same amount of STING agonist. Each of the animals received total of two doses (one week between doses) of the relevant treatment regimen. At day 7 post the second administration, the animals were sacrificed and the frequency of antigen-specific CD4+ and CD8+ T cells in the spleen was assessed using IFN-γ ELISPOT.

Figure 16C:
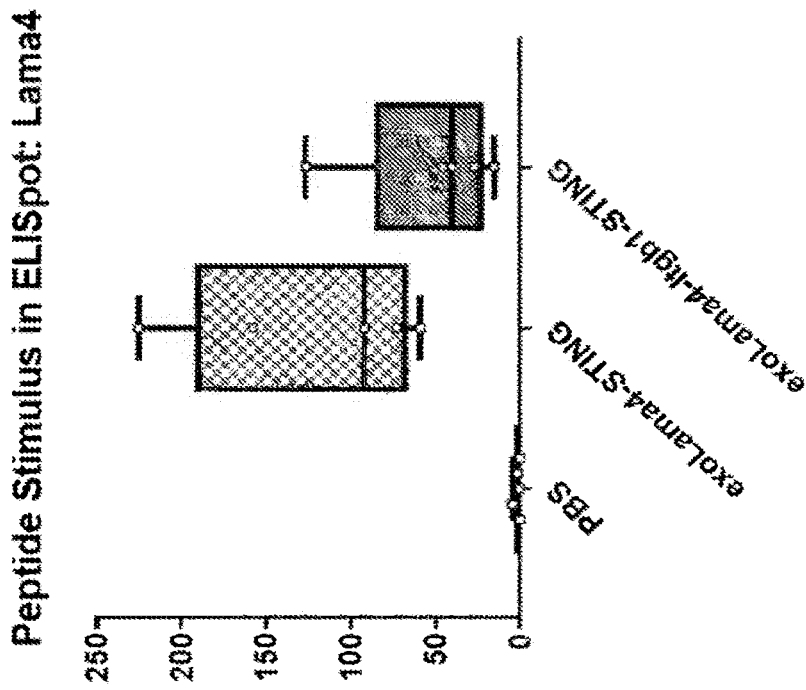
Figure 16B:
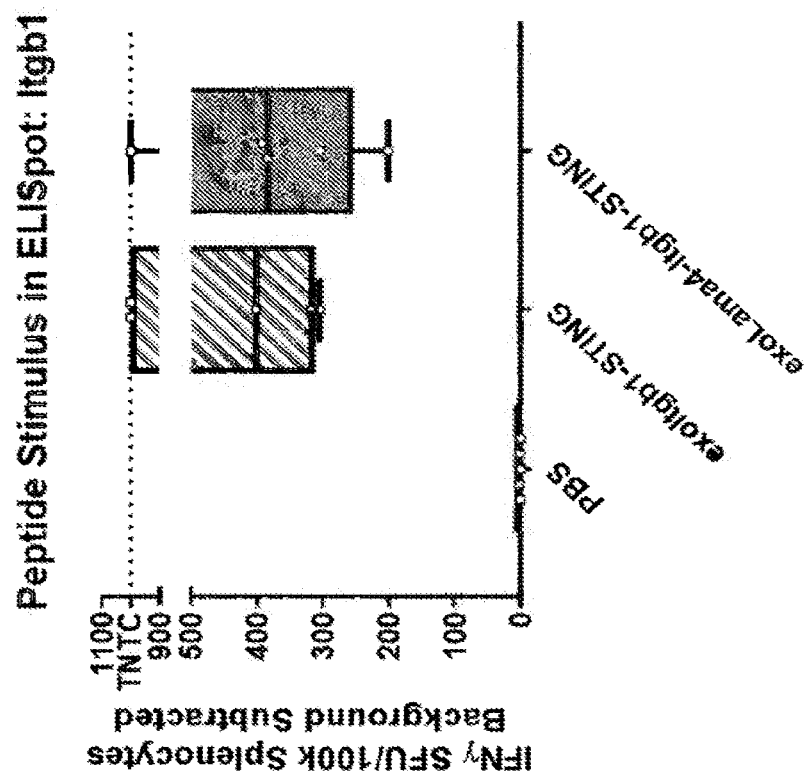
Figure 18B:
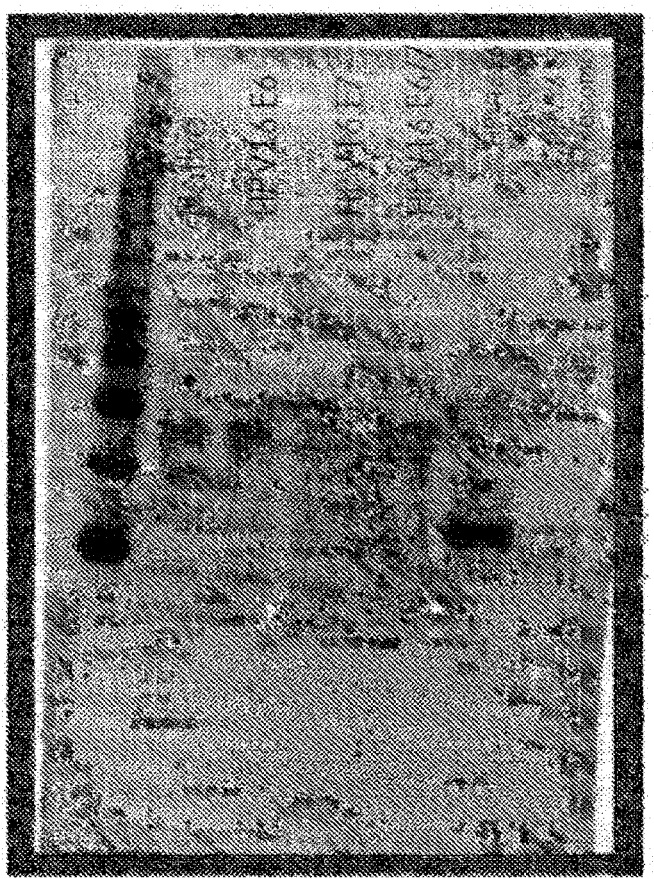
FIGS. 18A, 18B, 18C, 18D, 18E, 18F, 18G, 18H, 18I, 18J, 18K, and 18L show the expression of E6 and E7 proteins of HPV16 and HPV18 in the surface-engineered EVs (e.g., exosomes) disclosed herein, as measured by Western Blot.
Figure 18A:
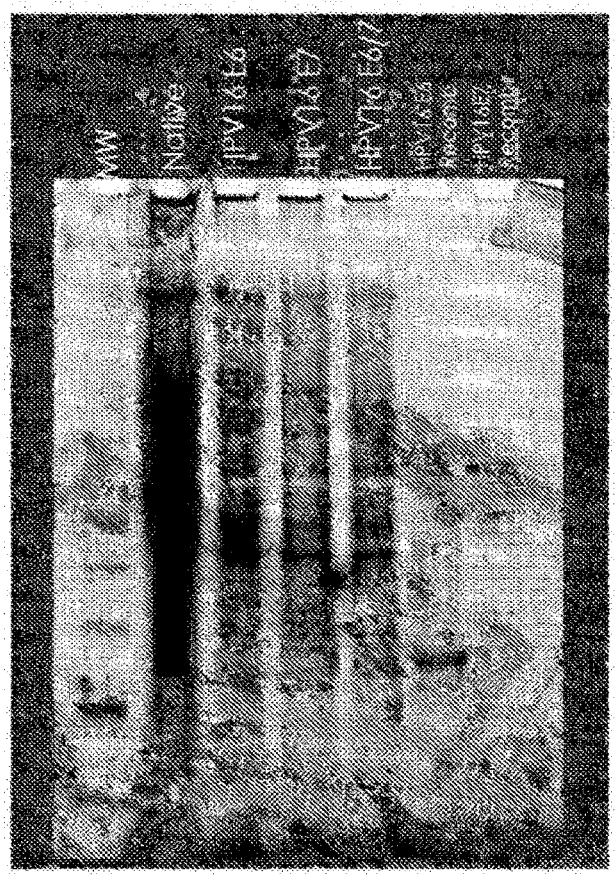
Figure 18D:
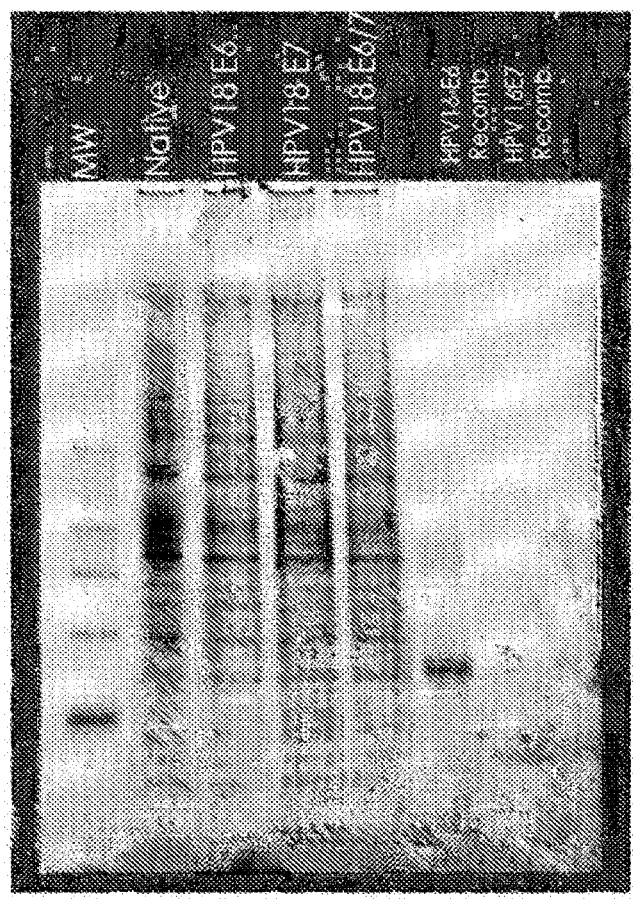
Figure 18C:
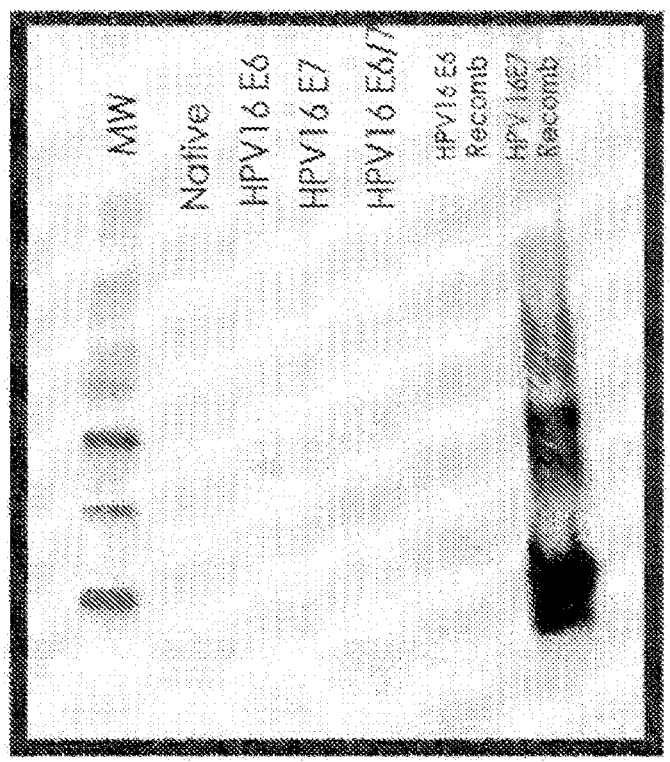
Figure 18F:
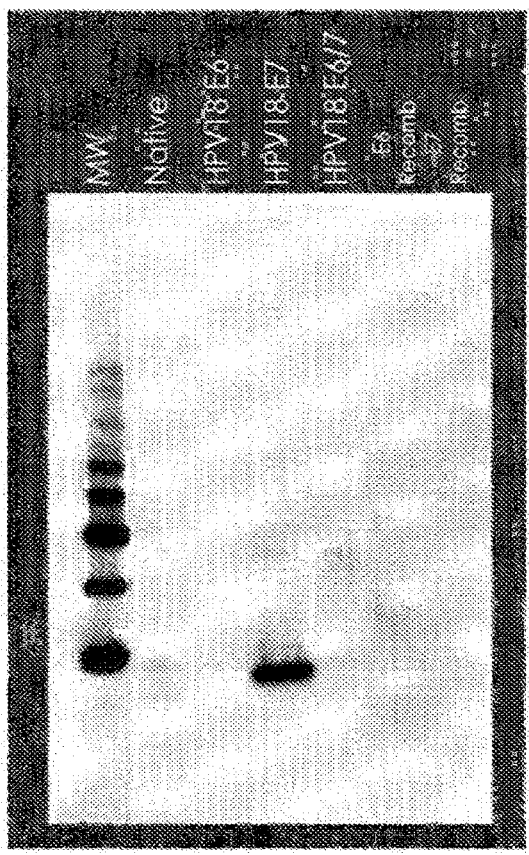
Figure 18E:
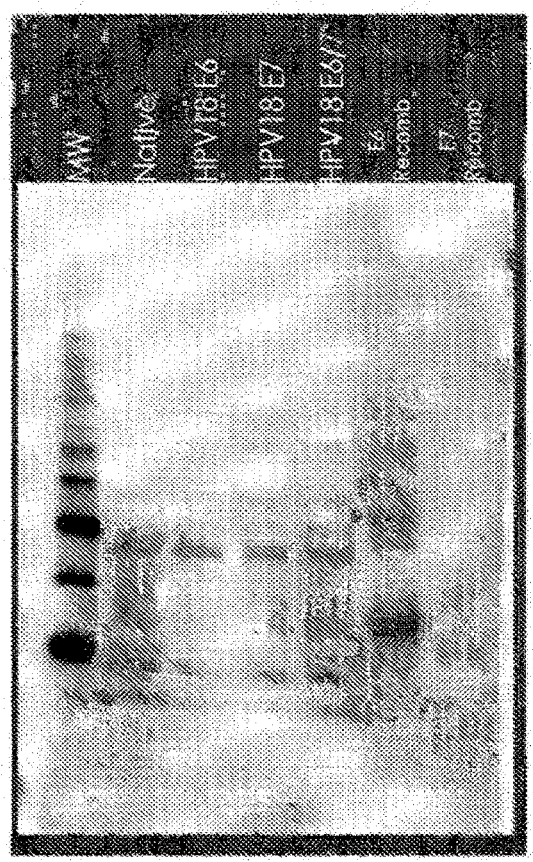
Figure 18H:
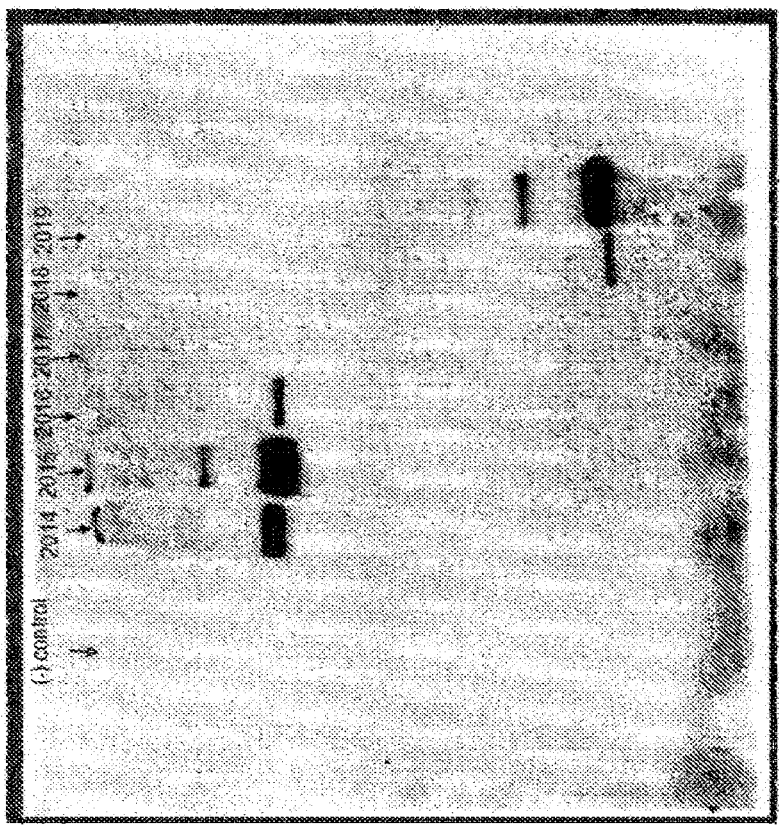
Figure 18G:
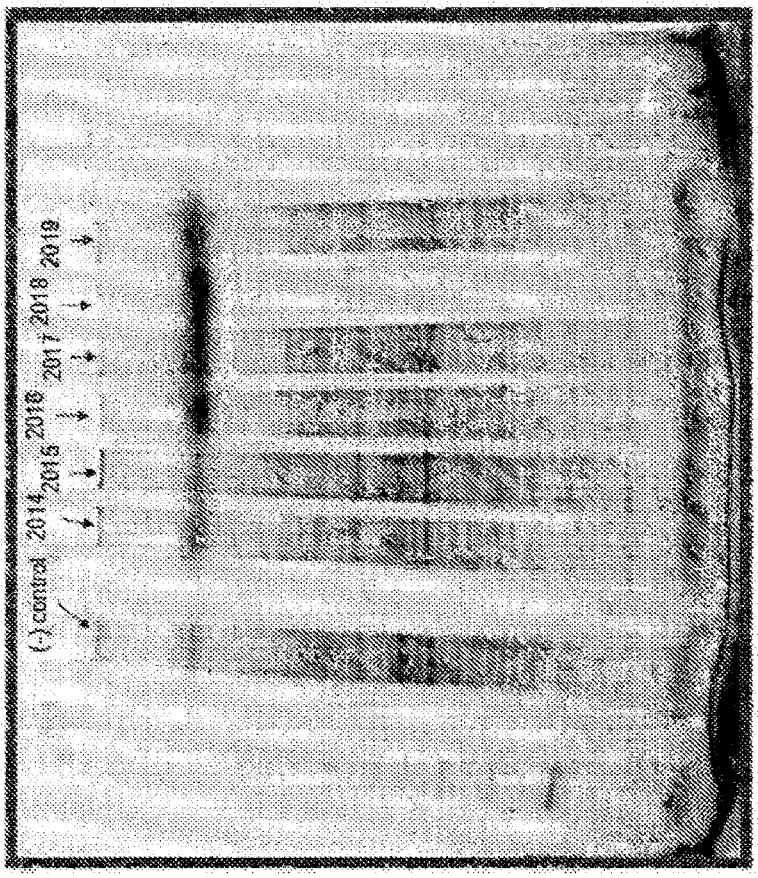
Figures 18I, 18J:
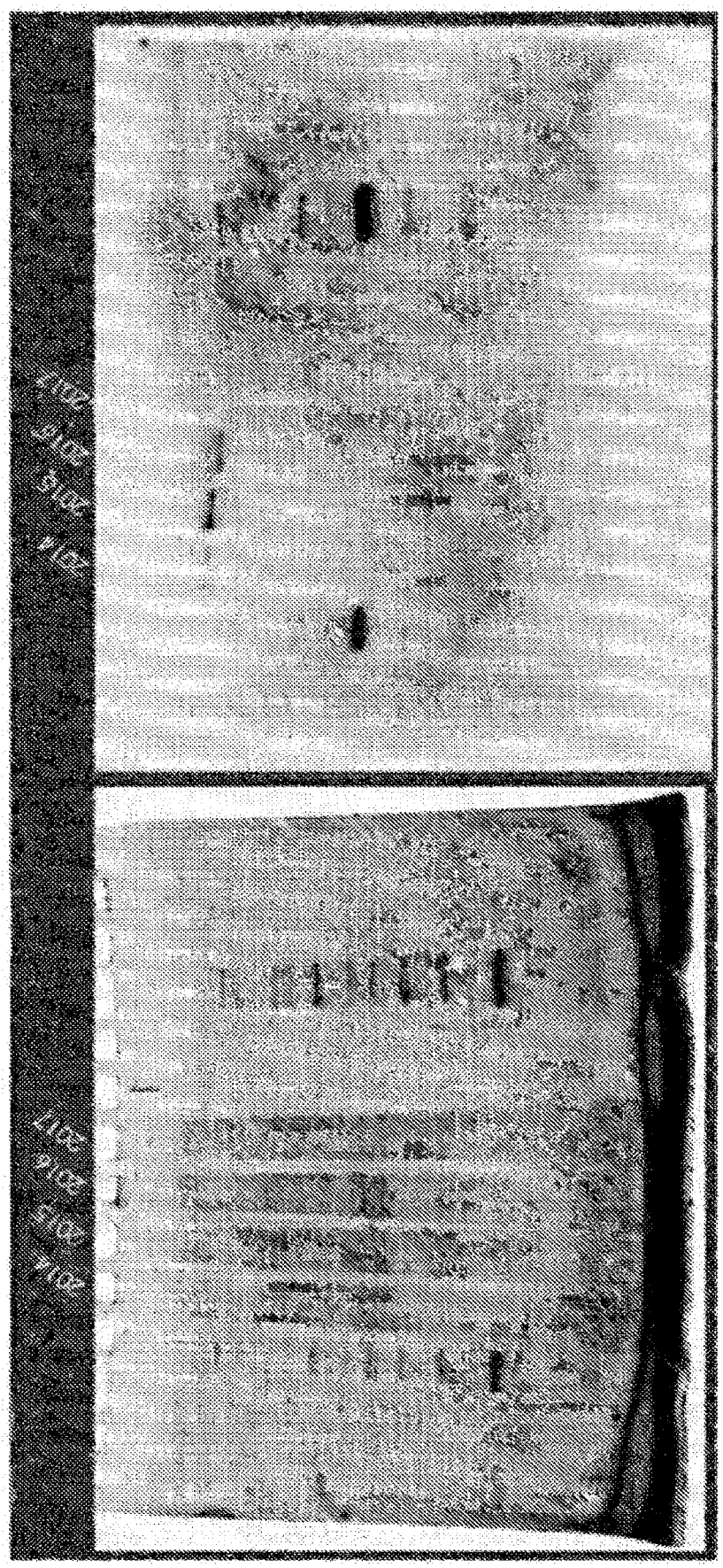
Figures 18K, 18L:
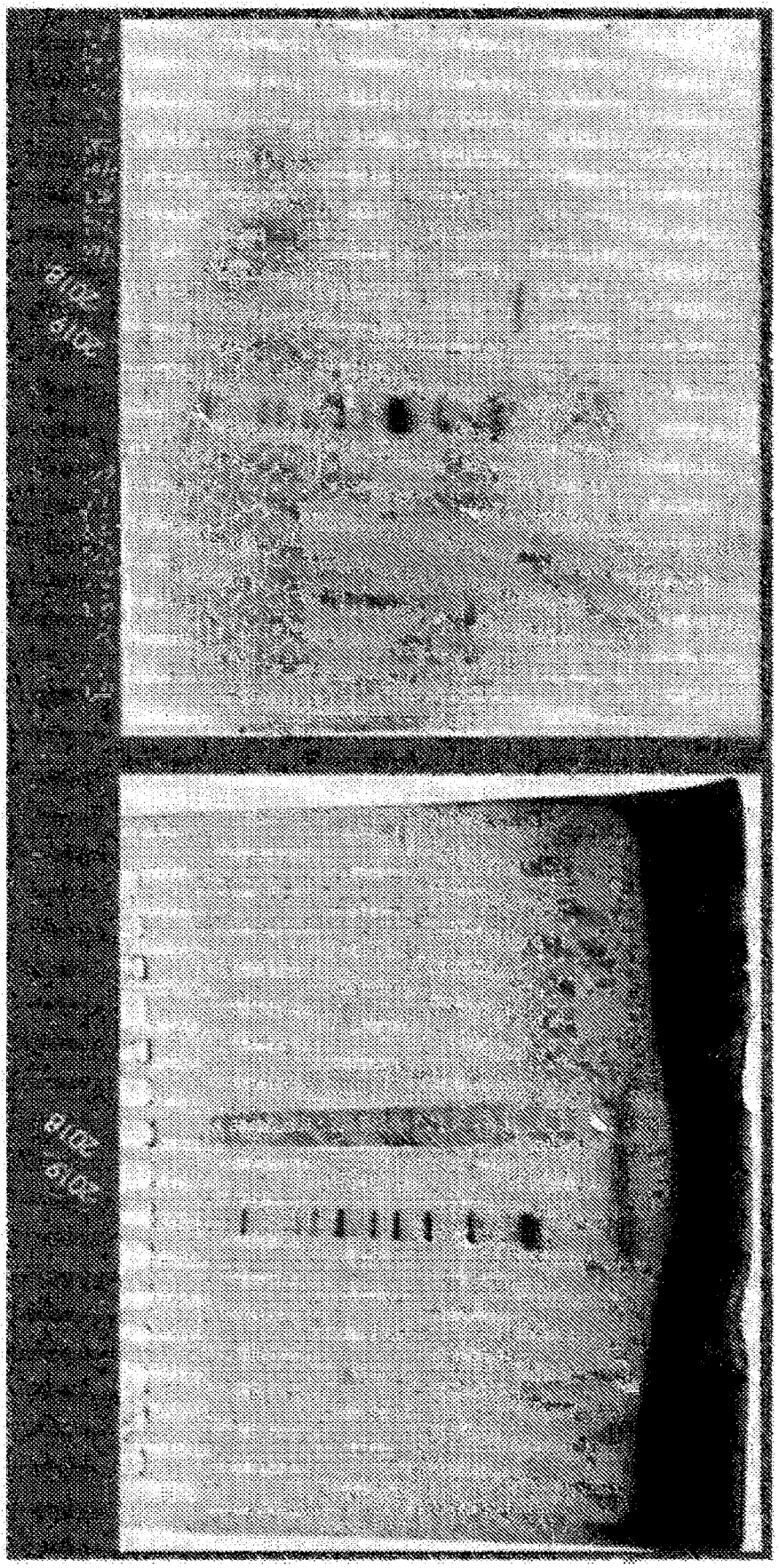

As shown in FIGS. 16B and 16C, robust Itgb1-specific CD8+ T cells and Lama4-specific CD4+ T cells were detected in animals from Group 2 (i.e., received Scaffold X-engineered EVs expressing the CD8 peptide alone) and Group 3 (i.e., received Scaffold X-engineered EVs expressing the CD4 peptide alone), respectively. Similarly, administering the Scaffold X-engineered EVs expressing both the CD4 peptide and the CD8 peptide to the animals resulted in strong antigen-specific CD8+ T cell and CD4+ T cell immune responses.

The results further confirm that the EVs (e.g., exosomes) disclosed herein can be used to induce robust immune responses against antigens of interest (e.g., tumor). The results also demonstrate the ability of the EVs (e.g., exosomes) disclosed herein to induce immune responses to multiple antigens, e.g., by expressing multiple antigens on the EVs.

Example 22: Efficacy of Scaffold X-Engineered EVs (e.g., Exosomes) Comprising Antigen and CpG Adjuvant in Inducing Antigen-Specific T Cell Responses To further assess the vaccine capabilities of the EVs (e.g., exosomes) disclosed herein, engineered EVs (e.g., exosomes) overexpressing Scaffold X ("Scaffold X-engineered EVs") were again generated (see, e.g., Example 1). CD8 peptide (Lama4) and/or CD4 peptide (Itgb1) containing maleimide linker were again cross-linked to the Scaffold X expressed on the surface of the engineered EVs as described in Example 21. In the current Example, the Scaffold X-engineered EVs were further loaded with CpG (i.e., a TLR9 agonist) instead of STING agonist. The Scaffold X-engineered EVs were then administered to mice as shown in FIG. 17A. Briefly, the animals received one of the following: (i) control EV (i.e., EV expressing Scaffold X alone) ("Empty PrX exos") (Group 1); (ii) Scaffold X-engineered EVs expressing the CD8 peptide (Lama4) alone ("exo-Lama4-CpG") (Group 2); and (iii) Scaffold X-engineered EVs expressing both the CD8 peptide (Lama4) and the CD4 peptide (Itgb1) ("exoItgb 1-Lama4-CpG") (Group 3). Each of the animals received two doses (one week between doses) of the relevant treatment regimen. And, at day 7 post second administration, the animals were sacrificed and the frequency of antigen-specific CD4+ and CD8+ T cells in the spleen was assessed using IFN-γ ELISPOT.

As shown in FIGS. 17B and 17C, treating the animals with the Scaffold X-engineered EVs expressing Lama4 alone ("exoLama4-CpG") resulted in the induction of a strong CD8+ T cell response specific for Lama4 (see FIG. FIG. 17C) but not to the Itgb1 peptide (see FIG. 17B). This result demonstrates the specificity of the CD8+ T cell response induced by the Scaffold X-engineered EVs. And, in agreement with the results provided in Example 21, Scaffold X-engineered EVs expressing both Lama4 and Itgb1 were able to induce robust T cell responses against both antigens.

These results further suggest that the EVs (e.g., exosomes) disclosed herein could be useful in inducing immune responses against variety of antigens.

Example 23: Expression of HPV Antigens in Surface-Engineered EVs (e.g., Exosomes)

To further assess the ability to express different antigens in the EVs (e.g., exosomes) of the present disclosure, 293 SF cells were transfected to express the E6 and/or E7 proteins of HPV16 or HPV18. Briefly, the cells were transfected with a plasmid encoding one of the following full length proteins: (i) HPV16 E6, (ii) HPV16 E7, (iii) HPV16 E6/E7, (iv) HPV18 E6, (v) HPV18 E7, and (vi) HPV18 E6/E7. Approximately 72 hours after the media change, cells were harvested and lysates were made from each of the transfected groups. Untransfected cells were used as negative control. Then, about 5 μL of each of the lysates were loaded on PAGE gel and blotted with the following antibodies: (i) HPV16/18 anti-E6 (AbCam, cat. #ab70), (ii) HPV16 anti-E7 (AbCam, cat. #1b30731), and (iii) HPV18 anti-E7 (AbCam, cat. #ab100953).

FIGS. 18A-18F provide the results. As shown, except perhaps for cells transfected with a plasmid encoding the HPV18 E7 protein, the transfected cells failed to express the full length HPV16 or HPV18 proteins as measured by Western Blot. This result suggested that at least the full length HPV16 E6, HPV16, and HPV18 E6 are not expressed in transient.

To address the above issue, a split protein expression strategy was used. Briefly, the 158 amino acid long HPV E6 protein was split in half at an unstructured region in the middle. This generated two peptides fragments: (i) the N-terminal nE6 (1-88aa) and (ii) the C-terminal cE6 (89-158aa). The codon optimized DNA sequences encoding the nE6 and the cE6 peptides fragments were used to assemble constructs expressing the split HPV E6 fused to Scaffold X (e.g., PTGFRN) at the N- or C-terminus and Scaffold Y at the C-terminus, respectively. The following plasmids were generated, which were used to transfect the 293SF cells: (i) pUC57-Kan-AAVS1HR-CAGGS-PTGFRN-FLAG-coHPV16nE6 ("pCB-2014"), (ii) pUC57-Kan-AAVS1HR-CAGGS-PTGFRN-FLAG-coHPV16cE6 ("pCB-2015"), (iii) pUC57-Kan-AAVS1HR-CAGGS-coHPV16nE6-FLAG-PTGFRN ("pCB-2016"), (iv) pUC57-Kan-AAVS1HR-CAGGS-coHPV16cE6-FLAG-PTGFRN ("pCB-2017"), (v) pUC57-Kan-AAVS1HR-CAGGS-PrY-FLAG-coHPV16nE6 ("pCB-2018"), and (vi) pUC57-Kan-AAVS1HR-CAGGS-PrY-FLAG-coHPV16cE6 ("pCB-2019"). (See Table 11, below). Then, the expression of the E6 and E7 proteins of HPV16 and HPV18 was assessed by Western Blot (as described above) and using an anti-FLAG antibody.

TABLE 11

Description of HPV Plasmids

| Name | Construct | Insert | Antigen |
|---|---|---|---|
| pCB-2014 | pUC57-Kan-AAVS1HR-CAGGS-PTGFRN-FLAG-coHPV16nE6 | PrX-FLAG-HPV-nE6 | nE6: N-terminal fragment of HPV16 E6 (1-88aa) |
| pCB-2015 | pUC57-Kan-AAVS1HR-CAGGS-PTGFRN-FLAG-coHPV16cE6 | PrX-FLAG-HPV-cE6 | cE6: C-terminal fragment of HPV16 E6 (89-158aa) |
| pCB-2016 | pUC57-Kan-AAVS1HR-CAGGS-coHPV16nE6-FLAG-PTGFRN | HPV-nE6-FLAG-PrX | nE6: N-terminal fragment of HPV16 E6 (1-88aa) |

TABLE 11-continued

Description of HPV Plasmids

| Name | Construct | Insert | Antigen |
|---|---|---|---|
| pCB-2017 | pUC57-Kan-AAVS1HR-CAGGS-coHPV16cE6-FLAG-PTGFRN | FLAG-HPV-cE6-FLAG-PrX | cE6: C-terminal fragment of HPV16 E6 (89-158aa) |
| pCB-2018 | pUC57-Kan-AAVS1HR-CAGGS-PrY-FLAG-coHPV16nE6 | PrY-FLAG-HPV-nE6 | nE6: N-terminal fragment of HPV16 E6 (1-88aa) |
| pCB-2019 | pUC57-Kan-AAVS1HR-CAGGS-PrY-FLAG-coHPV16cE6 | PrY-FLAG-HPV-cE6 | cE6: C-terminal fragment of HPV16 E6 (89-158aa) |

As shown in FIGS. 18G-18L, with the split protein expression strategy, each of the HPV proteins tested (i.e., HPV16 E6, HPV16 E7, HPV18 E6, and HPV18 E7) were expressed in both transient and stable cell lysates.

These results further confirm that the EVs (e.g., exosomes) disclosed herein can be engineered to express wide range of antigens, including different HPV proteins.

Example 24: Efficacy of Scaffold X-Engineered EVs (e.g., Exosomes) Comprising an Anti-Clec9a Targeting Moiety in Inducing an Antigen-Specific Immune Response Further to Examples 13 and 17 above, ability of an aCLEC9A-Px-OVA exoVACC to induce an antigen-specific immune response was assessed in an animal model. The aCLEC9A-Px-OVA exoVACC is an EV (e.g., exosome) loaded with a STING agonist and engineered to express the following: (i) aCLEC9A-Px (i.e., an anti-Clec9a antibody fragment linked to a Scaffold X) and (ii) OVA-Py (i.e., OVA linked to a Scaffold Y). Briefly, as shown in FIG. 19A, mice received one of the following: (i) OVA-expressing EVs (e.g., exosomes) loaded with STING agonist and expressing a control isotype antibody ("IgG-Px-OVA exoVACC") (Group 1), (ii) aCLEC9A-Px-OVA exoVACC (Group 2), and (iii) OVA-expressing EVs (e.g., exosomes) loaded with STING agonist (i.e., does not express Scaffold X) ("PyOVA exoVACC") (Group 3). Some of the animals received a single dose and then sacrificed a week later. Other animals received a second dose (one week after the first dose) and then sacrificed a week after the second dose. Splenocytes were harvested from the sacrificed animals and then, OVA-specific CD8+ T cells were analyzed using flow cytometry.

As shown in FIG. 19B, after a single administration of the EVs, there was no significant difference in the number of OVA-specific CD8+ effector memory T cells in the spleen. However, after a second dose, the number of OVA-specific CD8+ effector memory T cells in the spleen was significantly higher in animals treated with aCLEC9A-Px-OVA exoVACC (see FIG. 19C). This result highlights the benefits of expressing a targeting moiety (e.g., anti-Clec9a antibody fragment) in designing EVs (e.g., exosomes) for the treatment of diseases and disorders.

Example 25: Efficacy of Engineered-EVs (e.g., Exosomes) to Induce Antigen-Specific Antibody Response To determine whether EVs (e.g., exosomes) disclosed herein are also capable of inducing a robust humoral immune response, the ability of EVs (e.g., exosomes) to induce antigen-specific antibodies was observed in mice. Briefly, mice were intranasally administered with an engineered-exosome expressing OVA-Scaffold Y and loaded with the STING agonist CL656 ("Py-OVA exoVACC"). Control animals received one of the following: (i) soluble OVA ("OVA") (intranasally), (ii) soluble OVA+CL656 ("OVA+STING") (intranasally), (iii) exosome expressing only OVA-Scaffold Y fusion protein ("PyOVA") (intranasally), (iv) exosome expressing only OVA-Scaffold Y fusion protein+soluble CL656 (i.e., the STING agonist is not loaded into the exosomes) ("PyOVA+STING") (intranasally), and (v) soluble OVA+alum adjuvant ("OVA+Alum") (subcutaneously) (see FIG. 20A). Each of the treatment regiments were administered for a total of two doses (two weeks apart between doses). Then, two weeks after the last administration, sera was collected from the animals and the amount of OVA-specific IgG1 and IgA antibodies was determined using an ELISA assay.

Figures 20A, 20B, 20C:
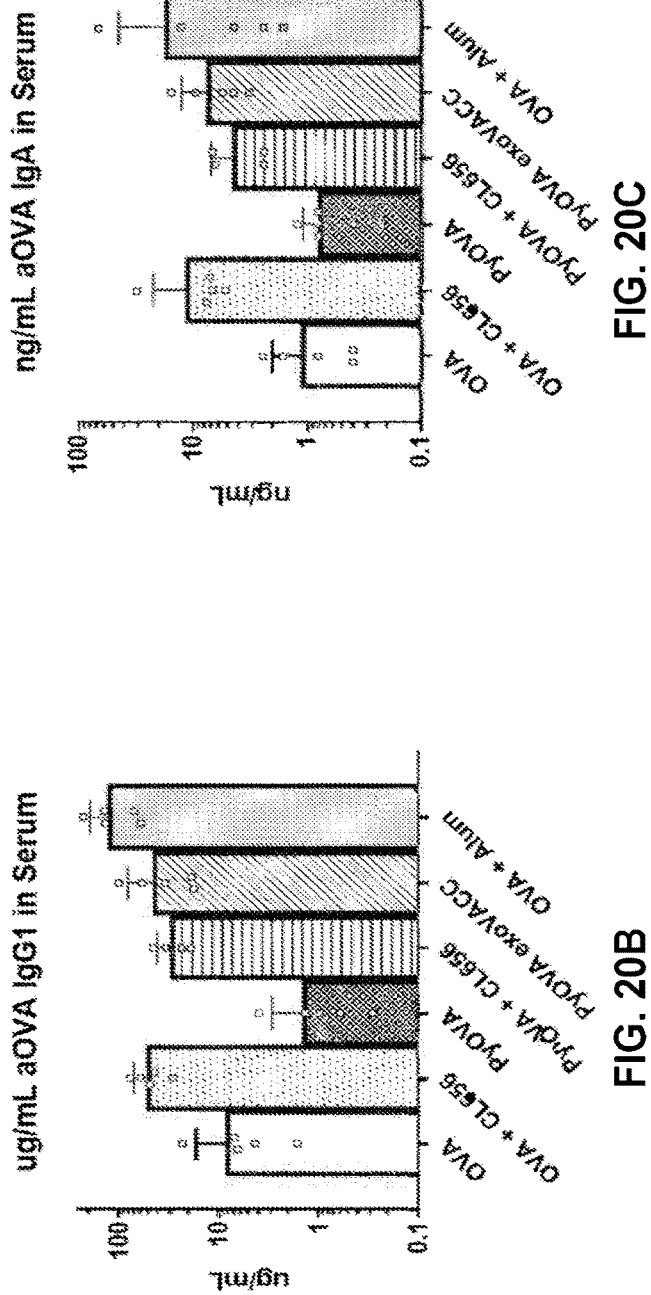
FIGS. 20A, 20B, and 20C show the ability of an EV (e.g., exosome) engineered to express OVA-Scaffold Y and loaded with a STING agonist to induce an antigen-specific humoral immune response after in vivo administration.

As seen in FIGS. 20A and 20B, EVs (e.g., exosomes) comprising OVA-Scaffold Y (i.e., antigen) and a STING agonist (i.e., adjuvant) were able to induce both antigen-specific IgG1 and IgA in the sera. This result demonstrates that the EVs (e.g., exosomes) disclosed herein are capable of inducing both antigen-specific cell-mediated and antibody-mediated immune responses after administration.

Figure 21:
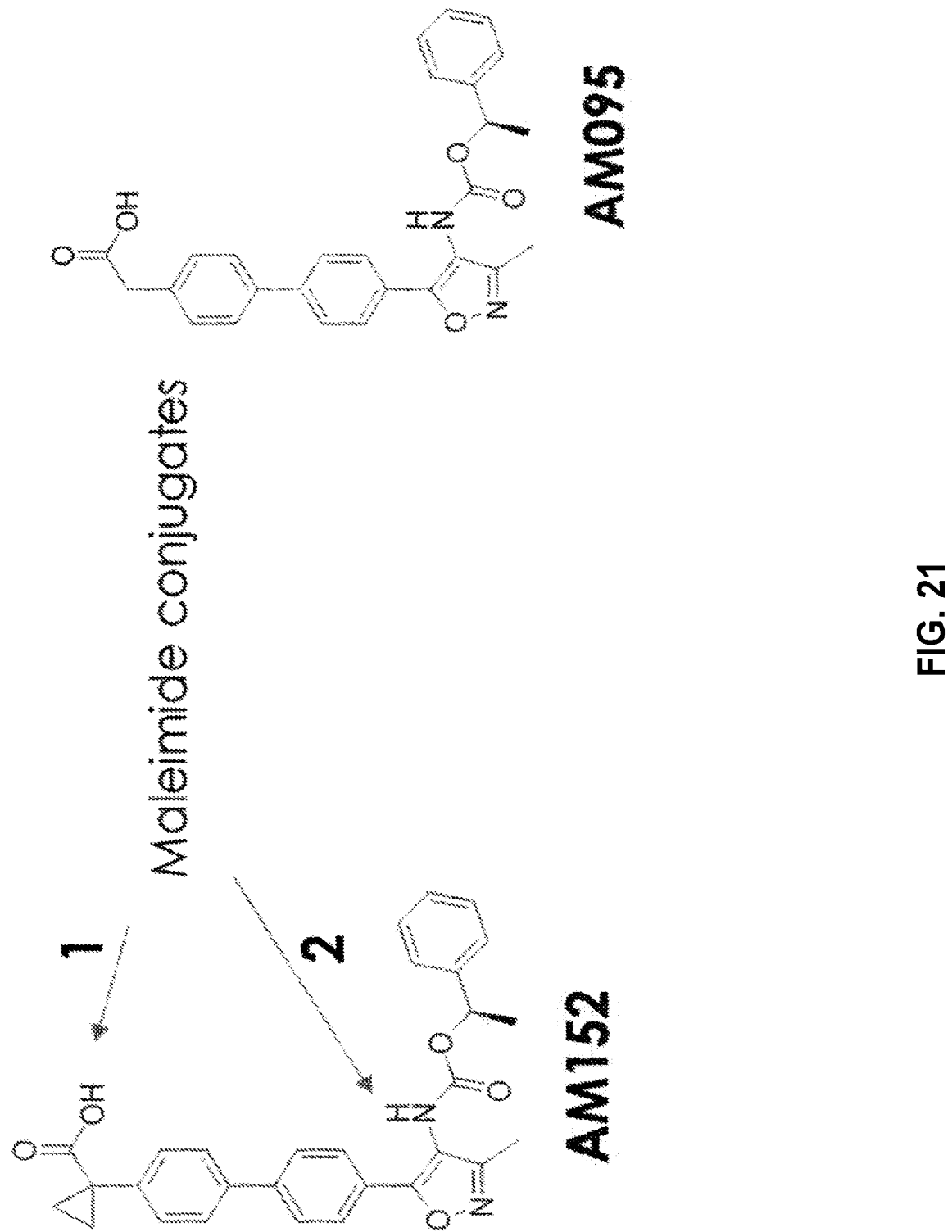
FIG. 21 shows the chemical structures of AM152 (Cyclopropanecarboxylic acid, 1-[4'-[3-methyl-4-[[[(1R)-1-phenylethoxy]carbonyl]amino]-5-isoxazolyl][1,1'-biphenyl]-4-yl]-) and AM095 (1,1'-Biphenyl]-4-acetic acid, 4'-[3-methyl-4-[[[(1R)-1-phenylethoxy]carbonyl]amino]-5-isoxazolyl[ ]-). Arrows labeled 1 and 2 indicate locations (carboxylic acid and carbamate) suitable for derivation to introduce a maleimide reactive group. The corresponding sites indicated in AM152 are also present in AM095.

Example 26: Surface-Engineered EVs (e.g., Exosomes) Comprising an LPA-1 Inhibitor As described herein, EVs (e.g., exosomes) of the present disclosure can be engineered to express an LPA-1 inhibitor on the surface of the EVs. Non-limiting examples of LPA-1 inhibitors that can be used with the present disclosure include AM152 and AM095. The chemical structures of AM152 and AM095 are presented in FIG. 21. The figure shows that maleimide-containing reagents can be conjugated to the carboxylic acid and/or carbamate groups of AM152. The same approach could be used to derivatize AM095 since the same reactive groups are present in AM095.

Figure 22:
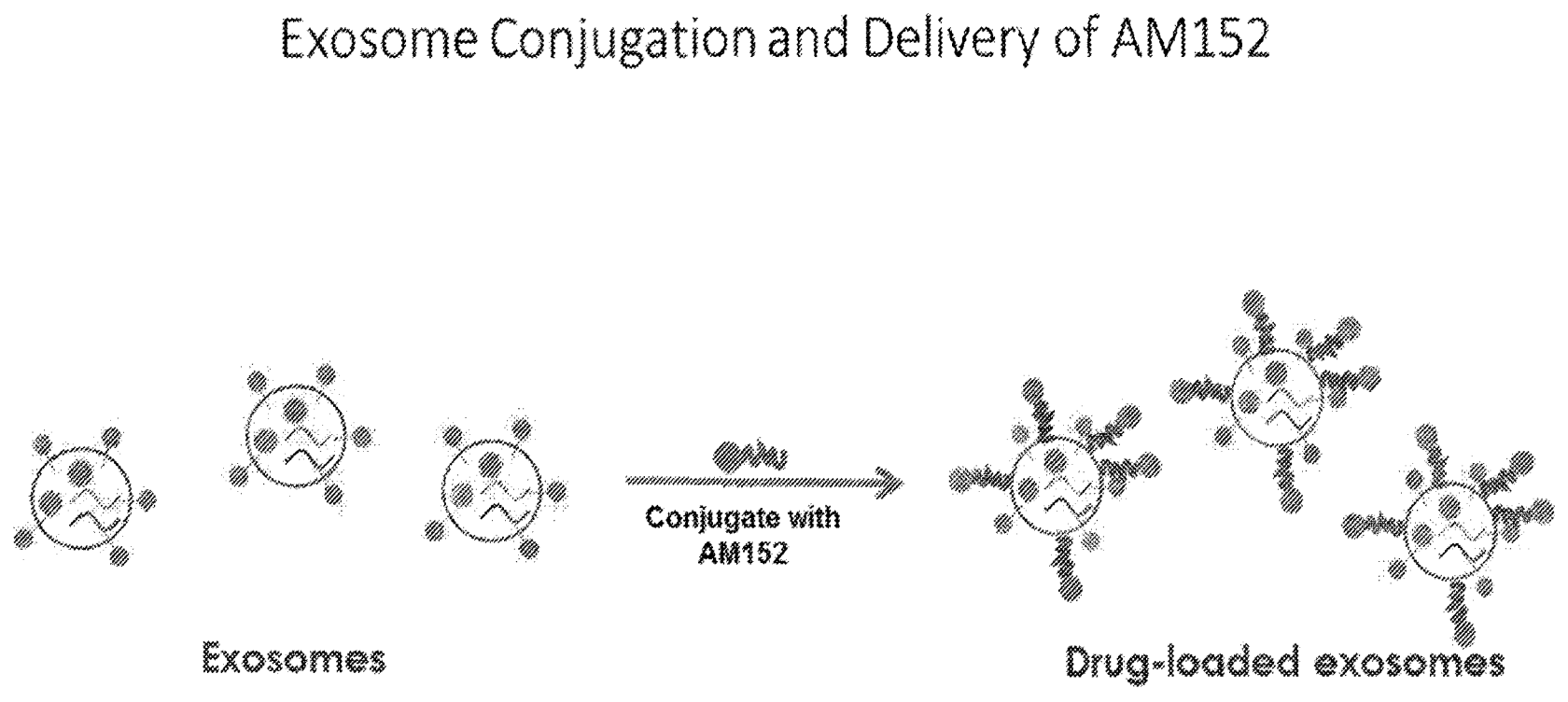

LPA-1 inhibitors such as AM095 and AM152 can be conjugated to the surface of EVs (e.g., exosomes) using the methods disclosed herein. The results would be an EV (e.g., exosome) comprising a plurality of inhibitors on the surface of the EV. See FIG. 22.

Figure 23:
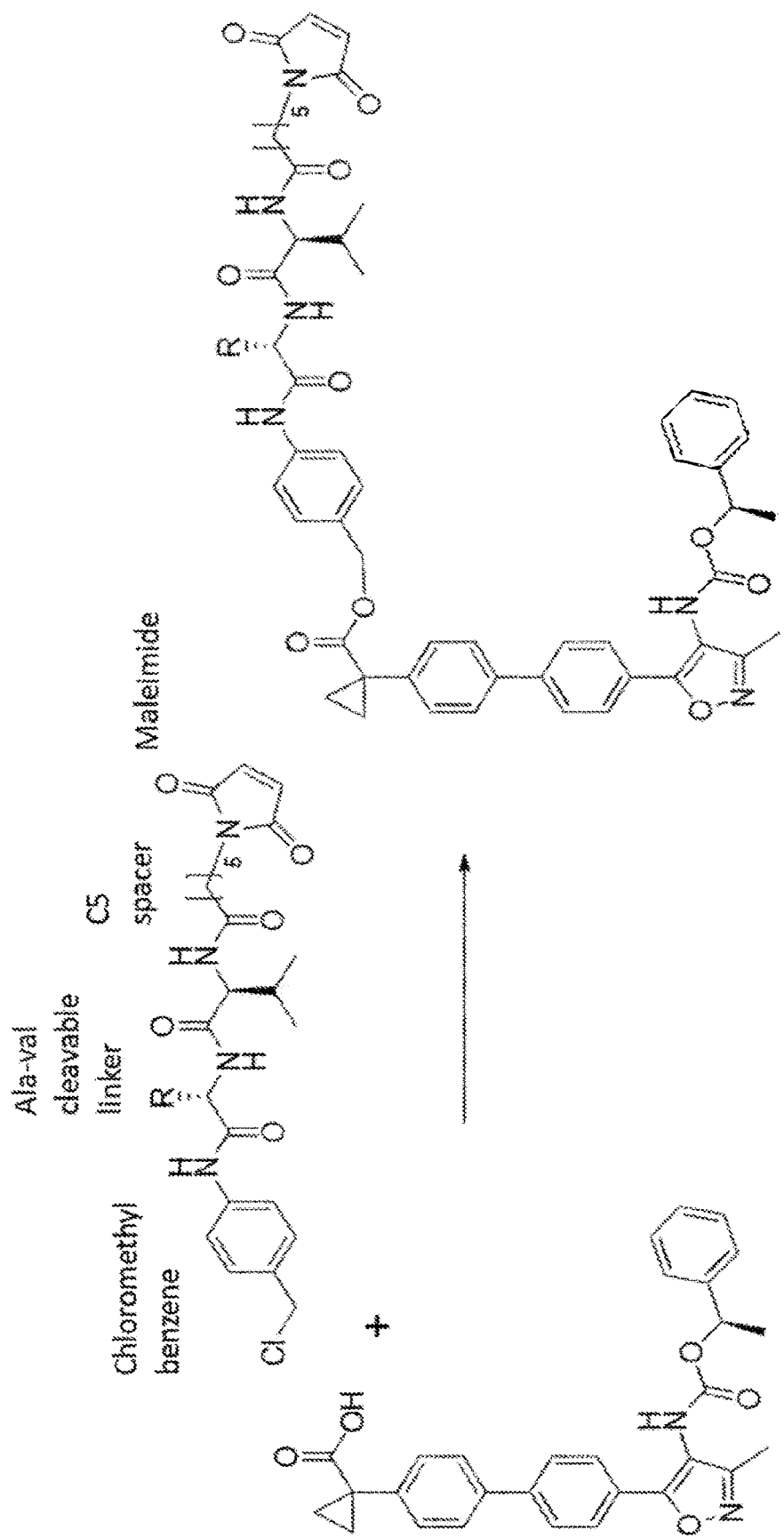
FIG. 23 shows an example of how a maleimide reactive group can be added to AM152 via its carboxylic acid group. The example shows the maleimide group as part of a reactive complex comprising an ala-val cleavable linker and a C5 spacer interposed between the maleimide group and the carboxylic acid-reactive chloromethyl benzene group.
Figure 24:
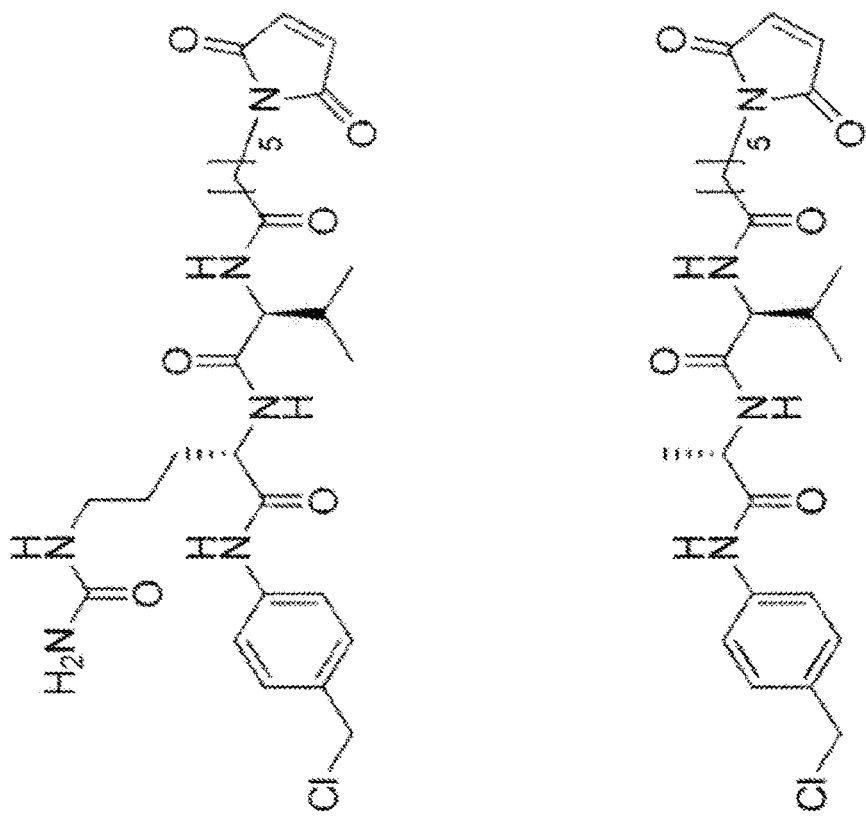
FIG. 24 shows two exemplary reagents that can be used to derivatize AM152. The top reagent comprises (i) a chloromethyl benzene group that can react with the carboxylic acid group of AM152 and (ii) a maleimide group; and interposed between them are a cleavable cit-val dipeptide and a C5 spacer. The bottom reagent comprises (i) a chloromethyl benzene group that can react with the carboxylic acid group of AM152 and (ii) a maleimide group, and interposed between them are a cleavable ala-val dipeptide and a C5 spacer.

FIG. 23 shows an example of how a maleimide reactive group can be added to AM152 via the acid group. The example shows the maleimide group as part of a complex comprising an ala-val cleavable linker interposed between the maleimide group and the carboxylic acid-reactive chloromethyl benzene group. FIG. 24 shows two exemplary reagents that can be used to derivatize AM152. The top reagent comprises (i) a chloromethyl benzene group that can react with the carboxylic acid group of AM152 and (ii) a maleimide group; and interposed between them are a cleavable cit-val dipeptide and a C5 spacer. The bottom reagent comprises (i) a chloromethyl benzene group that can react with the carboxylic acid group of AM152 and (ii) a maleimide group, and interposed between them are a cleavable ala-val dipeptide and a C5 spacer. The maleimide group would be subsequently used to attach the AM152 (or AM095), e.g., to a scaffold moiety either directly or indirectly via one or more spacers or linkers (e.g., disclosed herein).

Figure 25:
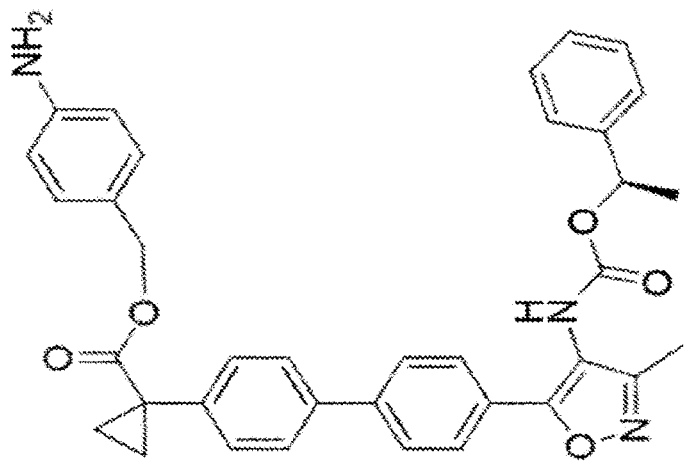
FIG. 25 shows the product that would result from cleaving the cit-val or ala-val dipeptide (e.g., by cathepsin B) in the conjugation product. The product, an AM152 aniline ester, could be further processed by an endogenous esterase to yield the free acid AM152 product.

FIG. 25 shows the product that would result from cleaving the cit-val or ala-val dipeptide (e.g., by cathepsin B) in the conjugation product. The product, an AM152 aniline ester, could be further processed by an endogenous esterase to yield the free acid AM152 product.

Figure 26:
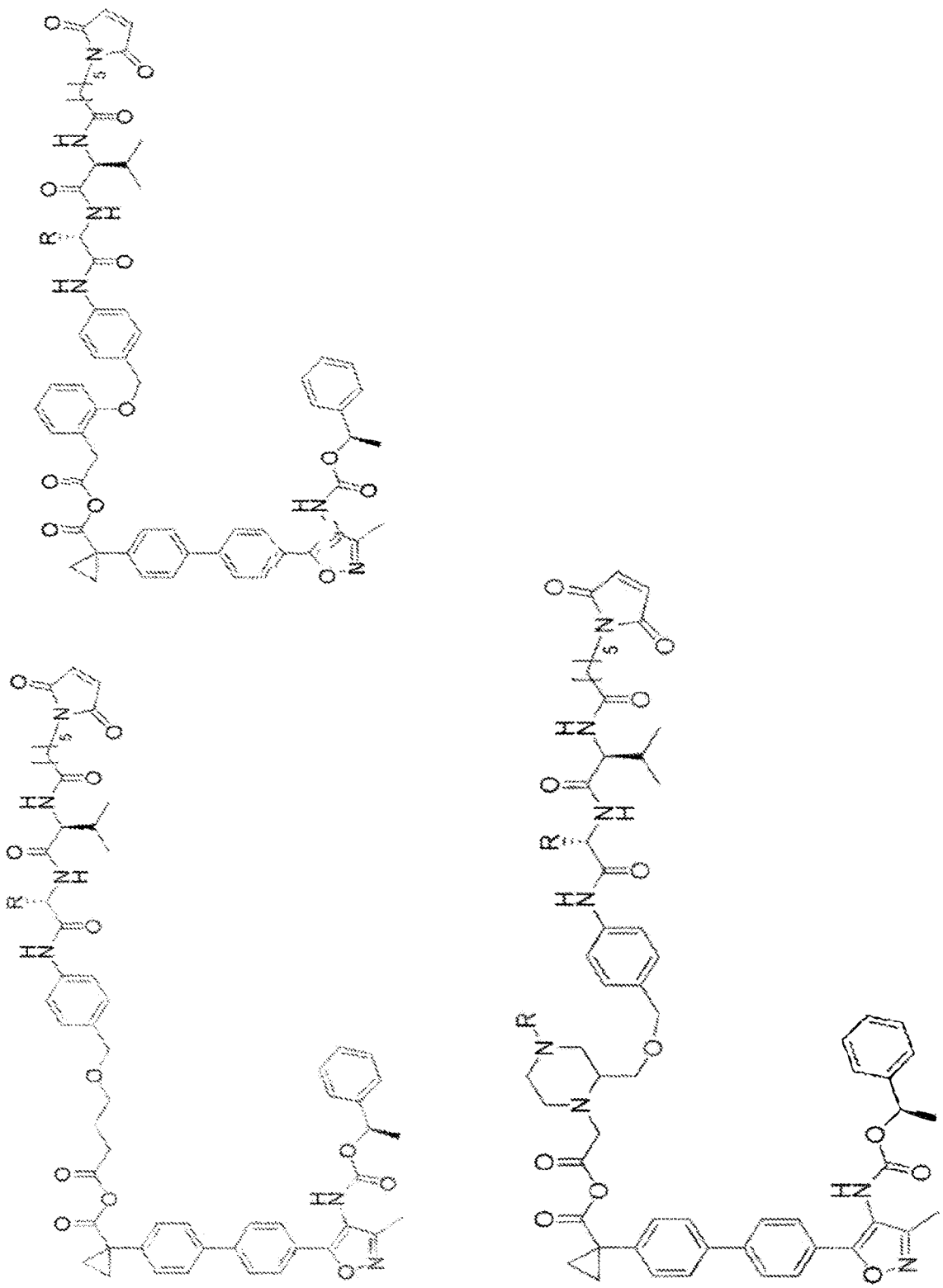
FIGS. 26 and 27 show several AM152 derivatives comprising a free maleimide group and different combinations of spacers.
Figure 27:
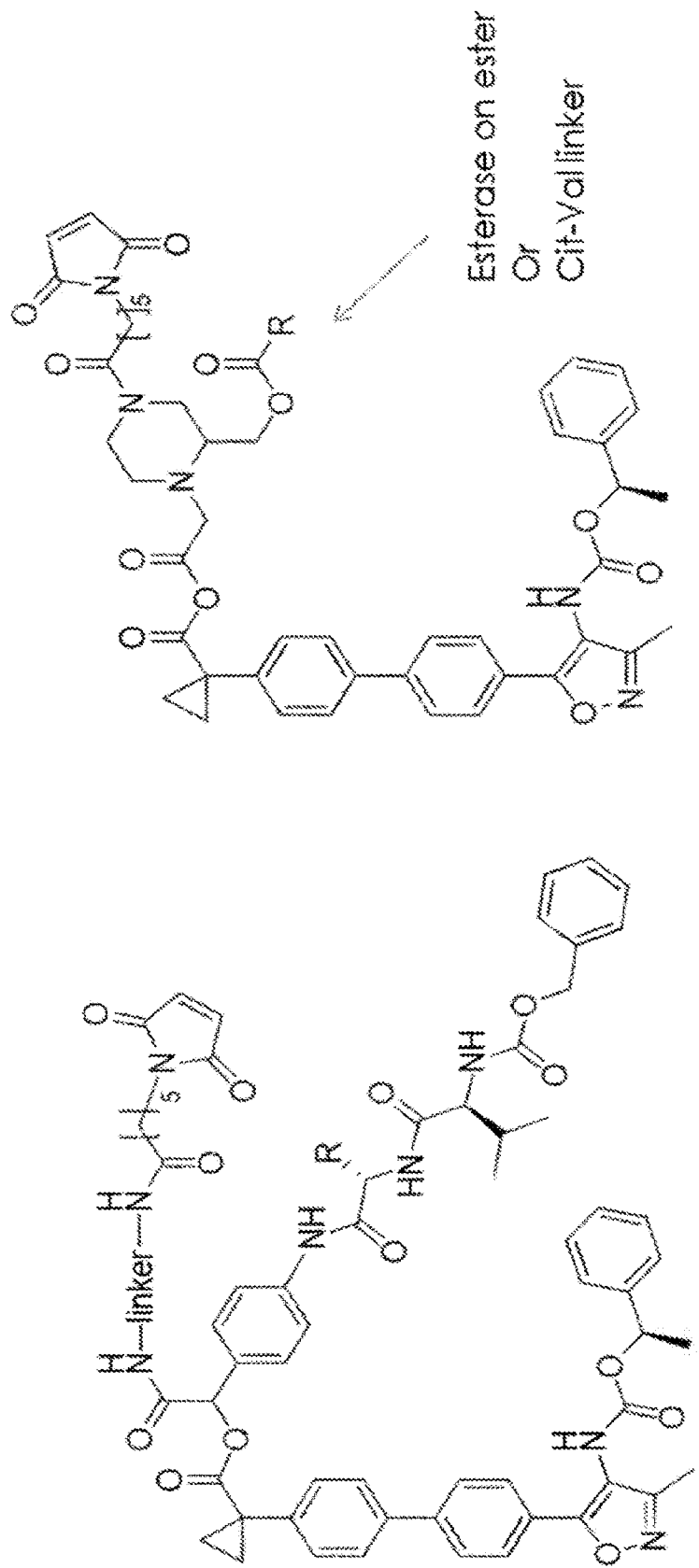

FIG. 26 shows several AM152 derivatives comprising a free maleimide group and different combinations of spacers. Additional derivatives are shown in FIG. 27.

FIG. 28 shows that after protection of the carboxylic acid group, it is possible to use the same reagents used to derivatize the carboxylic acid group to derivatize AM152 at its carbamate group. The resulting product would be subsequently deprotected to free the carboxylic acid group.

Figure 29:
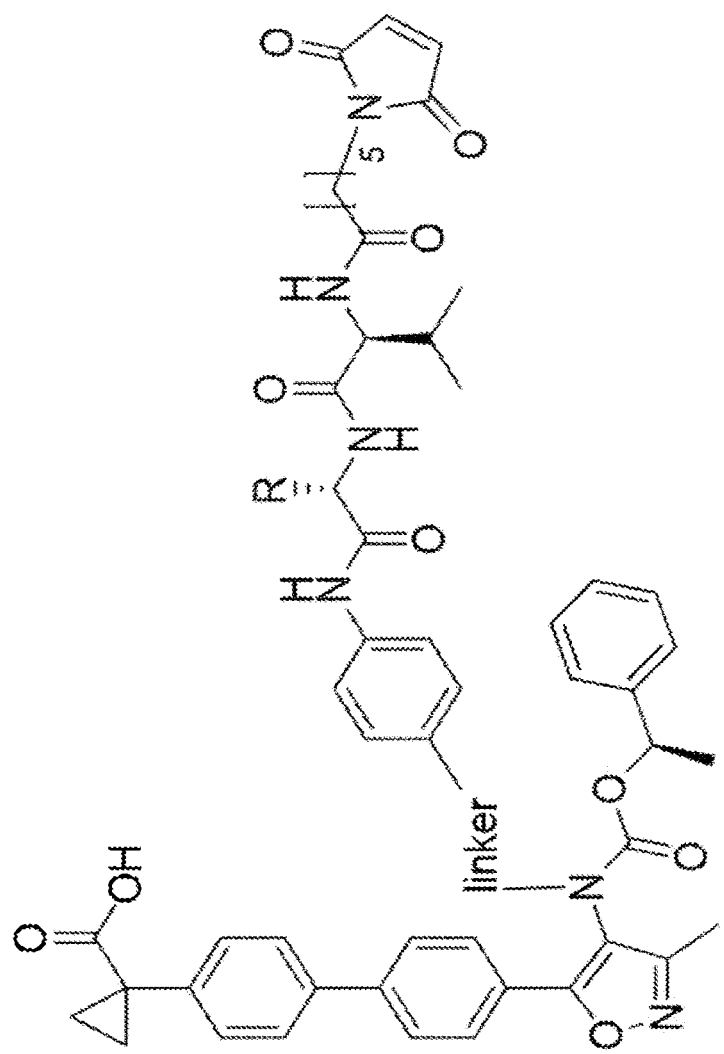
FIG. 29 shows illustrates an example in which the complex with the maleimide group is attached to the carbamate group of AM152 via a linker. Suitable linkers include any of the linkers disclosed in the present specification.

FIG. 29 illustrates an example in which the complex with the maleimide group is attached to the carbamate group of AM152 via a linker. Suitable linkers include any of the linkers disclosed in the present specification.

The processes disclosed in this example relate to the generation of an AM152 or AM095 derivative comprising a free maleimide reactive group, which could subsequently react with a scaffold moiety either directly or indirectly via one or more spacers or linkers. As a result, the AM152 or AM095 would be attached to the external surface of the EV, e.g., an exosome.

Figure 30:
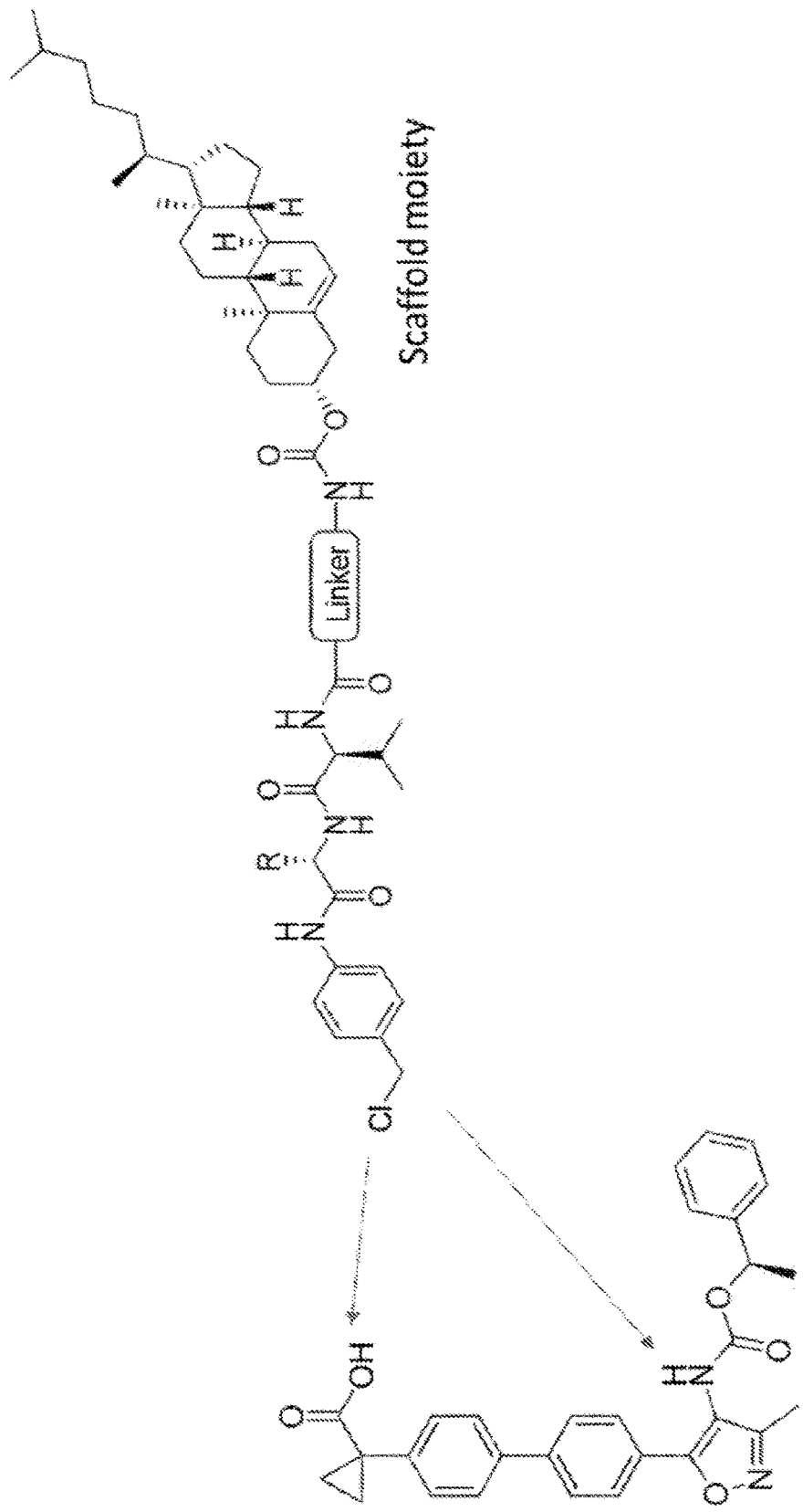
FIG. 30 shows that AM152 can be attached to a derivatized anchoring moiety instead of being derivatized and subsequently attached to an anchoring moiety via the reactive maleimide group.

However, the invention could also be practiced by derivatizing an anchoring moiety first, e.g., with a bifunctional group comprising maleimide, and then reacting the derivatized anchoring moiety, e.g., having a free chloromethyl benzene group, with either the carboxylic acid or the carbamate group of AM152, as shown in FIG. 30.

In some aspects, conjugating AM152 (or AM095) to the surface of EV, e.g., exosomes, improves at least one beneficial property of unconjugated AM152 (or AM095) and/or decreases at least one deleterious property of unconjugated AM152 or AM095 (e.g., toxicity, such as gall bladder toxicity and/or liver toxicity). In some aspects, conjugating AM152 (or AM095) to an EV, e.g., an exosome, improves the efficacy of AM512 or AM095 (compared to free AM152 or free AM095) in the treatment of a fibrotic disease, e.g., lung fibrosis, such as IPF.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific aspects have been illustrated and described, the above specification is not restrictive. It will be appreciated that various changes can be made without departing from the spirit and scope of the invention(s). Many variations will become apparent to those skilled in the art upon review of this specification.

What is claimed is:

1. An isolated extracellular vesicle (EV) having an exterior surface and a luminal surface and comprising (i) an antigen, (ii) a Scaffold X moiety, and (iii) a Scaffold Y moiety, wherein the antigen is fused to the Scaffold X moiety or the Scaffold Y moiety.

2. The EV of claim 1, wherein the antigen is fused to the N-terminus of the Scaffold X moiety or wherein the antigen is fused to the C-terminus of the Scaffold X moiety.

3. The EV of claim 1, wherein the antigen comprises a first antigen and a second antigen, and wherein: (i) the first antigen is fused to the Scaffold X moiety and the second antigen is fused to the Scaffold Y moiety or (ii) the first antigen is fused to the N-terminus of the Scaffold X moiety and the second antigen is fused to the C-terminus of the Scaffold X moiety.

4. The EV of claim 1, wherein the antigen is derived from a bacterium, virus, fungus, protozoa, or combinations thereof.

5. The EV of claim 4, wherein the antigen is derived from a human gamma herpes virus 4 (Epstein Barr virus), influenza A virus, influenza B virus, cytomegalovirus, *Staphylococcus aureus*, *Mycobacterium tuberculosis*, *Chlamydia trachomatis*, HIV, corona viruses, filoviruses, *Streptococcus pyogenes*, *Streptococcus pneumoniae*, Plasmodia species, Chikungunya virus, Human Papilloma virus (HPV), Hepatitis B, Hepatitis C, human herpes virus 8, Merkel cell polyomavirus (MCV), bunyavirus, arena virus, flavivirus, enterovirus, astrovirus, rhabdoviridae, *Borrelia burgdorferi* and Burrelia mayonii, herpes simplex virus 2 (HSV2), *Klebsiella* sp., *Pseudomonas aeruginosa*, *Enterococcus* sp., *Proteus* sp., *Enterobacter* sp., *Actinobacter* sp., coagulase-negative staphylococci (CoNS), *Mycoplasma* sp., Adenovirus, Adeno-associated virus (AAV), or combinations thereof.

6. The EV of claim 1, which further comprises a payload selected from an adjuvant, immune modulator, targeting moiety, or combinations thereof.

7. The EV of claim 6, wherein the payload is conjugated to the exterior surface and/or the luminal surface of the EV.

8. The EV of claim 7, wherein the payload is conjugated to the exterior surface and/or the luminal surface of the EV by a scaffold moiety.

9. The EV of claim 8, wherein the scaffold moiety comprises a Scaffold X moiety, Scaffold Y moiety, or both.

10. The EV of claim 6, wherein the payload is encapsulated within a lumen of the EV.

11. The EV of claim 6, wherein the adjuvant comprises a Stimulator of Interferon Genes (STING) agonist, a toll-like receptor (TLR) agonist, an inflammatory mediator, RIG-I agonists, alpha-gal-cer (NKT agonist), heat shock proteins, C-type lectin agonists, or any combination thereof.

12. The EV of claim 1, wherein (i) the Scaffold X moiety is a prostaglandin F2 receptor negative regulator (PTGFRN) protein or a fragment thereof, (ii) the Scaffold Y moiety is a brain acid soluble protein 1 (BASP1) protein or a fragment thereof, or (iii) both (i) and (ii).

13. An isolated extracellular vesicle (EV) having an exterior surface and a luminal surface and comprising (i) a first antigen, (ii) a second antigen, and (iii) a third antigen, wherein the first antigen, the second antigen, and/or the third antigen is fused to a Scaffold X moiety or a Scaffold Y moiety.

14. The EV of claim 13, wherein: (i) the first antigen is fused to the N-terminus of the Scaffold X moiety on the exterior surface of the EV, (ii) the second antigen is fused to the C-terminus of the Scaffold X moiety on the luminal surface of the EV, (iii) the third antigen is fused to the Scaffold Y moiety on the luminal surface of the EV, or (iv) any combination of (i) to (iii).

15. The EV of claim 13, which further comprises a payload selected from an adjuvant, immune modulator, targeting moiety, or combinations thereof.

16. The EV of claim 15, wherein the adjuvant comprises a STING agonist, a toll-like receptor (TLR) agonist, an inflammatory mediator, RIG-I agonists, alpha-gal-cer (NKT agonist), heat shock proteins, C-type lectin agonists, or any combination thereof.

17. The EV of claim 13, wherein (i) the Scaffold X moiety is a prostaglandin F2 receptor negative regulator (PTGFRN) protein or a fragment thereof, (ii) the Scaffold Y moiety is a brain acid soluble protein 1 (BASP1) protein or a fragment thereof, or (iii) both (i) and (ii).

18. The EV of claim 13, wherein the antigen is derived from a bacterium, virus, fungus, protozoa, or combinations thereof.

19. A pharmaceutical composition comprising the EV of claim 1 and a pharmaceutically acceptable carrier.

20. A method of treating a coronavirus infection in a subject in need thereof, comprising administering to the subject the EV of claim 1.

* * * * *

SEQUENCE LISTING

```
Sequence total quantity: 380
SEQ ID NO: 1              moltype = AA  length = 879
FEATURE                   Location/Qualifiers
source                    1..879
                          mol_type = protein
                          organism = Homo sapiens
SEQUENCE: 1
MGRLASRPLL LALLSLALCR GRVVRVPTAT LVRVVGTELV IPCNVSDYDG PSEQNFDWSF  60
SSLGSSFVEL ASTWEVGFPA QLYQERLQRG EILLRRTAND AVELHIKNVQ PSDQGHYKCS 120
TPSTDATVQG NYEDTVQVKV LADSLHVGPS ARPPPSLSLR EGEPFELRCT AASASPLHTH 180
LALLWEVHRG PARRSVLALT HEGRFHPGLG YEQRYHSGDV RLDTVGSDAY RLSVSRALSA 240
DQGSYRCIVS EWIAEQGNWQ EIQEKAVEVA TVVIQPSVLR AAVPKNVSVA EGKELDLTCN 300
ITTDRADDVR PEVTWSFSRM PDSTLPGSRV LARLDRDSLV HSSPHVALSH VDARSYHLLV 360
RDVSKENSGY YYCHVSLWAP GHNRSWHKVA EAVSSPAGVG VTWLEPDYQV YLNASKVPGF 420
ADDPTELACR VVDTKSGEAN VRFTVSWYYR MNRRSDNVVT SELLAVMDGD WTLKYGERSK 480
QRAQDGDFIF SKEHTDTFNF RIQRTTEEDR GNYYCVVSAW TKQRNNSWVK SKDVFSKPVN 540
IFWALEDSVL VVKARQPKPF FAAGNTFEMT CKVSSKNIKS PRYSVLIMAE KPVGDLSSPN 600
ETKYIISLDQ DSVVKLENWT DASRVDGVVL EKVQEDEFRY RMYQTQVSDA GLYRCMVTAW 660
SPVRGSLWRE AATSLSNPIE IDFQTSGPIF NASVHSDTPS VIRGDLIKLF CIITVEGAAL 720
DPDDMAFDVS WFAVHSFGLD KAPVLLSSLD RKGIVTTSRR DWKSDLSLER VSVLEFLLQV 780
HGSEDQDFGN YYCSVTPWVK SPTGSWQKEA EIHSKPVFIT VKMDVLNAFK YPLLIGVGLS 840
TVIGLLSCLI GYCSSHWCCK KEVQETRRER RRLMSMEMD                       879

SEQ ID NO: 2              moltype = AA  length = 731
FEATURE                   Location/Qualifiers
source                    1..731
                          mol_type = protein
                          organism = Homo sapiens
SEQUENCE: 2
PSARPPPSLS LREGEPFELR CTAASASPLH THLALLWEVH RGPARRSVLA LTHEGRFHPG  60
LGYEQRYHSG DVRLDTVGSD AYRLSVSRAL SADQGSYRCI VSEWIAEQGN WQEIQEKAVE 120
VATVVIQPSV LRAAVPKNVS VAEGKELDLT CNITTDRADD VRPEVTWSFS RMPDSTLPGS 180
RVLARLDRDS LVHSSPHVAL SHVDARSYHL LVRDVSKENS GYYYCHVSLW APGHNRSWHK 240
VAEAVSSPAG VGVTWLEPDY QVYLNASKVP GFADDPTELA CRVVDTKSGE ANVRFTVSWY 300
```

```
YRMNRRSDNV VTSELLAVMD GDWTLKYGER SKQRAQDGDF IFSKEHTDTF NFRIQRTTEE    360
DRGNYYCVVS AWTKQRNNSW VKSKDVFSKP VNIFWALEDS VLVVKARQPK PFFAAGNTFE    420
MTCKVSSKNI KSPRYSVLIM AEKPVGDLSS PNETKYIISL DQDSVVKLEN WTDASRVDGV    480
VLEKVQEDEF RYRMYQTQVS DAGLYRCMVT AWSPVRGSLW REAATSLSNP IEIDFQTSGP    540
IFNASVHSDT PSVIRGDLIK LFCIITVEGA ALDPDDMAFD VSWFAVHSFG LDKAPVLLSS    600
LDRKGIVTTS RRDWKSDLSL ERVSVLEFLL QVHGSEDQDF GNYYCSVTPW VKSPTGSWQK    660
EAEIHSKPVF ITVKMDVLNA FKYPLLIGVG LSTVIGLLSC LIGYCSSHWC CKKEVQETRR    720
ERRRLMSMEM D                                                        731

SEQ ID NO: 3              moltype = AA   length = 611
FEATURE                   Location/Qualifiers
source                    1..611
                          mol_type = protein
                          organism = Homo sapiens
SEQUENCE: 3
VATVVIQPSV LRAAVPKNVS VAEGKELDLT CNITTDRADD VRPEVTWSFS RMPDSTLPGS     60
RVLARLDRDS LVHSSPHVAL SHVDARSYHL LVRDVSKENS GYYYCHVSLW APGHNRSWHK    120
VAEAVSSPAG VGVTWLEPDY QVYLNASKVP GFADDPTELA CRVVDTKSGE ANVRFTVSWY    180
YRMNRRSDNV VTSELLAVMD GDWTLKYGER SKQRAQDGDF IFSKEHTDTF NFRIQRTTEE    240
DRGNYYCVVS AWTKQRNNSW VKSKDVFSKP VNIFWALEDS VLVVKARQPK PFFAAGNTFE    300
MTCKVSSKNI KSPRYSVLIM AEKPVGDLSS PNETKYIISL DQDSVVKLEN WTDASRVDGV    360
VLEKVQEDEF RYRMYQTQVS DAGLYRCMVT AWSPVRGSLW REAATSLSNP IEIDFQTSGP    420
IFNASVHSDT PSVIRGDLIK LFCIITVEGA ALDPDDMAFD VSWFAVHSFG LDKAPVLLSS    480
LDRKGIVTTS RRDWKSDLSL ERVSVLEFLL QVHGSEDQDF GNYYCSVTPW VKSPTGSWQK    540
EAEIHSKPVF ITVKMDVLNA FKYPLLIGVG LSTVIGLLSC LIGYCSSHWC CKKEVQETRR    600
ERRRLMSMEM D                                                        611

SEQ ID NO: 4              moltype = AA   length = 485
FEATURE                   Location/Qualifiers
source                    1..485
                          mol_type = protein
                          organism = Homo sapiens
SEQUENCE: 4
SPAGVGVTWL EPDYQVYLNA SKVPGFADDP TELACRVVDT KSGEANVRFT VSWYYRMNRR     60
SDNVVTSELL AVMDGDWTLK YGERSKQRAQ DGDFIFSKEH TDTFNFRIQR TTEEDRGNYY    120
CVVSAWTKQR NNSWVKSKDV FSKPVNIFWA LEDSVLVVKA RQPKPFFAAG NTFEMTCKVS    180
SKNIKSPRYS VLIMAEKPVG DLSSPNETKY IISLDQDSVV KLENWTDASR VDGVVLEKVQ    240
EDEFRYRMYQ TQVSDAGLYR CMVTAWSPVR GSLWREAATS LSNPIEIDFQ TSGPIFNASV    300
HSDTPSVIRG DLIKLFCIIT VEGAALDPDD MAFDVSWFAV HSFGLDKAPV LLSSLDRKGI    360
VTTSRRDWKS DLSLERVSVL EFLLQVHGSE DQDFGNYYCS VTPWVKSPTG SWQKEAEIHS    420
KPVFITVKMD VLNAFKYPLL IGVGLSTVIG LLSCLIGYCS SHWCCKKEVQ ETRRERRRLM    480
SMEMD                                                               485

SEQ ID NO: 5              moltype = AA   length = 343
FEATURE                   Location/Qualifiers
source                    1..343
                          mol_type = protein
                          organism = Homo sapiens
SEQUENCE: 5
KPVNIFWALE DSVLVVKARQ PKPFFAAGNT FEMTCKVSSK NIKSPRYSVL IMAEKPVGDL     60
SSPNETKYII SLDQDSVVKL ENWTDASRVD GVVLEKVQED EFRYRMYQTQ VSDAGLYRCM    120
VTAWSPVRGS LWREAATSLS NPIEIDFQTS GPIFNASVHS DTPSVIRGDL IKLFCIITVE    180
GAALDPDDMA FDVSWFAVHS FGLDKAPVLL SSLDRKGIVT TSRRDWKSDL SLERVSVLEF    240
LLQVHGSEDQ DFGNYYCSVT PWVKSPTGSW QKEAEIHSKP VFITVKMDVL NAFKYPLLIG    300
VGLSTVIGLL SCLIGYCSSH WCCKKEVQET RRERRRLMSM EMD                     343

SEQ ID NO: 6              moltype = AA   length = 217
FEATURE                   Location/Qualifiers
source                    1..217
                          mol_type = protein
                          organism = Homo sapiens
SEQUENCE: 6
VRGSLWREAA TSLSNPIEID FQTSGPIFNA SVHSDTPSVI RGDLIKLFCI ITVEGAALDP     60
DDMAFDVSWF AVHSFGLDKA PVLLSSLDRK GIVTTSRRDW KSDLSLERVS VLEFLLQVHG    120
SEDQDFGNYY CSVTPWVKSP TGSWQKEAEI HSKPVFITVK MDVLNAFKYP LLIGVGLSTV    180
IGLLSCLIGY CSSHWCCKKE VQETRRERRR LMSMEMD                            217

SEQ ID NO: 7              moltype = AA   length = 66
FEATURE                   Location/Qualifiers
source                    1..66
                          mol_type = protein
                          organism = Homo sapiens
SEQUENCE: 7
SKPVFITVKM DVLNAFKYPL LIGVGLSTVI GLLSCLIGYC SSHWCCKKEV QETRRERRRL     60
MSMEMD                                                               66

SEQ ID NO: 8              moltype = AA   length = 21
FEATURE                   Location/Qualifiers
source                    1..21
```

```
                         mol_type = protein
                         organism = Homo sapiens
SEQUENCE: 8
MGRLASRPLL LALLSLALCR G                                                21

SEQ ID NO: 9             moltype = AA   length = 385
FEATURE                  Location/Qualifiers
source                   1..385
                         mol_type = protein
                         organism = Homo sapiens
SEQUENCE: 9
MAAALFVLLG FALLGTHGAS GAAGFVQAPL SQQRWVGGSV ELHCEAVGSP VPEIQWWFEG        60
QGPNDTCSQL WDGARLDRVH IHATYHQHAA STISIDTLVE EDTGTYECRA SNDPDRNHLT       120
RAPRVKWVRA QAVVLVLEPG TVFTTVEDLG SKILLTCSLN DSATEVTGHR WLKGGVVLKE       180
DALPGQKTEF KVDSDDQWGE YSCVFLPEPM GTANIQLHGP PRVKAVKSSE HINEGETAML       240
VCKSESVPPV TDWAWYKITD SEDKALMNGS ESRFFVSSSQ GRSELHIENL NMEADPGQYR       300
CNGTSSKGSD QAIITLRVRS HLAALWPFLG IVAEVLVLVT IIFIYEKRRK PEDVLDDDDA       360
GSAPLKSSGQ HQNDKGKNVR QRNSS                                            385

SEQ ID NO: 10            moltype = AA   length = 247
FEATURE                  Location/Qualifiers
source                   1..247
                         mol_type = protein
                         organism = Homo sapiens
SEQUENCE: 10
PGTVFTTVED LGSKILLTCS LNDSATEVTG HRWLKGGVVL KEDALPGQKT EFKVDSDDQW        60
GEYSCVFLPE PMGTANIQLH GPPRVKAVKS SEHINEGETA MLVCKSESVP PVTDWAWYKI       120
TDSEDKALMN GSESRFFVSS SQGRSELHIE NLNMEADPGQ YRCNGTSSKG SDQAIITLRV       180
RSHLAALWPF LGIVAEVLVL VTIIFIYEKR RKPEDVLDDD DAGSAPLKSS GQHQNDKGKN       240
VRQRNSS                                                                247

SEQ ID NO: 11            moltype = AA   length = 168
FEATURE                  Location/Qualifiers
source                   1..168
                         mol_type = protein
                         organism = Homo sapiens
SEQUENCE: 11
HGPPRVKAVK SSEHINEGET AMLVCKSESV PPVTDWAWYK ITDSEDKALM NGSESRFFVS        60
SSQGRSELHI ENLNMEADPG QYRCNGTSSK GSDQAIITLR VRSHLAALWP FLGIVAEVLV       120
LVTIIFIYEK RRKPEDVLDD DDAGSAPLKS SGQHQNDKGK NVRQRNSS                   168

SEQ ID NO: 12            moltype = AA   length = 66
FEATURE                  Location/Qualifiers
source                   1..66
                         mol_type = protein
                         organism = Homo sapiens
SEQUENCE: 12
SHLAALWPFL GIVAEVLVLV TIIFIYEKRR KPEDVLDDDD AGSAPLKSSG QHQNDKGKNV        60
RQRNSS                                                                  66

SEQ ID NO: 13            moltype = AA   length = 18
FEATURE                  Location/Qualifiers
source                   1..18
                         mol_type = protein
                         organism = Homo sapiens
SEQUENCE: 13
MAAALFVLLG FALLGTHG                                                     18

SEQ ID NO: 14            moltype = AA   length = 613
FEATURE                  Location/Qualifiers
source                   1..613
                         mol_type = protein
                         organism = Homo sapiens
SEQUENCE: 14
MGALRPTLLP PSLPLLLLLM LGMGCWAREV LVPEGPLYRV AGTAVSISCN VTGYEGPAQQ        60
NFEWFLYRPE APDTALGIVS TKDTQFSYAV FKSRVVAGEV QVQRLQGDAV VLKIARLQAQ       120
DAGIYECHTP STDTRYLGSY SGKVELRVLP DVLQVSAAPP GPRGRQAPTS PPRMTVHEGQ       180
ELALGCLART STQKHTHLAV SFGRSVPEAP VGRSTLQEVV GIRSDLAVEA GAPYAERLAA       240
GELRLGKEGT DRYRMVVGGA QAGDAGTYHC TAAEWIQDPD GSWAQIAEKR AVLAHVDVQT       300
LSSQLAVTVG PGERRIGPGE PLELLCNVSG ALPPAGRHAA YSVGWEMAPA GAPGPGRLVA       360
QLDTEGVGSL GPGYEGRHIA MEKVASRTYR LRLEAARPGD AGTYRCLAKA YVRGSGTRLR       420
EAASARSRPL PVHVREEGVV LEAVAWLAGG TVYRGETASL LCNISVRGGP PGLRLAASWW       480
VERPEDGELS SVPAQLVGGV GQDGVAELGV RPGGGPVSVE LVGPRSHRLR LHSLGPEDEG       540
VYHCAPSAWV QHADYSWYQA GSARSGPVTV YPYMHALDTL FVPLLVGTGV ALVTGATVLG       600
TITCCFMKRL RKR                                                         613

SEQ ID NO: 15            moltype = AA   length = 456
FEATURE                  Location/Qualifiers
source                   1..456
```

```
                                mol_type = protein
                                organism = Homo sapiens
SEQUENCE: 15
APPGPRGRQA   PTSPPRMTVH   EGQELALGCL   ARTSTQKHTH   LAVSFGRSVP   EAPVGRSTLQ    60
EVVGIRSDLA   VEAGAPYAER   LAAGELRLGK   EGTDRYRMVV   GGAQAGDAGT   YHCTAAEWIQ   120
DPDGSWAQIA   EKRAVLAHVD   VQTLSSQLAV   TVGPGERRIG   PGEPLELLCN   VSGALPPAGR   180
HAAYSVGWEM   APAGAPGPGR   LVAQLDTEGV   GSLGPGYEGR   HIAMEKVASR   TYRLRLEAAR   240
PGDAGTYRCL   AKAYVRGSGT   RLREAASARS   RPLPVHVREE   GVVLEAVAWL   AGGTVYRGET   300
ASLLCNISVR   GGPPGLRLAA   SWWVERPEDG   ELSSVPAQLV   GGVGQDGVAE   LGVRPGGGPV   360
SVELVGPRSH   RLRLHSLGPE   DEGVYHCAPS   AWVQHADYSW   YQAGSARSGP   VTVYPYMHAL   420
DTLFVPLLVG   TGVALVTGAT   VLGTITCCFM   KRLRKR                                 456

SEQ ID NO: 16                   moltype = AA   length = 320
FEATURE                         Location/Qualifiers
source                          1..320
                                mol_type = protein
                                organism = Homo sapiens
SEQUENCE: 16
AHVDVQTLSS   QLAVTVGPGE   RRIGPGEPLE   LLCNVSGALP   PAGRHAAYSV   GWEMAPAGAP    60
GPGRLVAQLD   TEGVGSLGPG   YEGRHIAMEK   VASRTYRLRL   EAARPGDAGT   YRCLAKAYVR   120
GSGTRLREAA   SARSRPLPVH   VREEGVVLEA   VAWLAGGTVY   RGETASLLCN   ISVRGGPPGL   180
RLAASWWVER   PEDGELSSVP   AQLVGGVGQD   GVAELGVRPG   GGPVSVELVG   PRSHRLRLHS   240
LGPEDEGVYH   CAPSAWVQHA   DYSWYQAGSA   RSGPVTVYPY   MHALDTLFVP   LLVGTGVALV   300
TGATVLGTIT   CCFMKRLRKR                                                      320

SEQ ID NO: 17                   moltype = AA   length = 179
FEATURE                         Location/Qualifiers
source                          1..179
                                mol_type = protein
                                organism = Homo sapiens
SEQUENCE: 17
REEGVVLEAV   AWLAGGTVYR   GETASLLCNI   SVRGGPPGLR   LAASWWVERP   EDGELSSVPA    60
QLVGGVGQDG   VAELGVRPGG   GPVSVELVGP   RSHRLRLHSL   GPEDEGVYHC   APSAWVQHAD   120
YSWYQAGSAR   SGPVTVYPYM   HALDTLFVPL   LVGTGVALVT   GATVLGTITC   CFMKRLRKR    179

SEQ ID NO: 18                   moltype = AA   length = 24
FEATURE                         Location/Qualifiers
source                          1..24
                                mol_type = protein
                                organism = Homo sapiens
SEQUENCE: 18
VALVTGATVL   GTITCCFMKR   LRKR                                                24

SEQ ID NO: 19                   moltype = AA   length = 27
FEATURE                         Location/Qualifiers
source                          1..27
                                mol_type = protein
                                organism = Homo sapiens
SEQUENCE: 19
MGALRPTLLP   PSLPLLLLLM   LGMGCWA                                             27

SEQ ID NO: 20                   moltype = AA   length = 1195
FEATURE                         Location/Qualifiers
source                          1..1195
                                mol_type = protein
                                organism = Homo sapiens
SEQUENCE: 20
MKCFFPVLSC   LAVLGVVSAQ   RQVTVQEGPL   YRTEGSHITI   WCNVSGYQGP   SEQNFQWSIY    60
LPSSPEREVQ   IVSTMDSSFP   YAIYTQRVRG   GKIFIERVRG   NSTLLHITDL   QARDAGEYEC   120
HTPSTDKQYF   GSYSAKMNLV   VIPDSLQTTA   MPQTLHRVEQ   DPLELTCEVA   SETIQHSHLS   180
VAWLRQKVGE   KPVEVISLSR   DFMLHSSSEY   AQRQSLGEVR   LDKLGRTTFR   LTIFHLQPSD   240
QGEFYCEAAE   WIQDPDGSWY   AMTRKRSEGA   VVNVQPTDKE   FTVRLETEKR   LHTVGEPVEF   300
RCILEAQNVP   DRYFAVSWAF   NSSLIATMGP   NAVPVLNSEF   AHREARGQLK   VAKESDSVFV   360
LKIYHLRQED   SGKYNCRVTE   REKTVTGEFI   DKESKRPKNI   PIIVLPLKSS   ISVEVASNAS   420
VILEGEDLRF   SCSVRTAGRP   QGRFSVIWQL   VDRQNRRSNI   MWLDRDGTVQ   PGSSYWERSS   480
FGGVQMEQVQ   PNSFSLGIFN   SRKEDEGQYE   CHVTEWVRAV   DGEWQIVGER   RASTPISITA   540
LEMGFAVTAI   SRTPGVTYSD   SFDLQCIIKP   HYPAWVPVSV   TWRFQPVGTV   EFHDLVTFTR   600
DGGVQWGDRS   SSFRTRTAIE   KAESSNNVRL   SISRASDTEA   GKYQCVAELW   RKNYNNTWTR   660
LAERTSNLLE   IRVLQPVTKL   QVSKSKRTLT   LVENKPIQLN   CSVKSQTSQN   SHFAVLWYVH   720
KPSDADGKLI   LKTTHNSAFE   YGTYAEEEGL   RARLQFERHV   SGGLFSLTVQ   RAEVSDSGSY   780
YCHVEEWLLS   PNYAWYKLAE   EVSGRTEVTV   KQPDSRLRLS   QAQGNLSVLE   TRQVQLECVV   840
LNRTSITSQL   MVEWFVWKPN   HPERETVARL   SRDATFHYGE   QAAKNNLKGR   LHLESPSPGV   900
YRLFIQNVAV   QDSGTYSCHV   EEWLPSPSGM   WYKRAEDTAG   QTALTVMRPD   ASLQVDTVVP   960
NATVSEKAAF   QLDCSIVSRS   SQDSRFAVAW   YSLRTKAGGK   RSSPGLEEQE   EEREEEEEEE  1020
EDDDDDDPTE   RTALLSVGPD   AVFGPEGSPW   EGRLRFQRLS   PVLYRLTVLQ   ASPQDTGNYS  1080
CHVEEWLPSP   QKEWYRLTEE   ESAPIGIRVL   DTSPTLQSII   CSNDALFYFV   FFYPFPIFGI  1140
LIITILLVRF   KSRNSSKNSD   GKNGVPLLWI   KEPHLNYSPT   CLEPPVSLIH   PGAID       1195

SEQ ID NO: 21                   moltype = AA   length = 798
```

```
FEATURE                 Location/Qualifiers
source                  1..798
                        mol_type = protein
                        organism = Homo sapiens
SEQUENCE: 21
MNLQPIFWIG  LISSVCCVFA  QTDENRCLKA  NAKSCGECIQ  AGPNCGWCTN  STFLQEGMPT   60
SARCDDLEAL  KKKGCPPDDI  ENPRGSKDIK  KNKNVTNRSK  GTAEKLKPED  ITQIQPQQLV  120
LRLRSGEPQT  FTLKFKRAED  YPIDLYYLMD  LSYSMKDDLE  NVKSLGTDLM  NEMRRITSDF  180
RIGFGSFVEK  TVMPYISTTP  AKLRNPCTSE  QNCTSPFSYK  NVLSLTNKGE  VFNELVGKQR  240
ISGNLDSPEG  GFDAIMQVAV  CGSLIGWRNV  TRLLVFSTDA  GFHFAGDGKL  GGIVLPNDGQ  300
CHLENNMYTM  SHYYDYPSIA  HLVQKLSENN  IQTIFAVTEE  FQPVYKELKN  LIPKSAVGTL  360
SANSSNVIQL  IIDAYNSLSS  EVILENGKLS  EGVTISYKSY  CKNGVNGTGE  NGRKCSNISI  420
GDEVQFEISI  TSNKCPKKDS  DSFKIRPLGF  TEEVEVILQY  ICECECQSEG  IPESPKCHEG  480
NGTFECGACR  CNEGRVGRHC  ECSTDEVNSE  DMDAYCRKEN  SSEICSNNGE  CVCGQCVCRK  540
RDNTNEIYSG  KFCECDNFNC  DRSNGLICGG  NGVCKCRVCE  CNPNYTGSAC  DCSLDTSTCE  600
ASNGQICNGR  GICECGVCKC  TDPKFQGQTC  EMCQTCLGVC  AEHKECVQCR  AFNKGEKKDT  660
CTQECSYFNI  TKVESRDKLP  QPVQPDPVSH  CKEKDVDDCW  FYFTYSVNGN  NEVMVHVVEN  720
PECPTGPDII  PIVAGVVAGI  VLIGLALLLI  WKLLMIIHDR  REFAKFEKEK  MNAKWDTGEN  780
PIYKSAVTTV  VNPKYEGK                                                    798

SEQ ID NO: 22           moltype = AA   length = 1032
FEATURE                 Location/Qualifiers
source                  1..1032
                        mol_type = protein
                        organism = Homo sapiens
SEQUENCE: 22
MAWEARREPG  PRRAAVRETV  MLLLCLGVPT  GRPYNVDTES  ALLYQGPHNT  LFGYSVVLHS   60
HGANRWLLVG  APTANWLANA  SVINPGAIYR  CRIGKNPGQT  CEQLQLGSPN  GEPCGKTCLE  120
ERDNQWLGVT  LSRQPGENGS  IVTCGHRWKN  IFYIKNENKL  PTGGCYGVPP  DLRTELSKRI  180
APCYQDYVKK  FGENFASCQA  GISSFYTKDL  IVMGAPGSSY  WTGSLFVYNI  TTNKYKAFLD  240
KQNQVKFGSY  LGYSVGAGHF  RSQHTTEVVG  GAPQHEQIGK  AYIFSIDEKE  LNILHEMKGK  300
KLGSYFGASV  CAVDLNADGF  SDLLVGAPMQ  STIREEGRVF  VYINSGSGAV  MNAMETNLVG  360
SDKYAARFGE  SIVNLGDIDN  DGFEDVAIGA  PQEDDLQGAI  YIYNGRADGI  SSTFSQRIEG  420
LQISKSLSMF  GQSISGQIDA  DNNGYVDVAV  GAFRSDSAVL  LRTRPVVIVD  ASLSHPESVN  480
RTKFDCVENG  WPSVCIDLTL  CFSYKGKEVP  GYIVLFYNMS  LDVNRKAESP  PRFYFSSNGT  540
SDVITGSIQV  SSREANCRTH  QAFMRKDVRD  ILTPIQIEAA  YHLGPHVISK  RSTEEFPPLQ  600
PILQQKKEKD  IMKKTINFAR  FCAHENCSAD  LQVSAKIGFL  KPHENKTYLA  VGSMKTLMLN  660
VSLFNAGDDA  YETTLHVKLP  VGLYFIKILE  LEEKQINCEV  TDNSGVVQLD  CSIGYIYVDH  720
LSRIDISFLL  DVSSLSRAEE  DLSITVHATC  ENEEEMDNLK  HSRVTVAIPL  KYEVKLTVHG  780
FVNPTSFVYG  SNDENEPETC  MVEKMNLTFH  VINTGNSMAP  NVSVEIMVPN  SFSPQTDKLF  840
NILDVQTTTG  ECHFENYQRV  CALEQQKSAM  QTLKGIVRFL  SKTDKRLLYC  IKADPHCLNF  900
LCNFGKMESG  KEASVHIQLE  GRPSILEMDE  TSALKFEIRA  TGFPEPNPRV  IELNKDENVA  960
HVLLEGLHHQ  RPKRYFTIVI  ISSSLLLGLI  VLLLISYVMW  KAGFFKRQYK  SILQEENRRD 1020
SWSYINSKSN  DD                                                         1032

SEQ ID NO: 23           moltype = AA   length = 660
FEATURE                 Location/Qualifiers
source                  1..660
                        mol_type = protein
                        organism = Homo sapiens
SEQUENCE: 23
MELQPPEASI  AVVSIPRQLP  GSHSEAGVQG  LSAGDDSELG  SHCVAQTGLE  LLASGDPLPS   60
ASQNAEMIET  GSDCVTQAGL  QLLASSDPPA  LASKNAEVTE  TGFHHVSQAD  IEFLTSIDPT  120
ASASGSAGIT  GTMSQDTEVD  MKEVELNELE  PEKQPMNAAS  GAAMSLAGAE  KNGLVKIKVA  180
EDEAEAAAAA  KFTGLSKEEL  LKVAGSPGWV  RTRWALLLLF  WLGWLGMLAG  AVVIIVRAPR  240
CRELPAQKWW  HTGALYRIGD  LQAFQGHGAG  NLAGLKGRLD  YLSSLKVKGL  VLGPIHKNQK  300
DDVAQTDLLQ  IDPNFGSKED  FDSLLQSAKK  KSIRVILDLT  PNYRGENSWF  STQVDTVATK  360
VKDALEFWLQ  AGVDGFQVRD  IENLKDASSF  LAEWQNITKG  FSEDRLLIAG  TNSSDLQQIL  420
SLLESNKDLL  LTSSYLSDSG  STGEHTKSLV  TQYLNATGNR  WCSWSLSQAR  LLTSFLPAQL  480
LRLYQLMLFT  LPGTPVFSYG  DEIGLDAAAL  PGQPMEAPVM  LWDESSFPDI  PGAVSANMTV  540
KGQSEDPGSL  LSLFRRLSDQ  RSKERSLLHG  DFHAFSAGPG  LFSYIRHWDQ  NERFLVVLNF  600
GDVGLSAGLQ  ASDLPASASL  PAKADLLLST  QPGREEGSPL  ELERLKLEPH  EGLLLRFPYA  660

SEQ ID NO: 24           moltype = AA   length = 1023
FEATURE                 Location/Qualifiers
source                  1..1023
                        mol_type = protein
                        organism = Homo sapiens
SEQUENCE: 24
MGKGVGRDKY  EPAAVSEQGD  KKGKKGKKDR  DMDELKKEVS  MDDHKLSLDE  LHRKYGTDLS   60
RGLTSARAAE  ILARDGPNAL  TPPPTTPEWI  KFCRQLFGGF  SMLLWIGAIL  CFLAYSIQAA  120
TEEEPQNDNL  YLGVVLSAVV  IITGCFSYYQ  EAKSSKIMES  FKNMVPQQAL  VIRNGEKMSI  180
NAEEVVVGDL  VEVKGGDRIP  ADLRIISANG  CKVDNSSLTG  ESEPQTRSPD  FTNENPLETR  240
NIAFFSTNCV  EGTARGIVVY  TGDRTVMGRI  ATLASGLEGG  QTPIAAEIEH  FIHIITGVAV  300
FLGVSFFILS  LILEYTWLEA  VIFLIGIIVA  NVPEGLLATV  TVCLTLTAKR  MARKNCLVKN  360
LEAVETLGST  STICSDKTGT  LTQNRMTVAH  MWFDNQIHEA  DTTENQSGVS  FDKTSATWLA  420
LSRIAGLCNR  AVFQANQENL  PILKRAVAGD  ASESALLKCI  ELCCGSVKEM  RERYAKIVEI  480
PFNSTNKYQL  SIHKNPNTSE  PQHLLVMKGA  PERILDRCSS  ILLHGKEQPL  DEELKDAFQN  540
AYLELGGLGE  RVLGFCHLFL  PDEQFPEGFQ  FDTDDVNFPI  DNLCFVGLIS  MIDPPRAAVP  600
```

```
DAVGKCRSAG IKVIMVTGDH PITAKAIAKG VGIISEGNET VEDIAARLNI PVSQVNPRDA    660
KACVVHGSDL KDMTSEQLDD ILKYHTEIVF ARTSPQQKLI IVEGCQRQGA IVAVTGDGVN    720
DSPALKKADI GVAMGIAGSD VSKQAADMIL LDDNFASIVT GVEEGRLIFD NLKKSIAYTL    780
TSNIPEITPF LIFIIANIPL PLGTVTILCI DLGTDMVPAI SLAYEQAESD IMKRQPRNPK    840
TDKLVNERLI SMAYGQIGMI QALGGFFTYF VILAENGFLP IHLLGLRVDW DDRWINDVED    900
SYGQQWTYEQ RKIVEFTCHT AFFVSIVVVQ WADLVICKTR RNSVFQQGMK NKILIFGLFE    960
ETALAAFLSY CPGMGVALRM YPLKPTWWFC AFPYSLLIFV YDEVRKLIIR RRPGGWVEKE   1020
TYY                                                                1023

SEQ ID NO: 25           moltype = AA   length = 1020
FEATURE                 Location/Qualifiers
source                  1..1020
                        mol_type = protein
                        organism = Homo sapiens
SEQUENCE: 25
MGRGAGREYS PAATTAENGG GKKKQKEKEL DELKKEVAMD DHKLSLDELG RKYQVDLSKG     60
LTNQRAQDVL ARDGPNALTP PPTTPEWVKF CRQLFGGFSI LLWIGAILCF LAYGIQAAME   120
DEPSNDNLYL GVVLAAVVIV TGCFSYYQEA KSSKIMDSFK NMVPQQALVI REGEKMQINA   180
EEVVVGDLVE VKGGDRVPAD LRIISSHGCK VDNSSLTGES EPQTRSPEFT HENPLETRNI   240
CFFSTNCVEG TARGIVIATG DRTVMGRIAT LASGLEVGRT PIAMEIEHFI QLITGVAVFL   300
GVSFFVLSLI LGYSWLEAVI FLIGIIVANV PEGLLATVTV CLTLTAKRMA RKNCLVKNLE   360
AVETLGSTST ICSDKTGTLT QNRMTVAHMW FDNQIHEADT TEDQSGATFD KRSPTWTALS   420
RIAGLCNRAV FKAGQENISV SKRDTAGDAS ESALLKCIEL SCGSVRKMRD RNPKVAEIPF   480
NSTNKYQLSI HEREDSPQSH VLVMKGAPER ILDRCSTILV QGKEIPLDKE MQDAFQNAYM   540
ELGGLGERVL GFCQLNLPSG KFPRGFKFDT DELNFPTEKL CFVGLMSMID PPRAAVPDAV   600
GKCRSAGIKV IMVTGDHPIT AKAIAKGVGI ISEGNETVED IAARLNIPMS QVNPREAKAC   660
VVHGSDLKDM TSEQLDEILK NHTEIVFART SPQQKLIIVE GCQRQGAIVA VTGDGVNDSP   720
ALKKADIGIA MGISGSDVSK QAADMILLDD NFASIVTGVE EGRLIFDNLK KSIAYTLTSN   780
IPEITPFLLF IIANIPLPLG TVTILCIDLG TDMVPAISLA YEAAESDIMK RQPRNSQTDK   840
LVNERLISMA YGQIGMIQAL GGFFTYFVIL AENGFLPSAL LIRLDWDDR TMNDLEDSYG    900
QEWTYEQRKV VEFTCHTAFF ASIVVVQWAD LIICKTRRNS VFQQGMKNKI LIFGLLEETA   960
LAAFLSYCPG MGVALRMYPL KVTWWFCAFP YSLLIFIYDE VRKLILRRYP GGWVEKETYY  1020

SEQ ID NO: 26           moltype = AA   length = 1026
FEATURE                 Location/Qualifiers
source                  1..1026
                        mol_type = protein
                        organism = Homo sapiens
SEQUENCE: 26
MGSGGSDSYR IATSQDKKDD KDSPKKNKGK ERRDLDDLKK EVAMTEHKMS VEEVCRKYNT    60
DCVQGLTHSK AQEILARDGP NALTPPPTTP EWVKFCRQLF GGFSILLWIG AILCFLAYGI   120
QAGTEDDPSG DNLYLGIVLA AVVIITGCFS YYQEAKSSKI MESFKNMVPQ QALVIREGEK   180
MQVNAEEVVV GDLVEIKGGD RVPADLRIIS AHGCKVDNSS LTGESEPQTR SPDCTHDNPL   240
ETRNITFFST NCVEGTARGV VVATGDRTVM GRIATLASGL EVGKTPIAIE IEHFIQLITG   300
VAVFLGVSFF ILSLILGYTW LEAVIFLIGI IVANVPEGLL ATVTVCLTLT AKRMARKNCL   360
VKNLEAVETL GSTSTICSDK TGTLTQNRMT VAHMWFDNQI HEADTTEDQS GTSFDKSSHT   420
WVALSHIAGL CNRAVFKGGQ DNIPVLKRDV AGDASESALL KCIELSSGSV KLMRERNKKV   480
AEIPFNSTNK YQLSIHETED PNDNRYLLVM KGAPERILDR CSTILLQGKE QPLDEEMKEA   540
FQNAYLELGG LGERVLGFCH YYLPEEQFPK GFAFDCDDVN FTTDNLCFVG LMSMIDPPRA   600
AVPDAVGKCR SAGIKVIMVT GDHPITAKAI AKGVGIISEG NETVEDIAAR LNIPVSQVNP   660
RDAKACVIHG TDLKDFTSEQ IDEILQNHTE IVFARTSPQQ KLIIVEGCQR QGAIVAVTGD   720
GVNDSPALKK ADIGVAMGIA GSDVSKQAAD MILLDDNFAS IVTGVEEGRL IFDNLKKSIA   780
YTLTSNIPEI TPFLLFIMAN IPLPLGTITI LCIDLGTDMV PAISLAYEAA ESDIMKRQPR   840
NPRTDKLVNE RLISMAYGQI GMIQALGGFF SYFVILAENG FLPGNLVGIR LNWDDRTVND   900
LEDSYGQQWT YEQRKVVEFT CHTAFFVSIV VVQWADLIIC KTRRNSVFQQ GMKNKILIFG   960
LFEETALAAF LSYCPGMDVA LRMYPLKPSW WFCAFPYSFL IFVYDEIRKL ILRRNPGGWV  1020
EKETYY                                                            1026

SEQ ID NO: 27           moltype = AA   length = 1029
FEATURE                 Location/Qualifiers
source                  1..1029
                        mol_type = protein
                        organism = Homo sapiens
SEQUENCE: 27
MGLWGKKGTV APHDQSPRRR PKKGLIKKKM VKREKQKRNM EELKKEVVMD DHKLTLEELS    60
TKYSVDLTKG HSHQRAKEIL TRGGPNTVTP PPTTPEWVKF CKQLFGGFSL LLWTGAILCF   120
VAYSIQIYFN EEPTKDNLYL SIVLSVVVIV TGCFSYYQEA KSSKIMESFK NMVPQQALVI   180
RGGEKMQINV QEVVLGDLVE IKGGDRVPAD LRLISAQGCK VDNSSLTGES EPQSRSPDFT   240
HENPLETRNI CFFSTNCVEG TARGIVIATG DSTVMGRIAS LTSGLAVGQT PIAAEIEHFI   300
HLITVVAVFL GVTFFALSLL LGYGWLEAII FLIGIIVANV PEGLLATVTV CLTLTAKRMA   360
RKNCLVKNLE AVETLGSTST ICSDKTGTLT QNRMTVAHMW FDMTVYEADT TEEQTGKTFT   420
KSSDTWFMLA RIAGLCNRAD FKANQEILPI AKRATTGDAS ESALLKFIEQ SYSSVAEMRE   480
KNPKVAEIPF NSTNKYQMSI HLREDSSQTH VLMMKGAPER ILEFCSTFLL NGQEYSMNDE   540
MKEAFQNAYL ELGGLGERVL GFCFLNLPSS FSKGFPFNTD EINFPMDNLC FVGLISMIDP   600
PRAAVPDAVS KCRSAGIKVI MVTGDHPITA KAIAKGVGII SEGTETAEEV AARLKIPISK   660
VDASAAKAIV VHGAELKDIQ SKQLDQILQN HPEIVFARTS PQQKLIIVEG CQRLGAVVAV   720
TGDGVNDSPA LKKADIGIAM GISGSDVSKQ AADMILLDDN FASIVTGVEE GRLIFDNLKK   780
SIMYTLTSNI PEITPFLMFI ILGIPLPLGT ITILCIDLGT DMVPAISLAY ESAESDIMKR   840
LPRNPKTDNL VNHRLIGMAY GQIGMIQALA GFFTYFVILA ENGFRPVDLL GIRLHWEDKY   900
```

```
LNDLEDSYGQ QWTYEQRKVV EFTCQTAFFV TIVVVQWADL IISKTRRNSL FQQGMRNKVL    960
IFGILEETLL AAFLSYTPGM DVALRMYPLK ITWWLCAIPY SILIFVYDEI RKLLIRQHPD   1020
GWVERETYY                                                           1029

SEQ ID NO: 28           moltype = AA   length = 279
FEATURE                 Location/Qualifiers
source                  1..279
                        mol_type = protein
                        organism = Homo sapiens
SEQUENCE: 28
MTKNEKKSLN QSLAEWKLFI YNPTTGEFLG RTAKSWGLIL LFYLVFYGFL AALFSFTMWV    60
MLQTLNDEVP KYRDQIPSPG LMVFPKPVTA LEYTFSRSDP TSYAGYIEDL KKFLKPYTLE   120
EQKNLTVCPD GALFEQKGPV YVACQFPISL LQACSGMNDP DFGYSQGNPC ILVKMNRIIG   180
LKPEGVPRID CVSKNEDIPN VAVYPHNGMI DLKYFPYYGK KLHVGYLQPL VAVQVSFAPN   240
NTGKEVTVEC KIDGSANLKS QDDRDKFLGR VMFKITARA                         279

SEQ ID NO: 29           moltype = AA   length = 1258
FEATURE                 Location/Qualifiers
source                  1..1258
                        mol_type = protein
                        organism = Homo sapiens
SEQUENCE: 29
MGDMANNSVA YSGVKNSLKE ANHDGDFGIT LAELRALMEL RSTDALRKIQ ESYGDVYGIC    60
TKLKTSPNEG LSGNPADLER REAVFGKNFI PPKKPKTFLQ LVWEALQDVT LIILEIAAIV   120
SLGLSFYQPP EGDNALCGEV SVGEEEGEGE TGWIEGAAIL LSVVCVVLVT AFNDWSKEKQ   180
FRGLQSRIEQ EQKFTVIRGG QVIQIPVADI TVGDIAQVKY GDLLPADGIL IQGNDLKIDE   240
SSLTGESDHV KKSLDKDPLL LSGTHVMEGS GRMVVTAVGV NSQTGIIFTL LGAGGEEEEK   300
KDEKKKEKKN KKQDGAIENR NKAKAQDGAA MEMQPLKSEE GGDGDEKDKK KANLPKKEKS   360
VLQGKLTKLA VQIGKAGLLM SAITVIILVL YFVIDTFWVQ KRPWLAECTP IYIQYFVKFF   420
IIGVTVLVVA VPEGLPLAVT ISLAYSVKKM MKDNNLVRHL DACETMGNAT AICSDKTGTL   480
TMNRMTVVQA YINEKHYKKV PEPEAIPPNI LSYLVTGISV NCAYTSKILP PEKEGGLPRH   540
VGNKTECALL GLLLDLKRDY QDVRNEIPEE ALYKVYTFNS VRKSMSTVLK NSDGSYRIFS   600
KGASEIIILKK CFKILSANGE AKVFRPRDRD DIVKTVIEPM ASEGLRTICL AFRDFPAGEP   660
EPEWDNENDI VTGLTCIAVV GIEDPVRPEV PDAIKKCQRA GITVRMVTGD NINTARAIAT   720
KCGILHPGED FLCLEGKDFN RRIRNEKGEI EQERIDKIWP KLRVLARSSP TDKHTLVKGI   780
IDSTVSDQRQ VVAVTGDGTN DGPALKKADV GFAMGIAGTD VAKEASDIIL TDDNFTSIVK   840
AVMWGRNVYD SISKFLQFQL TVNVAVIVA FTGACITQDS PLKAVQMLWV NLIMDTLASL    900
ALATEPPTES LLLRKPYGRN KPLISRTMMK NILGHAFYQL VVVFTLLFAG EKFFDIDSGR   960
NAPLHAPPSE HYTIVFNTFV LMQLFNEINA RKIHGERNVF EGIFNNAIFC TIVLGTFVVQ   1020
IIIVQFGGKP FSCSELSIEQ WLWSIFLGMG TLLWGQLIST IPTSRLKFLK EAGHGTQKEE   1080
IPEEELAEDV EEIDHAEREL RRGQILWFRG LNRIQTQMDV VNAFQSGSSI QGALRRQPSI   1140
ASQHHDVTNI STPTHIRVVN AFRSSLYEGL EKPESRSSIH NFMTHPEFRI EDSEPHIPLI   1200
DDTDAEDDAP TKRNSSPPPS PNKNNNAVDS GIHLTIEMNK SATSSSPGSP LHSLETSL    1258

SEQ ID NO: 30           moltype = AA   length = 1272
FEATURE                 Location/Qualifiers
source                  1..1272
                        mol_type = protein
                        organism = Homo sapiens
SEQUENCE: 30
MGDMTNSDFY SKNQRNESSH GGEFGCTMEE LRSLMELRGT EAVVKIKETY GDTEAICRRL    60
KTSPVEGLPG TAPDLEKRKQ IFGQNFIPPK PKTFLQLVW EALQDVTLII LEIAAIISLG   120
LSFYHPPGEG NEGCATAQGG AEDEGEAEAG WIEGAAILLS VICVVLVTAF NDWSKEKQFR   180
GLQSRIEQEQ KFTVVRAGQV VQIPVAEIVV GDIAQVKYGD LLPADGLFIQ GNDLKIDESS   240
LTGESDQVRK SVDKDPMLLS GTHVMEGSGR MLVTAVGVNS QTGIIFTLLG AGGEEEEKKD   300
KKGVKKGDGL QLPAADGAAA SNAADSANAS LVNGKMQDGN VDASQSKAKQ QDGAAAMEMQ   360
PLKSAEGGDA DDRKKASMHK KEKSVLQGKL TKLAVQIGKA GLVMSAITVI ILVLYFTVDT   420
FVVNKKPWLP ECTPVYVQYF VKFFIIGVTV LVVAVPEGLP LAVTISLAYS VKKMMKDNNL   480
VRHLDACETM GNATAICSDK TGTLTTNRMT VVQAYVGDVH YKEIPDPSSI NTKTMELLIN   540
AIAINSAYTT KILPPEKEGA LPRQVGNKTE CGLLGFVLDL KQDYEPVRSQ MPEEKLYKVY   600
TFNSVRKSMS TVIKLPDESF RMYSKGASEI VLKKCCKILN GAGEPRVFRP RDRDEMVKKV   660
IEPMACDGLR TICVAYRDFP SSPEPDWDNE NDILNELTCI CVVGIEDPVR PEVPEAIRKC   720
QRAGITVRMV TGDNINTARA IAIKCGIIHP GEDFLCLEGK EFNRRIRNEK GEIEQERIDK   780
IWPKLRVLAR SSPTDKHTLV KGIIDSTHTE QRQVVAVTGD GTNDGPALKK ADVGFAMGIA   840
GTDVAKEASD IILTDDNFSS IVKAVMWGRN VYDSISKFLQ FQLTVNVAV IVAFTGACIT    900
QDSPLKAVQM LWVNLIMDTF ASLALATEPP TETLLLRKPY GRNKPLISRT MMKNILGHAV   960
YQLALIFTLL FVGEKMFQID SGRNAPLHSP PSEHYTIIFN TFVMMQLFNE INARKIHGER   1020
NVFDGIFRNP IFCTIVLGTF AIQIVIVQFG GKPFSCSPLG LDQWMWCIFI GLGELVWGQV   1080
IATIPTSRLK FLKEAGRLTQ KEEIPEEELN EDVEEIDHAE RELRRGQILW FRGLNRIQTQ   1140
IEVVNTFKSG ASFQGALRRQ SSVTSQSQDI RVVKAFRSSL YEGLEKPESR TSIHNFMAHP   1200
EFRIEDSQPH IPLIDDTDLE EDAALKQNSS PPSSLNKNNS AIDSGINLTT DTSKSATSSS   1260
PGSPIHSLET SL                                                      1272

SEQ ID NO: 31           moltype = AA   length = 1241
FEATURE                 Location/Qualifiers
source                  1..1241
                        mol_type = protein
                        organism = Homo sapiens
SEQUENCE: 31
```

```
MTNPSDRVLP ANSMAESREG DFGCTVMELR KLMELRSRDA LTQINVHYGG VQNLCSRLKT    60
SPVEGLSGNP ADLEKRRQVF GHNVIPPKKP KTFLELVWEA LQDVTLIILE IAAIISLVLS   120
FYRPAGEENE LCGQVATTPE DENEAQAGWI EGAAILFSVI IVVLVTAFND WSKEKQFRGL   180
QCRIEQEQKF SIIRNGQLIQ LPVAEIVVGD IAQVKYGDLL PADGILIQGN DLKIDESSLT   240
GESDHVKKSL DKDPMLLSGT HVMEGSGRMV VTAVGVNSQT GIILTLLGVN EDDEGEKKKK   300
GKKQGVPENR NKAKTQDGVA LEIQPLNSQE GIDNEEKDKK AVKVPKKEKS VLQGKLTRLA   360
VQIGKAGLLM SALTVFILIL YFVIDNFVIN RRPWLPECTP IYIQYFVKFF IIGITVLVVA   420
VPEGLPLAVT ISLAYSVKKM MKDNNLVRHL DACETMGNAT AICSDKTGTL TMNRMTVVQA   480
YIGGIHYRQI PSPDVFLPKV LDLIVNGISI NSAYTSKILP PEKEGGLPRQ VGNKTECALL   540
GFVTDLKQDY QAVRNEVPEE KLYKVYTFNS VRKSMSTVIR NPNGGFRMYS KGASEIILRK   600
CNRILDRKGE AVPFKNKDRD DMVRTVIEPM ACDGLRTICI AYRDFDDTEP SWDNENEILT   660
ELTCIAVVGI EDPVRPEVPD AIAKCKQAGI TVRMVTGDNI NTARAIATKC GILTPGDDFL   720
CLEGKEFNRL IRNEKGEVEQ EKLDKIWPKL RVLARSSPTD KHTLVKGIID STVGEHRQVV   780
AVTGDGTNDG PALKKADVGF AMGIAGTDVA KEASDIILTD DNFTSIVKAV MWGRNVYDSI   840
SKFLQFQLTV NVVAVIVAFT GACITQDSPL KAVQMLWVNL IMDTFASLAL ATEPPTESLL   900
KRRPYGRNKP LISRTMMKNI LGHAFYQLIV IFILVFAGEK FFDIDSGRKA PLHSPPSQHY   960
TIVFNTFVLM QLFNEINSRK IHGEKNVFSG IYRNIIFCSV VLGTFICQIF IVEFGGKPFS  1020
CTSLSLSQWL WCLFIGIGEL LWGQFISAIP TRSLKFLKEA GHGTTKEEIT KDAEGLDEID  1080
HAEMELRRGQ ILWFRGLNRI QTQIDVINTF QTGASFKGVL RRQNMGQHLD VKLVPSSSYI  1140
KVVKAFHSSL HESIQKPYNQ KSIHSFMTHP EFAIEEELPR TPLLDEEEEE NPDKASKFGT  1200
RVLLLDGEVT PYANTNNNAV DCNQVQLPQS DSSLQSLETS V                     1241

SEQ ID NO: 32           moltype = AA   length = 1241
FEATURE                 Location/Qualifiers
source                  1..1241
                        mol_type = protein
                        organism = Homo sapiens
SEQUENCE: 32
MTNPSDRVLP ANSMAESREG DFGCTVMELR KLMELRSRDA LTQINVHYGG VQNLCSRLKT    60
SPVEGLSGNP ADLEKRRQVF GHNVIPPKKP KTFLELVWEA LQDVTLIILE IAAIISLVLS   120
FYRPAGEENE LCGQVATTPE DENEAQAGWI EGAAILFSVI IVVLVTAFND WSKEKQFRGL   180
QCRIEQEQKF SIIRNGQLIQ LPVAEIVVGD IAQVKYGDLL PADGILIQGN DLKIDESSLT   240
GESDHVKKSL DKDPMLLSGT HVMEGSGRMV VTAVGVNSQT GIILTLLGVN EDDEGEKKKK   300
GKKQGVPENR NKAKTQDGVA LEIQPLNSQE GIDNEEKDKK AVKVPKKEKS VLQGKLTRLA   360
VQIGKAGLLM SALTVFILIL YFVIDNFVIN RRPWLPECTP IYIQYFVKFF IIGITVLVVA   420
VPEGLPLAVT ISLAYSVKKM MKDNNLVRHL DACETMGNAT AICSDKTGTL TMNRMTVVQA   480
YIGGIHYRQI PSPDVFLPKV LDLIVNGISI NSAYTSKILP PEKEGGLPRQ VGNKTECALL   540
GFVTDLKQDY QAVRNEVPEE KLYKVYTFNS VRKSMSTVIR NPNGGFRMYS KGASEIILRK   600
CNRILDRKGE AVPFKNKDRD DMVRTVIEPM ACDGLRTICI AYRDFDDTEP SWDNENEILT   660
ELTCIAVVGI EDPVRPEVPD AIAKCKQAGI TVRMVTGDNI NTARAIATKC GILTPGDDFL   720
CLEGKEFNRL IRNEKGEVEQ EKLDKIWPKL RVLARSSPTD KHTLVKGIID STVGEHRQVV   780
AVTGDGTNDG PALKKADVGF AMGIAGTDVA KEASDIILTD DNFTSIVKAV MWGRNVYDSI   840
SKFLQFQLTV NVVAVIVAFT GACITQDSPL KAVQMLWVNL IMDTFASLAL ATEPPTESLL   900
KRRPYGRNKP LISRTMMKNI LGHAFYQLIV IFILVFAGEK FFDIDSGRKA PLHSPPSQHY   960
TIVFNTFVLM QLFNEINSRK IHGEKNVFSG IYRNIIFCSV VLGTFICQIF IVEFGGKPFS  1020
CTSLSLSQWL WCLFIGIGEL LWGQFISAIP TRSLKFLKEA GHGTTKEEIT KDAEGLDEID  1080
HAEMELRRGQ ILWFRGLNRI QTQIDVINTF QTGASFKGVL RRQNMGQHLD VKLVPSSSYI  1140
KVVKAFHSSL HESIQKPYNQ KSIHSFMTHP EFAIEEELPR TPLLDEEEEE NPDKASKFGT  1200
RVLLLDGEVT PYANTNNNAV DCNQVQLPQS DSSLQSLETS V                     1241

SEQ ID NO: 33           moltype = AA   length = 193
FEATURE                 Location/Qualifiers
source                  1..193
                        mol_type = protein
                        organism = Homo sapiens
SEQUENCE: 33
GPIFNASVHS DTPSVIRGDL IKLFCIITVE GAALDPDDMA FDVSWFAVHS FGLDKAPVLL    60
SSLDRKGIVT TSRRDWKSDL SLERVSVLEF LLQVHGSEDQ DFGNYYCSVT PWVKSPTGSW   120
QKEAEIHSKP VFITVKMDVL NAFKYPLLIG VGLSTVIGLL SCLIGYCSSH WCCKKEVQET   180
RRERRRLMSM EMD                                                     193

SEQ ID NO: 34           moltype = AA   length = 1021
FEATURE                 Location/Qualifiers
source                  1..1021
                        mol_type = protein
                        organism = Homo sapiens
SEQUENCE: 34
MAGISYVASF FLLLTKLSIG QREVTVQKGP LFRAEGYPVS IGCNVTGHQG PSEQHFQWSV    60
YLPTNPTQEV QIISTKDAAF SYAVYTQRVR SGDVYVERVQ GNSVLLHISK LQMKDAGEYE   120
CHTPNTDEKY YGSYSAKTNL IVIPDTLSAT MSSQTLGKEE GEPLALTCEA SKATAQHTHL   180
SVTWYLTQDG GGSQATEIIS LSKDPILVPG PLYTERFAAS DVQLNKLGPT TFRLSIERLQ   240
SSDQGQLFCE ATEWIQDPDE TWMFITKKQT DQTTLRIQPA VKDFQVNITA DSLFAEGKPL   300
ELVCLVVSSG RDPQLQGIWF FNGTEIAHID AGGVLGLNQN YKERASQGEL QVSKLGPKAF   360
SLKIFSLGPE DEGAYRCVVA EVMKTRTGSW QVLRQRKQSP SHVHLRKPAA RSVVMSTKNK   420
QQVVWEGETL AFLCKAGGAE SPLSVSWWHI PRDQTQPEFV AGMGQDGIVQ LGASYGVPSY   480
HGNTRLEKMD WATFQLEITF TAITDSGTYE CRVSEKSRNQ ARDLSWTQKI SVTVKSLESS   540
LQVSLMSRQP QVMLTNTFDL SCVVRAGYSD LKVPLTVTWQ FQPASSHIFH QLIRITHNGT   600
IEWGNFLSRF QKKTKVSQSL FRSQLLVHDA TEEETGVYQC EVEVYDRNSL YNNRPPRASA   660
ISHPLRIAVT LPESKLKVNS RSQVQELSIN SNTDIECSIL SRSNGNLQLA IIWYFSPVST   720
```

```
NASWLKILEM DQTNVIKTGD EFHTPQRKQK FHTEKVSQDL FQLHILNVED SDRGKYHCAV   780
EEWLLSTNGT WHKLGEKKSG LTELKLKPTG SKVRVSKVYW TENVTEHREV AIRCSLESVG   840
SSATLYSVMW YWNRENSGSK LLVHLQHDGL LEYGEEGLRR HLHCYRSSST DFVLKLHQVE   900
MEDAGMYWCR VAEWQLHGHP SKWINQASDE SQRMVLTVLP SEPTLPSRIC SSAPLLYFLF   960
ICPFVLLLLL LISLLCLYWK ARKLSTLRSN TRKEKALWVD LKEAGGVTTN RREDEEEDEG  1020
N                                                                1021

SEQ ID NO: 35           moltype = AA   length = 20
FEATURE                 Location/Qualifiers
source                  1..20
                        mol_type = protein
                        organism = Homo sapiens
SEQUENCE: 35
MAGISYVASF FLLLTKLSIG                                               20

SEQ ID NO: 36           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 36
cgttggcagt ccgccttaac                                               20

SEQ ID NO: 37           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 37
catagtcact gacgttgcag                                               20

SEQ ID NO: 38           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 38
ttgtggagct tgcaagcacc                                               20

SEQ ID NO: 39           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 39
gttctttatg tggagctcca                                               20

SEQ ID NO: 40           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 40
tatcccttgc tgatcggcgt                                               20

SEQ ID NO: 41           moltype = DNA  length = 20
FEATURE                 Location/Qualifiers
source                  1..20
                        mol_type = other DNA
                        note = Synthetic  Oligonucleotide
                        organism = synthetic construct
SEQUENCE: 41
gctgcagtac ccgatgagac                                               20

SEQ ID NO: 42           moltype = AA   length = 38
FEATURE                 Location/Qualifiers
source                  1..38
                        mol_type = protein
                        note = Synthetic Polypeptide
                        organism = synthetic construct
SEQUENCE: 42
EHSAGGGGSD YKDDDDKGGG GSLSNPIEID FQTSGPIF                           38

SEQ ID NO: 43           moltype = AA   length = 34
```

```
FEATURE                 Location/Qualifiers
source                  1..34
                        mol_type = protein
                        note = Synthetic Polypeptide
                        organism = synthetic construct
SEQUENCE: 43
EHSAGGGGSD YKDDDDKGGG GSIEIDFQTS GPIF                              34

SEQ ID NO: 44           moltype = AA  length = 30
FEATURE                 Location/Qualifiers
source                  1..30
                        mol_type = protein
                        note = Synthetic Polypeptide
                        organism = synthetic construct
SEQUENCE: 44
EHSAGGGGSD YKDDDDKGGG GSFQTSGPIF                                   30

SEQ ID NO: 45           moltype = AA  length = 26
FEATURE                 Location/Qualifiers
source                  1..26
                        mol_type = protein
                        note = Synthetic Polypeptide
                        organism = synthetic construct
SEQUENCE: 45
EHSAGGGGSD YKDDDDKGGG GSGPIF                                       26

SEQ ID NO: 46           moltype = AA  length = 42
FEATURE                 Location/Qualifiers
source                  1..42
                        mol_type = protein
                        note = Synthetic Polypeptide
                        organism = synthetic construct
SEQUENCE: 46
FITVKMDTLD PRSFLLRNPN DKYEPFWEDE EKNESGSDKT HT                     42

SEQ ID NO: 47           moltype = AA  length = 332
FEATURE                 Location/Qualifiers
source                  1..332
                        mol_type = protein
                        organism = Homo sapiens
SEQUENCE: 47
MGAQFSKTAA KGEAAAERPG EAAVASSPSK ANGQENGHVK VNGDASPAAA ESGAKEELQA  60
NGSAPAADKE EPAAAGSGAA SPSAAEKGEP AAAAAPEAGA SPVEKEAPAE GEAAEPGSPT  120
AAEGEAASAA SSTSSPKAED GATPSPSNET PKKKKKRFSF KKSFKLSGFS FKKNKKEAGE  180
GGEAEAPAAE GGKDEAAGGA AAAAAEAGAA SGEQAAAPGE EAAAGEEGAA GGDPQEAKPQ  240
EAAVAPEKPP ASDETKAAEE PSKVEEKKAE EAGASAAACE APSAAGPGAP PEQEAAPAEE  300
PAAAAASSAC AAPSQEAQPE CSPEAPPAEA AE                                332

SEQ ID NO: 48           moltype = AA  length = 195
FEATURE                 Location/Qualifiers
source                  1..195
                        mol_type = protein
                        organism = Homo sapiens
SEQUENCE: 48
MGSQSSKAPR GDVTAEEAAG ASPAKANGQE NGHVKSNGDL SPKGEGESPP VNGTDEAAGA  60
TGDAIEPAPP SQGAEAKGEV PPKETPKKKK KFSFKKPFKL SGLSFKRNRK EGGGDSSASS  120
PTEEEQEQGE IGACSDEGTA QEGKAAATPE SQEPQAKGAE ASAASEEEAG PQATEPSTPS  180
GPESGPTPAS AEQNE                                                   195

SEQ ID NO: 49           moltype = AA  length = 227
FEATURE                 Location/Qualifiers
source                  1..227
                        mol_type = protein
                        organism = Homo sapiens
SEQUENCE: 49
MGGKLSKKKK GYNVNDEKAK EKDKKAEGAA TEEEGTPKES EPQAAAEPAE AKEGKEKPDQ  60
DAEGKAEEKE GEKDAAAAKE EAPKAEPEKT EGAAEAKAEP PKAPEQEQAA PGPAAGGEAP  120
KAAEAAAAPA ESAAPAAGEE PSKEEGEPKK TEAPAAPAAQ ETKSDGAPAS DSKPGSSEAA  180
PSSKETPAAT EAPSSTPKAQ GPAASAEEPK PVEAPAANSD QTVTVKE                227

SEQ ID NO: 50           moltype = AA  length = 30
FEATURE                 Location/Qualifiers
source                  1..30
                        mol_type = protein
                        note = Synthetic peptide
                        organism = synthetic construct
SEQUENCE: 50
MGGKLSKKKK GYNVNDEKAK EKDKKAEGAA                                   30
```

```
SEQ ID NO: 51          moltype = AA   length = 27
FEATURE                Location/Qualifiers
source                 1..27
                       mol_type = protein
                       note = Synthetic peptide
                       organism = synthetic construct
SEQUENCE: 51
MGGKLSKKKK GYNVNDEKAK EKDKKAE                                              27

SEQ ID NO: 52          moltype = AA   length = 24
FEATURE                Location/Qualifiers
source                 1..24
                       mol_type = protein
                       note = Synthetic peptide
                       organism = synthetic construct
SEQUENCE: 52
MGGKLSKKKK GYNVNDEKAK EKDK                                                 24

SEQ ID NO: 53          moltype = AA   length = 21
FEATURE                Location/Qualifiers
source                 1..21
                       mol_type = protein
                       note = Synthetic peptide
                       organism = synthetic construct
SEQUENCE: 53
MGGKLSKKKK GYNVNDEKAK E                                                    21

SEQ ID NO: 54          moltype = AA   length = 18
FEATURE                Location/Qualifiers
source                 1..18
                       mol_type = protein
                       note = Synthetic peptide
                       organism = synthetic construct
SEQUENCE: 54
MGGKLSKKKK GYNVNDEK                                                        18

SEQ ID NO: 55          moltype = AA   length = 15
FEATURE                Location/Qualifiers
source                 1..15
                       mol_type = protein
                       note = Synthetic peptide
                       organism = synthetic construct
SEQUENCE: 55
MGGKLSKKKK GYNVN                                                           15

SEQ ID NO: 56          moltype = AA   length = 12
FEATURE                Location/Qualifiers
source                 1..12
                       mol_type = protein
                       note = Synthetic peptide
                       organism = synthetic construct
SEQUENCE: 56
MGGKLSKKKK GY                                                              12

SEQ ID NO: 57          moltype = AA   length = 11
FEATURE                Location/Qualifiers
source                 1..11
                       mol_type = protein
                       note = Synthetic peptide
                       organism = synthetic construct
SEQUENCE: 57
MGGKLSKKKK G                                                               11

SEQ ID NO: 58          moltype = AA   length = 10
FEATURE                Location/Qualifiers
source                 1..10
                       mol_type = protein
                       note = Synthetic peptide
                       organism = synthetic construct
SEQUENCE: 58
MGGKLSKKKK                                                                 10

SEQ ID NO: 59          moltype = AA   length = 9
FEATURE                Location/Qualifiers
source                 1..9
                       mol_type = protein
                       note = Synthetic peptide
                       organism = synthetic construct
SEQUENCE: 59
```

```
MGGKLSKKK                                                                  9

SEQ ID NO: 60         moltype = AA  length = 8
FEATURE               Location/Qualifiers
source                1..8
                      mol_type = protein
                      note = Synthetic peptide
                      organism = synthetic construct
SEQUENCE: 60
MGGKLSKK                                                                   8

SEQ ID NO: 61         moltype = AA  length = 7
FEATURE               Location/Qualifiers
source                1..7
                      mol_type = protein
                      note = Synthetic peptide
                      organism = synthetic construct
SEQUENCE: 61
MGGKLSK                                                                    7

SEQ ID NO: 62         moltype = AA  length = 8
FEATURE               Location/Qualifiers
source                1..8
                      mol_type = protein
                      note = Synthetic peptide
                      organism = synthetic construct
SEQUENCE: 62
MGGKLAKK                                                                   8

SEQ ID NO: 63         moltype = AA  length = 8
FEATURE               Location/Qualifiers
source                1..8
                      mol_type = protein
                      note = Synthetic peptide
                      organism = synthetic construct
SEQUENCE: 63
MGGKFSKK                                                                   8

SEQ ID NO: 64         moltype = AA  length = 8
FEATURE               Location/Qualifiers
source                1..8
                      mol_type = protein
                      note = Synthetic peptide
                      organism = synthetic construct
SEQUENCE: 64
MGGKFAKK                                                                   8

SEQ ID NO: 65         moltype = AA  length = 8
FEATURE               Location/Qualifiers
source                1..8
                      mol_type = protein
                      note = Synthetic peptide
                      organism = synthetic construct
SEQUENCE: 65
MGGKSSKK                                                                   8

SEQ ID NO: 66         moltype = AA  length = 8
FEATURE               Location/Qualifiers
source                1..8
                      mol_type = protein
                      note = Synthetic peptide
                      organism = synthetic construct
SEQUENCE: 66
MGGKSAKK                                                                   8

SEQ ID NO: 67         moltype = AA  length = 8
FEATURE               Location/Qualifiers
source                1..8
                      mol_type = protein
                      note = Synthetic peptide
                      organism = synthetic construct
SEQUENCE: 67
MGGKQSKK                                                                   8

SEQ ID NO: 68         moltype = AA  length = 8
FEATURE               Location/Qualifiers
source                1..8
                      mol_type = protein
                      note = Synthetic peptide
```

```
                        organism = synthetic construct
SEQUENCE: 68
MGGKQAKK                                                                        8

SEQ ID NO: 69           moltype = AA   length = 8
FEATURE                 Location/Qualifiers
source                  1..8
                        mol_type = protein
                        note = Synthetic peptide
                        organism = synthetic construct
SEQUENCE: 69
MGGQLSKK                                                                        8

SEQ ID NO: 70           moltype = AA   length = 8
FEATURE                 Location/Qualifiers
source                  1..8
                        mol_type = protein
                        note = Synthetic peptide
                        organism = synthetic construct
SEQUENCE: 70
MGGQLAKK                                                                        8

SEQ ID NO: 71           moltype = AA   length = 8
FEATURE                 Location/Qualifiers
source                  1..8
                        mol_type = protein
                        note = Synthetic peptide
                        organism = synthetic construct
SEQUENCE: 71
MGGQFSKK                                                                        8

SEQ ID NO: 72           moltype = AA   length = 8
FEATURE                 Location/Qualifiers
source                  1..8
                        mol_type = protein
                        note = Synthetic peptide
                        organism = synthetic construct
SEQUENCE: 72
MGGQFAKK                                                                        8

SEQ ID NO: 73           moltype = AA   length = 8
FEATURE                 Location/Qualifiers
source                  1..8
                        mol_type = protein
                        note = Synthetic peptide
                        organism = synthetic construct
SEQUENCE: 73
MGGQSSKK                                                                        8

SEQ ID NO: 74           moltype = AA   length = 8
FEATURE                 Location/Qualifiers
source                  1..8
                        mol_type = protein
                        note = Synthetic peptide
                        organism = synthetic construct
SEQUENCE: 74
MGGQSAKK                                                                        8

SEQ ID NO: 75           moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 75
MGGQQSKK                                                                        8

SEQ ID NO: 76           moltype = AA   length = 8
FEATURE                 Location/Qualifiers
source                  1..8
                        mol_type = protein
                        note = Synthetic peptide
                        organism = synthetic construct
SEQUENCE: 76
MGGQQAKK                                                                        8

SEQ ID NO: 77           moltype = AA   length = 8
FEATURE                 Location/Qualifiers
```

| | | |
|---|---|---|
| source | 1..8<br>mol_type = protein<br>note = Synthetic peptide<br>organism = synthetic construct | |
| SEQUENCE: 77<br>MGAKLSKK | | 8 |
| SEQ ID NO: 78<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 78<br>MGAKLAKK | | 8 |
| SEQ ID NO: 79<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 79<br>MGAKFSKK | | 8 |
| SEQ ID NO: 80<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 80<br>MGAKFAKK | | 8 |
| SEQ ID NO: 81<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 81<br>MGAKSSKK | | 8 |
| SEQ ID NO: 82<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 82<br>MGAKSAKK | | 8 |
| SEQ ID NO: 83<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 83<br>MGAKQSKK | | 8 |
| SEQ ID NO: 84<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 84<br>MGAKQAKK | | 8 |
| SEQ ID NO: 85<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 85<br>MGAQLSKK | | 8 |

| | | |
|---|---|---|
| SEQ ID NO: 86<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 86<br>MGAQLAKK | | 8 |
| SEQ ID NO: 87<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 87<br>MGAQFSKK | | 8 |
| SEQ ID NO: 88<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 88<br>MGAQFAKK | | 8 |
| SEQ ID NO: 89<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 89<br>MGAQSSKK | | 8 |
| SEQ ID NO: 90<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 90<br>MGAQSAKK | | 8 |
| SEQ ID NO: 91<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 91<br>MGAQQSKK | | 8 |
| SEQ ID NO: 92<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 92<br>MGAQQAKK | | 8 |
| SEQ ID NO: 93<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 93<br>MGSKLSKK | | 8 |
| SEQ ID NO: 94<br>FEATURE<br>source | moltype = AA   length = 8<br>Location/Qualifiers<br>1..8<br>mol_type = protein<br>note = Synthetic peptide<br>organism = synthetic construct | |
| SEQUENCE: 94 | | |

```
MGSKLAKK                                                                          8

SEQ ID NO: 95          moltype = AA  length = 8
FEATURE                Location/Qualifiers
source                 1..8
                       mol_type = protein
                       note = Synthetic peptide
                       organism = synthetic construct
SEQUENCE: 95
MGSKFSKK                                                                          8

SEQ ID NO: 96          moltype = AA  length = 8
FEATURE                Location/Qualifiers
source                 1..8
                       mol_type = protein
                       note = Synthetic peptide
                       organism = synthetic construct
SEQUENCE: 96
MGSKFAKK                                                                          8

SEQ ID NO: 97          moltype = AA  length = 8
FEATURE                Location/Qualifiers
source                 1..8
                       mol_type = protein
                       note = Synthetic peptide
                       organism = synthetic construct
SEQUENCE: 97
MGSKSSKK                                                                          8

SEQ ID NO: 98          moltype = AA  length = 8
FEATURE                Location/Qualifiers
source                 1..8
                       mol_type = protein
                       note = Synthetic peptide
                       organism = synthetic construct
SEQUENCE: 98
MGSKSAKK                                                                          8

SEQ ID NO: 99          moltype = AA  length = 8
FEATURE                Location/Qualifiers
source                 1..8
                       mol_type = protein
                       note = Synthetic peptide
                       organism = synthetic construct
SEQUENCE: 99
MGSKQSKK                                                                          8

SEQ ID NO: 100         moltype = AA  length = 8
FEATURE                Location/Qualifiers
source                 1..8
                       mol_type = protein
                       note = Synthetic peptide
                       organism = synthetic construct
SEQUENCE: 100
MGSKQAKK                                                                          8

SEQ ID NO: 101         moltype = AA  length = 8
FEATURE                Location/Qualifiers
source                 1..8
                       mol_type = protein
                       note = Synthetic peptide
                       organism = synthetic construct
SEQUENCE: 101
MGSQLSKK                                                                          8

SEQ ID NO: 102         moltype = AA  length = 8
FEATURE                Location/Qualifiers
source                 1..8
                       mol_type = protein
                       note = Synthetic peptide
                       organism = synthetic construct
SEQUENCE: 102
MGSQLAKK                                                                          8

SEQ ID NO: 103         moltype = AA  length = 8
FEATURE                Location/Qualifiers
source                 1..8
                       mol_type = protein
                       note = Synthetic peptide
```

```
                          -continued

SEQUENCE: 103
MGSQFSKK                                                                8

SEQ ID NO: 104        moltype = AA  length = 8
FEATURE               Location/Qualifiers
source                1..8
                      mol_type = protein
                      note = Synthetic peptide
                      organism = synthetic construct
SEQUENCE: 104
MGSQFAKK                                                                8

SEQ ID NO: 105        moltype = AA  length = 8
FEATURE               Location/Qualifiers
source                1..8
                      mol_type = protein
                      note = Synthetic peptide
                      organism = synthetic construct
SEQUENCE: 105
MGSQSSKK                                                                8

SEQ ID NO: 106        moltype = AA  length = 8
FEATURE               Location/Qualifiers
source                1..8
                      mol_type = protein
                      note = Synthetic peptide
                      organism = synthetic construct
SEQUENCE: 106
MGSQSAKK                                                                8

SEQ ID NO: 107        moltype = AA  length = 8
FEATURE               Location/Qualifiers
source                1..8
                      mol_type = protein
                      note = Synthetic peptide
                      organism = synthetic construct
SEQUENCE: 107
MGSQQSKK                                                                8

SEQ ID NO: 108        moltype = AA  length = 8
FEATURE               Location/Qualifiers
source                1..8
                      mol_type = protein
                      note = Synthetic peptide
                      organism = synthetic construct
SEQUENCE: 108
MGSQQAKK                                                                8

SEQ ID NO: 109        moltype = AA  length = 7
FEATURE               Location/Qualifiers
source                1..7
                      mol_type = protein
                      note = Synthetic peptide
                      organism = synthetic construct
SEQUENCE: 109
MGGKLAK                                                                 7

SEQ ID NO: 110        moltype = AA  length = 7
FEATURE               Location/Qualifiers
source                1..7
                      mol_type = protein
                      note = Synthetic peptide
                      organism = synthetic construct
SEQUENCE: 110
MGGKFSK                                                                 7

SEQ ID NO: 111        moltype = AA  length = 7
FEATURE               Location/Qualifiers
source                1..7
                      mol_type = protein
                      note = Synthetic peptide
                      organism = synthetic construct
SEQUENCE: 111
MGGKFAK                                                                 7

SEQ ID NO: 112        moltype = AA  length = 7
FEATURE               Location/Qualifiers
source                1..7
```

```
                            mol_type = protein
                            note = Synthetic peptide
                            organism = synthetic construct
SEQUENCE: 112
MGGKSSK                                                                   7

SEQ ID NO: 113              moltype = AA   length = 7
FEATURE                     Location/Qualifiers
source                      1..7
                            mol_type = protein
                            note = Synthetic peptide
                            organism = synthetic construct
SEQUENCE: 113
MGGKSAK                                                                   7

SEQ ID NO: 114              moltype = AA   length = 7
FEATURE                     Location/Qualifiers
source                      1..7
                            mol_type = protein
                            note = Synthetic peptide
                            organism = synthetic construct
SEQUENCE: 114
MGGKQSK                                                                   7

SEQ ID NO: 115              moltype = AA   length = 7
FEATURE                     Location/Qualifiers
source                      1..7
                            mol_type = protein
                            note = Synthetic peptide
                            organism = synthetic construct
SEQUENCE: 115
MGGKQAK                                                                   7

SEQ ID NO: 116              moltype = AA   length = 7
FEATURE                     Location/Qualifiers
source                      1..7
                            mol_type = protein
                            note = Synthetic peptide
                            organism = synthetic construct
SEQUENCE: 116
MGGQLSK                                                                   7

SEQ ID NO: 117              moltype = AA   length = 7
FEATURE                     Location/Qualifiers
source                      1..7
                            mol_type = protein
                            note = Synthetic peptide
                            organism = synthetic construct
SEQUENCE: 117
MGGQLAK                                                                   7

SEQ ID NO: 118              moltype = AA   length = 7
FEATURE                     Location/Qualifiers
source                      1..7
                            mol_type = protein
                            note = Synthetic peptide
                            organism = synthetic construct
SEQUENCE: 118
MGGQFSK                                                                   7

SEQ ID NO: 119              moltype = AA   length = 7
FEATURE                     Location/Qualifiers
source                      1..7
                            mol_type = protein
                            note = Synthetic peptide
                            organism = synthetic construct
SEQUENCE: 119
MGGQFAK                                                                   7

SEQ ID NO: 120              moltype = AA   length = 7
FEATURE                     Location/Qualifiers
source                      1..7
                            mol_type = protein
                            note = Synthetic peptide
                            organism = synthetic construct
SEQUENCE: 120
MGGQSSK                                                                   7

SEQ ID NO: 121              moltype = AA   length = 7
```

| | | |
|---|---|---|
| FEATURE | Location/Qualifiers | |
| source | 1..7 | |
| | mol_type = protein | |
| | note = Synthetic peptide | |
| | organism = synthetic construct | |
| SEQUENCE: 121 | | |
| MGGQSAK | | 7 |
| | | |
| SEQ ID NO: 122 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 122 | | |
| MGGQQSK | | 7 |
| | | |
| SEQ ID NO: 123 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 123 | | |
| MGGQQAK | | 7 |
| | | |
| SEQ ID NO: 124 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 124 | | |
| MGAKLSK | | 7 |
| | | |
| SEQ ID NO: 125 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 125 | | |
| MGAKLAK | | 7 |
| | | |
| SEQ ID NO: 126 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 126 | | |
| MGAKFSK | | 7 |
| | | |
| SEQ ID NO: 127 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 127 | | |
| MGAKFAK | | 7 |
| | | |
| SEQ ID NO: 128 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 128 | | |
| MGAKSSK | | 7 |
| | | |
| SEQ ID NO: 129 | moltype = AA  length = 7 | |
| FEATURE | Location/Qualifiers | |
| source | 1..7 | |
| | mol_type = protein | |
| | note = Synthetic peptide | |
| | organism = synthetic construct | |
| SEQUENCE: 129 | | |
| MGAKSAK | | 7 |

```
SEQ ID NO: 130          moltype = AA  length = 7
FEATURE                 Location/Qualifiers
source                  1..7
                        mol_type = protein
                        note = Synthetic peptide
                        organism = synthetic construct
SEQUENCE: 130
MGAKQSK                                                                 7

SEQ ID NO: 131          moltype = AA  length = 7
FEATURE                 Location/Qualifiers
source                  1..7
                        mol_type = protein
                        note = Synthetic peptide
                        organism = synthetic construct
SEQUENCE: 131
MGAKQAK                                                                 7

SEQ ID NO: 132          moltype = AA  length = 7
FEATURE                 Location/Qualifiers
source                  1..7
                        mol_type = protein
                        note = Synthetic peptide
                        organism = synthetic construct
SEQUENCE: 132
MGAQLSK                                                                 7

SEQ ID NO: 133          moltype = AA  length = 7
FEATURE                 Location/Qualifiers
source                  1..7
                        mol_type = protein
                        note = Synthetic peptide
                        organism = synthetic construct
SEQUENCE: 133
MGAQLAK                                                                 7

SEQ ID NO: 134          moltype = AA  length = 7
FEATURE                 Location/Qualifiers
source                  1..7
                        mol_type = protein
                        note = Synthetic peptide
                        organism = synthetic construct
SEQUENCE: 134
MGAQFSK                                                                 7

SEQ ID NO: 135          moltype = AA  length = 7
FEATURE                 Location/Qualifiers
source                  1..7
                        mol_type = protein
                        note = Synthetic peptide
                        organism = synthetic construct
SEQUENCE: 135
MGAQFAK                                                                 7

SEQ ID NO: 136          moltype = AA  length = 7
FEATURE                 Location/Qualifiers
source                  1..7
                        mol_type = protein
                        note = Synthetic peptide
                        organism = synthetic construct
SEQUENCE: 136
MGAQSSK                                                                 7

SEQ ID NO: 137          moltype = AA  length = 7
FEATURE                 Location/Qualifiers
source                  1..7
                        mol_type = protein
                        note = Synthetic peptide
                        organism = synthetic construct
SEQUENCE: 137
MGAQSAK                                                                 7

SEQ ID NO: 138          moltype = AA  length = 7
FEATURE                 Location/Qualifiers
source                  1..7
                        mol_type = protein
                        note = Synthetic peptide
                        organism = synthetic construct
```

```
SEQUENCE: 138
MGAQQSK                                                                          7

SEQ ID NO: 139          moltype = AA  length = 7
FEATURE                 Location/Qualifiers
source                  1..7
                        mol_type = protein
                        note = Synthetic peptide
                        organism = synthetic construct
SEQUENCE: 139
MGAQQAK                                                                          7

SEQ ID NO: 140          moltype = AA  length = 7
FEATURE                 Location/Qualifiers
source                  1..7
                        mol_type = protein
                        note = Synthetic peptide
                        organism = synthetic construct
SEQUENCE: 140
MGSKLSK                                                                          7

SEQ ID NO: 141          moltype = AA  length = 7
FEATURE                 Location/Qualifiers
source                  1..7
                        mol_type = protein
                        note = Synthetic peptide
                        organism = synthetic construct
SEQUENCE: 141
MGSKLAK                                                                          7

SEQ ID NO: 142          moltype = AA  length = 7
FEATURE                 Location/Qualifiers
source                  1..7
                        mol_type = protein
                        note = Synthetic peptide
                        organism = synthetic construct
SEQUENCE: 142
MGSKFSK                                                                          7

SEQ ID NO: 143          moltype = AA  length = 7
FEATURE                 Location/Qualifiers
source                  1..7
                        mol_type = protein
                        note = Synthetic peptide
                        organism = synthetic construct
SEQUENCE: 143
MGSKFAK                                                                          7

SEQ ID NO: 144          moltype = AA  length = 7
FEATURE                 Location/Qualifiers
source                  1..7
                        mol_type = protein
                        note = Synthetic peptide
                        organism = synthetic construct
SEQUENCE: 144
MGSKSSK                                                                          7

SEQ ID NO: 145          moltype = AA  length = 7
FEATURE                 Location/Qualifiers
source                  1..7
                        mol_type = protein
                        note = Synthetic peptide
                        organism = synthetic construct
SEQUENCE: 145
MGSKSAK                                                                          7

SEQ ID NO: 146          moltype = AA  length = 7
FEATURE                 Location/Qualifiers
source                  1..7
                        mol_type = protein
                        note = Synthetic peptide
                        organism = synthetic construct
SEQUENCE: 146
MGSKQSK                                                                          7

SEQ ID NO: 147          moltype = AA  length = 7
FEATURE                 Location/Qualifiers
source                  1..7
                        mol_type = protein
```

```
                        note = Synthetic peptide
                        organism = synthetic construct
SEQUENCE: 147
MGSKQAK                                                              7

SEQ ID NO: 148          moltype = AA  length = 7
FEATURE                 Location/Qualifiers
source                  1..7
                        mol_type = protein
                        note = Synthetic peptide
                        organism = synthetic construct
SEQUENCE: 148
MGSQLSK                                                              7

SEQ ID NO: 149          moltype = AA  length = 7
FEATURE                 Location/Qualifiers
source                  1..7
                        mol_type = protein
                        note = Synthetic peptide
                        organism = synthetic construct
SEQUENCE: 149
MGSQLAK                                                              7

SEQ ID NO: 150          moltype = AA  length = 7
FEATURE                 Location/Qualifiers
source                  1..7
                        mol_type = protein
                        note = Synthetic peptide
                        organism = synthetic construct
SEQUENCE: 150
MGSQFSK                                                              7

SEQ ID NO: 151          moltype = AA  length = 7
FEATURE                 Location/Qualifiers
source                  1..7
                        mol_type = protein
                        note = Synthetic peptide
                        organism = synthetic construct
SEQUENCE: 151
MGSQFAK                                                              7

SEQ ID NO: 152          moltype = AA  length = 7
FEATURE                 Location/Qualifiers
source                  1..7
                        mol_type = protein
                        note = Synthetic peptide
                        organism = synthetic construct
SEQUENCE: 152
MGSQSSK                                                              7

SEQ ID NO: 153          moltype = AA  length = 7
FEATURE                 Location/Qualifiers
source                  1..7
                        mol_type = protein
                        note = Synthetic peptide
                        organism = synthetic construct
SEQUENCE: 153
MGSQSAK                                                              7

SEQ ID NO: 154          moltype = AA  length = 7
FEATURE                 Location/Qualifiers
source                  1..7
                        mol_type = protein
                        note = Synthetic peptide
                        organism = synthetic construct
SEQUENCE: 154
MGSQQSK                                                              7

SEQ ID NO: 155          moltype = AA  length = 7
FEATURE                 Location/Qualifiers
source                  1..7
                        mol_type = protein
                        note = Synthetic peptide
                        organism = synthetic construct
SEQUENCE: 155
MGSQQAK                                                              7

SEQ ID NO: 156          moltype = AA  length = 9
FEATURE                 Location/Qualifiers
```

```
source                  1..9
                        mol_type = protein
                        note = Synthetic peptide
                        organism = synthetic construct
SEQUENCE: 156
MGAKLSKKK                                                                 9

SEQ ID NO: 157          moltype = AA   length = 167
FEATURE                 Location/Qualifiers
source                  1..167
                        mol_type = protein
                        note = Synthetic polypeptide
                        organism = synthetic construct
SEQUENCE: 157
MGGKLSKKKK GYNVNDEKAK EKDKKAEGAA SGGSGGSDYK DDDDKGGGSG MASNFTQFVL         60
VDNGGTGDVT VAPSNFANGI AEWISSNSRS QAYKVTCSVR QSSAQNRKYT IKVEVPKGAW        120
RSYLNMELTI PIFATNSDCE LIVKAMQGLL KDGNPIPSAI AANSGIY                      167

SEQ ID NO: 158          moltype = AA   length = 167
FEATURE                 Location/Qualifiers
source                  1..167
                        mol_type = protein
                        note = Synthetic polypeptide
                        organism = synthetic construct
SEQUENCE: 158
MGGKLSKKKK GYNVNDEKAK EKDKKAEGAA SGGSGGSDYK DDDDKGGGSG MASNFTQFVL         60
VDNGGTGDVT VAPSNFANGI AEWISSNSRS QAYKVTCSVR QSSAQKRKYT IKVEVPKGAW        120
RSYLNMELTI PIFATNSDCE LIVKAMQGLL KDGNPIPSAI AANSGIY                      167

SEQ ID NO: 159          moltype = AA   length = 296
FEATURE                 Location/Qualifiers
source                  1..296
                        mol_type = protein
                        note = Synthetic polypeptide
                        organism = synthetic construct
SEQUENCE: 159
MGGKLSKKKK GYNVNDEKAK EKDKKAEGAA SGGSGGSDYK DDDDKGGGSG MASNFTQFVL         60
VDNGGTGDVT VAPSNFANGI AEWISSNSRS QAYKVTCSVR QSSAQNRKYT IKVEVPKGAW        120
RSYLNMELTI PIFATNSDCE LIVKAMQGLL KDGNPIPSAI AANSGIYGSG GSGGSGGSGM        180
ASNFTQFVLV DNGGTGDVTV APSNFANGIA EWISSNSRSQ AYKVTCSVRQ SSAQNRKYTI        240
KVEVPKGAWR SYLNMELTIP IFATNSDCEL IVKAMQGLLK DGNPIPSAIA ANSGIY            296

SEQ ID NO: 160          moltype = AA   length = 296
FEATURE                 Location/Qualifiers
source                  1..296
                        mol_type = protein
                        note = Synthetic polypeptide
                        organism = synthetic construct
SEQUENCE: 160
MGGKLSKKKK GYNVNDEKAK EKDKKAEGAA SGGSGGSDYK DDDDKGGGSG MASNFTQFVL         60
VDNGGTGDVT VAPSNFANGI AEWISSNSRS QAYKVTCSVR QSSAQKRKYT IKVEVPKGAW        120
RSYLNMELTI PIFATNSDCE LIVKAMQGLL KDGNPIPSAI AANSGIYGSG GSGGSGGSGM        180
ASNFTQFVLV DNGGTGDVTV APSNFANGIA EWISSNSRSQ AYKVTCSVRQ SSAQKRKYTI        240
KVEVPKGAWR SYLNMELTIP IFATNSDCEL IVKAMQGLLK DGNPIPSAIA ANSGIY            296

SEQ ID NO: 161          moltype = RNA   length = 680
FEATURE                 Location/Qualifiers
source                  1..680
                        mol_type = other RNA
                        note = Synthetic polynucleotide
                        organism = synthetic construct
SEQUENCE: 161
atgaagccca ccgagaacaa cgaagacttc aacatcgtgg ccgtggccag caacttcgcg         60
accacggatc tcgatgctga ccgcgggaag ttgcccggca agaagctgcc gctggaggtg        120
ctcaaagagt tggaagccaa tgcccggaaa gctggctgca ccaggggctg tctgatctgc        180
ctgtcccaca tcaagtgcac gcccaagatg aagaagttca tcccaggacg ctgccacacc        240
tacgaaggcg acaaagagtc cgcacagggc ggcataggcg aggcgatcgt cgacattcct        300
gagattcctg ggttcaagga cttggagccc ttggagcagt tcatcgcaca ggtctgatctg       360
tgtgtggact gcacaactgg ctgcctcaaa gggcttgcca acgtgcagtg ttctgacctg        420
ctcaagaagt ggctgccgca acgctgtgcg accttttgcca gcaagatcca gggccaggtg      480
gacaagatca agggggccgg tggtgactaa ggatccatcg ataagcttca tcgaaacatg        540
aggatcaccc atatctgcag tcgacatcga aacatgagga tcacccatgt ctgcagtcga        600
catcgaaaca tgaggatcac ccatgtctgc agtcgacatc gaaacatgag gatcacccat        660
gtctgcagtc gacatcgaaa                                                    680

SEQ ID NO: 162          moltype = AA   length = 9
FEATURE                 Location/Qualifiers
source                  1..9
                        mol_type = protein
```

```
                        note = Synthetic peptide
                        organism = synthetic construct
SEQUENCE: 162
MGXKLSKKK                                                               9

SEQ ID NO: 163          moltype = AA   length = 9
FEATURE                 Location/Qualifiers
MOD_RES                 3
                        note = See specification as filed for detailed description
                         of substitutions and preferred embodiments
source                  1..9
                        mol_type = protein
                        note = Synthetic peptide
                        organism = synthetic construct
SEQUENCE: 163
MGXKLSKKK                                                               9

SEQ ID NO: 164          moltype = AA   length = 8
FEATURE                 Location/Qualifiers
MOD_RES                 3
                        note = G or A or S
MOD_RES                 4
                        note = K or Q
MOD_RES                 5
                        note = L or F or S or Q
MOD_RES                 6
                        note = S or A
MOD_RES                 6
                        note = See specification as filed for detailed description
                         of substitutions and preferred embodiments
source                  1..8
                        mol_type = protein
                        note = Synthetic peptide
                        organism = synthetic construct
SEQUENCE: 164
MGXXXXKK                                                                8

SEQ ID NO: 165          moltype = DNA   length = 20
FEATURE                 Location/Qualifiers
source                  1..20
                        mol_type = other DNA
                        note = Synthetic primer
                        organism = synthetic construct
SEQUENCE: 165
tggaggtgct caaagagttg                                                  20

SEQ ID NO: 166          moltype = DNA   length = 17
FEATURE                 Location/Qualifiers
source                  1..17
                        mol_type = other DNA
                        note = Synthetic primer
                        organism = synthetic construct
SEQUENCE: 166
ttgggcgtgc acttgat                                                     17

SEQ ID NO: 167          moltype = DNA   length = 13
FEATURE                 Location/Qualifiers
source                  1..13
                        mol_type = other DNA
                        note = Synthetic probe
                        organism = synthetic construct
SEQUENCE: 167
gggcattggc ttc                                                         13

SEQ ID NO: 168          moltype = AA   length = 60
FEATURE                 Location/Qualifiers
source                  1..60
                        mol_type = protein
                        note = Synthetic polypeptide
                        organism = synthetic construct
SEQUENCE: 168
MGGKLSKKKK GYNVNDEKAK EKDKKAEGAA SAGGGGSDYK DDDDKGGGGS VSKGEELFTG       60

SEQ ID NO: 169          moltype = AA   length = 60
FEATURE                 Location/Qualifiers
source                  1..60
                        mol_type = protein
                        note = Synthetic polypeptide
                        organism = synthetic construct
```

```
SEQUENCE: 169
MAGKLSKKKK GYNVNDEKAK EKDKKAEGAA SAGGGGSDYK DDDDKGGGGS VSKGEELFTG    60

SEQ ID NO: 170          moltype = AA  length = 60
FEATURE                 Location/Qualifiers
source                  1..60
                        mol_type = protein
                        note = Synthetic polypeptide
                        organism = synthetic construct
SEQUENCE: 170
MGAKLSKKKK GYNVNDEKAK EKDKKAEGAA SAGGGGSDYK DDDDKGGGGS VSKGEELFTG    60

SEQ ID NO: 171          moltype = AA  length = 60
FEATURE                 Location/Qualifiers
source                  1..60
                        mol_type = protein
                        note = Synthetic polypeptide
                        organism = synthetic construct
SEQUENCE: 171
MAAKLSKKKK GYNVNDEKAK EKDKKAEGAA SAGGGGSDYK DDDDKGGGGS VSKGEELFTG    60

SEQ ID NO: 172          moltype = AA  length = 57
FEATURE                 Location/Qualifiers
source                  1..57
                        mol_type = protein
                        note = Synthetic polypeptide
                        organism = synthetic construct
SEQUENCE: 172
MGGKLSKKKK GYNVNDEKAK EKDKKAESAG GGGSDYKDDD DKGGGGSVSK GEELFTG       57

SEQ ID NO: 173          moltype = AA  length = 54
FEATURE                 Location/Qualifiers
source                  1..54
                        mol_type = protein
                        note = Synthetic polypeptide
                        organism = synthetic construct
SEQUENCE: 173
MGGKLSKKKK GYNVNDEKAK EKDKSAGGGG SDYKDDDDKG GGGSVSKGEE LFTG          54

SEQ ID NO: 174          moltype = AA  length = 51
FEATURE                 Location/Qualifiers
source                  1..51
                        mol_type = protein
                        note = Synthetic polypeptide
                        organism = synthetic construct
SEQUENCE: 174
MGGKLSKKKK GYNVNDEKAK ESAGGGGSDY KDDDDKGGGG SVSKGEELFT G             51

SEQ ID NO: 175          moltype = AA  length = 48
FEATURE                 Location/Qualifiers
source                  1..48
                        mol_type = protein
                        note = Synthetic polypeptide
                        organism = synthetic construct
SEQUENCE: 175
MGGKLSKKKK GYNVNDEKSA GGGGSDYKDD DDKGGGGSVS KGEELFTG                 48

SEQ ID NO: 176          moltype = AA  length = 45
FEATURE                 Location/Qualifiers
source                  1..45
                        mol_type = protein
                        note = Synthetic polypeptide
                        organism = synthetic construct
SEQUENCE: 176
MGGKLSKKKK GYNVNSAGGG GSDYKDDDDK GGGGSVSKGE ELFTG                    45

SEQ ID NO: 177          moltype = AA  length = 42
FEATURE                 Location/Qualifiers
source                  1..42
                        mol_type = protein
                        note = Synthetic polypeptide
                        organism = synthetic construct
SEQUENCE: 177
MGGKLSKKKK GYSAGGGGSD YKDDDDKGGG GSVSKGEELF TG                       42

SEQ ID NO: 178          moltype = AA  length = 39
FEATURE                 Location/Qualifiers
source                  1..39
                        mol_type = protein
```

```
                         note = Synthetic polypeptide
                         organism = synthetic construct
SEQUENCE: 178
MGGKLSKKKS AGGGGSDYKD DDDKGGGGSV SKGEELFTG                                 39

SEQ ID NO: 179           moltype = AA   length = 36
FEATURE                  Location/Qualifiers
source                   1..36
                         mol_type = protein
                         note = Synthetic polypeptide
                         organism = synthetic construct
SEQUENCE: 179
MGGKLSSAGG GGSDYKDDDD KGGGGSVSKG EELFTG                                    36

SEQ ID NO: 180           moltype = AA   length = 33
FEATURE                  Location/Qualifiers
source                   1..33
                         mol_type = protein
                         note = Synthetic polypeptide
                         organism = synthetic construct
SEQUENCE: 180
MGGSAGGGGS DYKDDDDKGG GGSVSKGEEL FTG                                       33

SEQ ID NO: 181           moltype = AA   length = 54
FEATURE                  Location/Qualifiers
source                   1..54
                         mol_type = protein
                         note = Synthetic polypeptide
                         organism = synthetic construct
SEQUENCE: 181
MGGKLSKKKK GYNVNDEKAK EKDKKAEGAA SAGGGGSDYK DDDDKGGGGS VSKG                54

SEQ ID NO: 182           moltype = AA   length = 36
FEATURE                  Location/Qualifiers
source                   1..36
                         mol_type = protein
                         note = Synthetic polypeptide
                         organism = synthetic construct
SEQUENCE: 182
MGGKLSKKKK GYSAGGGGSD YKDDDDKGGG GSVSKG                                    36

SEQ ID NO: 183           moltype = AA   length = 35
FEATURE                  Location/Qualifiers
source                   1..35
                         mol_type = protein
                         note = Synthetic polypeptide
                         organism = synthetic construct
SEQUENCE: 183
MGGKLSKKKK GSAGGGGSDY KDDDDKGGGG SVSKG                                     35

SEQ ID NO: 184           moltype = AA   length = 34
FEATURE                  Location/Qualifiers
source                   1..34
                         mol_type = protein
                         note = Synthetic polypeptide
                         organism = synthetic construct
SEQUENCE: 184
MGGKLSKKKK SAGGGGSDYK DDDDKGGGGS VSKG                                      34

SEQ ID NO: 185           moltype = AA   length = 33
FEATURE                  Location/Qualifiers
source                   1..33
                         mol_type = protein
                         note = Synthetic polypeptide
                         organism = synthetic construct
SEQUENCE: 185
MGGKLSKKKS AGGGGSDYKD DDDKGGGGSV SKG                                       33

SEQ ID NO: 186           moltype = AA   length = 32
FEATURE                  Location/Qualifiers
source                   1..32
                         mol_type = protein
                         note = Synthetic polypeptide
                         organism = synthetic construct
SEQUENCE: 186
MGGKLSKKSA GGGGSDYKDD DDKGGGGSVS KG                                        32

SEQ ID NO: 187           moltype = AA   length = 31
FEATURE                  Location/Qualifiers
```

```
source                   1..31
                         mol_type = protein
                         note = Synthetic polypeptide
                         organism = synthetic construct
SEQUENCE: 187
MGGKLSKSAG GGGSDYKDDD DKGGGGSVSK G                               31

SEQ ID NO: 188           moltype = AA   length = 30
FEATURE                  Location/Qualifiers
source                   1..30
                         mol_type = protein
                         note = Synthetic polypeptide
                         organism = synthetic construct
SEQUENCE: 188
MGGKLSSAGG GGSDYKDDDD KGGGGSVSKG                                 30

SEQ ID NO: 189           moltype = AA   length = 30
FEATURE                  Location/Qualifiers
source                   1..30
                         mol_type = protein
                         note = Synthetic polypeptide
                         organism = synthetic construct
SEQUENCE: 189
MGGKLDKKKK GYNVNDEKAK EKDKKAEGAA                                 30

SEQ ID NO: 190           moltype = AA   length = 30
FEATURE                  Location/Qualifiers
source                   1..30
                         mol_type = protein
                         note = Synthetic polypeptide
                         organism = synthetic construct
SEQUENCE: 190
MGGKLAKKKK GYNVNDEKAK EKDKKAEGAA                                 30

SEQ ID NO: 191           moltype = AA   length = 30
FEATURE                  Location/Qualifiers
source                   1..30
                         mol_type = protein
                         note = Synthetic polypeptide
                         organism = synthetic construct
SEQUENCE: 191
MGGKQSKKKK GYNVNDEKAK EKDKKAEGAA                                 30

SEQ ID NO: 192           moltype = AA   length = 30
FEATURE                  Location/Qualifiers
source                   1..30
                         mol_type = protein
                         note = Synthetic polypeptide
                         organism = synthetic construct
SEQUENCE: 192
MGAKKKKKRF SFKKSFKLSG FSFKKNKKEA                                 30

SEQ ID NO: 193           moltype = AA   length = 30
FEATURE                  Location/Qualifiers
source                   1..30
                         mol_type = protein
                         note = Synthetic polypeptide
                         organism = synthetic construct
SEQUENCE: 193
MAAKKKKKRF SFKKSFKLSG FSFKKNKKEA                                 30

SEQ ID NO: 194           moltype = AA   length = 30
FEATURE                  Location/Qualifiers
source                   1..30
                         mol_type = protein
                         note = Synthetic polypeptide
                         organism = synthetic construct
SEQUENCE: 194
MGAKKSKKRF SFKKSFKLSG FSFKKNKKEA                                 30

SEQ ID NO: 195           moltype = AA   length = 30
FEATURE                  Location/Qualifiers
source                   1..30
                         mol_type = protein
                         note = Synthetic polypeptide
                         organism = synthetic construct
SEQUENCE: 195
MGAKKAKKRF SFKKPFKLSG FSFKKNKKEA                                 30
```

```
SEQ ID NO: 196           moltype = AA  length = 153
FEATURE                  Location/Qualifiers
source                   1..153
                         mol_type = protein
                         note = Synthetic polypeptide
                         organism = synthetic construct
SEQUENCE: 196
MGGKLSKKKK SAGGSGGSTS GSGDYKDDDD KGSGFEMDQV QLVESGGALV QPGGSLRLSC    60
AASGFPVNRY SMRWYRQAPG KEREWVAGMS SAGDRSSYED SVKGRFTISR DDARNTVYLQ   120
MNSLKPEDTA VYYCNVNVGF EYWGQGTQVT VSS                                153

SEQ ID NO: 197           moltype = AA  length = 4
FEATURE                  Location/Qualifiers
source                   1..4
                         mol_type = protein
                         note = Peptide Linker
                         organism = synthetic construct
SEQUENCE: 197
GGGG                                                                  4

SEQ ID NO: 198           moltype = AA  length = 7
FEATURE                  Location/Qualifiers
source                   1..7
                         mol_type = protein
                         note = Peptide Linker
                         organism = synthetic construct
SEQUENCE: 198
SGGSGGS                                                               7

SEQ ID NO: 199           moltype = AA  length = 15
FEATURE                  Location/Qualifiers
source                   1..15
                         mol_type = protein
                         note = Peptide Linker
                         organism = synthetic construct
SEQUENCE: 199
GGSGGSGGSG GSGGG                                                     15

SEQ ID NO: 200           moltype = AA  length = 16
FEATURE                  Location/Qualifiers
source                   1..16
                         mol_type = protein
                         note = Peptide Linker
                         organism = synthetic construct
SEQUENCE: 200
GGSGGSGGGG SGGGGS                                                    16

SEQ ID NO: 201           moltype = AA  length = 18
FEATURE                  Location/Qualifiers
source                   1..18
                         mol_type = protein
                         note = Peptide Linker
                         organism = synthetic construct
SEQUENCE: 201
GGSGGSGGSG GSGGSGGS                                                  18

SEQ ID NO: 202           moltype = AA  length = 15
FEATURE                  Location/Qualifiers
source                   1..15
                         mol_type = protein
                         note = Peptide Linker
                         organism = synthetic construct
SEQUENCE: 202
GGGGSGGGGS GGGGS                                                     15

SEQ ID NO: 203           moltype = AA  length = 5
FEATURE                  Location/Qualifiers
SITE                     5
                         note = Wherein X can be any integer from 1 to 100
source                   1..5
                         mol_type = protein
                         note = Peptide Linker
                         organism = synthetic construct
SEQUENCE: 203
GGGSX                                                                 5

SEQ ID NO: 204           moltype = AA  length = 10
FEATURE                  Location/Qualifiers
SITE                     4
```

```
                        note = Wherein X can be any integer from 1 to 100
SITE                    10
                        note = Wherein X can be any integer from 1 to 100
source                  1..10
                        mol_type = protein
                        note = Peptide Linker
                        organism = synthetic construct
SEQUENCE: 204
GGSXGGGGSX                                                              10

SEQ ID NO: 205          moltype = AA  length = 4
FEATURE                 Location/Qualifiers
source                  1..4
                        mol_type = protein
                        note = Effector Domain Sequence
                        organism = synthetic construct
SEQUENCE: 205
KKKK                                                                     4

SEQ ID NO: 206          moltype = AA  length = 5
FEATURE                 Location/Qualifiers
source                  1..5
                        mol_type = protein
                        note = Effector Domain Sequence
                        organism = synthetic construct
SEQUENCE: 206
KKKKK                                                                    5

SEQ ID NO: 207          moltype = AA  length = 4
FEATURE                 Location/Qualifiers
source                  1..4
                        mol_type = protein
                        note = Effector Domain Sequence
                        organism = synthetic construct
SEQUENCE: 207
RRRR                                                                     4

SEQ ID NO: 208          moltype = AA  length = 5
FEATURE                 Location/Qualifiers
source                  1..5
                        mol_type = protein
                        note = Effector Domain Sequence
                        organism = synthetic construct
SEQUENCE: 208
RRRRR                                                                    5

SEQ ID NO: 209          moltype =     length =
SEQUENCE: 209
000

SEQ ID NO: 210          moltype =     length =
SEQUENCE: 210
000

SEQ ID NO: 211          moltype = AA  length = 7
FEATURE                 Location/Qualifiers
source                  1..7
                        mol_type = protein
                        note = N Terminus Domain Sequence
                        organism = synthetic construct
SEQUENCE: 211
GGKLSKK                                                                  7

SEQ ID NO: 212          moltype = AA  length = 7
FEATURE                 Location/Qualifiers
source                  1..7
                        mol_type = protein
                        note = N Terminus Domain Sequence
                        organism = synthetic construct
SEQUENCE: 212
GAKLSKK                                                                  7

SEQ ID NO: 213          moltype = AA  length = 7
FEATURE                 Location/Qualifiers
source                  1..7
                        mol_type = protein
                        note = N Terminus Domain Sequence
                        organism = synthetic construct
SEQUENCE: 213
```

```
GGKQSKK                                                                         7

SEQ ID NO: 214         moltype = AA  length = 7
FEATURE                Location/Qualifiers
source                 1..7
                       mol_type = protein
                       note = N Terminus Domain Sequence
                       organism = synthetic construct
SEQUENCE: 214
GGKLAKK                                                                         7

SEQ ID NO: 215         moltype = AA  length = 6
FEATURE                Location/Qualifiers
source                 1..6
                       mol_type = protein
                       note = N Terminus Domain Sequence
                       organism = synthetic construct
SEQUENCE: 215
GGKLSK                                                                          6

SEQ ID NO: 216         moltype = AA  length = 6
FEATURE                Location/Qualifiers
source                 1..6
                       mol_type = protein
                       note = N Terminus Domain Sequence
                       organism = synthetic construct
SEQUENCE: 216
GAKLSK                                                                          6

SEQ ID NO: 217         moltype = AA  length = 6
FEATURE                Location/Qualifiers
source                 1..6
                       mol_type = protein
                       note = N Terminus Domain Sequence
                       organism = synthetic construct
SEQUENCE: 217
GGKQSK                                                                          6

SEQ ID NO: 218         moltype = AA  length = 6
FEATURE                Location/Qualifiers
source                 1..6
                       mol_type = protein
                       note = N Terminus Domain Sequence
                       organism = synthetic construct
SEQUENCE: 218
GGKLAK                                                                          6

SEQ ID NO: 219         moltype = AA  length = 4
FEATURE                Location/Qualifiers
source                 1..4
                       mol_type = protein
                       note = N Terminus Domain Sequence
                       organism = synthetic construct
SEQUENCE: 219
KKKG                                                                            4

SEQ ID NO: 220         moltype = AA  length = 5
FEATURE                Location/Qualifiers
source                 1..5
                       mol_type = protein
                       note = N Terminus Domain Sequence
                       organism = synthetic construct
SEQUENCE: 220
KKKGY                                                                           5

SEQ ID NO: 221         moltype = AA  length = 6
FEATURE                Location/Qualifiers
source                 1..6
                       mol_type = protein
                       note = N Terminus Domain Sequence
                       organism = synthetic construct
SEQUENCE: 221
KKKGYN                                                                          6

SEQ ID NO: 222         moltype = AA  length = 7
FEATURE                Location/Qualifiers
source                 1..7
                       mol_type = protein
                       note = N Terminus Domain Sequence
```

```
                           -continued organism = synthetic construct
SEQUENCE: 222
KKKGYNV                                                                 7

SEQ ID NO: 223         moltype = AA   length = 8
FEATURE                Location/Qualifiers
source                 1..8
                       mol_type = protein
                       note = N Terminus Domain Sequence
                       organism = synthetic construct
SEQUENCE: 223
KKKGYNVN                                                                8

SEQ ID NO: 224         moltype = AA   length = 6
FEATURE                Location/Qualifiers
source                 1..6
                       mol_type = protein
                       note = N Terminus Domain Sequence
                       organism = synthetic construct
SEQUENCE: 224
KKKGYS                                                                  6

SEQ ID NO: 225         moltype = AA   length = 6
FEATURE                Location/Qualifiers
source                 1..6
                       mol_type = protein
                       note = N Terminus Domain Sequence
                       organism = synthetic construct
SEQUENCE: 225
KKKGYG                                                                  6

SEQ ID NO: 226         moltype = AA   length = 7
FEATURE                Location/Qualifiers
source                 1..7
                       mol_type = protein
                       note = N Terminus Domain Sequence
                       organism = synthetic construct
SEQUENCE: 226
KKKGYGG                                                                 7

SEQ ID NO: 227         moltype = AA   length = 5
FEATURE                Location/Qualifiers
source                 1..5
                       mol_type = protein
                       note = N Terminus Domain Sequence
                       organism = synthetic construct
SEQUENCE: 227
KKKGS                                                                   5

SEQ ID NO: 228         moltype = AA   length = 6
FEATURE                Location/Qualifiers
source                 1..6
                       mol_type = protein
                       note = N Terminus Domain Sequence
                       organism = synthetic construct
SEQUENCE: 228
KKKGSG                                                                  6

SEQ ID NO: 229         moltype = AA   length = 7
FEATURE                Location/Qualifiers
source                 1..7
                       mol_type = protein
                       note = N Terminus Domain Sequence
                       organism = synthetic construct
SEQUENCE: 229
KKKGSGS                                                                 7

SEQ ID NO: 230         moltype = AA   length = 4
FEATURE                Location/Qualifiers
source                 1..4
                       mol_type = protein
                       note = N Terminus Domain Sequence
                       organism = synthetic construct
SEQUENCE: 230
KKKS                                                                    4

SEQ ID NO: 231         moltype = AA   length = 5
FEATURE                Location/Qualifiers
source                 1..5
```

-continued

```
                         mol_type = protein
                         note = N Terminus Domain Sequence
                         organism = synthetic construct
SEQUENCE: 231
KKKSG                                                                   5

SEQ ID NO: 232           moltype = AA  length = 6
FEATURE                  Location/Qualifiers
source                   1..6
                         mol_type = protein
                         note = N Terminus Domain Sequence
                         organism = synthetic construct
SEQUENCE: 232
KKKSGG                                                                  6

SEQ ID NO: 233           moltype = AA  length = 7
FEATURE                  Location/Qualifiers
source                   1..7
                         mol_type = protein
                         note = N Terminus Domain Sequence
                         organism = synthetic construct
SEQUENCE: 233
KKKSGGS                                                                 7

SEQ ID NO: 234           moltype = AA  length = 8
FEATURE                  Location/Qualifiers
source                   1..8
                         mol_type = protein
                         note = N Terminus Domain Sequence
                         organism = synthetic construct
SEQUENCE: 234
KKKSGGSG                                                                8

SEQ ID NO: 235           moltype = AA  length = 8
FEATURE                  Location/Qualifiers
source                   1..8
                         mol_type = protein
                         note = N Terminus Domain Sequence
                         organism = synthetic construct
SEQUENCE: 235
KKSGGSGG                                                                8

SEQ ID NO: 236           moltype = AA  length = 10
FEATURE                  Location/Qualifiers
source                   1..10
                         mol_type = protein
                         note = N Terminus Domain Sequence
                         organism = synthetic construct
SEQUENCE: 236
KKKSGGSGGS                                                             10

SEQ ID NO: 237           moltype = AA  length = 8
FEATURE                  Location/Qualifiers
source                   1..8
                         mol_type = protein
                         note = N Terminus Domain Sequence
                         organism = synthetic construct
SEQUENCE: 237
KRFSFKKS                                                                8

SEQ ID NO: 238           moltype = AA  length = 8
FEATURE                  Location/Qualifiers
source                   1..8
                         mol_type = protein
                         note = N Terminus Domain Sequence
                         organism = synthetic construct
SEQUENCE: 238
GGKLSKKK                                                                8

SEQ ID NO: 239           moltype = AA  length = 8
FEATURE                  Location/Qualifiers
source                   1..8
                         mol_type = protein
                         note = N Terminus Domain Sequence
                         organism = synthetic construct
SEQUENCE: 239
GGKLSKKS                                                                8

SEQ ID NO: 240           moltype = AA  length = 8
```

```
FEATURE                     Location/Qualifiers
source                      1..8
                            mol_type = protein
                            note = N Terminus Domain Sequence
                            organism = synthetic construct
SEQUENCE: 240
GAKLSKKK                                                                    8

SEQ ID NO: 241              moltype = AA  length = 8
FEATURE                     Location/Qualifiers
source                      1..8
                            mol_type = protein
                            note = N Terminus Domain Sequence
                            organism = synthetic construct
SEQUENCE: 241
GAKLSKKS                                                                    8

SEQ ID NO: 242              moltype = AA  length = 8
FEATURE                     Location/Qualifiers
source                      1..8
                            mol_type = protein
                            note = N Terminus Domain Sequence
                            organism = synthetic construct
SEQUENCE: 242
GGKQSKKK                                                                    8

SEQ ID NO: 243              moltype = AA  length = 8
FEATURE                     Location/Qualifiers
source                      1..8
                            mol_type = protein
                            note = N Terminus Domain Sequence
                            organism = synthetic construct
SEQUENCE: 243
GGKQSKKS                                                                    8

SEQ ID NO: 244              moltype = AA  length = 8
FEATURE                     Location/Qualifiers
source                      1..8
                            mol_type = protein
                            note = N Terminus Domain Sequence
                            organism = synthetic construct
SEQUENCE: 244
GGKLAKKK                                                                    8

SEQ ID NO: 245              moltype = AA  length = 8
FEATURE                     Location/Qualifiers
source                      1..8
                            mol_type = protein
                            note = N Terminus Domain Sequence
                            organism = synthetic construct
SEQUENCE: 245
GGKLAKKS                                                                    8

SEQ ID NO: 246              moltype = AA  length = 14
FEATURE                     Location/Qualifiers
source                      1..14
                            mol_type = protein
                            note = Scaffold Y Sequence
                            organism = synthetic construct
SEQUENCE: 246
GGKLSKKKKG YNVN                                                            14

SEQ ID NO: 247              moltype = AA  length = 14
FEATURE                     Location/Qualifiers
source                      1..14
                            mol_type = protein
                            note = Scaffold Y Sequence
                            organism = synthetic construct
SEQUENCE: 247
GAKLSKKKKG YNVN                                                            14

SEQ ID NO: 248              moltype = AA  length = 14
FEATURE                     Location/Qualifiers
source                      1..14
                            mol_type = protein
                            note = Scaffold Y Sequence
                            organism = synthetic construct
SEQUENCE: 248
GGKQSKKKKG YNVN                                                            14
```

```
SEQ ID NO: 249         moltype = AA   length = 14
FEATURE                Location/Qualifiers
source                 1..14
                       mol_type = protein
                       note = Scaffold Y Sequence
                       organism = synthetic construct
SEQUENCE: 249
GGKLAKKKKG YNVN                                                          14

SEQ ID NO: 250         moltype = AA   length = 14
FEATURE                Location/Qualifiers
source                 1..14
                       mol_type = protein
                       note = Scaffold Y Sequence
                       organism = synthetic construct
SEQUENCE: 250
GGKLSKKKKG YSGG                                                          14

SEQ ID NO: 251         moltype = AA   length = 14
FEATURE                Location/Qualifiers
source                 1..14
                       mol_type = protein
                       note = Scaffold Y Sequence
                       organism = synthetic construct
SEQUENCE: 251
GGKLSKKKKG SGGS                                                          14

SEQ ID NO: 252         moltype = AA   length = 14
FEATURE                Location/Qualifiers
source                 1..14
                       mol_type = protein
                       note = Scaffold Y Sequence
                       organism = synthetic construct
SEQUENCE: 252
GGKLSKKKKS GGSG                                                          14

SEQ ID NO: 253         moltype = AA   length = 14
FEATURE                Location/Qualifiers
source                 1..14
                       mol_type = protein
                       note = Scaffold Y Sequence
                       organism = synthetic construct
SEQUENCE: 253
GGKLSKKKSG GSGG                                                          14

SEQ ID NO: 254         moltype = AA   length = 14
FEATURE                Location/Qualifiers
source                 1..14
                       mol_type = protein
                       note = Scaffold Y Sequence
                       organism = synthetic construct
SEQUENCE: 254
GGKLSKKSGG SGGS                                                          14

SEQ ID NO: 255         moltype = AA   length = 14
FEATURE                Location/Qualifiers
source                 1..14
                       mol_type = protein
                       note = Scaffold Y Sequence
                       organism = synthetic construct
SEQUENCE: 255
GGKLSKSGGS GGSV                                                          14

SEQ ID NO: 256         moltype = AA   length = 14
FEATURE                Location/Qualifiers
source                 1..14
                       mol_type = protein
                       note = Scaffold Y Sequence
                       organism = synthetic construct
SEQUENCE: 256
GAKKSKKRFS FKKS                                                          14

SEQ ID NO: 257         moltype = AA   length = 29
FEATURE                Location/Qualifiers
source                 1..29
                       mol_type = protein
                       note = Scaffold Y Sequence
                       organism = synthetic construct
```

```
SEQUENCE: 257
GGKLSKKKKG YNVNDEKAKE KDKKAEGAA                                         29

SEQ ID NO: 258          moltype = AA  length = 28
FEATURE                 Location/Qualifiers
source                  1..28
                        mol_type = protein
                        note = Scaffold Y Sequence
                        organism = synthetic construct
SEQUENCE: 258
GGKLSKKKKG YNVNDEKAKE KDKKAEGA                                          28

SEQ ID NO: 259          moltype = AA  length = 27
FEATURE                 Location/Qualifiers
source                  1..27
                        mol_type = protein
                        note = Scaffold Y Sequence
                        organism = synthetic construct
SEQUENCE: 259
GGKLSKKKKG YNVNDEKAKE KDKKAEG                                           27

SEQ ID NO: 260          moltype = AA  length = 26
FEATURE                 Location/Qualifiers
source                  1..26
                        mol_type = protein
                        note = Scaffold Y Sequence
                        organism = synthetic construct
SEQUENCE: 260
GGKLSKKKKG YNVNDEKAKE KDKKAE                                            26

SEQ ID NO: 261          moltype = AA  length = 25
FEATURE                 Location/Qualifiers
source                  1..25
                        mol_type = protein
                        note = Scaffold Y Sequence
                        organism = synthetic construct
SEQUENCE: 261
GGKLSKKKKG YNVNDEKAKE KDKKA                                             25

SEQ ID NO: 262          moltype = AA  length = 24
FEATURE                 Location/Qualifiers
source                  1..24
                        mol_type = protein
                        note = Scaffold Y Sequence
                        organism = synthetic construct
SEQUENCE: 262
GGKLSKKKKG YNVNDEKAKE KDKK                                              24

SEQ ID NO: 263          moltype = AA  length = 23
FEATURE                 Location/Qualifiers
source                  1..23
                        mol_type = protein
                        note = Scaffold Y Sequence
                        organism = synthetic construct
SEQUENCE: 263
GGKLSKKKKG YNVNDEKAKE KDK                                               23

SEQ ID NO: 264          moltype = AA  length = 22
FEATURE                 Location/Qualifiers
source                  1..22
                        mol_type = protein
                        note = Scaffold Y Sequence
                        organism = synthetic construct
SEQUENCE: 264
GGKLSKKKKG YNVNDEKAKE KD                                                22

SEQ ID NO: 265          moltype = AA  length = 21
FEATURE                 Location/Qualifiers
source                  1..21
                        mol_type = protein
                        note = Scaffold Y Sequence
                        organism = synthetic construct
SEQUENCE: 265
GGKLSKKKKG YNVNDEKAKE K                                                 21

SEQ ID NO: 266          moltype = AA  length = 20
FEATURE                 Location/Qualifiers
source                  1..20
                        mol_type = protein
```

```
                              note = Scaffold Y Sequence
                              organism = synthetic construct
SEQUENCE: 266
GGKLSKKKKG YNVNDEKAKE                                                     20

SEQ ID NO: 267                moltype = AA   length = 19
FEATURE                       Location/Qualifiers
source                        1..19
                              mol_type = protein
                              note = Scaffold Y Sequence
                              organism = synthetic construct
SEQUENCE: 267
GGKLSKKKKG YNVNDEKAK                                                      19

SEQ ID NO: 268                moltype = AA   length = 18
FEATURE                       Location/Qualifiers
source                        1..18
                              mol_type = protein
                              note = Scaffold Y Sequence
                              organism = synthetic construct
SEQUENCE: 268
GGKLSKKKKG YNVNDEKA                                                       18

SEQ ID NO: 269                moltype = AA   length = 17
FEATURE                       Location/Qualifiers
source                        1..17
                              mol_type = protein
                              note = Scaffold Y Sequence
                              organism = synthetic construct
SEQUENCE: 269
GGKLSKKKKG YNVNDEK                                                        17

SEQ ID NO: 270                moltype = AA   length = 16
FEATURE                       Location/Qualifiers
source                        1..16
                              mol_type = protein
                              note = Scaffold Y Sequence
                              organism = synthetic construct
SEQUENCE: 270
GGKLSKKKKG YNVNDE                                                         16

SEQ ID NO: 271                moltype = AA   length = 15
FEATURE                       Location/Qualifiers
source                        1..15
                              mol_type = protein
                              note = Scaffold Y Sequence
                              organism = synthetic construct
SEQUENCE: 271
GGKLSKKKKG YNVND                                                          15

SEQ ID NO: 272                moltype = AA   length = 13
FEATURE                       Location/Qualifiers
source                        1..13
                              mol_type = protein
                              note = Scaffold Y Sequence
                              organism = synthetic construct
SEQUENCE: 272
GGKLSKKKKG YNV                                                            13

SEQ ID NO: 273                moltype = AA   length = 12
FEATURE                       Location/Qualifiers
source                        1..12
                              mol_type = protein
                              note = Scaffold Y Sequence
                              organism = synthetic construct
SEQUENCE: 273
GGKLSKKKKG YN                                                             12

SEQ ID NO: 274                moltype = AA   length = 11
FEATURE                       Location/Qualifiers
source                        1..11
                              mol_type = protein
                              note = Scaffold Y Sequence
                              organism = synthetic construct
SEQUENCE: 274
GGKLSKKKKG Y                                                              11

SEQ ID NO: 275                moltype = AA   length = 10
FEATURE                       Location/Qualifiers
```

```
source                          1..10
                                mol_type = protein
                                note = Scaffold Y Sequence
                                organism = synthetic construct
SEQUENCE: 275
GGKLSKKKKG                                                                  10

SEQ ID NO: 276                  moltype = AA  length = 9
FEATURE                         Location/Qualifiers
source                          1..9
                                mol_type = protein
                                note = Scaffold Y Sequence
                                organism = synthetic construct
SEQUENCE: 276
GGKLSKKKK                                                                    9

SEQ ID NO: 277                  moltype = AA  length = 28
FEATURE                         Location/Qualifiers
source                          1..28
                                mol_type = protein
                                note = Scaffold Y Sequence
                                organism = synthetic construct
SEQUENCE: 277
GAKKSKKRFS FKKSFKLSGF SFKKNKKE                                               28

SEQ ID NO: 278                  moltype = AA  length = 27
FEATURE                         Location/Qualifiers
source                          1..27
                                mol_type = protein
                                note = Scaffold Y Sequence
                                organism = synthetic construct
SEQUENCE: 278
GAKKSKKRFS FKKSFKLSGF SFKKNKK                                                27

SEQ ID NO: 279                  moltype = AA  length = 26
FEATURE                         Location/Qualifiers
source                          1..26
                                mol_type = protein
                                note = Scaffold Y Sequence
                                organism = synthetic construct
SEQUENCE: 279
GAKKSKKRFS FKKSFKLSGF SFKKNK                                                 26

SEQ ID NO: 280                  moltype = AA  length = 25
FEATURE                         Location/Qualifiers
source                          1..25
                                mol_type = protein
                                note = Scaffold Y Sequence
                                organism = synthetic construct
SEQUENCE: 280
GAKKSKKRFS FKKSFKLSGF SFKKN                                                  25

SEQ ID NO: 281                  moltype = AA  length = 24
FEATURE                         Location/Qualifiers
source                          1..24
                                mol_type = protein
                                note = Scaffold Y Sequence
                                organism = synthetic construct
SEQUENCE: 281
GAKKSKKRFS FKKSFKLSGF SFKK                                                   24

SEQ ID NO: 282                  moltype = AA  length = 23
FEATURE                         Location/Qualifiers
source                          1..23
                                mol_type = protein
                                note = Scaffold Y Sequence
                                organism = synthetic construct
SEQUENCE: 282
GAKKSKKRFS FKKSFKLSGF SFK                                                    23

SEQ ID NO: 283                  moltype = AA  length = 22
FEATURE                         Location/Qualifiers
source                          1..22
                                mol_type = protein
                                note = Scaffold Y Sequence
                                organism = synthetic construct
SEQUENCE: 283
GAKKSKKRFS FKKSFKLSGF SF                                                     22
```

```
SEQ ID NO: 284           moltype = AA  length = 21
FEATURE                  Location/Qualifiers
source                   1..21
                         mol_type = protein
                         note = Scaffold Y Sequence
                         organism = synthetic construct
SEQUENCE: 284
GAKKSKKRFS FKKSFKLSGF S                                                    21

SEQ ID NO: 285           moltype = AA  length = 20
FEATURE                  Location/Qualifiers
source                   1..20
                         mol_type = protein
                         note = Scaffold Y Sequence
                         organism = synthetic construct
SEQUENCE: 285
GAKKSKKRFS FKKSFKLSGF                                                      20

SEQ ID NO: 286           moltype = AA  length = 19
FEATURE                  Location/Qualifiers
source                   1..19
                         mol_type = protein
                         note = Scaffold Y Sequence
                         organism = synthetic construct
SEQUENCE: 286
GAKKSKKRFS FKKSFKLSG                                                       19

SEQ ID NO: 287           moltype = AA  length = 18
FEATURE                  Location/Qualifiers
source                   1..18
                         mol_type = protein
                         note = Scaffold Y Sequence
                         organism = synthetic construct
SEQUENCE: 287
GAKKSKKRFS FKKSFKLS                                                        18

SEQ ID NO: 288           moltype = AA  length = 17
FEATURE                  Location/Qualifiers
source                   1..17
                         mol_type = protein
                         note = Scaffold Y Sequence
                         organism = synthetic construct
SEQUENCE: 288
GAKKSKKRFS FKKSFKL                                                         17

SEQ ID NO: 289           moltype = AA  length = 16
FEATURE                  Location/Qualifiers
source                   1..16
                         mol_type = protein
                         note = Scaffold Y Sequence
                         organism = synthetic construct
SEQUENCE: 289
GAKKSKKRFS FKKSFK                                                          16

SEQ ID NO: 290           moltype = AA  length = 15
FEATURE                  Location/Qualifiers
source                   1..15
                         mol_type = protein
                         note = Scaffold Y Sequence
                         organism = synthetic construct
SEQUENCE: 290
GAKKSKKRFS FKKSF                                                           15

SEQ ID NO: 291           moltype =     length =
SEQUENCE: 291
000

SEQ ID NO: 292           moltype = AA  length = 13
FEATURE                  Location/Qualifiers
source                   1..13
                         mol_type = protein
                         note = Scaffold Y Sequence
                         organism = synthetic construct
SEQUENCE: 292
GAKKSKKRFS FKK                                                             13

SEQ ID NO: 293           moltype = AA  length = 12
FEATURE                  Location/Qualifiers
source                   1..12
```

-continued

```
                        mol_type = protein
                        note = Scaffold Y Sequence
                        organism = synthetic construct
SEQUENCE: 293
GAKKSKKRFS FK                                                              12

SEQ ID NO: 294          moltype = AA  length = 11
FEATURE                 Location/Qualifiers
source                  1..11
                        mol_type = protein
                        note = Scaffold Y Sequence
                        organism = synthetic construct
SEQUENCE: 294
GAKKSKKRFS F                                                               11

SEQ ID NO: 295          moltype = AA  length = 10
FEATURE                 Location/Qualifiers
source                  1..10
                        mol_type = protein
                        note = Scaffold Y Sequence
                        organism = synthetic construct
SEQUENCE: 295
GAKKSKKRFS                                                                 10

SEQ ID NO: 296          moltype = AA  length = 9
FEATURE                 Location/Qualifiers
source                  1..9
                        mol_type = protein
                        note = Scaffold Y Sequence
                        organism = synthetic construct
SEQUENCE: 296
GAKKSKKRF                                                                   9

SEQ ID NO: 297          moltype = AA  length = 8
FEATURE                 Location/Qualifiers
source                  1..8
                        mol_type = protein
                        note = Scaffold Y Sequence
                        organism = synthetic construct
SEQUENCE: 297
GAKKSKKR                                                                    8

SEQ ID NO: 298          moltype = AA  length = 7
FEATURE                 Location/Qualifiers
source                  1..7
                        mol_type = protein
                        note = Scaffold Y Sequence
                        organism = synthetic construct
SEQUENCE: 298
GAKKSKK                                                                     7

SEQ ID NO: 299          moltype =     length =
SEQUENCE: 299
000

SEQ ID NO: 300          moltype = AA  length = 29
FEATURE                 Location/Qualifiers
source                  1..29
                        mol_type = protein
                        note = Scaffold Y Sequence
                        organism = synthetic construct
SEQUENCE: 300
GAKKSKKRFS FKKSFKLSGF SFKKNKKEA                                            29

SEQ ID NO: 301          moltype = AA  length = 29
FEATURE                 Location/Qualifiers
source                  1..29
                        mol_type = protein
                        note = Scaffold Y Sequence
                        organism = synthetic construct
SEQUENCE: 301
GAKKAKKRFS FKKSFKLSGF SFKKNKKEA                                            29

SEQ ID NO: 302          moltype = AA  length = 28
FEATURE                 Location/Qualifiers
source                  1..28
                        mol_type = protein
                        note = Scaffold Y Sequence
                        organism = synthetic construct
```

```
SEQUENCE: 302
GAQESKKKKK KRFSFKKSFK LSGFSFKK                                           28

SEQ ID NO: 303          moltype = AA   length = 27
FEATURE                 Location/Qualifiers
source                  1..27
                        mol_type = protein
                        note = Scaffold Y Sequence
                        organism = synthetic construct
SEQUENCE: 303
GAQESKKKKK KRFSFKKSFK LSGFSFK                                            27

SEQ ID NO: 304          moltype = AA   length = 26
FEATURE                 Location/Qualifiers
source                  1..26
                        mol_type = protein
                        note = Scaffold Y Sequence
                        organism = synthetic construct
SEQUENCE: 304
GAQESKKKKK KRFSFKKSFK LSGFSF                                             26

SEQ ID NO: 305          moltype = AA   length = 25
FEATURE                 Location/Qualifiers
source                  1..25
                        mol_type = protein
                        note = Scaffold Y Sequence
                        organism = synthetic construct
SEQUENCE: 305
GAQESKKKKK KRFSFKKSFK LSGFS                                              25

SEQ ID NO: 306          moltype = AA   length = 24
FEATURE                 Location/Qualifiers
source                  1..24
                        mol_type = protein
                        note = Scaffold Y Sequence
                        organism = synthetic construct
SEQUENCE: 306
GAQESKKKKK KRFSFKKSFK LSGF                                               24

SEQ ID NO: 307          moltype = AA   length = 23
FEATURE                 Location/Qualifiers
source                  1..23
                        mol_type = protein
                        note = Scaffold Y Sequence
                        organism = synthetic construct
SEQUENCE: 307
GAQESKKKKK KRFSFKKSFK LSG                                                23

SEQ ID NO: 308          moltype = AA   length = 22
FEATURE                 Location/Qualifiers
source                  1..22
                        mol_type = protein
                        note = Scaffold Y Sequence
                        organism = synthetic construct
SEQUENCE: 308
GAQESKKKKK KRFSFKKSFK LS                                                 22

SEQ ID NO: 309          moltype = AA   length = 21
FEATURE                 Location/Qualifiers
source                  1..21
                        mol_type = protein
                        note = Scaffold Y Sequence
                        organism = synthetic construct
SEQUENCE: 309
GAQESKKKKK KRFSFKKSFK L                                                  21

SEQ ID NO: 310          moltype = AA   length = 20
FEATURE                 Location/Qualifiers
source                  1..20
                        mol_type = protein
                        note = Scaffold Y Sequence
                        organism = synthetic construct
SEQUENCE: 310
GAQESKKKKK KRFSFKKSFK                                                    20

SEQ ID NO: 311          moltype = AA   length = 19
FEATURE                 Location/Qualifiers
source                  1..19
                        mol_type = protein
```

```
                              -continued note = Scaffold Y Sequence
                          organism = synthetic construct
SEQUENCE: 311
GAQESKKKKK KRFSFKKSF                                                   19

SEQ ID NO: 312            moltype = AA   length = 18
FEATURE                   Location/Qualifiers
source                    1..18
                          mol_type = protein
                          note = Scaffold Y Sequence
                          organism = synthetic construct
SEQUENCE: 312
GAQESKKKKK KRFSFKKS                                                    18

SEQ ID NO: 313            moltype = AA   length = 17
FEATURE                   Location/Qualifiers
source                    1..17
                          mol_type = protein
                          note = Scaffold Y Sequence
                          organism = synthetic construct
SEQUENCE: 313
GAQESKKKKK KRFSFKK                                                     17

SEQ ID NO: 314            moltype = AA   length = 16
FEATURE                   Location/Qualifiers
source                    1..16
                          mol_type = protein
                          note = Scaffold Y Sequence
                          organism = synthetic construct
SEQUENCE: 314
GAQESKKKKK KRFSFK                                                      16

SEQ ID NO: 315            moltype = AA   length = 15
FEATURE                   Location/Qualifiers
source                    1..15
                          mol_type = protein
                          note = Scaffold Y Sequence
                          organism = synthetic construct
SEQUENCE: 315
GAQESKKKKK KRFSF                                                       15

SEQ ID NO: 316            moltype = AA   length = 14
FEATURE                   Location/Qualifiers
source                    1..14
                          mol_type = protein
                          note = Scaffold Y Sequence
                          organism = synthetic construct
SEQUENCE: 316
GAQESKKKKK KRFS                                                        14

SEQ ID NO: 317            moltype = AA   length = 13
FEATURE                   Location/Qualifiers
source                    1..13
                          mol_type = protein
                          note = Scaffold Y Sequence
                          organism = synthetic construct
SEQUENCE: 317
GAQESKKKKK KRF                                                         13

SEQ ID NO: 318            moltype = AA   length = 12
FEATURE                   Location/Qualifiers
source                    1..12
                          mol_type = protein
                          note = Scaffold Y Sequence
                          organism = synthetic construct
SEQUENCE: 318
GAQESKKKKK KR                                                          12

SEQ ID NO: 319            moltype = AA   length = 11
FEATURE                   Location/Qualifiers
source                    1..11
                          mol_type = protein
                          note = Scaffold Y Sequence
                          organism = synthetic construct
SEQUENCE: 319
GAQESKKKKK K                                                           11

SEQ ID NO: 320            moltype = AA   length = 10
FEATURE                   Location/Qualifiers
```

```
source                          1..10
                                mol_type = protein
                                note = Scaffold Y Sequence
                                organism = synthetic construct
SEQUENCE: 320
GAQESKKKKK                                                                       10

SEQ ID NO: 321                  moltype = AA  length = 9
FEATURE                         Location/Qualifiers
source                          1..9
                                mol_type = protein
                                note = Scaffold Y Sequence
                                organism = synthetic construct
SEQUENCE: 321
GAQESKKKK                                                                         9

SEQ ID NO: 322                  moltype = AA  length = 8
FEATURE                         Location/Qualifiers
source                          1..8
                                mol_type = protein
                                note = Scaffold Y Sequence
                                organism = synthetic construct
SEQUENCE: 322
GAQESKKK                                                                          8

SEQ ID NO: 323                  moltype = AA  length = 7
FEATURE                         Location/Qualifiers
source                          1..7
                                mol_type = protein
                                note = Scaffold Y Sequence
                                organism = synthetic construct
SEQUENCE: 323
GAQESKK                                                                           7

SEQ ID NO: 324                  moltype = AA  length = 30
FEATURE                         Location/Qualifiers
source                          1..30
                                mol_type = protein
                                note = Scaffold Y Sequence
                                organism = synthetic construct
SEQUENCE: 324
GSQSSKKKKK KFSFKKPFKL SGLSFKRNRK                                                 30

SEQ ID NO: 325                  moltype = AA  length = 29
FEATURE                         Location/Qualifiers
source                          1..29
                                mol_type = protein
                                note = Scaffold Y Sequence
                                organism = synthetic construct
SEQUENCE: 325
GSQSSKKKKK KFSFKKPFKL SGLSFKRNR                                                  29

SEQ ID NO: 326                  moltype = AA  length = 28
FEATURE                         Location/Qualifiers
source                          1..28
                                mol_type = protein
                                note = Scaffold Y Sequence
                                organism = synthetic construct
SEQUENCE: 326
GSQSSKKKKK KFSFKKPFKL SGLSFKRN                                                   28

SEQ ID NO: 327                  moltype = AA  length = 27
FEATURE                         Location/Qualifiers
source                          1..27
                                mol_type = protein
                                note = Scaffold Y Sequence
                                organism = synthetic construct
SEQUENCE: 327
GSQSSKKKKK KFSFKKPFKL SGLSFKR                                                    27

SEQ ID NO: 328                  moltype = AA  length = 26
FEATURE                         Location/Qualifiers
source                          1..26
                                mol_type = protein
                                note = Scaffold Y Sequence
                                organism = synthetic construct
SEQUENCE: 328
GSQSSKKKKK KFSFKKPFKL SGLSFK                                                     26
```

| | | |
|---|---|---|
| SEQ ID NO: 329 | moltype = AA length = 25 | |
| FEATURE | Location/Qualifiers | |
| source | 1..25 | |
| | mol_type = protein | |
| | note = Scaffold Y Sequence | |
| | organism = synthetic construct | |
| SEQUENCE: 329 | | |
| GSQSSKKKKK KFSFKKPFKL SGLSF | | 25 |
| | | |
| SEQ ID NO: 330 | moltype = AA length = 24 | |
| FEATURE | Location/Qualifiers | |
| source | 1..24 | |
| | mol_type = protein | |
| | note = Scaffold Y Sequence | |
| | organism = synthetic construct | |
| SEQUENCE: 330 | | |
| GSQSSKKKKK KFSFKKPFKL SGLS | | 24 |
| | | |
| SEQ ID NO: 331 | moltype = AA length = 23 | |
| FEATURE | Location/Qualifiers | |
| source | 1..23 | |
| | mol_type = protein | |
| | note = Scaffold Y Sequence | |
| | organism = synthetic construct | |
| SEQUENCE: 331 | | |
| GSQSSKKKKK KFSFKKPFKL SGL | | 23 |
| | | |
| SEQ ID NO: 332 | moltype = AA length = 22 | |
| FEATURE | Location/Qualifiers | |
| source | 1..22 | |
| | mol_type = protein | |
| | note = Scaffold Y Sequence | |
| | organism = synthetic construct | |
| SEQUENCE: 332 | | |
| GSQSSKKKKK KFSFKKPFKL SG | | 22 |
| | | |
| SEQ ID NO: 333 | moltype = AA length = 21 | |
| FEATURE | Location/Qualifiers | |
| source | 1..21 | |
| | mol_type = protein | |
| | note = Scaffold Y Sequence | |
| | organism = synthetic construct | |
| SEQUENCE: 333 | | |
| GSQSSKKKKK KFSFKKPFKL S | | 21 |
| | | |
| SEQ ID NO: 334 | moltype = AA length = 20 | |
| FEATURE | Location/Qualifiers | |
| source | 1..20 | |
| | mol_type = protein | |
| | note = Scaffold Y Sequence | |
| | organism = synthetic construct | |
| SEQUENCE: 334 | | |
| GSQSSKKKKK KFSFKKPFKL | | 20 |
| | | |
| SEQ ID NO: 335 | moltype = AA length = 19 | |
| FEATURE | Location/Qualifiers | |
| source | 1..19 | |
| | mol_type = protein | |
| | note = Scaffold Y Sequence | |
| | organism = synthetic construct | |
| SEQUENCE: 335 | | |
| GSQSSKKKKK KFSFKKPFK | | 19 |
| | | |
| SEQ ID NO: 336 | moltype = AA length = 18 | |
| FEATURE | Location/Qualifiers | |
| source | 1..18 | |
| | mol_type = protein | |
| | note = Scaffold Y Sequence | |
| | organism = synthetic construct | |
| SEQUENCE: 336 | | |
| GSQSSKKKKK KFSFKKPF | | 18 |
| | | |
| SEQ ID NO: 337 | moltype = AA length = 17 | |
| FEATURE | Location/Qualifiers | |
| source | 1..17 | |
| | mol_type = protein | |
| | note = Scaffold Y Sequence | |
| | organism = synthetic construct | |
| SEQUENCE: 337 | | |

```
GSQSSKKKKK KFSFKKP                                                        17

SEQ ID NO: 338           moltype = AA   length = 16
FEATURE                  Location/Qualifiers
source                   1..16
                         mol_type = protein
                         note = Scaffold Y Sequence
                         organism = synthetic construct
SEQUENCE: 338
GSQSSKKKKK KFSFKK                                                         16

SEQ ID NO: 339           moltype = AA   length = 15
FEATURE                  Location/Qualifiers
source                   1..15
                         mol_type = protein
                         note = Scaffold Y Sequence
                         organism = synthetic construct
SEQUENCE: 339
GSQSSKKKKK KFSFK                                                          15

SEQ ID NO: 340           moltype = AA   length = 14
FEATURE                  Location/Qualifiers
source                   1..14
                         mol_type = protein
                         note = Scaffold Y Sequence
                         organism = synthetic construct
SEQUENCE: 340
GSQSSKKKKK KFSF                                                           14

SEQ ID NO: 341           moltype = AA   length = 13
FEATURE                  Location/Qualifiers
source                   1..13
                         mol_type = protein
                         note = Scaffold Y Sequence
                         organism = synthetic construct
SEQUENCE: 341
GSQSSKKKKK KFS                                                            13

SEQ ID NO: 342           moltype = AA   length = 12
FEATURE                  Location/Qualifiers
source                   1..12
                         mol_type = protein
                         note = Scaffold Y Sequence
                         organism = synthetic construct
SEQUENCE: 342
GSQSSKKKKK KF                                                             12

SEQ ID NO: 343           moltype = AA   length = 11
FEATURE                  Location/Qualifiers
source                   1..11
                         mol_type = protein
                         note = Scaffold Y Sequence
                         organism = synthetic construct
SEQUENCE: 343
GSQSSKKKKK K                                                              11

SEQ ID NO: 344           moltype = AA   length = 10
FEATURE                  Location/Qualifiers
source                   1..10
                         mol_type = protein
                         note = Scaffold Y Sequence
                         organism = synthetic construct
SEQUENCE: 344
GSQSSKKKKK                                                                10

SEQ ID NO: 345           moltype = AA   length = 9
FEATURE                  Location/Qualifiers
source                   1..9
                         mol_type = protein
                         note = Scaffold Y Sequence
                         organism = synthetic construct
SEQUENCE: 345
GSQSSKKKK                                                                 9

SEQ ID NO: 346           moltype = AA   length = 8
FEATURE                  Location/Qualifiers
source                   1..8
                         mol_type = protein
                         note = Scaffold Y Sequence
```

```
                          organism = synthetic construct
SEQUENCE: 346
GSQSSKKK                                                                     8

SEQ ID NO: 347            moltype = AA   length = 7
FEATURE                   Location/Qualifiers
source                    1..7
                          mol_type = protein
                          note = Scaffold Y Sequence
                          organism = synthetic construct
SEQUENCE: 347
GSQSSKK                                                                      7

SEQ ID NO: 348            moltype = AA   length = 28
FEATURE                   Location/Qualifiers
source                    1..28
                          mol_type = protein
                          note = Scaffold Y Sequence
                          organism = synthetic construct
SEQUENCE: 348
GAKKAKKRFS FKKSFKLSGF SFKKNKKE                                               28

SEQ ID NO: 349            moltype = AA   length = 27
FEATURE                   Location/Qualifiers
source                    1..27
                          mol_type = protein
                          note = Scaffold Y Sequence
                          organism = synthetic construct
SEQUENCE: 349
GAKKAKKRFS FKKSFKLSGF SFKKNKK                                                27

SEQ ID NO: 350            moltype = AA   length = 26
FEATURE                   Location/Qualifiers
source                    1..26
                          mol_type = protein
                          note = Scaffold Y Sequence
                          organism = synthetic construct
SEQUENCE: 350
GAKKAKKRFS FKKSFKLSGF SFKKNK                                                 26

SEQ ID NO: 351            moltype = AA   length = 25
FEATURE                   Location/Qualifiers
source                    1..25
                          mol_type = protein
                          note = Scaffold Y Sequence
                          organism = synthetic construct
SEQUENCE: 351
GAKKAKKRFS FKKSFKLSGF SFKKN                                                  25

SEQ ID NO: 352            moltype = AA   length = 24
FEATURE                   Location/Qualifiers
source                    1..24
                          mol_type = protein
                          note = Scaffold Y Sequence
                          organism = synthetic construct
SEQUENCE: 352
GAKKAKKRFS FKKSFKLSGF SFKK                                                   24

SEQ ID NO: 353            moltype = AA   length = 23
FEATURE                   Location/Qualifiers
source                    1..23
                          mol_type = protein
                          note = Scaffold Y Sequence
                          organism = synthetic construct
SEQUENCE: 353
GAKKAKKRFS FKKSFKLSGF SFK                                                    23

SEQ ID NO: 354            moltype = AA   length = 22
FEATURE                   Location/Qualifiers
source                    1..22
                          mol_type = protein
                          note = Scaffold Y Sequence
                          organism = synthetic construct
SEQUENCE: 354
GAKKAKKRFS FKKSFKLSGF SF                                                     22

SEQ ID NO: 355            moltype = AA   length = 21
FEATURE                   Location/Qualifiers
source                    1..21
```

```
                              mol_type = protein
                              note = Scaffold Y Sequence
                              organism = synthetic construct
SEQUENCE: 355
GAKKAKKRFS FKKSFKLSGF S                                            21

SEQ ID NO: 356                moltype = AA   length = 20
FEATURE                       Location/Qualifiers
source                        1..20
                              mol_type = protein
                              note = Scaffold Y Sequence
                              organism = synthetic construct
SEQUENCE: 356
GAKKAKKRFS FKKSFKLSGF                                              20

SEQ ID NO: 357                moltype = AA   length = 19
FEATURE                       Location/Qualifiers
source                        1..19
                              mol_type = protein
                              note = Scaffold Y Sequence
                              organism = synthetic construct
SEQUENCE: 357
GAKKAKKRFS FKKSFKLSG                                               19

SEQ ID NO: 358                moltype = AA   length = 18
FEATURE                       Location/Qualifiers
source                        1..18
                              mol_type = protein
                              note = Scaffold Y Sequence
                              organism = synthetic construct
SEQUENCE: 358
GAKKAKKRFS FKKSFKLS                                                18

SEQ ID NO: 359                moltype = AA   length = 17
FEATURE                       Location/Qualifiers
source                        1..17
                              mol_type = protein
                              note = Scaffold Y Sequence
                              organism = synthetic construct
SEQUENCE: 359
GAKKAKKRFS FKKSFKL                                                 17

SEQ ID NO: 360                moltype = AA   length = 16
FEATURE                       Location/Qualifiers
source                        1..16
                              mol_type = protein
                              note = Scaffold Y Sequence
                              organism = synthetic construct
SEQUENCE: 360
GAKKAKKRFS FKKSFK                                                  16

SEQ ID NO: 361                moltype = AA   length = 15
FEATURE                       Location/Qualifiers
source                        1..15
                              mol_type = protein
                              note = Scaffold Y Sequence
                              organism = synthetic construct
SEQUENCE: 361
GAKKAKKRFS FKKSF                                                   15

SEQ ID NO: 362                moltype = AA   length = 14
FEATURE                       Location/Qualifiers
source                        1..14
                              mol_type = protein
                              note = Scaffold Y Sequence
                              organism = synthetic construct
SEQUENCE: 362
GAKKAKKRFS FKKS                                                    14

SEQ ID NO: 363                moltype = AA   length = 13
FEATURE                       Location/Qualifiers
source                        1..13
                              mol_type = protein
                              note = Scaffold Y Sequence
                              organism = synthetic construct
SEQUENCE: 363
GAKKAKKRFS FKK                                                     13

SEQ ID NO: 364                moltype = AA   length = 12
```

```
FEATURE            Location/Qualifiers
source             1..12
                   mol_type = protein
                   note = Scaffold Y Sequence
                   organism = synthetic construct
SEQUENCE: 364
GAKKAKKRFS FK                                                          12

SEQ ID NO: 365     moltype = AA  length = 11
FEATURE            Location/Qualifiers
source             1..11
                   mol_type = protein
                   note = Scaffold Y Sequence
                   organism = synthetic construct
SEQUENCE: 365
GAKKAKKRFS F                                                           11

SEQ ID NO: 366     moltype = AA  length = 10
FEATURE            Location/Qualifiers
source             1..10
                   mol_type = protein
                   note = Scaffold Y Sequence
                   organism = synthetic construct
SEQUENCE: 366
GAKKAKKRFS                                                             10

SEQ ID NO: 367     moltype = AA  length = 9
FEATURE            Location/Qualifiers
source             1..9
                   mol_type = protein
                   note = Scaffold Y Sequence
                   organism = synthetic construct
SEQUENCE: 367
GAKKAKKRF                                                               9

SEQ ID NO: 368     moltype = AA  length = 8
FEATURE            Location/Qualifiers
source             1..8
                   mol_type = protein
                   note = Scaffold Y Sequence
                   organism = synthetic construct
SEQUENCE: 368
GAKKAKKR                                                                8

SEQ ID NO: 369     moltype = AA  length = 7
FEATURE            Location/Qualifiers
source             1..7
                   mol_type = protein
                   note = Scaffold Y Sequence
                   organism = synthetic construct
SEQUENCE: 369
GAKKAKK                                                                 7

SEQ ID NO: 370     moltype = AA  length = 94
FEATURE            Location/Qualifiers
source             1..94
                   mol_type = protein
                   note = ESAT6 Protein Sequence
                   organism = synthetic construct
SEQUENCE: 370
MTEQQWNFAG IEAAASAIQG NVTSIHSLDE GKQSLTKLAA AWGGSGSEAY QGVQQKWDAT       60
ATELNNALQN LARTISEAGQ AMASTEGNVT GMFA                                  94

SEQ ID NO: 371     moltype = AA  length = 96
FEATURE            Location/Qualifiers
source             1..96
                   mol_type = protein
                   note = TB10.4 Protein Sequence
                   organism = synthetic construct
SEQUENCE: 371
MSQIMYNYPA MLGHAGDMAG YAGTLQSLGA EIAVEQAALQ SAWQGDTGIT YQAWQAQWNQ       60
AMEDLVRAYH AMSSTHEANT MAMMARDTAE AAKWGG                                96

SEQ ID NO: 372     moltype = AA  length = 8
FEATURE            Location/Qualifiers
source             1..8
                   mol_type = protein
                   note = Scaffold Y Sequence
                   organism = synthetic construct
```

```
SEQUENCE: 372
GXKLSKKK                                                                     8

SEQ ID NO: 373         moltype = AA  length = 5
FEATURE                Location/Qualifiers
SITE                   5
                       note = Wherein X is any integer between 1-100
source                 1..5
                       mol_type = protein
                       note = Linker
                       organism = synthetic construct
SEQUENCE: 373
GGGGX                                                                        5

SEQ ID NO: 374         moltype =   length =
SEQUENCE: 374
000

SEQ ID NO: 375         moltype =   length =
SEQUENCE: 375
000

SEQ ID NO: 376         moltype =   length =
SEQUENCE: 376
000

SEQ ID NO: 377         moltype =   length =
SEQUENCE: 377
000

SEQ ID NO: 378         moltype =   length =
SEQUENCE: 378
000

SEQ ID NO: 379         moltype = AA  length = 28
FEATURE                Location/Qualifiers
source                 1..28
                       mol_type = protein
                       note = Lama4 Peptide
                       organism = synthetic construct
SEQUENCE: 379
QKISFFDGFE VGFNFRTLQP NGLLFYYT                                              28

SEQ ID NO: 380         moltype = AA  length = 23
FEATURE                Location/Qualifiers
source                 1..23
                       mol_type = protein
                       note = Itgb1 Peptide
                       organism = synthetic construct
SEQUENCE: 380
WFYFTYSVNG YNEAIVHVVE TPD                                                   23
```